US009382535B2

(12) United States Patent
Ladner et al.

(10) Patent No.: US 9,382,535 B2
(45) Date of Patent: Jul. 5, 2016

(54) METHODS OF CONSTRUCTING LIBRARIES OF GENETIC PACKAGES THAT COLLECTIVELY DISPLAY THE MEMBERS OF A DIVERSE FAMILY OF PEPTIDES, POLYPEPTIDES OR PROTEINS

(75) Inventors: Robert C. Ladner, Ijamsville, MD (US); Edward H. Cohen, Belmont, MA (US); Horacio G. Nastri, Newton, MA (US); Kristin L. Rookey, St. Revere, MA (US); Rene Hoet, Maastricht (NL)

(73) Assignee: Dyax Corp., Burlington, MA (US)

( * ) Notice: Subject to any disclaimer, the term of this patent is extended or adjusted under 35 U.S.C. 154(b) by 385 days.

(21) Appl. No.: 11/365,556

(22) Filed: Feb. 28, 2006

(65) Prior Publication Data
US 2006/0166252 A1 Jul. 27, 2006

Related U.S. Application Data

(62) Division of application No. 09/837,306, filed on Apr. 17, 2001, now abandoned.

(60) Provisional application No. 60/198,069, filed on Apr. 17, 2000.

(51) Int. Cl.
*C12Q 1/68* (2006.01)
*C12Q 1/70* (2006.01)
*C12N 15/00* (2006.01)
*C07H 21/02* (2006.01)
*C07H 21/04* (2006.01)
*C12N 15/10* (2006.01)
*C12N 15/66* (2006.01)
*C40B 40/02* (2006.01)

(52) U.S. Cl.
CPC ............ *C12N 15/1093* (2013.01); *C12N 15/10* (2013.01); *C12N 15/1037* (2013.01); *C12N 15/66* (2013.01); *C40B 40/02* (2013.01)

(58) Field of Classification Search
None
See application file for complete search history.

(56) References Cited

U.S. PATENT DOCUMENTS

| | | | |
|---|---|---|---|
| 5,118,605 A | 6/1992 | Urdea | |
| 5,223,409 A * | 6/1993 | Ladner et al. | 506/1 |
| 5,380,833 A | 1/1995 | Urdea | |
| 5,565,332 A * | 10/1996 | Hoogenboom et al. | 435/69.1 |
| 5,618,920 A | 4/1997 | Robinson et al. | |
| 5,658,727 A | 8/1997 | Barbas et al. | |
| 5,688,666 A | 11/1997 | Bass et al. | |
| 5,714,320 A * | 2/1998 | Kool | 435/6.16 |
| 5,723,323 A | 3/1998 | Kauffman et al. | |
| 5,733,743 A | 3/1998 | Johnson et al. | |
| 5,739,281 A | 4/1998 | Thogersen et al. | |
| 5,750,373 A | 5/1998 | Garrard et al. | |
| 5,780,279 A | 7/1998 | Matthews et al. | |
| 5,798,208 A | 8/1998 | Crea | |
| 5,814,476 A | 9/1998 | Kauffman et al. | |
| 5,817,483 A | 10/1998 | Kauffman et al. | |
| 5,821,047 A | 10/1998 | Garrard et al. | |
| 5,824,514 A | 10/1998 | Kauffman et al. | |
| 5,830,663 A | 11/1998 | Embleton et al. | |
| 5,837,242 A | 11/1998 | Holliger et al. | |
| 5,840,479 A | 11/1998 | Little et al. | |
| 5,846,765 A | 12/1998 | Matthews et al. | |
| 5,854,033 A * | 12/1998 | Lizardi | 435/91.2 |
| 5,858,657 A | 1/1999 | Winter et al. | |
| 5,858,671 A | 1/1999 | Jones | |
| 5,871,907 A | 2/1999 | Winter et al. | |
| 5,871,911 A | 2/1999 | Dahlberg et al. | |
| 5,872,215 A | 2/1999 | Osbourne et al. | |
| 5,885,793 A | 3/1999 | Griffiths et al. | |
| 5,917,018 A | 6/1999 | Thogersen et al. | |
| 5,935,831 A * | 8/1999 | Quax et al. | 435/228 |
| 5,962,255 A | 10/1999 | Griffiths et al. | |
| 5,962,271 A | 10/1999 | Chenchik et al. | |
| 5,962,272 A | 10/1999 | Chenchik et al. | |
| 5,969,108 A | 10/1999 | McCafferty et al. | |
| 5,976,862 A | 11/1999 | Kauffman et al. | |
| 5,994,519 A | 11/1999 | Osbourne et al. | |
| 6,010,884 A | 1/2000 | Griffiths et al. | |
| 6,017,732 A | 1/2000 | Jespers et al. | |
| 6,040,136 A | 3/2000 | Garrard et al. | |
| 6,057,098 A | 5/2000 | Buechler et al. | |
| 6,140,471 A | 10/2000 | Johnson et al. | |
| 6,172,197 B1 | 1/2001 | McCafferty et al. | |
| 6,180,336 B1 | 1/2001 | Osbourn et al. | |
| 6,225,447 B1 | 5/2001 | Winter et al. | |
| 6,238,904 B1 * | 5/2001 | Morgan et al. | 435/199 |
| 6,248,516 B1 | 6/2001 | Winter et al. | |
| 6,291,158 B1 | 9/2001 | Winter et al. | |

(Continued)

FOREIGN PATENT DOCUMENTS

DE 19624562 1/1998
JP 2000-500647 A1 1/2000

(Continued)

OTHER PUBLICATIONS

Gushiken et al., Jun. 1999, Polymorphism of b2-glycoprotein I at codons 306 and 316 in patients with systemic lupus erythematosus and antiphospholipid syndrome, Arthritis & Rheumatism, 42(6): 1189-1193.*

(Continued)

Primary Examiner — Robert T. Crow
Assistant Examiner — Joseph G Dauner
(74) Attorney, Agent, or Firm — Wolf, Greenfield & Sacks, P.C.

(57) ABSTRACT

Methods useful in constructing libraries that collectively display members of diverse families of peptides, polypeptides or proteins and the libraries produced using those methods. Methods of screening those libraries and the peptides, polypeptides or proteins identified by such screens.

27 Claims, 6 Drawing Sheets

(56) References Cited

U.S. PATENT DOCUMENTS

| | | | |
|---|---|---|---|
| 6,291,159 | B1 | 9/2001 | Winter et al. |
| 6,291,160 | B1 | 9/2001 | Lerner et al. |
| 6,291,161 | B1 | 9/2001 | Lerner et al. |
| 6,291,650 | B1 | 9/2001 | Winter et al. |
| 6,300,064 | B1 | 10/2001 | Knappik et al. |
| 6,319,690 | B1 | 11/2001 | Little et al. |
| 6,342,588 | B1 | 1/2002 | Osbourn et al. |
| 6,420,113 | B1 | 7/2002 | Buechler et al. |
| 6,489,123 | B2 | 12/2002 | Osbourn et al. |
| 6,492,107 | B1 | 12/2002 | Kauffman et al. |
| 6,492,123 | B1 | 12/2002 | Holliger et al. |
| 6,492,160 | B1 | 12/2002 | Griffiths et al. |
| 6,521,404 | B1 | 2/2003 | Griffiths et al. |
| 6,531,580 | B1 | 3/2003 | Huse et al. |
| 6,544,731 | B1 | 4/2003 | Griffiths et al. |
| 6,545,142 | B1 | 4/2003 | Winter et al. |
| 6,555,313 | B1 | 4/2003 | Griffiths et al. |
| 6,569,641 | B1 | 5/2003 | Kauffman et al. |
| 6,582,915 | B1 | 6/2003 | Griffiths et al. |
| 6,589,527 | B1 | 7/2003 | Griffiths et al. |
| 6,593,081 | B1 | 7/2003 | Griffiths et al. |
| 6,680,192 | B1 | 1/2004 | Lerner et al. |
| 6,696,245 | B2 | 2/2004 | Winter et al. |
| 6,696,248 | B1 | 2/2004 | Knappik et al. |
| 6,706,484 | B1 | 3/2004 | Knappik et al. |
| 6,753,136 | B2 | 6/2004 | Lohning |
| 6,806,079 | B1 | 10/2004 | McCafferty et al. |
| 6,828,422 | B1 | 12/2004 | Achim et al. |
| 6,846,634 | B1 | 1/2005 | Tomilson et al. |
| 6,916,605 | B1 | 7/2005 | McCafferty et al. |
| 6,969,586 | B1 | 11/2005 | Lerner et al. |
| 7,063,943 | B1 | 6/2006 | McCafferty et al. |
| 7,189,841 | B2 | 3/2007 | Lerner et al. |
| 8,288,322 | B2 | 10/2012 | Ladner et al. |
| 2002/0004215 | A1 | 1/2002 | Osbourn et al. |
| 2003/0114659 | A1 | 6/2003 | Winter et al. |
| 2003/0130496 | A1 | 7/2003 | Winter et al. |
| 2003/0148372 | A1 | 8/2003 | Tomlinson et al. |
| 2003/0190674 | A1 | 10/2003 | Griffiths et al. |
| 2003/0232333 | A1 | 12/2003 | Ladner et al. |
| 2004/0029113 | A1 | 2/2004 | Ladner et al. |
| 2004/0038921 | A1 | 2/2004 | Kreutzer et al. |
| 2004/0110941 | A2 | 6/2004 | Winter et al. |
| 2004/0157214 | A1 | 8/2004 | McCafferty et al. |
| 2004/0157215 | A1 | 8/2004 | McCafferty et al. |
| 2005/0202512 | A1 | 9/2005 | Tomlinson et al. |
| 2006/0003334 | A1 | 1/2006 | Achim et al. |
| 2006/0019260 | A1 | 1/2006 | Lerner et al. |
| 2006/0166252 | A1 | 7/2006 | Ladner et al. |
| 2006/0257937 | A1 | 11/2006 | Ladner |
| 2007/0031879 | A1 | 2/2007 | Ley |
| 2013/0040861 | A1 | 2/2013 | Ladner et al. |

FOREIGN PATENT DOCUMENTS

| | | | |
|---|---|---|---|
| WO | WO 9201047 | A1 * | 1/1992 |
| WO | WO 94/07922 | | 4/1994 |
| WO | 96/35781 | A1 | 11/1996 |
| WO | 9708320 | | 3/1997 |
| WO | WO 97/15690 | A1 | 5/1997 |
| WO | WO 97/20923 | | 6/1997 |
| WO | WO 97/49809 | | 12/1997 |
| WO | 9906834 | | 2/1999 |
| WO | 99/55367 | | 11/1999 |
| WO | WO 99/55367 | A1 | 11/1999 |
| WO | 00/18905 | | 4/2000 |
| WO | WO 00/18905 | A1 | 4/2000 |
| WO | 0179481 | A2 | 10/2001 |

OTHER PUBLICATIONS

Persic. Gene. 1997. 187: 9-18.*
Roben. J. Clin. Invest. 1996. 98(12): 2827-2837.*
Matthyssens. PNAS. 1980. 77(11): 6561-6565.*
NEB Heat Inactivation Chart (retrieved on Sep. 18, 2013 from the internet: <https://www.neb.com/tools-and-resources/usage-guidelines/heat-inactivation>).*
Podhajska. Gene. 1985. 40: 175-182.*
Heddle, R.J.; Rowley, D. "Dog immunoglobulins. I. Immunochemical characterization of dog serum, parotid saliva, colostrum, milk and small bowel fluid." Immunology, 29 (1) pp. 185-195 (1975).
Hrncir et al. "Anticardiolipin antibodies in diffuse connective tissue diseases in the IgG, IgM and IgA isotypes" Vnitmi Lekarstvi. 36 (11), 1041-1049, translation (provided by USPTO) p. 1-13 (1999).
Roitt, I.; Brostoff, J.; Male, D. Immunology Sixth Edition. New York: Mosby pp. 67-70 and 80 (2001).
Arden, "Conserved motifs in T-cell receptor CDR1 and CDR2: implications for ligand and CD8 co-receptor binding" Current Opinion in Immunology, Current Biology Ltd., 10(1):74-81, 1998, XP004313624.
Barbas et al., "Human Autoantibody Recognition of DNA" Proc. Natl. Acad. Sci. 92:2529-2533, 1995, XP002927212.
Davies et al., "Affinity improvement of single antibody VH domains: residues in all three hypervariable regions affect antigen binding", Immunotechnology 2(3):169-179, 1996, XP004070292.
de Haard et al., "A Large Non-immunized Human Fab Fragment Phage Library That Permits Rapid Isolation and Kinetic Analysis of High Affinity Antibodies" Journal of Biological Chemistry, 274(26):18218-18230, 1999, XP002128301.
Hoogenboom et al., "By-passing Immunisation Human Antibodies from Synthetic Repertoires of Germline $V_H$ Gene Segments Rearranged in Vitro" Journal of Molecular Biology, 227:381-388, 1992, XP002974448.
"The Immune Diversity in a Test Tube—Non-Immunised Antibody Libraries and Functional Variability in Defined Protein Scaffolds" Combinotorial Chemistry & High Throughput Screening, 4:409-416, 2001, Soderlind et al.
Tomlinson et al., The Repertoire of Human Germline $V_H$ Sequences Reveals about Fifty Groups of $V_H$ Segments with Different Hypervariable Loops, Journal of Molecular Biology, 227:776-798, 1992, XP000990787.
Aujame et al., "High affinity human antibodies by phage display", Human Antibodies, 8(4):155-168 (1997).
Barbas et al., "Semisynthetic combinatorial antibody libraries: a chemical solution to the diversity problem," Proceedings of the National Academy of Sciences of USA, 89:4457-4461 (1992).
Corbett et al., "Sequence of the human immunoglobulin diversity (D) segment locus: a systematic analysis provides no evidence for the use of DIR segments, inverted D segments, "minor" D segments or D-D recombination", J. Mol. Biol. 270(4): 587-597 (1997).
Hoogenboom et al., "Antibody phage display technology and its applications," Immunotechnology, 4(1):1-20 (1998).
Jirholt et al., "Exploiting sequence space: shuffling in vivo formed complementarity determining regions into a master framework," Gene, 1998, vol. 215, No. 2, pp. 471-476.
Knappik et al., "Fully Synthetic Human Combinatorial Antibody Libraries (HuCAL) Based on Modular Consensus Frameworks and CDRs Randomized with Trinucleotides", J. Mol. Biol., 296:57-86 (2000).
Kruif et al., "Selection and application of human single chain Fv antibody fragments from a semi-synthetic phage antibody display library with designed CDR3 regions", J. Mol. Biol., 248(1):97-105 (1995).
Powell et al., "Construction, assembly and selection of combinatorial antibody libraries", pp. 155-172 in Genetic Engineering with PCR (Horton and Tait, Eds. 1998), vol. 5 of The Current Innovations in Molecular Biology series, Horizon Scientific Press.
Ryu et al., "Recent Progress in Biomolecular Engineering", Biotechnology Progress, 2000, vol. 15, No. 1, pp. 2-16.
Short et al., "Contribution of Antibody Heavy Chain CDR1 to Digoxin Binding Analyzed by Random Mutagenesis of Phage-displayed Fab 26-10", Journal of Biol. Chem., vol. 270 (1):28541-28550 (1995).
Soderlind et al., "Domain libraries: Synthetic diversity for de novo design of antibody V-regions", Gene, 1995, vol. 160, No. 2, pp. 269-272.

(56) References Cited

OTHER PUBLICATIONS

Zucconi et al., "Domain repertoires as a tool to derive protein recognition rules", 2000, FEBS Letters, vol. 480, No. 1, pp. 49-54.
Balint et al., "Antibody engineering by parsimonious mutagenesis," Gene, 1993, vol. 137, pp. 109-118.
Saviranta et al., "Engineering the steroid-specificity of an anti-17B-estradiol Fab by random mutagenesis and competitive phage panning," Protein Engineering, 1998, vol. 11, No. 2, pp. 143-152.
Sheets et al., "Efficient construction of a large nonimmune phage antibody library: The production of high-affinity human single-chain antibodies to protein antigens," Proc. Natl. Acad. Sci. USA, 1998, vol. 95, pp. 6157-6162.
Alves, J. et al., "Accuracy of the EcoRV restriction endonuclease: binding and cleavage studies with oligodeoxynucleotide substrates containing degenerate recognition sequences," Biochemistry, 34(35):11191-11197 (1995).
Grimes E., et al., "Achilles' heel cleavage: creation of rare restriction sites in λ phage genomes and evaluation of additional operators, repressors and restriction/modification systems," Gene, 90(1):1-7 (1990).
Guo-Rong Qi et al., "Restriction of a Single Stranded M13 DNA Using Synthetic Oligonucleotides: The Structural Requirement of Restriction Enzymes," Cell Biol., 65:50-55 (1986).
Hasan N. and Szybalski W., "Control of cloned gene expression by promoter inversion in vivo: construction of improved vectors with a multiple cloning site and the $P_{tac}$ promoter," Gene, 56(1):145-151 (1987).
Hoet, et al., "The Importance of the Light Chain for the Epitope Specificity of Human Anti-U1 Small Nuclear RNA Autoantibodies Present in Systemic Lupus Erythematosus Patients" Journal of Immunology 163(6):3304-3312 (1999).
Kaczorowski T. and Szybalski W., "Genomic DNA sequencing by SPEL-6 primer walking using hexamer ligation," Gene, 223(1-2):83-91 (1998).
Kim S.C. et al., "Cleaving DNA at any predetermined site with adapter-primers and class-IIS restriction enzymes," Science 240(4851):504-506 (1988).
Kim S.C. et al., "Structural requirements for FokI-DNA interaction and oligodeoxyribonucleotide-instructed cleavage," J. Mol. Biol., 258(4):638-649 (1996).
Koob M. and Szybalski W., "Cleaving yeast and *Escherichia coli* genomes at a single site," Science, 250(4978):271-273 (1990).
Koob M. et al., "Conferring new specificity upon restriction endonucleases by combining repressor-operator interaction and methylation," Gene, 74(1):165-167 (1988).
Koob M. et al., "Conferring operator specificity on restriction endonucleases," Science, 241(4869):1084-1086 (1988).
Koob M. et al., "RecA-AC: single-site cleavage of plasmids and chromosomes at any predetermined restriction site," Nucleic Acids Re., 20(21):5831-5836 (1992).
Kur J. et al., "A novel method for converting common restriction enzymes into rare cutters: integration host factor-mediated Achilles' cleavage (IHF-AC)," Gene, 110(1):1-7 (1992).
Lowman, H. B..; Wells, J. A., "Affinity Maturation of Human Growth Hormone by Monovalent Phage Display", J. Mol. Biol. 234:564-578 (1993).
Podhajska A. J. and Szybalski W., "Conversion of the Fok-I endonuclease to a universal restriction enzyme: cleavage of phage M13mp7 DNA at predetermined sites," Gene, 40(1):175-182 (1985).
Podhajska A. J. et al., "Conferring new specificities on restriction enzymes: cleavage at any predetermined site by combining adapter oligodeoxynucleotide and class-IIS enzyme," Methods Enzymol. 216(G):303-309 (1992).
Posfai G. and Szybalski W., "A simple method for locating methylated bases in DNA using class-IIS restriction enzymes," Gene, 74(1):179-1781 (1988).
Robert W. Blakesley et al., "Duplex Regions in "Single-Stranded" ØX174 DNA Are Cleaved by a Restriction Endonuclease from Haemophilus Aegyptius," The Journal of Biological Chemistry, 252:7300-7306 (1977).

Seed, B., "Developments in expression cloning", Current Opinion in Biotechnology, 6:567-573 (1995).
Suzuki, M., Takemura, H., Suzuki, H., Sumida, T., "Light Chain Determines the Binding Property of Human Anti-dsDNA IgG Autoantibodies" Biochem. Biophys. Res. Commun. 271:240-243 (Apr. 29, 2000).
Szybalski W. and Skalka A., "Nobel prizes and restriction enzymes," Gene, 4(3):181-182 (1978).
Szybalski W. et al., "Class-IIS restriction enzymes—a review," Gene, 100:13-26 (1991).
Szybalski W., "Reasons and risks to study restriction/modification enzymes form extreme thermophiles: chilly coldrooms, $13^{th}$ sample, and 13-codon overlap," Gene, 112(1):1-2 (1992).
Szybalski W., "Universal restriction endonucleases: designing novel cleavage specificities by combining adapter oligodeoxynucleotide and enzyme moieties," Gene, 40(2-3):169-173 (1985).
Thielking V. et al., "Accuracy of the EcoRI restriction endonuclease: binding and cleavage studies with oligodeoxynucleotide substrates containing degenerate recognition sequences," Biochemistry, 29(19):4682-4691 (1990).
Zhu D., "Oligodeoxynucleotide-directed cleavage and repair of a single-stranded vector: a method of site-specific mutagenesis," Analytical Biochemistry, 177(1):120-124 (1989).
Koichi Nishigaki et al., "Type II Restriction Endonucleases Cleave Single-Stranded DNAs in General," Nucleic Acids Research, 13:5747-5760 (1985).
Extended European Search Report dated Mar. 10, 2011 from European Application No. 10179786.8.
Podhajska A J Szybalski W.: "Conversion of the Fok- I Endonuclease to a Universal Restriction Enzyme Cleavage of Phage M-13-MP-7 DNA at Predetermined Sites", Gene (Amsterdam), vol. 40, No. 2-3, pp. 175-182 (1985).
Zhu D: "Oligodeoxynucleotide-Directed Cleavage and Repair of a Single-Stranded Vector a Method of Site-Specific Mutagenesis", Analytical Biochemistry, vol. 177, No. 1, pp. 120-124 (1989).
Extended European Search Report from European Application No. 10179777.7 dated Feb. 2, 2011.
Barbas, C.F., "Assembly of Combinatorial antibody libraries on phage surfaces: The gene III site", Proc. Natl. Acad. Sci., vol. 88, pp. 7978-7982, Sep. 1991.
Clackson, T., "In Vitro Selection from Protein and Peptide Libraries", Elsevier Science Ltd., vol. 12, pp. 173-184, May 1, 1994.
Courtney, B.C., "A phage display vector with improved stability, applicability and ease of manipulation", Gene, vol. 165, No. 1, pp. 139-140, Nov. 7, 1995.
Extended European Search Report dated May 26, 2010 from European Application No. 10156326.0.
Fan, Z-C, "Three-dimensional Structure of an Fv from a Human IgM Immunoglobulin", J. Mol. Biol., vol. 228, No. 1, pp. 188-207, Nov. 5, 1992.
Hoet, R.M., "Generation of high-affinity human antibodies by combining donor-derived and synthetic complementarity-determining-region diversity", Nature Biotechnology, vol. 23, No. 3, pp. 344-348, Mar. 2005.
Hoogenboom, H.R., "Multi-subunit proteins on the surface of filamentous phage: methodologies for displaying antibody (Fab) heavy and light chains", Nucleic Acids Research, vol. 19, No. 15, pp. 4133-4137, Jan. 1, 1991.
Schoonbroodt, S, "Oligonucleotide-assisted cleavage and ligation: a novel directional DNA cloning technology to capture cDNAs. Application in the construction of a human immune antibody phage-display library", Nucleic Acids Research, vol. 33, No. 9, p. E81, 2005.
Smith, G.P., "Phage Display", Chem. Rev., vol. 97, No. 2, pp. 391-410, Mar. 1, 1997.
Brezinschek (May 1997) Journal of Clinical Investigation vol. 99 pp. 2488 to 2501.
Pini (Aug. 21, 1998) Journal of Biological Chemistry vol. 273 pp. 21769 to 21776.
Stewart (Feb. 1, 1993) Journal of Experimental Medicine vol. 177 pp. 409 to 418.
Yang (1995) Journal of Molecular Biology vol. 254 pp. 392 to 403.
Opposition from European Serial No. EP1578903.

(56) References Cited

OTHER PUBLICATIONS

Barbas et al., Assembly of combinatorial antibody libraries on phage surfaces: the gene III site. Proc Natl Acad Sci U S A. Sep. 15, 1991;88(18):7978-82.
Barbas et al., Selection and evolution of high-affinity human antiviral antibodies. Trends Biotechnol. Jul. 1996;14(7):230-4.
Beers et al., Immunotoxins with increased activity against epidermal growth factor receptor vIII-expressing cells produced by antibody phage display. Clin Cancer Res. Jul. 2000;6(7):2835-43.
Brezinschek et al., Analysis of the human VH gene repertoire. Differential effects of selection and somatic hypermutation on human peripheral CD5(+)/IgM+ and CD5(−)/IgM+ B cells. J Clin Invest. May 15, 1997;99(10):2488-501.
Clackson et al., In vitro selection from protein and peptide libraries. Trends Biotechnol. May 1994;12(5):173-84.
Courtney et al., A phage display vector with improved stability, applicability and ease of manipulation. Gene. Nov. 7, 1995;165(1):139-40.
Deng et al., Basis for selection of improved carbohydrate-binding single-chain antibodies from synthetic gene libraries. Proc Natl Acad Sci U S A. May 23, 1995;92(11):4992-6.
Fan et al., Three-dimensional structure of an Fv from a human IgM immunoglobulin. J Mol Biol. Nov. 5, 1992;228(1):188-207.
Griffin et al., A human monoclonal antibody specific for the leucine-33 (P1A1, HPA-1a) form of platelet glycoprotein IIIa from a V gene phage display library. Blood. Dec. 15, 1995;86(12):4430-6.
Hemminki et al., Fine tuning of an anti-testosterone antibody binding site by stepwise optimisation of the CDRs. Immunotechnology. Jun. 1998;4(1):59-69.
Hoet et al., Generation of high-affinity human antibodies by combining donor-derived and synthetic complementarity-determining-region diversity. Nat Biotechnol. Mar. 2005;23(3):344-8. Epub Feb. 20, 2005.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Jackson et al., In vitro antibody maturation. Improvement of a high affinity, neutralizing antibody against IL-1 beta. J Immunol. Apr. 1, 1995;154(7):3310-9.
Marks et al., By-passing immunization: building high affinity human antibodies by chain shuffling. Biotechnology (N Y). Jul. 1992;10(7):779-83.
Pini et al., Design and use of a phage display library: human antibodies with subnanomolar affinity against a marker of angiogenesis eluted from a two-dimensional gel. J Biol Chem. Aug. 21, 1998;273(34):21769-76.
Schoonbroodt et al., Oligonucleotide-assisted cleavage and ligation: a novel directional DNA cloning technology to capture cDNAs. Application in the construction of a human immune antibody phage-display library. Nucleic Acids Res. May 19, 2005;33(9):e81.
Smith et al., Building synthetic antibodies as adhesive ligands for integrins. J Biol Chem. Dec. 30, 1994;269(52):32788-95.
Smith et al., Phage Display. Chem Rev. Apr. 1, 1997;97(2):391-410.
Soderlind et al., Recombining germline-derived CDR sequences for creating diverse single-framework antibody libraries. Nat Biotechnol. Aug. 2000;18(8):852-6.
Stewart et al., High-frequency representation of a single VH gene in the expressed human B cell repertoire. J Exp Med. Feb. 1, 1993;177(2):409-18. Erratum in: J Exp Med. Apr. 1, 1993;177(4):1227.
Van Den Beucken et al., Building novel binding ligands to B7.1 and B7.2 based on human antibody single variable light chain domains. J Mol Biol. Jul. 13, 2001;310(3):591-601.
Wang et al., Phage display of proteases and macromolecular inhibitors. Methods Enzymol. 1996;267:52-68.
Wu et al., Length distribution of CDRH3 in antibodies. Proteins. May 1993;16(1):1-7.
Yang et al., CDR walking mutagenesis for the affinity maturation of a potent human anti-HIV-1 antibody into the picomolar range. J Mol Biol. Dec. 1, 1995;254(3):392-403.
Zemlin et al., Expressed murine and human CDR-H3 intervals of equal length exhibit distinct repertoires that differ in their amino acid composition and predicted range of structures. J Mol Biol. Dec. 5, 2003;334(4):733-49.

* cited by examiner

SEQUENCE LISTING

<160> NUMBER OF SEQ ID NOS: 504

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catgtgtatt actgtgc                                                  17

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cacatccgtg cttcttgcac ggatgtggca cagtaataca catg                    44

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gtgtattaga ctgctgcc                                                 18

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggcagcagtc taatacacca catccgtgtt cttcacggat gtg                     43

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cacatccgtg tttgttacac ggatgtggtg tcttacagtc cattctg                 47

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagaatggac tgtaagacac                                               20

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atcgagtctc actgagccac atccgtggtt ttccacggat gtg                     43

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctcagtgag actcgat                                                    17

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgaccgaat tgctacaag                                                  19

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gactcctcag cttcttgctg aggagtcctt gtagcaattc ggtcat                    46

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acctcactgg cttccggatt cactttctct                                      30

<210> SEQ ID NO 12
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agaaacccac tccaaacctt taccaggagc ttggcgaacc ca                        42

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggaaggcagt gatctagaga tagtgaagcg acctttaacg gagtcagcat a              51

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 14
ggaaggcagt gatctagaga tag                                          23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(24)
<223> OTHER INFORMATION: a, c, g, t, unknown or other

<400> SEQUENCE: 15
cacggatgtg nnnnnnnnnn nnnn                                         24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(14)
<223> OTHER INFORMATION: a, c, g, t, unknown or other

<400> SEQUENCE: 16
nnnnnnnnnn nnnncacatc cgtg                                         24

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgtattact gtgc                                                    14

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cacatccgtg cacggatgtg gcacagtaat acac                              34

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtgtattaga ctgc                                                    14
```

-continued

```
<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcagtctaat acaccacatc cgtgcacgga tgtg                                 34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cacatccgtg cacggatgtg gtgtcttaca gtcc                                 34

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggactgtaag acac                                                       14

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagtctcact gagccacatc cgtgcacgga tgtg                                 34

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gctcagtgag actc                                                       14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgtattact gtgc                                                       14
```

```
<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtatattact gtgc                                                       14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtgtattact gtaa                                                       14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gtgtattact gtac                                                       14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttgtattact gtgc                                                       14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttgtatcact gtgc                                                       14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acatattact gtgc                                                       14
```

```
<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
acgtattact gtgc                                                          14

<210> SEQ ID NO 33
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
atgtattact gtgc                                                          14

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tggaagaggc acgttctttt cttt                                               24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaagaaaaga acgtgcctct tcca                                               24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acactctccc ctgttgaagc tctt                                               24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgaacattct gtaggggcca ctg                                                23
```

```
<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agagcattct gcaggggcca ctg                                           23

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
accgcctcca ccgggcgcgc cttattaaca ctctcccctg ttgaagctct t             51

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
accgcctcca ccgggcgcgc cttattatga acattctgta ggggccactg               50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
accgcctcca ccgggcgcgc cttattaaga gcattctgca ggggccactg               50

<210> SEQ ID NO 42
<211> LENGTH: 98
<212> TYPE: DNA
<213> ORGANISM: Homo sapiens

<400> SEQUENCE: 42
agggtcacca tgaccaggga cacgtccatc agcacagcct acatggagct gagcaggctg    60
agatctgacg acacggccgt gtattactgt gcgagaga                           98

<210> SEQ ID NO 43
<211> LENGTH: 98
<212> TYPE: DNA
<213> ORGANISM: Homo sapiens

<400> SEQUENCE: 43
agagtcacca ttaccaggga cacatccgcg agcacagcct acatggagct gagcagcctg    60
agatctgaag acacggctgt gtattactgt gcgagaga                           98

<210> SEQ ID NO 44
```

```
<211> LENGTH: 98
<212> TYPE: DNA
<213> ORGANISM: Homo sapiens

<400> SEQUENCE: 44
agagtcacca tgaccaggaa cacctccata agcacagcct acatggagct gagcagcctg      60
agatctgagg acacggccgt gtattactgt gcgagagg                              98

<210> SEQ ID NO 45
<211> LENGTH: 98
<212> TYPE: DNA
<213> ORGANISM: Homo sapiens

<400> SEQUENCE: 45
agagtcacca tgaccacaga cacatccacg agcacagcct acatggagct gaggagcctg      60
agatctgacg acacggccgt gtattactgt gcgagaga                              98

<210> SEQ ID NO 46
<211> LENGTH: 98
<212> TYPE: DNA
<213> ORGANISM: Homo sapiens

<400> SEQUENCE: 46
agagtcacca tgaccgagga cacatctaca gacacagcct acatggagct gagcagcctg      60
agatctgagg acacggccgt gtattactgt gcaacaga                              98

<210> SEQ ID NO 47
<211> LENGTH: 98
<212> TYPE: DNA
<213> ORGANISM: Homo sapiens

<400> SEQUENCE: 47
agagtcacca ttaccaggga caggtctatg agcacagcct acatggagct gagcagcctg      60
agatctgagg acacagccat gtattactgt gcaagata                              98

<210> SEQ ID NO 48
<211> LENGTH: 98
<212> TYPE: DNA
<213> ORGANISM: Homo sapiens

<400> SEQUENCE: 48
agagtcacca tgaccaggga cacgtccacg agcacagtct acatggagct gagcagcctg      60
agatctgagg acacggccgt gtattactgt gcgagaga                              98

<210> SEQ ID NO 49
<211> LENGTH: 98
<212> TYPE: DNA
<213> ORGANISM: Homo sapiens

<400> SEQUENCE: 49
agagtcacca ttaccaggga catgtccaca agcacagcct acatggagct gagcagcctg      60
agatccgagg acacggccgt gtattactgt gcggcaga                              98

<210> SEQ ID NO 50
<211> LENGTH: 98
<212> TYPE: DNA
<213> ORGANISM: Homo sapiens

<400> SEQUENCE: 50
agagtcacga ttaccgcgga cgaatccacg agcacagcct acatggagct gagcagcctg      60
```
agatctgagg acacggccgt gtattactgt gcgagaga                                98

<210> SEQ ID NO 51
<211> LENGTH: 98
<212> TYPE: DNA
<213> ORGANISM: Homo sapiens

<400> SEQUENCE: 51
agagtcacga ttaccgcgga caaatccacg agcacagcct acatggagct gagcagcctg        60
agatctgagg acacggccgt gtattactgt gcgagaga                                98

<210> SEQ ID NO 52
<211> LENGTH: 98
<212> TYPE: DNA
<213> ORGANISM: Homo sapiens

<400> SEQUENCE: 52
agagtcacca taaccgcgga cacgtctaca gacacagcct acatggagct gagcagcctg        60
agatctgagg acacggccgt gtattactgt gcaacaga                                98

<210> SEQ ID NO 53
<211> LENGTH: 100
<212> TYPE: DNA
<213> ORGANISM: Homo sapiens

<400> SEQUENCE: 53
aggctcacca tcaccaagga cacctccaaa aaccaggtgg tccttacaat gaccaacatg        60
gaccctgtgg acacagccac atattactgt gcacacagac                              100

<210> SEQ ID NO 54
<211> LENGTH: 100
<212> TYPE: DNA
<213> ORGANISM: Homo sapiens

<400> SEQUENCE: 54
aggctcacca tctccaagga cacctccaaa agccaggtgg tccttaccat gaccaacatg        60
gaccctgtgg acacagccac atattactgt gcacggatac                              100

<210> SEQ ID NO 55
<211> LENGTH: 100
<212> TYPE: DNA
<213> ORGANISM: Homo sapiens

<400> SEQUENCE: 55
aggctcacca tctccaagga cacctccaaa aaccaggtgg tccttacaat gaccaacatg        60
gaccctgtgg acacagccac gtattactgt gcacggatac                              100

<210> SEQ ID NO 56
<211> LENGTH: 98
<212> TYPE: DNA
<213> ORGANISM: Homo sapiens

<400> SEQUENCE: 56
cgattcacca tctccagaga caacgccaag aactcactgt atctgcaaat gaacagcctg        60
agagccgagg acacggctgt gtattactgt gcgagaga                                98

<210> SEQ ID NO 57
<211> LENGTH: 100
<212> TYPE: DNA

<213> ORGANISM: Homo sapiens

<400> SEQUENCE: 57
cgattcacca tctccagaga caacgccaag aactccctgt atctgcaaat gaacagtctg    60
agagctgagg acacggcctt gtattactgt gcaaaagata                         100

<210> SEQ ID NO 58
<211> LENGTH: 98
<212> TYPE: DNA
<213> ORGANISM: Homo sapiens

<400> SEQUENCE: 58
cgattcacca tctccaggga caacgccaag aactcactgt atctgcaaat gaacagcctg    60
agagccgagg acacggccgt gtattactgt gcgagaga                           98

<210> SEQ ID NO 59
<211> LENGTH: 98
<212> TYPE: DNA
<213> ORGANISM: Homo sapiens

<400> SEQUENCE: 59
cgattcacca tctccagaga aaatgccaag aactccttgt atcttcaaat gaacagcctg    60
agagccgggg acacggctgt gtattactgt gcaagaga                           98

<210> SEQ ID NO 60
<211> LENGTH: 98
<212> TYPE: DNA
<213> ORGANISM: Homo sapiens

<400> SEQUENCE: 60
agattcacca tctcaagaga tgattcaaaa aacacgctgt atctgcaaat gaacagcctg    60
aaaaccgagg acacagccgt gtattactgt accacaga                           98

<210> SEQ ID NO 61
<211> LENGTH: 98
<212> TYPE: DNA
<213> ORGANISM: Homo sapiens

<400> SEQUENCE: 61
cgattcacca tctccagaga caacgccaag aactccctgt atctgcaaat gaacagtctg    60
agagccgagg acacggcctt gtatcactgt gcgagaga                           98

<210> SEQ ID NO 62
<211> LENGTH: 98
<212> TYPE: DNA
<213> ORGANISM: Homo sapiens

<400> SEQUENCE: 62
cgattcacca tctccagaga caacgccaag aactcactgt atctgcaaat gaacagcctg    60
agagccgagg acacggctgt gtattactgt gcgagaga                           98

<210> SEQ ID NO 63
<211> LENGTH: 98
<212> TYPE: DNA
<213> ORGANISM: Homo sapiens

<400> SEQUENCE: 63
cggttcacca tctccagaga caattccaag aacacgctgt atctgcaaat gaacagcctg    60
agagccgagg acacggccgt atattactgt gcgaaaga                           98

<210> SEQ ID NO 64
<211> LENGTH: 98
<212> TYPE: DNA
<213> ORGANISM: Homo sapiens

<400> SEQUENCE: 64
cgattcacca tctccagaga caattccaag aacacgctgt atctgcaaat gaacagcctg    60
agagctgagg acacggctgt gtattactgt gcgaaaga                            98

<210> SEQ ID NO 65
<211> LENGTH: 98
<212> TYPE: DNA
<213> ORGANISM: Homo sapiens

<400> SEQUENCE: 65
cgattcacca tctccagaga caattccaag aacacgctgt atctgcaaat gaacagcctg    60
agagctgagg acacggctgt gtattactgt gcgagaga                            98

<210> SEQ ID NO 66
<211> LENGTH: 98
<212> TYPE: DNA
<213> ORGANISM: Homo sapiens

<400> SEQUENCE: 66
cgattcacca tctccagaga caattccaag aacacgctgt atctgcaaat gaacagcctg    60
agagctgagg acacggctgt gtattactgt gcgaaaga                            98

<210> SEQ ID NO 67
<211> LENGTH: 98
<212> TYPE: DNA
<213> ORGANISM: Homo sapiens

<400> SEQUENCE: 67
cgattcacca tctccagaga caattccaag aacacgctgt atctgcaaat gaacagcctg    60
agagccgagg acacggctgt gtattactgt gcgagaga                            98

<210> SEQ ID NO 68
<211> LENGTH: 100
<212> TYPE: DNA
<213> ORGANISM: Homo sapiens

<400> SEQUENCE: 68
cgattcacca tctccagaga caacagcaaa aactccctgt atctgcaaat gaacagtctg    60
agaactgagg acaccgcctt gtattactgt gcaaaagata                          100

<210> SEQ ID NO 69
<211> LENGTH: 98
<212> TYPE: DNA
<213> ORGANISM: Homo sapiens

<400> SEQUENCE: 69
cgattcacca tctccagaga caatgccaag aactcactgt atctgcaaat gaacagcctg    60
agagacgagg acacggctgt gtattactgt gcgagaga                            98

<210> SEQ ID NO 70
<211> LENGTH: 98
<212> TYPE: DNA
<213> ORGANISM: Homo sapiens

<400> SEQUENCE: 70
agattcacca tctcaagaga tggttccaaa agcatcgcct atctgcaaat gaacagcctg    60
aaaaccgagg acacagccgt gtattactgt actagaga                           98

<210> SEQ ID NO 71
<211> LENGTH: 98
<212> TYPE: DNA
<213> ORGANISM: Homo sapiens

<400> SEQUENCE: 71
cgattcacca tctccagaga caattccaag aacacgctgt atcttcaaat gaacagcctg    60
agagccgagg acacggccgt gtattactgt gcgagaga                           98

<210> SEQ ID NO 72
<211> LENGTH: 98
<212> TYPE: DNA
<213> ORGANISM: Homo sapiens

<400> SEQUENCE: 72
agattcacca tctccagaga caattccaag aacacgctgt atcttcaaat gggcagcctg    60
agagctgagg acatggctgt gtattactgt gcgagaga                           98

<210> SEQ ID NO 73
<211> LENGTH: 98
<212> TYPE: DNA
<213> ORGANISM: Homo sapiens

<400> SEQUENCE: 73
agattcacca tctccagaga caattccaag aacacgctgt atcttcaaat gaacagcctg    60
agagctgagg acacggctgt gtattactgt gcgagaga                           98

<210> SEQ ID NO 74
<211> LENGTH: 98
<212> TYPE: DNA
<213> ORGANISM: Homo sapiens

<400> SEQUENCE: 74
agattcacca tctcaagaga tgattcaaag aactcactgt atctgcaaat gaacagcctg    60
aaaaccgagg acacggccgt gtattactgt gctagaga                           98

<210> SEQ ID NO 75
<211> LENGTH: 98
<212> TYPE: DNA
<213> ORGANISM: Homo sapiens

<400> SEQUENCE: 75
aggttcacca tctccagaga tgattcaaag aacacggcgt atctgcaaat gaacagcctg    60
aaaaccgagg acacggccgt gtattactgt actagaca                           98

<210> SEQ ID NO 76
<211> LENGTH: 98
<212> TYPE: DNA
<213> ORGANISM: Homo sapiens

<400> SEQUENCE: 76
cgattcacca tctccagaga caacgccaag aacacgctgt atctgcaaat gaacagtctg    60
agagccgagg acacggctgt gtattactgt gcaagaga                           98

```
<210> SEQ ID NO 77
<211> LENGTH: 98
<212> TYPE: DNA
<213> ORGANISM: Homo sapiens

<400> SEQUENCE: 77
agattcacca tctccagaga caattccaag aacacgctgc atcttcaaat gaacagcctg      60
agagctgagg acacggctgt gtattactgt aagaaaga                             98

<210> SEQ ID NO 78
<211> LENGTH: 98
<212> TYPE: DNA
<213> ORGANISM: Homo sapiens

<400> SEQUENCE: 78
cgagtcacca tatcagtaga caagtccaag aaccagttct ccctgaagct gagctctgtg      60
accgccgcgg acacggccgt gtattactgt gcgagaga                             98

<210> SEQ ID NO 79
<211> LENGTH: 98
<212> TYPE: DNA
<213> ORGANISM: Homo sapiens

<400> SEQUENCE: 79
cgagtcacca tgtcagtaga cacgtccaag aaccagttct ccctgaagct gagctctgtg      60
accgccgtgg acacggccgt gtattactgt gcgagaaa                             98

<210> SEQ ID NO 80
<211> LENGTH: 98
<212> TYPE: DNA
<213> ORGANISM: Homo sapiens

<400> SEQUENCE: 80
cgagttacca tatcagtaga cacgtctaag aaccagttct ccctgaagct gagctctgtg      60
actgccgcgg acacggccgt gtattactgt gcgagaga                             98

<210> SEQ ID NO 81
<211> LENGTH: 98
<212> TYPE: DNA
<213> ORGANISM: Homo sapiens

<400> SEQUENCE: 81
cgagtcacca tatcagtaga caggtccaag aaccagttct ccctgaagct gagctctgtg      60
accgccgcgg acacggccgt gtattactgt gccagaga                             98

<210> SEQ ID NO 82
<211> LENGTH: 98
<212> TYPE: DNA
<213> ORGANISM: Homo sapiens

<400> SEQUENCE: 82
cgagttacca tatcagtaga cacgtccaag aaccagttct ccctgaagct gagctctgtg      60
actgccgcag acacggccgt gtattactgt gccagaga                             98

<210> SEQ ID NO 83
<211> LENGTH: 98
<212> TYPE: DNA
<213> ORGANISM: Homo sapiens

<400> SEQUENCE: 83
```

```
cgagttacca tatcagtaga cacgtctaag aaccagttct ccctgaagct gagctctgtg    60
actgccgcgg acacggccgt gtattactgt gcgagaga                            98
```

<210> SEQ ID NO 84
<211> LENGTH: 98
<212> TYPE: DNA
<213> ORGANISM: Homo sapiens

<400> SEQUENCE: 84

```
cgagtcacca tatcagtaga cacgtccaag aaccagttct ccctgaagct gagctctgtg    60
accgccgcgg acacggctgt gtattactgt gcgagaga                            98
```

<210> SEQ ID NO 85
<211> LENGTH: 98
<212> TYPE: DNA
<213> ORGANISM: Homo sapiens

<400> SEQUENCE: 85

```
cgagtcacca tatccgtaga cacgtccaag aaccagttct ccctgaagct gagctctgtg    60
accgccgcag acacggctgt gtattactgt gcgagaca                            98
```

<210> SEQ ID NO 86
<211> LENGTH: 98
<212> TYPE: DNA
<213> ORGANISM: Homo sapiens

<400> SEQUENCE: 86

```
cgagtcacca tatcagtaga cacgtccaag aaccagttct ccctgaagct gagctctgtg    60
accgctgcgg acacggccgt gtattactgt gcgagaga                            98
```

<210> SEQ ID NO 87
<211> LENGTH: 98
<212> TYPE: DNA
<213> ORGANISM: Homo sapiens

<400> SEQUENCE: 87

```
cgagtcacca tatcagtaga cacgtccaag aaccagttct ccctgaagct gagctctgtg    60
accgctgcgg acacggccgt gtattactgt gcgagaga                            98
```

<210> SEQ ID NO 88
<211> LENGTH: 98
<212> TYPE: DNA
<213> ORGANISM: Homo sapiens

<400> SEQUENCE: 88

```
cgagtcacca tatcagtaga cacgtccaag aaccagttct ccctgaagct gagctctgtg    60
accgccgcag acacggccgt gtattactgt gcgagaga                            98
```

<210> SEQ ID NO 89
<211> LENGTH: 98
<212> TYPE: DNA
<213> ORGANISM: Homo sapiens

<400> SEQUENCE: 89

```
caggtcacca tctcagccga caagtccatc agcaccgcct acctgcagtg gagcagcctg    60
aaggcctcgg acaccgccat gtattactgt gcgagaca                            98
```

<210> SEQ ID NO 90
<211> LENGTH: 96

```
<212> TYPE: DNA
<213> ORGANISM: Homo sapiens

<400> SEQUENCE: 90
cacgtcacca tctcagctga caagtccatc agcactgcct acctgcagtg gagcagcctg      60
aaggcctcgg acaccgccat gtattactgt gcgaga                                96

<210> SEQ ID NO 91
<211> LENGTH: 98
<212> TYPE: DNA
<213> ORGANISM: Homo sapiens

<400> SEQUENCE: 91
cgaataacca tcaacccaga cacatccaag aaccagttct ccctgcagct gaactctgtg      60
actcccgagg acacggctgt gtattactgt gcaagaga                              98

<210> SEQ ID NO 92
<211> LENGTH: 98
<212> TYPE: DNA
<213> ORGANISM: Homo sapiens

<400> SEQUENCE: 92
cggtttgtct tctccttgga cacctctgtc agcacggcat atctgcagat ctgcagccta      60
aaggctgagg acactgccgt gtattactgt gcgagaga                              98

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
agttctccct gcagctgaac tc                                               22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
cactgtatct gcaaatgaac ag                                               22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ccctgtatct gcaaatgaac ag                                               22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                              probe

<400> SEQUENCE: 96
ccgcctacct gcagtggagc ag                                            22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
cgctgtatct gcaaatgaac ag                                            22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
cggcatatct gcagatctgc ag                                            22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
cggcgtatct gcaaatgaac ag                                            22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
ctgcctacct gcagtggagc ag                                            22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
tcgcctatct gcaaatgaac ag                                            22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 102
agttctccct gcagctgaac tc                                              22

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ttctccctgc agctgaactc                                                 20

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
ttctccctgc agctgaac                                                   18

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
cgctgtatct gcaaatgaac ag                                              22

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ctgtatctgc aaatgaacag                                                 20

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ctgtatctgc aaatgaac                                                   18

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 108
cactgtatct gcaaatgaac ag                                          22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ccgcctacct gcagtggagc ag                                          22

<210> SEQ ID NO 110
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cgcttcacta agtctagaga caactctaag aatactctct acttgcagat gaacagctta    60
agg                                                                  63

<210> SEQ ID NO 111
<211> LENGTH: 4
<212> TYPE: PRT
<213> ORGANISM: Unknown
<220> FEATURE:
<223> OTHER INFORMATION: Description of Unknown: MALIA3 peptide

<400> SEQUENCE: 111

Ser Val Leu Val
1

<210> SEQ ID NO 112
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
caagtagaga gtattcttag agttgtctct agacttagtg aagcg                 45

<210> SEQ ID NO 113
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
cgcttcacta agtctagaga caactctaag aatactctct acttgcagct gaac       54

<210> SEQ ID NO 114
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 114
cgcttcacta agtctagaga caactctaag aatactctct acttgcaaat gaac            54

<210> SEQ ID NO 115
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cgcttcacta agtctagaga caactctaag aatactctct acttgcagtg gagc            54

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cgcttcacta agtctagaga c                                               21

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
acatggagct gagcagcctg ag                                              22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
acatggagct gagcaggctg ag                                              22

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
acatggagct gaggagcctg ag                                              22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 120
acctgcagtg gagcagcctg aa                                              22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
atctgcaaat gaacagcctg aa                                              22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
atctgcaaat gaacagcctg ag                                              22

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
atctgcaaat gaacagtctg ag                                              22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
atctgcagat ctgcagccta aa                                              22

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
atcttcaaat gaacagcctg ag                                              22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
```
atcttcaaat gggcagcctg ag				22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
ccctgaagct gagctctgtg ac				22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
ccctgcagct gaactctgtg ac				22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 129
tccttacaat gaccaacatg ga				22

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
tccttaccat gaccaacatg ga				22

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
acatggagct gagcagcctg ag				22

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccctgaagct gagctctgtg ac                                               22

<210> SEQ ID NO 133
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cgcttcacta agtctagaga caactctaag aatactctct acttgcagat gaacagctta    60
agg                                                                   63

<210> SEQ ID NO 134
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cgcttcactc agtctagaga taacagtaaa aatactttgt acttgcagct gagcagcctg    60

<210> SEQ ID NO 135
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cgcttcactc agtctagaga taacagtaaa aatactttgt acttgcagct gagctctgtg    60

<210> SEQ ID NO 136
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tcagctgcaa gtacaaagta tttttactgt tatctctaga ctgagtgaag cg            52

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
cgcttcactc agtctagaga taac                                            24

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138

-continued ccgtgtatta ctgtgcgaga ga                                             22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ctgtgtatta ctgtgcgaga ga                                             22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ccgtgtatta ctgtgcgaga gg                                             22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccgtgtatta ctgtgcaaca ga                                             22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ccatgtatta ctgtgcaaga ta                                             22

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ccgtgtatta ctgtgcggca ga                                             22

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ccacatatta ctgtgcacac ag                                              22

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ccacatatta ctgtgcacgg at                                              22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ccacgtatta ctgtgcacgg at                                              22

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ccttgtatta ctgtgcaaaa ga                                              22

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
ctgtgtatta ctgtgcaaga ga                                              22

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
ccgtgtatta ctgtaccaca ga                                              22

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
ccttgtatca ctgtgcgaga ga                                              22

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ccgtatatta ctgtgcgaaa ga                                              22

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctgtgtatta ctgtgcgaaa ga                                              22

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ccgtgtatta ctgtactaga ga                                              22

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ccgtgtatta ctgtgctaga ga                                              22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
ccgtgtatta ctgtactaga ca                                              22

<210> SEQ ID NO 156
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ctgtgtatta ctgtaagaaa ga                                              22

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ccgtgtatta ctgtgcgaga aa                                               22

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
ccgtgtatta ctgtgccaga ga                                               22

<210> SEQ ID NO 159
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
ctgtgtatta ctgtgcgaga ca                                               22

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ccatgtatta ctgtgcgaga ca                                               22

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ccatgtatta ctgtgcgaga                                                  20

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ccgtgtatta ctgtgcgaga g                                                21

-continued

```
<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ctgtgtatta ctgtgcgaga g                                                   21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ccgtgtatta ctgtgcgaga g                                                   21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ccgtatatta ctgtgcgaaa g                                                   21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ctgtgtatta ctgtgcgaaa g                                                   21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
ctgtgtatta ctgtgcgaga c                                                   21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
ccatgtatta ctgtgcgaga c                                                   21

<210> SEQ ID NO 169
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ccatgtatta ctgtgcgaga                                                    20

<210> SEQ ID NO 170
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggtgtagtga tctagtgaca actctaagaa tactctctac ttgcagatga acagctttag        60
ggctgaggac actgcagtct actattgtgc gaga                                    94

<210> SEQ ID NO 171
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ggtgtagtga tctagtgaca actctaagaa tactctctac ttgcagatga acagctttag        60
ggctgaggac actgcagtct actattgtgc gaaa                                    94

<210> SEQ ID NO 172
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
atagtagact gcagtgtcct cagcccttaa gctgttcatc tgcaagtaga gagtattctt        60
agagttgtct ctagatcact acacc                                              85

<210> SEQ ID NO 173
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ggtgtagtga tctagagaca ac                                                 22

<210> SEQ ID NO 174
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
```
ggtgtagtga aacagcttta gggctgagga cactgcagtc tactattgtg cgaga         55

<210> SEQ ID NO 175
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ggtgtagtga aacagcttta gggctgagga cactgcagtc tactattgtg cgaaa         55

<210> SEQ ID NO 176
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
atagtagact gcagtgtcct cagcccttaa gctgtttcac tacacc                   46

<210> SEQ ID NO 177
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ggtgtagtga aacagcttaa gggctg                                         26

<210> SEQ ID NO 178
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
cacatccgtg ttgttcacgg atgtg                                          25

<210> SEQ ID NO 179
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aatagtagac tgcagtgtcc tcagcccttp agctgttcat ctgcaagtag agagtattct    60
tagagttgtc tctagactta gtgaagcg                                       88

<210> SEQ ID NO 180
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cgcttcacta agtctagaga caactctaag aatactctct acttgcagat gaacagctta    60
agggctgagg acactgcagt ctactattgt gcgag    95

<210> SEQ ID NO 181
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cgcttcacta agtctagaga caactctaag aatactctct acttgcagat gaacagctta    60
agggctgagg acactgcagt ctactattgt acgag    95

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cgcttcacta agtctagaga caac    24

<210> SEQ ID NO 183
<211> LENGTH: 419
<212> TYPE: DNA
<213> ORGANISM: Unknown
<220> FEATURE:
<223> OTHER INFORMATION: Description of Unknown: V3-23 polynucleotide

<400> SEQUENCE: 183
ctgtctgaac ggcccagccg gccatggccg aagttcaatt gttagagtct ggtggcggtc    60
ttgttcagcc tggtggttct ttacgtcttt cttgcgctgc ttccggattc actttctctt   120
cgtacgctat gtcttgggtt cgccaagctc ctggtaaagg tttggagtgg gtttctgcta   180
tctctggttc tggtggcagt acttactatg ctgactccgt aaaggtcgc ttcactatct   240 ctagagacaa ctctaagaat actctctact tgcagatgaa cagcttaagg gctgaggaca   300
ctgcagtcta ctattgcgct aaagactatg aaggtactgg ttatgctttc gacatatggg   360
gtcaaggtac tatggtcacc gtctctagtg cctccaccaa gggcccatcg gtcttcccc    419

<210> SEQ ID NO 184
<211> LENGTH: 136
<212> TYPE: PRT
<213> ORGANISM: Unknown
<220> FEATURE:
<223> OTHER INFORMATION: Description of Unknown: V3-23 polypeptide

<400> SEQUENCE: 184

Ala Gln Pro Ala Met Ala Glu Val Gln Leu Leu Glu Ser Gly Gly Gly
1               5                   10                  15

Leu Val Gln Pro Gly Gly Ser Leu Arg Leu Ser Cys Ala Ala Ser Gly
            20                  25                  30

Phe Thr Phe Ser Ser Tyr Ala Met Ser Trp Val Arg Gln Ala Pro Gly
        35                  40                  45

Lys Gly Leu Glu Trp Val Ser Ala Ile Ser Gly Ser Gly Gly Ser Thr
    50                  55                  60

Tyr Tyr Ala Asp Ser Val Lys Gly Arg Phe Thr Ile Ser Arg Asp Asn
65                  70                  75                  80

Ser Lys Asn Thr Leu Tyr Leu Gln Met Asn Ser Leu Arg Ala Glu Asp
            85                  90                  95

Thr Ala Val Tyr Tyr Cys Ala Lys Asp Tyr Glu Gly Thr Gly Tyr Ala
        100                 105                 110

Phe Asp Ile Trp Gly Gln Gly Thr Met Val Thr Val Ser Ser Ala Ser
    115                 120                 125

Thr Lys Gly Pro Ser Val Phe Pro
    130             135

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ctgtctgaac ggcccagccg                                               20

<210> SEQ ID NO 186
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ctgtctgaac ggcccagccg gccatggccg aagttcaatt gttagagtct ggtggcggtc    60
ttgttcagcc tggtggttct tta                                           83

<210> SEQ ID NO 187
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gaaagtgaat ccggaagcag cgcaagaaag acgtaaagaa ccaccaggct gaac          54

<210> SEQ ID NO 188
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
agaaacccac tccaaacctt taccaggagc ttggcgaacc ca                      42

<210> SEQ ID NO 189
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 189
agtgtcctca gcccttaagc tgttcatctg caagtagaga gtattcttag agttgtctct    60
agagatagtg aagcgacctt taacggagtc agca                                94

<210> SEQ ID NO 190
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gcttaagggc tgaggacact gcagtctact attgcgctaa agactatgaa ggtactggtt    60
atgctttcga catatggggt c                                              81

<210> SEQ ID NO 191
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ggggaagacc gatgggccct tggtggaggc actagagacg gtgaccatag taccttgacc    60
ccatatgtcg aaagc                                                     75

<210> SEQ ID NO 192
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(24)
<223> OTHER INFORMATION: a, c, g, t, unknown or other and encodes any
      amino acid except Cys
<220> FEATURE:
<221> NAME/KEY: modified_base
<222> LOCATION: (28)..(30)
<223> OTHER INFORMATION: a, c, g, t, unknown or other and encodes any
      amino acid except Cys
<220> FEATURE:
<221> NAME/KEY: modified_base
<222> LOCATION: (34)..(36)
<223> OTHER INFORMATION: a, c, g, t, unknown or other and encodes any
      amino acid except Cys

<400> SEQUENCE: 192
gcttccggat tcactttctc tnnntacnnn atgnnntggg ttcgccaagc tcctgg        56

<210> SEQ ID NO 193
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, g, t, unknown or other and encodes any
      amino acid except Ala, Cys, Asp, Glu, Phe, His, Ile, Lys, Leu,
      Met, Asn, Pro, Gln or Thr
<220> FEATURE:
```

```
<221> NAME/KEY: modified_base
<222> LOCATION: (25)..(27)
<223> OTHER INFORMATION: a, c, g, t, unknown or other and encodes any
      amino acid except Ala, Cys, Asp, Glu, Phe, His, Ile, Lys, Leu,
      Met, Asn, Pro, Gln or Thr
<220> FEATURE:
<221> NAME/KEY: modified_base
<222> LOCATION: (28)..(30)
<223> OTHER INFORMATION: a, c, g, t, unknown or other and encodes any
      amino acid except Ala, Cys, Asp, Glu, Phe, Gly, His, Ile, Lys,
      Leu, Met, Asn, Gln, Arg, Thr, Val, Trp or Tyr
<220> FEATURE:
<221> NAME/KEY: modified_base
<222> LOCATION: (40)..(42)
<223> OTHER INFORMATION: a, c, g, t, unknown or other and encodes any
      amino acid except Cys
<220> FEATURE:
<221> NAME/KEY: modified_base
<222> LOCATION: (46)..(48)
<223> OTHER INFORMATION: a, c, g, t, unknown or other and encodes any
      amino acid except Cys

<400> SEQUENCE: 193
ggtttggagt gggtttctnn natcnnnnnn tctggtggcn nnactnnnta tgctgactcc    60
gttaaagg                                                            68

<210> SEQ ID NO 194
<211> LENGTH: 9535
<212> TYPE: DNA
<213> ORGANISM: Unknown
<220> FEATURE:
<223> OTHER INFORMATION: Description of Unknown: MALIA3 polynucleotide

<400> SEQUENCE: 194
aatgctacta ctattagtag aattgatgcc acctttttcag ctcgcgcccc aaatgaaaat    60
atagctaaac aggttattga ccatttgcga aatgtatcta atggtcaaac taaatctact   120
cgttcgcaga attgggaatc aactgttaca tggaatgaaa cttccagaca ccgtacttta   180
gttgcatatt taaaacatgt tgagctacag caccagattc agcaattaag ctctaagcca   240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag   360
tctttcgggc ttcctcttaa tcttttttgat gcaatccgct ttgcttctga ctataatagt   420
cagggtaaag acctgatttt tgatttatgg tcattctcgt tttctgaact gtttaaagca   480
tttgaggggg attcaatgaa tatttatgac gattccgcag tattggacgc tatccagtct   540
aaacatttta ctattacccc ctctggcaaa acttcttttg caaaagcctc tcgctatttt   600
ggtttttatc gtcgtctggt aaacgagggt tatgatagtg ttgctcttac tatgcctcgt   660
aattcctttt ggcgttatgt atctgcatta gttgaatgtg gtattcctaa atctcaactg   720
atgaatcttt ctacctgtaa taatgttgtt ccgttagttc gttttattaa cgtagatttt   780
tcttcccaac gtcctgactg gtataatgag ccagttctta aaatcgcata aggtaattca   840
caatgattaa agttgaaatt aaaccatctc aagcccaatt tactactcgt tctggtgttt   900
ctcgtcaggg caagccttat tcactgaatg agcagctttg ttacgttgat ttgggtaatg   960
aatatccggt tcttgtcaag attactcttg atgaaggtca gccagcctat gcgcctggtc  1020
tgtacaccgt tcatctgtcc tctttcaaag ttggtcagtt cggttcccct atgattgacc  1080
gtctgcgcct cgttccggct aagtaacatg gagcaggtcg cggatttcga cacaattttat  1140 caggcgatga tacaaatctc cgttgtactt tgtttcgcgc ttggtataat cgctgggggt  1200
caaagatgag tgttttagtg tattctttcg cctctttcgt tttaggttgg tgccttcgta  1260
```

```
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagccttttc  1560 ttttggaga ttttcaacgt gaaaaaatta ttattcgcaa ttcctttagt tgttcctttc   1620
tattctcaca gtgcacagtc tgtcgtgacg cagccgccct cagtgtctgg ggccccaggg   1680
cagagggtca ccatctcctg cactgggagc agctccaaca tcggggcagg ttatgatgta   1740
cactggtacc agcagcttcc aggaacagcc cccaaactcc tcatctatgg taacagcaat   1800
cggccctcag gggtccctga ccgattctct ggctccaagt ctggcacctc agcctccctg   1860
gccatcactg gctccaggc tgaggatgag gctgattatt actgccagtc ctatgacagc   1920
agcctgagtg gcctttatgt cttcggaact gggaccaagg tcaccgtcct aggtcagccc   1980
aaggccaacc ccactgtcac tctgttcccg ccctcctctg aggagctcca agccaacaag   2040
gccacactag tgtgtctgat cagtgacttc tacccgggag ctgtgacagt ggcctggaag   2100
gcagatagca gccccgtcaa ggcgggagtg gagaccacca cccctccaa acaaagcaac   2160 aacaagtacg cggccagcag ctatctgagc ctgacgcctg agcagtggaa gtcccacaga   2220
agctacagct gccaggtcac gcatgaaggg agcaccgtgg agaagacagt ggcccctaca   2280
gaatgttcat aataaaccgc ctccaccggg cgcgccaatt ctatttcaag agacagtca   2340 taatgaaata cctattgcct acggcagccg ctggattgtt attactcgcg gcccagccgg   2400
ccatggccga agttcaattg ttagagtctg gtggcggtct tgttcagcct ggtggttctt   2460
tacgtctttc ttgcgctgct tccggattca ctttctcttc gtacgctatg tcttgggttc   2520
gccaagctcc tggtaaaggt ttggagtggg tttctgctat ctctggttct ggtggcagta   2580
cttactatgc tgactccgtt aaaggtcgct tcactatctc tagagacaac tctaagaata   2640
ctctctactt gcagatgaac agcttaaggg ctgaggacac tgcagtctac tattgcgcta   2700
aagactatga aggtactggt tatgctttcg acatatgggg tcaaggtact atggtcaccg   2760
tctctagtgc ctccaccaag ggcccatcgg tcttcccct ggcaccctcc tccaagagca   2820
cctctggggg cacagcggcc ctgggctgcc tggtcaagga ctacttcccc gaaccggtga   2880
cggtgtcgtg gaactcaggc gccctgacca gcggcgtcca caccttcccg gctgtcctac   2940
agtctagcgg actctactcc ctcagcagcg tagtgaccgt gccctcttct agcttgggca   3000
cccagaccta catctgcaac gtgaatcaca agcccagcaa caccaaggtg gacaagaaag   3060
ttgagcccaa atcttgtgcg gccgctcatc accaccatca tcactctgct gaacaaaaac   3120
tcatctcaga agaggatctg aatggtgccg cagatatcaa cgatgatcgt atggctagcg   3180
gcgccgctga aactgttgaa agttgtttag caaaaccccca tacagaaaat tcatttacta   3240
acgtctggaa agacgacaaa actttagatc gttacgctaa ctatgagggt tgtctgtgga   3300
atgctacagg cgttgtagtt tgtactggtg acgaaactca gtgttacggt acatgggttc   3360
ctattgggct tgctatccct gaaaatgagg gtggtggctc tgagggtggc ggttctgagg   3420
gtggcggttc tgagggtggc ggtactaaac ctcctgagta cggtgataca cctattccgg   3480
gctatactta tatcaaccct ctcgacggca cttatccgcc tggtactgag caaaaccccg   3540
ctaatcctaa tccttctctt gaggagtctc agcctcttaa tactttcatg tttcagaata   3600
```

```
ataggttccg aaataggcag ggggcattaa ctgtttatac gggcactgtt actcaaggca    3660
ctgaccccgt taaaacttat taccagtaca ctcctgtatc atcaaaagcc atgtatgacg    3720
cttactggaa cggtaaattc agagactgcg cttttccattc tggctttaat gaagatccat   3780
tcgtttgtga atatcaaggc caatcgtctg acctgcctca acctcctgtc aatgctggcg    3840
gcggctctgg tggtggttct ggtggcggct ctgagggtgg tggctctgag ggtggcggtt    3900
ctgagggtgg cggctctgag ggaggcggtt ccggtggtgg ctctggttcc ggtgattttg    3960
attatgaaaa gatggcaaac gctaataagg gggctatgac cgaaaatgcc gatgaaaacg    4020
cgctacagtc tgacgctaaa ggcaaacttg attctgtcgc tactgattac ggtgctgcta    4080
tcgatggttt cattggtgac gtttccggcc ttgctaatgg taatggtgct actggtgatt    4140
ttgctggctc taattcccaa atggctcaag tcggtgacgg tgataattca cctttaatga    4200
ataatttccg tcaatattta ccttccctcc ctcaatcggt tgaatgtcgc ccttttgtct    4260
ttagcgctgg taaaccatat gaattttcta ttgattgtga caaaataaac ttattccgtg    4320
gtgtctttgc gtttctttta tatgttgcca cctttatgta tgtattttct acgtttgcta    4380
acatactgcg taataaggag tcttaatcat gccagttctt ttgggtattc cgttattatt    4440
gcgtttcctc ggtttccttc tggtaacttt gttcggctat ctgcttactt ttcttaaaaa    4500
gggcttcggt aagatagcta ttgctatttc attgtttctt gctcttatta ttgggcttaa    4560
ctcaattctt gtgggttatc tctctgatat tagcgctcaa ttaccctctg actttgttca    4620
gggtgttcag ttaattctcc cgtctaatgc gcttccctgt ttttatgtta ttctctctgt    4680
aaaggctgct atttcatttt tgacgttaa acaaaaaatc gtttcttatt tggattggga    4740
taaataatat ggctgtttat tttgtaactg gcaaattagg ctctggaaag acgctcgtta    4800
gcgttggtaa gattcaggat aaaattgtag ctgggtgcaa aatagcaact aatcttgatt    4860
taaggcttca aaacctcccg caagtcggga ggttcgctaa aacgcctcgc gttcttagaa    4920
taccggataa gccttctata tctgatttgc ttgctattgg gcgcggtaat gattcctacg    4980
atgaaaataa aaacggcttg cttgttctcg atgagtgcgg tacttggttt aatacccgtt    5040
cttggaatga taaggaaaga cagccgatta ttgattggtt tctacatgct cgtaaattag    5100
gatgggatat tatttttctt gttcaggact tatctattgt tgataaacag gcgcgttctg    5160
cattagctga acatgttgtt tattgtcgtc gtctggacag aattacttta ccttttgtcg    5220
gtactttata ttctcttatt actggctcga aaatgcctct gcctaaatta catgttggcg    5280
ttgttaaata tggcgattct caattaagcc ctactgttga gcgttggctt tatactggta    5340
agaatttgta taacgcatat gatactaaac aggctttttc tagtaattat gattccggtg    5400
tttattctta tttaacgcct tatttatcac acgtcggta tttcaaacca ttaaatttag    5460
gtcagaagat gaaattaact aaaatatatt tgaaaaagtt ttctcgcgtt ctttgtcttg    5520
cgattggatt tgcatcagca tttacatata gttatataac ccaacctaag ccggaggtta    5580
aaaaggtagt ctctcagacc tatgattttg ataaattcac tattgactct tctcagcgtc    5640
ttaatctaag ctatcgctat gttttcaagg attctaaggg aaaattaatt aatagcgacg    5700
atttacagaa gcaaggttat tcactcacat atattgattt atgtactgtt tccattaaaa    5760
aaggtaattc aaatgaaatt gttaaatgta attaattttg ttttcttgat gtttgtttca    5820
tcatcttctt ttgctcaggt aattgaaatg aataattcgc ctctgcgcga ttttgtaact    5880
tggtattcaa agcaatcagg cgaatccgtt attgtttctc ccgatgtaaa aggtactgtt    5940
actgtatatt catctgacgt taaacctgaa aatctacgca atttctttat ttctgtttta    6000
```

```
cgtgctaata attttgatat ggttggttca attccttcca taattcagaa gtataatcca    6060
aacaatcagg attatattga tgaattgcca tcatctgata atcaggaata tgatgataat    6120
tccgctcctt ctggtggttt ctttgttccg caaaatgata atgttactca aacttttaaa    6180
attaataacg ttcgggcaaa ggatttaata cgagttgtcg aattgtttgt aaagtctaat    6240
acttctaaat cctcaaatgt attatctatt gacggctcta atctattagt tgtttctgca    6300
cctaaagata ttttagataa ccttcctcaa ttcctttcta ctgttgattt gccaactgac    6360
cagatattga ttgagggttt gatatttgag gttcagcaag gtgatgcttt agattttca    6420
tttgctgctg gctctcagcg tggcactgtt gcaggcggtg ttaatactga ccgcctcacc    6480
tctgttttat cttctgctgg tggttcgttc ggtatttta atggcgatgt tttagggcta    6540
tcagttcgcg cattaaagac taatagccat tcaaaaatat tgtctgtgcc acgtattctt    6600
acgctttcag gtcagaaggg ttctatctct gttggccaga atgtcccttt tattactggt    6660
cgtgtgactg gtgaatctgc caatgtaaat aatccatttc agacgattga gcgtcaaaat    6720
gtaggtattt ccatgagcgt ttttcctgtt gcaatggctg gcggtaatat tgttctggat    6780
attaccagca aggccgatag tttgagttct tctactcagg caagtgatgt tattactaat    6840
caaagaagta ttgctacaac ggttaatttg cgtgatggac agactctttt actcggtggc    6900
ctcactgatt ataaaaacac ttctcaagat tctggcgtac cgttcctgtc taaaatccct    6960
ttaatcggcc tcctgtttag ctcccgctct gattccaacg aggaaagcac gttatacgtg    7020
ctcgtcaaag caaccatagt acgcgccctg tagcggcgca ttaagcgcgg cgggtgtggt    7080
ggttacgcgc agcgtgaccg ctacacttgc cagcgcccta gcgcccgctc ctttcgcttt    7140
cttcccttcc tttctcgcca cgttcgccgg ctttccccgt caagctctaa atcgggggct    7200
ccctttaggg ttccgattta gtgctttacg gcacctcgac cccaaaaaac ttgatttggg    7260
tgatggttca cgtagtgggc catcgccctg atagacggtt tttcgccctt tgacgttgga    7320
gtccacgttc tttaatagtg gactcttgtt ccaaactgga acaacactca accctatctc    7380
gggctattct tttgatttat aagggatttt gccgatttcg gaaccaccat caaacaggat    7440
tttcgcctgc tggggcaaac cagcgtggac cgcttgctgc aactctctca gggccaggcg    7500
gtgaagggca atcagctgtt gcccgtctca ctggtgaaaa gaaaaaccac cctggatcca    7560
agcttgcagg tggcactttt cggggaaatg tgcgcggaac ccctatttgt ttatttttct    7620
aaatacattc aaatatgtat ccgctcatga caataaacc ctgataaatg cttcaataat    7680
attgaaaaag gaagagtatg agtattcaac atttccgtgt cgcccttatt ccctttttg    7740
cggcattttg ccttcctgtt tttgctcacc cagaaacgct ggtgaaagta aaagatgctg    7800
aagatcagtt gggcgcacga gtgggttaca tcgaactgga tctcaacagc ggtaagatcc    7860
ttgagagttt tcgccccgaa gaacgttttc caatgatgag cacttttaaa gttctgctat    7920
gtcatacact attatcccgt attgacgccg gcaagagcaa ctcggtcgc cgggcgcggt    7980
attctcagaa tgacttggtt gagtactcac cagtcacaga aaagcatctt acggatggca    8040
tgacagtaag agaattatgc agtgctgcca taaccatgag tgataacact gcggccaact    8100
tacttctgac aacgatcgga ggaccgaagg agctaaccgc ttttttgcac aacatgggg    8160
atcatgtaac tcgccttgat cgttgggaac cggagctgaa tgaagccata ccaaacgacg    8220
agcgtgacac cacgatgcct gtagcaatgc caacaacgtt gcgcaaacta ttaactggcg    8280
aactacttac tctagcttcc cggcaacaat taatagactg gatggaggcg gataaagttg    8340
```

```
caggaccact tctgcgctcg gcccttccgg ctggctggtt tattgctgat aaatctggag    8400
ccggtgagcg tgggtctcgc ggtatcattg cagcactggg gccagatggt aagccctccc    8460
gtatcgtagt tatctacacg acggggagtc aggcaactat ggatgaacga aatagacaga    8520
tcgctgagat aggtgcctca ctgattaagc attggtaact gtcagaccaa gtttactcat    8580
atatacttta gattgattta aacttcatt tttaatttaa aaggatctag gtgaagatcc      8640
tttttgataa tctcatgacc aaaatcccctt aacgtgagtt ttcgttccac tgtacgtaag   8700 accccccaagc ttgtcgactg aatggcgaat ggcgctttgc ctggtttccg gcaccagaag   8760
cggtgccgga agctggctg gagtgcgatc ttcctgaggc cgatactgtc gtcgtcccct     8820
caaactggca gatgcacggt tacgatgcgc ccatctacac caacgtaacc tatcccatta   8880
cggtcaatcc gccgtttgtt cccacggaga atccgacggg ttgttactcg ctcacattta   8940
atgttgatga agctggcta caggaaggcc agacgcgaat tatttttgat ggcgttccta    9000
ttggttaaaa aatgagctga tttaacaaaa atttaacgcg aatttaaca aaatattaac    9060 gtttacaatt taaatatttg cttatacaat cttcctgttt ttggggcttt tctgattatc   9120
aaccggggta catatgattg acatgctagt tttacgatta ccgttcatcg attctcttgt   9180
ttgctccaga ctctcaggca atgacctgat agcctttgta gatctctcaa aaatagctac   9240
cctctccggc atgaatttat cagctagaac ggttgaatat catattgatg gtgatttgac   9300
tgtctccggc ctttctcacc cttttgaatc tttacctaca cattactcag gcattgcatt   9360
taaaatatat gagggttcta aaattttta tccttgcgtt gaaataaagg cttctcccgc    9420
aaaagtatta cagggtcata atgttttttgg tacaaccgat ttagctttat gctctgaggc  9480
tttattgctt aattttgcta attctttgcc ttgcctgtat gatttattgg atgtt         9535

<210> SEQ ID NO 195
<211> LENGTH: 20
<212> TYPE: PRT
<213> ORGANISM: Unknown
<220> FEATURE:
<223> OTHER INFORMATION: Description of Unknown: MALIA3 peptide

<400> SEQUENCE: 195

Met Lys Lys Leu Leu Phe Ala Ile Pro Leu Val Val Pro Phe Tyr Ser
1               5                   10                  15

His Ser Ala Gln
            20

<210> SEQ ID NO 196
<211> LENGTH: 368
<212> TYPE: PRT
<213> ORGANISM: Unknown
<220> FEATURE:
<223> OTHER INFORMATION: Description of Unknown: MALIA3 polypeptide

<400> SEQUENCE: 196

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ala Ile Ser Gly Ser Gly Gly Ser Thr
```

```
                65                  70                  75                  80
        Tyr Tyr Ala Asp Ser Val Lys Gly Arg Phe Thr Ile Ser Arg Asp Asn
                        85                  90                  95

Ser Lys Asn Thr Leu Tyr Leu Gln Met Asn Ser Leu Arg Ala Glu Asp
                        100                 105                 110

Thr Ala Val Tyr Tyr Cys Ala Lys Asp Tyr Glu Gly Thr Gly Tyr Ala
                        115                 120                 125

Phe Asp Ile Trp Gly Gln Gly Thr Met Val Thr Val Ser Ser Ala Ser
                130                 135                 140

Thr Lys Gly Pro Ser Val Phe Pro Leu Ala Pro Ser Ser Lys Ser Thr
        145                 150                 155                 160

Ser Gly Gly Thr Ala Ala Leu Gly Cys Leu Val Lys Asp Tyr Phe Pro
                        165                 170                 175

Glu Pro Val Thr Val Ser Trp Asn Ser Gly Ala Leu Thr Ser Gly Val
                        180                 185                 190

His Thr Phe Pro Ala Val Leu Gln Ser Ser Gly Leu Tyr Ser Leu Ser
                        195                 200                 205

Ser Val Val Thr Val Pro Ser Ser Ser Leu Gly Thr Gln Thr Tyr Ile
                210                 215                 220

Cys Asn Val Asn His Lys Pro Ser Asn Thr Lys Val Asp Lys Lys Val
        225                 230                 235                 240

Glu Pro Lys Ser Cys Ala Ala Ala His His His His His His Ser Ala
                        245                 250                 255

Glu Gln Lys Leu Ile Ser Glu Glu Asp Leu Asn Gly Ala Ala Asp Ile
                        260                 265                 270

Asn Asp Asp Arg Met Ala Ser Gly Ala Ala Glu Thr Val Glu Ser Cys
                        275                 280                 285

Leu Ala Lys Pro His Thr Glu Ile Ser Phe Thr Asn Val Trp Lys Asp
                290                 295                 300

Asp Lys Thr Leu Asp Arg Tyr Ala Asn Tyr Glu Gly Cys Leu Trp Asn
        305                 310                 315                 320

Ala Thr Gly Val Val Val Cys Thr Gly Asp Glu Thr Gln Cys Tyr Gly
                        325                 330                 335

Thr Trp Val Pro Ile Gly Leu Ala Ile Pro Glu Asn Glu Gly Gly Gly
                        340                 345                 350

Ser Glu Gly Gly Gly Ser Glu Gly Gly Ser Glu Gly Gly Gly Thr
                        355                 360                 365

<210> SEQ ID NO 197
<211> LENGTH: 152
<212> TYPE: PRT
<213> ORGANISM: Unknown
<220> FEATURE:
<223> OTHER INFORMATION: Description of Unknown: MALIA3 polypeptide

<400> SEQUENCE: 197

Ser Gly Asp Phe Asp Tyr Glu Lys Met Ala Asn Ala Asn Lys Gly Ala
        1               5                   10                  15

Met Thr Glu Asn Ala Asp Glu Asn Ala Leu Gln Ser Asp Ala Lys Gly
                        20                  25                  30

Lys Leu Asp Ser Val Ala Thr Asp Tyr Gly Ala Ala Ile Asp Gly Phe
                        35                  40                  45

Ile Gly Asp Val Ser Gly Leu Ala Asn Gly Asn Gly Ala Thr Gly Asp
                        50                  55                  60

Phe Ala Gly Ser Asn Ser Gln Met Ala Gln Val Gly Asp Gly Asp Asn
```

-continued

```
                65                  70                  75                  80

Ser Pro Leu Met Asn Asn Phe Arg Gln Tyr Leu Pro Ser Leu Pro Gln
                85                  90                  95

Ser Val Glu Cys Arg Pro Phe Val Phe Ser Ala Gly Lys Pro Tyr Glu
               100                 105                 110

Phe Ser Ile Asp Cys Asp Lys Ile Asn Leu Phe Arg Gly Val Phe Ala
               115                 120                 125

Phe Leu Leu Tyr Val Ala Thr Phe Met Tyr Val Phe Ser Thr Phe Ala
               130                 135                 140

Asn Ile Leu Arg Asn Lys Glu Ser
145                 150

<210> SEQ ID NO 198
<211> LENGTH: 15
<212> TYPE: PRT
<213> ORGANISM: Unknown
<220> FEATURE:
<223> OTHER INFORMATION: Description of Unknown: MALIA3 peptide

<400> SEQUENCE: 198

Met Pro Val Leu Leu Gly Ile Pro Leu Leu Leu Arg Phe Leu Gly
1               5                  10                  15

<210> SEQ ID NO 199
<211> LENGTH: 336
<212> TYPE: PRT
<213> ORGANISM: Unknown
<220> FEATURE:
<223> OTHER INFORMATION: Description of Unknown: MALIA3 polypeptide

<400> SEQUENCE: 199

Gly Lys Thr Leu Val Ser Val Gly Lys Ile Gln Asp Lys Ile Val Ala
1               5                  10                  15

Gly Cys Lys Ile Ala Thr Asn Leu Asp Leu Arg Leu Gln Asn Leu Pro
                20                  25                  30

Gln Val Gly Arg Phe Ala Lys Thr Pro Arg Val Leu Arg Ile Pro Asp
                35                  40                  45

Lys Pro Ser Ile Ser Asp Leu Leu Ala Ile Gly Arg Gly Asn Asp Ser
                50                  55                  60

Tyr Asp Glu Asn Lys Asn Gly Leu Leu Val Leu Asp Glu Cys Gly Thr
65                  70                  75                  80

Trp Phe Asn Thr Arg Ser Trp Asn Asp Lys Glu Arg Gln Pro Ile Ile
                85                  90                  95

Asp Trp Phe Leu His Ala Arg Lys Leu Gly Trp Asp Ile Ile Phe Leu
               100                 105                 110

Val Gln Asp Leu Ser Ile Val Asp Lys Gln Ala Arg Ser Ala Leu Ala
               115                 120                 125

Glu His Val Val Tyr Cys Arg Arg Leu Asp Arg Ile Thr Leu Pro Phe
               130                 135                 140

Val Gly Thr Leu Tyr Ser Leu Ile Thr Gly Ser Lys Met Pro Leu Pro
145                 150                 155                 160

Lys Leu His Val Gly Val Val Lys Tyr Gly Asp Ser Gln Leu Ser Pro
                165                 170                 175

Thr Val Glu Arg Trp Leu Tyr Thr Gly Lys Asn Leu Tyr Asn Ala Tyr
                180                 185                 190

Asp Thr Lys Gln Ala Phe Ser Ser Asn Tyr Asp Ser Gly Val Tyr Ser
                195                 200                 205
```

```
Tyr Leu Thr Pro Tyr Leu Ser His Gly Arg Tyr Phe Lys Pro Leu Asn
            210                 215                 220

Leu Gly Gln Lys Met Lys Leu Thr Lys Ile Tyr Leu Lys Phe Ser
225                 230                 235                 240

Arg Val Leu Cys Leu Ala Ile Gly Phe Ala Ser Ala Phe Thr Tyr Ser
                245                 250                 255

Tyr Ile Thr Gln Pro Lys Pro Glu Val Lys Val Val Ser Gln Thr
                260                 265                 270

Tyr Asp Phe Asp Lys Phe Thr Ile Asp Ser Ser Gln Arg Leu Asn Leu
                275                 280                 285

Ser Tyr Arg Tyr Val Phe Lys Asp Ser Lys Gly Lys Leu Ile Asn Ser
290                 295                 300

Asp Asp Leu Gln Lys Gln Gly Tyr Ser Leu Thr Tyr Ile Asp Leu Cys
305                 310                 315                 320

Thr Val Ser Ile Lys Lys Gly Asn Ser Asn Glu Ile Val Lys Cys Asn
                325                 330                 335
```

```
<210> SEQ ID NO 200
<211> LENGTH: 10
<212> TYPE: PRT
<213> ORGANISM: Unknown
<220> FEATURE:
<223> OTHER INFORMATION: Description of Unknown: MALIA3 peptide

<400> SEQUENCE: 200

Met Lys Leu Leu Asn Val Ile Asn Phe Val
1               5                   10

<210> SEQ ID NO 201
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cgcttcacta tctctagaga caactctaag aatactctct acttgcagat gaacagctta       60
agggctgagg acactgcagt ctactattgc gctaaa                                 96

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
                20                  25                  30

<210> SEQ ID NO 203
<211> LENGTH: 96
<212> TYPE: DNA
<213> ORGANISM: Artificial Sequence
<220> FEATURE:
<223> OTHER INFORMATION: Description of Artificial Sequence: Synthetic
      consensus oligonucleotide
<220> FEATURE:
<221> NAME/KEY: modified_base
```

```
<222> LOCATION: (3)..(3)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (15)..(15)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other
<220> FEATURE:
<221> NAME/KEY: modified_base
<222> LOCATION: (57)..(57)
<223> OTHER INFORMATION: a, c, g, t, unknown or other
<220> FEATURE:
<221> NAME/KEY: modified_base
<222> LOCATION: (63)..(63)
<223> OTHER INFORMATION: a, c, g, t, unknown or other
<220> FEATURE:
<221> NAME/KEY: modified_base
<222> LOCATION: (66)..(66)
<223> OTHER INFORMATION: a, c, g, t, unknown or other
<220> FEATURE:
<221> NAME/KEY: modified_base
<222> LOCATION: (75)..(75)
<223> OTHER INFORMATION: a, c, g, t, unknown or other
<220> FEATURE:
<221> NAME/KEY: modified_base
<222> LOCATION: (78)..(78)
<223> OTHER INFORMATION: a, c, g, t, unknown or other
<220> FEATURE:
<221> NAME/KEY: modified_base
<222> LOCATION: (81)..(81)
<223> OTHER INFORMATION: a, c, g, t, unknown or other
<220> FEATURE:
<221> NAME/KEY: modified_base
<222> LOCATION: (93)..(93)
<223> OTHER INFORMATION: a, c, g, t, unknown or other

<400> SEQUENCE: 203
cgnttyacna thtcncgnga yaaytcnaar aayacnttrt ayttrcarat gaaytcnttr    60
cgngcngarg ayacngcngt ntaytaytgy gcnaar                              96

<210> SEQ ID NO 204
<211> LENGTH: 90
<212> TYPE: DNA
<213> ORGANISM: Homo sapiens

<400> SEQUENCE: 204
caggtgcagc tggtgcagtc tggggctgag gtgaagaagc ctggggcctc agtgaaggtc    60
tcctgcaagg cttctggata caccttcacc                                    90

<210> SEQ ID NO 205
<211> LENGTH: 90
<212> TYPE: DNA
<213> ORGANISM: Homo sapiens

<400> SEQUENCE: 205
caggtccagc ttgtgcagtc tggggctgag gtgaagaagc ctggggcctc agtgaaggtt    60
```

```
tcctgcaagg cttctggata caccttcact                                   90

<210> SEQ ID NO 206
<211> LENGTH: 90
<212> TYPE: DNA
<213> ORGANISM: Homo sapiens

<400> SEQUENCE: 206
caggtgcagc tggtgcagtc tggggctgag gtgaagaagc ctggggcctc agtgaaggtc   60
tcctgcaagg cttctggata caccttcacc                                   90

<210> SEQ ID NO 207
<211> LENGTH: 90
<212> TYPE: DNA
<213> ORGANISM: Homo sapiens

<400> SEQUENCE: 207
caggttcagc tggtgcagtc tggagctgag gtgaagaagc ctggggcctc agtgaaggtc   60
tcctgcaagg cttctggtta cacctttacc                                   90

<210> SEQ ID NO 208
<211> LENGTH: 90
<212> TYPE: DNA
<213> ORGANISM: Homo sapiens

<400> SEQUENCE: 208
caggtccagc tggtacagtc tggggctgag gtgaagaagc ctggggcctc agtgaaggtc   60
tcctgcaagg tttccggata caccctcact                                   90

<210> SEQ ID NO 209
<211> LENGTH: 90
<212> TYPE: DNA
<213> ORGANISM: Homo sapiens

<400> SEQUENCE: 209
cagatgcagc tggtgcagtc tggggctgag gtgaagaaga ctgggtcctc agtgaaggtt   60
tcctgcaagg cttccggata caccttcacc                                   90

<210> SEQ ID NO 210
<211> LENGTH: 90
<212> TYPE: DNA
<213> ORGANISM: Homo sapiens

<400> SEQUENCE: 210
caggtgcagc tggtgcagtc tggggctgag gtgaagaagc ctggggcctc agtgaaggtt   60
tcctgcaagg catctggata caccttcacc                                   90

<210> SEQ ID NO 211
<211> LENGTH: 90
<212> TYPE: DNA
<213> ORGANISM: Homo sapiens

<400> SEQUENCE: 211
caaatgcagc tggtgcagtc tgggcctgag gtgaagaagc ctgggacctc agtgaaggtc   60
tcctgcaagg cttctggatt caccttact                                    90

<210> SEQ ID NO 212
<211> LENGTH: 90
<212> TYPE: DNA
```

```
<400> SEQUENCE: 212
caggtgcagc tggtgcagtc tggggctgag gtgaagaagc ctgggtcctc ggtgaaggtc      60
tcctgcaagg cttctggagg caccttcagc                                       90

<210> SEQ ID NO 213
<211> LENGTH: 90
<212> TYPE: DNA
<213> ORGANISM: Homo sapiens

<400> SEQUENCE: 213
caggtgcagc tggtgcagtc tggggctgag gtgaagaagc ctgggtcctc ggtgaaggtc      60
tcctgcaagg cttctggagg caccttcagc                                       90

<210> SEQ ID NO 214
<211> LENGTH: 90
<212> TYPE: DNA
<213> ORGANISM: Homo sapiens

<400> SEQUENCE: 214
gaggtccagc tggtacagtc tggggctgag gtgaagaagc ctggggctac agtgaaaatc      60
tcctgcaagg tttctggata caccttcacc                                       90

<210> SEQ ID NO 215
<211> LENGTH: 90
<212> TYPE: DNA
<213> ORGANISM: Homo sapiens

<400> SEQUENCE: 215
cagatcacct tgaaggagtc tggtcctacg ctggtgaaac ccacacagac cctcacgctg      60
acctgcacct tctctgggtt ctcactcagc                                       90

<210> SEQ ID NO 216
<211> LENGTH: 90
<212> TYPE: DNA
<213> ORGANISM: Homo sapiens

<400> SEQUENCE: 216
caggtcacct tgaaggagtc tggtcctgtg ctggtgaaac ccacagagac cctcacgctg      60
acctgcaccg tctctgggtt ctcactcagc                                       90

<210> SEQ ID NO 217
<211> LENGTH: 90
<212> TYPE: DNA
<213> ORGANISM: Homo sapiens

<400> SEQUENCE: 217
caggtcacct tgaaggagtc tggtcctgcg ctggtgaaac ccacacagac cctcacactg      60
acctgcacct tctctgggtt ctcactcagc                                       90

<210> SEQ ID NO 218
<211> LENGTH: 90
<212> TYPE: DNA
<213> ORGANISM: Homo sapiens

<400> SEQUENCE: 218
gaggtgcagc tggtggagtc tgggggaggc ttggtccagc ctgggggtc cctgagactc       60 tcctgtgcag cctctggatt caccttagt                                        90
```

```
<210> SEQ ID NO 219
<211> LENGTH: 90
<212> TYPE: DNA
<213> ORGANISM: Homo sapiens

<400> SEQUENCE: 219
gaagtgcagc tggtggagtc tgggggaggc ttggtacagc ctggcaggtc cctgagactc      60
tcctgtgcag cctctggatt cacctttgat                                       90

<210> SEQ ID NO 220
<211> LENGTH: 90
<212> TYPE: DNA
<213> ORGANISM: Homo sapiens

<400> SEQUENCE: 220
caggtgcagc tggtggagtc tgggggaggc ttggtcaagc ctggagggtc cctgagactc      60
tcctgtgcag cctctggatt caccttcagt                                       90

<210> SEQ ID NO 221
<211> LENGTH: 90
<212> TYPE: DNA
<213> ORGANISM: Homo sapiens

<400> SEQUENCE: 221
gaggtgcagc tggtggagtc tgggggaggc ttggtacagc ctgggggtc cctgagactc       60 tcctgtgcag cctctggatt caccttcagt                                       90

<210> SEQ ID NO 222
<211> LENGTH: 90
<212> TYPE: DNA
<213> ORGANISM: Homo sapiens

<400> SEQUENCE: 222
gaggtgcagc tggtggagtc tgggggaggc ttggtaaagc ctgggggtc ccttagactc       60 tcctgtgcag cctctggatt cactttcagt                                       90

<210> SEQ ID NO 223
<211> LENGTH: 90
<212> TYPE: DNA
<213> ORGANISM: Homo sapiens

<400> SEQUENCE: 223
gaggtgcagc tggtggagtc tgggggaggt gtggtacggc ctgggggtc cctgagactc       60 tcctgtgcag cctctggatt cacctttgat                                       90

<210> SEQ ID NO 224
<211> LENGTH: 90
<212> TYPE: DNA
<213> ORGANISM: Homo sapiens

<400> SEQUENCE: 224
gaggtgcagc tggtggagtc tgggggaggc ctggtcaagc ctgggggtc cctgagactc       60 tcctgtgcag cctctggatt caccttcagt                                       90

<210> SEQ ID NO 225
<211> LENGTH: 90
<212> TYPE: DNA
<213> ORGANISM: Homo sapiens

<400> SEQUENCE: 225
```

```
gaggtgcagc tgttggagtc tgggggaggc ttggtacagc ctgggggggtc cctgagactc    60 tcctgtgcag cctctggatt cacctttagc                                      90

<210> SEQ ID NO 226
<211> LENGTH: 90
<212> TYPE: DNA
<213> ORGANISM: Homo sapiens

<400> SEQUENCE: 226
caggtgcagc tgtggagtc tgggggaggc gtggtccagc ctgggaggtc cctgagactc      60
tcctgtgcag cctctggatt caccttcagt                                      90

<210> SEQ ID NO 227
<211> LENGTH: 90
<212> TYPE: DNA
<213> ORGANISM: Homo sapiens

<400> SEQUENCE: 227
caggtgcagc tgtggagtc tgggggaggc gtggtccagc ctgggaggtc cctgagactc      60
tcctgtgcag cctctggatt caccttcagt                                      90

<210> SEQ ID NO 228
<211> LENGTH: 90
<212> TYPE: DNA
<213> ORGANISM: Homo sapiens

<400> SEQUENCE: 228
caggtgcagc tgtggagtc tgggggaggc gtggtccagc ctgggaggtc cctgagactc      60
tcctgtgcag cctctggatt caccttcagt                                      90

<210> SEQ ID NO 229
<211> LENGTH: 90
<212> TYPE: DNA
<213> ORGANISM: Homo sapiens

<400> SEQUENCE: 229
caggtgcagc tgtggagtc tgggggaggc gtggtccagc ctgggaggtc cctgagactc      60
tcctgtgcag cgtctggatt caccttcagt                                      90

<210> SEQ ID NO 230
<211> LENGTH: 90
<212> TYPE: DNA
<213> ORGANISM: Homo sapiens

<400> SEQUENCE: 230
gaagtgcagc tggtggagtc tgggggagtc gtggtacagc ctgggggtc cctgagactc      60 tcctgtgcag cctctggatt cacctttgat                                      90

<210> SEQ ID NO 231
<211> LENGTH: 90
<212> TYPE: DNA
<213> ORGANISM: Homo sapiens

<400> SEQUENCE: 231
gaggtgcagc tggtggagtc tgggggaggc ttggtacagc ctgggggtc cctgagactc      60 tcctgtgcag cctctggatt caccttcagt                                      90

<210> SEQ ID NO 232
```

```
<211> LENGTH: 90
<212> TYPE: DNA
<213> ORGANISM: Homo sapiens

<400> SEQUENCE: 232
gaggtgcagc tggtggagtc tggggggaggc ttggtacagc cagggcggtc cctgagactc    60
tcctgtacag cttctggatt cacctttggt                                      90

<210> SEQ ID NO 233
<211> LENGTH: 90
<212> TYPE: DNA
<213> ORGANISM: Homo sapiens

<400> SEQUENCE: 233
gaggtgcagc tggtggagac tgaggaggc ttgatccagc ctgggggtc cctgagactc       60 tcctgtgcag cctctgggtt caccgtcagt                                      90

<210> SEQ ID NO 234
<211> LENGTH: 90
<212> TYPE: DNA
<213> ORGANISM: Homo sapiens

<400> SEQUENCE: 234
gaggtgcagc tggtggagtc tggggggaggc ttggtccagc ctgggggtc cctgagactc     60 tcctgtgcag cctctggatt caccttcagt                                      90

<210> SEQ ID NO 235
<211> LENGTH: 90
<212> TYPE: DNA
<213> ORGANISM: Homo sapiens

<400> SEQUENCE: 235
gaggtgcagc tggtggagtc tggggggaggc ttggtccagc ctgggggtc cctgagactc     60 tcctgtgcag cctctggatt caccgtcagt                                      90

<210> SEQ ID NO 236
<211> LENGTH: 90
<212> TYPE: DNA
<213> ORGANISM: Homo sapiens

<400> SEQUENCE: 236
gaggtgcagc tggtggagtc tggggggaggc ttggtccagc ctggagggtc cctgagactc    60
tcctgtgcag cctctggatt caccttcagt                                      90

<210> SEQ ID NO 237
<211> LENGTH: 90
<212> TYPE: DNA
<213> ORGANISM: Homo sapiens

<400> SEQUENCE: 237
gaggtgcagc tggtggagtc tggggggaggc ttggtccagc ctgggggtc cctgaaactc     60 tcctgtgcag cctctgggtt caccttcagt                                      90

<210> SEQ ID NO 238
<211> LENGTH: 90
<212> TYPE: DNA
<213> ORGANISM: Homo sapiens

<400> SEQUENCE: 238
gaggtgcagc tggtggagtc cggggggaggc ttagttcagc ctgggggtc cctgagactc     60
```

```
tcctgtgcag cctctggatt caccttcagt                                        90

<210> SEQ ID NO 239
<211> LENGTH: 90
<212> TYPE: DNA
<213> ORGANISM: Homo sapiens

<400> SEQUENCE: 239
gaggtgcagc tggtggagtc tcggggagtc ttggtacagc ctgggggtc cctgagactc         60 tcctgtgcag cctctggatt caccgtcagt                                        90

<210> SEQ ID NO 240
<211> LENGTH: 90
<212> TYPE: DNA
<213> ORGANISM: Homo sapiens

<400> SEQUENCE: 240
caggtgcagc tgcaggagtc gggcccagga ctggtgaagc cttcggggac cctgtccctc        60
acctgcgctg tctctggtgg ctccatcagc                                        90

<210> SEQ ID NO 241
<211> LENGTH: 90
<212> TYPE: DNA
<213> ORGANISM: Homo sapiens

<400> SEQUENCE: 241
caggtgcagc tgcaggagtc gggcccagga ctggtgaagc cttcggacac cctgtccctc        60
acctgcgctg tctctggtta ctccatcagc                                        90

<210> SEQ ID NO 242
<211> LENGTH: 90
<212> TYPE: DNA
<213> ORGANISM: Homo sapiens

<400> SEQUENCE: 242
caggtgcagc tgcaggagtc gggcccagga ctggtgaagc cttcacagac cctgtccctc        60
acctgcactg tctctggtgg ctccatcagc                                        90

<210> SEQ ID NO 243
<211> LENGTH: 90
<212> TYPE: DNA
<213> ORGANISM: Homo sapiens

<400> SEQUENCE: 243
cagctgcagc tgcaggagtc cggctcagga ctggtgaagc cttcacagac cctgtccctc        60
acctgcgctg tctctggtgg ctccatcagc                                        90

<210> SEQ ID NO 244
<211> LENGTH: 90
<212> TYPE: DNA
<213> ORGANISM: Homo sapiens

<400> SEQUENCE: 244
caggtgcagc tgcaggagtc gggcccagga ctggtgaagc cttcacagac cctgtccctc        60
acctgcactg tctctggtgg ctccatcagc                                        90

<210> SEQ ID NO 245
<211> LENGTH: 90
<212> TYPE: DNA
```

```
<213> ORGANISM: Homo sapiens

<400> SEQUENCE: 245
caggtgcagc tgcaggagtc gggcccagga ctggtgaagc cttcacagac cctgtccctc    60
acctgcactg tctctggtgg ctccatcagc                                     90

<210> SEQ ID NO 246
<211> LENGTH: 90
<212> TYPE: DNA
<213> ORGANISM: Homo sapiens

<400> SEQUENCE: 246
caggtgcagc tacagcagtg gggcgcagga ctgttgaagc cttcggagac cctgtccctc    60
acctgcgctg tctatggtgg gtccttcagt                                     90

<210> SEQ ID NO 247
<211> LENGTH: 90
<212> TYPE: DNA
<213> ORGANISM: Homo sapiens

<400> SEQUENCE: 247
cagctgcagc tgcaggagtc gggcccagga ctggtgaagc cttcggagac cctgtccctc    60
acctgcactg tctctggtgg ctccatcagc                                     90

<210> SEQ ID NO 248
<211> LENGTH: 90
<212> TYPE: DNA
<213> ORGANISM: Homo sapiens

<400> SEQUENCE: 248
caggtgcagc tgcaggagtc gggcccagga ctggtgaagc cttcggagac cctgtccctc    60
acctgcactg tctctggtgg ctccatcagt                                     90

<210> SEQ ID NO 249
<211> LENGTH: 90
<212> TYPE: DNA
<213> ORGANISM: Homo sapiens

<400> SEQUENCE: 249
caggtgcagc tgcaggagtc gggcccagga ctggtgaagc cttcggagac cctgtccctc    60
acctgcactg tctctggtgg ctccgtcagc                                     90

<210> SEQ ID NO 250
<211> LENGTH: 90
<212> TYPE: DNA
<213> ORGANISM: Homo sapiens

<400> SEQUENCE: 250
caggtgcagc tgcaggagtc gggcccagga ctggtgaagc cttcggagac cctgtccctc    60
acctgcgctg tctctggtta ctccatcagc                                     90

<210> SEQ ID NO 251
<211> LENGTH: 90
<212> TYPE: DNA
<213> ORGANISM: Homo sapiens

<400> SEQUENCE: 251
gaggtgcagc tggtgcagtc tggagcagag gtgaaaaagc ccggggagtc tctgaagatc    60
tcctgtaagg gttctggata cagctttacc                                     90
```

<210> SEQ ID NO 252
<211> LENGTH: 90
<212> TYPE: DNA
<213> ORGANISM: Homo sapiens

<400> SEQUENCE: 252
gaagtgcagc tggtgcagtc tggagcagag gtgaaaaagc ccggggagtc tctgaggatc    60
tcctgtaagg gttctggata cagctttacc                                     90

<210> SEQ ID NO 253
<211> LENGTH: 90
<212> TYPE: DNA
<213> ORGANISM: Homo sapiens

<400> SEQUENCE: 253
caggtacagc tgcagcagtc aggtccagga ctggtgaagc cctcgcagac cctctcactc    60
acctgtgcca tctccgggga cagtgtctct                                     90

<210> SEQ ID NO 254
<211> LENGTH: 90
<212> TYPE: DNA
<213> ORGANISM: Homo sapiens

<400> SEQUENCE: 254
caggtgcagc tggtgcaatc tgggtctgag ttgaagaagc ctggggcctc agtgaaggtt    60
tcctgcaagg cttctggata caccttcact                                     90

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
agttctccct gcagctgaac tc                                             22

<210> SEQ ID NO 256
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
cactgtatct gcaaatgaac ag                                             22

<210> SEQ ID NO 257
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
ccctgtatct gcaaatgaac ag                                             22

<210> SEQ ID NO 258
<211> LENGTH: 22

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
ccgcctacct gcagtggagc ag                                            22

<210> SEQ ID NO 259
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
cgctgtatct gcaaatgaac ag                                            22

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
cggcatatct gcagatctgc ag                                            22

<210> SEQ ID NO 261
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
cggcgtatct gcaaatgaac ag                                            22

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
ctgcctacct gcagtggagc ag                                            22

<210> SEQ ID NO 263
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
tcgcctatct gcaaatgaac ag                                            22

<210> SEQ ID NO 264
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 264
acatggagct gagcagcctg ag                                              22

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
acatggagct gagcaggctg ag                                              22

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
acatggagct gaggagcctg ag                                              22

<210> SEQ ID NO 267
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
acctgcagtg gagcagcctg aa                                              22

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
atctgcaaat gaacagcctg aa                                              22

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
atctgcaaat gaacagcctg ag                                              22

<210> SEQ ID NO 270
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 270
atctgcaaat gaacagtctg ag                                            22

<210> SEQ ID NO 271
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
atctgcagat ctgcagccta aa                                            22

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
atcttcaaat gaacagcctg ag                                            22

<210> SEQ ID NO 273
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
atcttcaaat gggcagcctg ag                                            22

<210> SEQ ID NO 274
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
ccctgaagct gagctctgtg ac                                            22

<210> SEQ ID NO 275
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ccctgcagct gaactctgtg ac                                            22

<210> SEQ ID NO 276
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 276
tccttacaat gaccaacatg ga                                              22

<210> SEQ ID NO 277
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tccttaccat gaccaacatg ga                                              22

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ccgtgtatta ctgtgcgaga ga                                              22

<210> SEQ ID NO 279
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
ctgtgtatta ctgtgcgaga ga                                              22

<210> SEQ ID NO 280
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccgtgtatta ctgtgcgaga gg                                              22

<210> SEQ ID NO 281
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
ccgtgtatta ctgtgcaaca ga                                              22

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 282
ccatgtatta ctgtgcaaga ta                                              22

<210> SEQ ID NO 283
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
ccgtgtatta ctgtgcggca ga                                              22

<210> SEQ ID NO 284
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ccacatatta ctgtgcacac ag                                              22

<210> SEQ ID NO 285
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccacatatta ctgtgcacgg at                                              22

<210> SEQ ID NO 286
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ccacgtatta ctgtgcacgg at                                              22

<210> SEQ ID NO 287
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
ccttgtatta ctgtgcaaaa ga                                              22

<210> SEQ ID NO 288
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 288
ctgtgtatta ctgtgcaaga ga                                              22

<210> SEQ ID NO 289
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ccgtgtatta ctgtaccaca ga                                              22

<210> SEQ ID NO 290
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
ccttgtatca ctgtgcgaga ga                                              22

<210> SEQ ID NO 291
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ccgtatatta ctgtgcgaaa ga                                              22

<210> SEQ ID NO 292
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
ctgtgtatta ctgtgcgaaa ga                                              22

<210> SEQ ID NO 293
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ccgtgtatta ctgtactaga ga                                              22

<210> SEQ ID NO 294
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 294
ccgtgtatta ctgtgctaga ga                                              22

<210> SEQ ID NO 295
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
ccgtgtatta ctgtactaga ca                                              22

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
ctgtgtatta ctgtaagaaa ga                                              22

<210> SEQ ID NO 297
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
ccgtgtatta ctgtgcgaga aa                                              22

<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ccgtgtatta ctgtgccaga ga                                              22

<210> SEQ ID NO 299
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ctgtgtatta ctgtgcgaga ca                                              22

<210> SEQ ID NO 300
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
```

```
ccatgtatta ctgtgcgaga ca                                              22
```

<210> SEQ ID NO 301
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301

```
ccatgtatta ctgtgcgaga aa                                              22
```

<210> SEQ ID NO 302
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 302

```
gacatccaga tgacccagtc tccatcctcc ctgtctgcat ctgtaggaga cagagtcacc      60
atcacttgc                                                             69
```

<210> SEQ ID NO 303
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 303

```
cagtctgtgc tgactcagcc accctcggtg tctgaagccc caggcagag ggtcaccatc       60 tcctgt                                                                66
```

<210> SEQ ID NO 304
<211> LENGTH: 668
<212> TYPE: DNA
<213> ORGANISM: Unknown
<220> FEATURE:
<223> OTHER INFORMATION: Description of Unknown: h3401-h2 polynucleotide

<400> SEQUENCE: 304

```
agtgcacaag acatccagat gacccagtct ccagccaccc tgtctgtgtc tccaggggaa      60
agggccaccc tctcctgcag ggccagtcag agtgttagta caacttagc ctggtaccag      120 cagaaacctg gccaggttcc caggctcctc atctatggtg catccaccag gccactgat      180 atcccagcca ggttcagtgg cagtgggtct gggacagact tcactctcac catcagcaga      240
ctggagcctg aagattttgc agtgtattac tgtcagcggt atggtagctc accggggtgg      300
acgttcggcc aagggaccaa ggtggaaatc aaacgaactg tggctgcacc atctgtcttc      360
atcttcccgc catctgatga gcagttgaaa tctggaactg cctctgttgt gtgcctgctg      420 ataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc      600 acccatcagg gcctgagctc gcctgtcaca aagagcttca caaaggaga gtgtaagggc      660 gaattcgc                                                              668
```

<210> SEQ ID NO 305
<211> LENGTH: 223
<212> TYPE: PRT
<213> ORGANISM: Unknown
<220> FEATURE:
<223> OTHER INFORMATION: Description of Unknown: h3401-h2 polypeptide

<400> SEQUENCE: 305

Ser Ala Gln Asp Ile Gln Met Thr Gln Ser Pro Ala Thr Leu Ser Val
1               5                   10                  15

Ser Pro Gly Glu Arg Ala Thr Leu Ser Cys Arg Ala Ser Gln Ser Val
            20                  25                  30

Ser Asn Asn Leu Ala Trp Tyr Gln Gln Lys Pro Gly Gln Val Pro Arg
        35                  40                  45

Leu Leu Ile Tyr Gly Ala Ser Thr Arg Ala Thr Asp Ile Pro Ala Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Arg Tyr Gly Ser
                85                  90                  95

Ser Pro Gly Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Lys Gly Glu Cys Lys Gly Glu Phe Ala
    210                 215                 220

<210> SEQ ID NO 306
<211> LENGTH: 667
<212> TYPE: DNA
<213> ORGANISM: Unknown
<220> FEATURE:
<223> OTHER INFORMATION: Description of Unknown: h3401-d8 KAPPA
      polynucleotide

<400> SEQUENCE: 306
agtgcacaag acatccagat gacccagtct cctgccaccc tgtctgtgtc tccaggtgaa      60
agagccaccc tctcctgcag ggccagtcag aatcttctca gcaacttagc ctggtaccag     120
cagaaacctg gccaggctcc caggctcctc atctatggtg cttccaccgg ggccattggt     180
atcccagcca ggttcagtgg cagtgggtct gggacagagt tcactctcac catcagcagc     240
ctgcagtctg aagattttgc agtgtatttc tgtcagcagt atggtacctc accgcccact     300
ttcggcggag ggaccaaggt ggagatcaaa cgaactgtgg ctgcaccatc tgtcttcatc     360
ttcccgccat ctgatgagca gttgaaatct ggaactgcct ctgttgtgtg cccgctgaat     420
aacttctatc ccagagaggc caaagtacag tggaaggtgg ataacgccct ccaatcgggt     480

```
aactcccagg agagtgtcac agagcaggac aacaaggaca gcacctacag cctcagcagc       540
accctgacgc tgagcaaagt agactacgag aaacacgaag tctacgcctg cgaagtcacc       600
catcagggcc ttagctcgcc cgtcacgaag agcttcaaca ggggagagtg taagaaagaa       660
ttcgttt                                                                 667
```

<210> SEQ ID NO 307
<211> LENGTH: 222
<212> TYPE: PRT
<213> ORGANISM: Unknown
<220> FEATURE:
<223> OTHER INFORMATION: Description of Unknown: h3401-d8 KAPPA
      polypeptide

<400> SEQUENCE: 307

```
Ser Ala Gln Asp Ile Gln Met Thr Gln Ser Pro Ala Thr Leu Ser Val
1               5                   10                  15

Ser Pro Gly Glu Arg Ala Thr Leu Ser Cys Arg Ala Ser Gln Asn Leu
            20                  25                  30

Leu Ser Asn Leu Ala Trp Tyr Gln Gln Lys Pro Gly Gln Ala Pro Arg
        35                  40                  45

Leu Leu Ile Tyr Gly Ala Ser Thr Gly Ala Ile Gly Ile Pro Ala Arg
    50                  55                  60

Phe Ser Gly Ser Gly Ser Gly Thr Glu Phe Thr Leu Thr Ile Ser Ser
65                  70                  75                  80

Leu Gln Ser Glu Asp Phe Ala Val Tyr Phe Cys Gln Gln Tyr Gly Thr
                85                  90                  95

Ser Pro Pro Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Pro Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Asn Lys Asp Ser Thr Tyr
                165                 170                 175

Ser Leu Ser Ser Thr Leu Thr Leu Ser Lys Val Asp Tyr Glu Lys His
            180                 185                 190

Glu Val Tyr Ala Cys Glu Val Thr His Gln Gly Leu Ser Ser Pro Val
        195                 200                 205

Thr Lys Ser Phe Asn Arg Gly Glu Cys Lys Lys Glu Phe Val
    210                 215                 220
```

<210> SEQ ID NO 308
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308

```
gctgtgtatt actgtgcgag cacatccgtg ttgttcacgg atgtg                        45
```

<210> SEQ ID NO 309
<211> LENGTH: 45
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 309
gccgtgtatt actgtgcgag cacatccgtg ttgttcacgg atgtg            45

<210> SEQ ID NO 310
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gccgtatatt actgtgcgag cacatccgtg ttgttcacgg atgtg            45

<210> SEQ ID NO 311
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gccgtgtatt actgtacgag cacatccgtg ttgttcacgg atgtg            45

<210> SEQ ID NO 312
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
gccatgtatt actgtgcgag cacatccgtg ttgttcacgg atgtg            45

<210> SEQ ID NO 313
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
aatagtagac tgcagtgtcc tcagcccttaa agctgttcat ctgcaagtag agagtattct   60
tagagttgtc tctagactta gtgaagcg                               88

<210> SEQ ID NO 314
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
cgcttcacta agtctagaga caactctaag aatactctct acttgcagat gaacagctta   60
agggctgagg acactgcagt ctactattgt gcgag                       95

```
<210> SEQ ID NO 315
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
cgcttcacta agtctagaga caactctaag aatactctct acttgcagat gaacagctta    60
agggctgagg acactgcagt ctactattgt acgag                                95

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cgcttcacta agtctagaga caac                                            24

<210> SEQ ID NO 317
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
cacatccgtg ttgttcacgg atgtgggagg atggagactg ggtc                      44

<210> SEQ ID NO 318
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
cacatccgtg ttgttcacgg atgtgggaga gtggagactg agtc                      44

<210> SEQ ID NO 319
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
cacatccgtg ttgttcacgg atgtgggtgc ctggagactg cgtc                      44

<210> SEQ ID NO 320
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
cacatccgtg ttgttcacgg atgtgggtgg ctggagactg cgtc                      44
```

<210> SEQ ID NO 321
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
cctctactct tgtcacagtg cacaagacat ccag                                34

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
cctctactct tgtcacagtg                                                20

<210> SEQ ID NO 323
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
ggaggatgga ctggatgtct tgtgcactgt gacaagagta gagg                     44

<210> SEQ ID NO 324
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ggagagtgga ctggatgtct tgtgcactgt gacaagagta gagg                     44

<210> SEQ ID NO 325
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ggtgcctgga ctggatgtct tgtgcactgt gacaagagta gagg                     44

<210> SEQ ID NO 326
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
ggtggctgga ctggatgtct tgtgcactgt gacaagagta gagg                     44

<210> SEQ ID NO 327
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 327
cacatccgtg ttgttcacgg atgtggatcg actgtccagg agac    44

<210> SEQ ID NO 328
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 328
cacatccgtg ttgttcacgg atgtggactg tctgtcccaa ggcc    44

<210> SEQ ID NO 329
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 329
cacatccgtg ttgttcacgg atgtggactg actgtccagg agac    44

<210> SEQ ID NO 330
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 330
cacatccgtg ttgttcacgg atgtggaccc tctgccctgg ggcc    44

<210> SEQ ID NO 331
<211> LENGTH: 59
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 331
cctctgactg agtgcacaga gtgctttaac ccaaccggct agtgttagcg gttccccgg    59

<210> SEQ ID NO 332
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 332
cctctgactg agtgcacaga gtgctttaac ccaaccggct agtgttagcg gttccccggg    60
acagtcgat    69

<210> SEQ ID NO 333
<211> LENGTH: 69
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 333
cctctgactg agtgcacaga gtgctttaac ccaaccggct agtgttagcg gttccccggg    60
acagacagt                                                           69

<210> SEQ ID NO 334
<211> LENGTH: 69
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 334
cctctgactg agtgcacaga gtgctttaac ccaaccggct agtgttagcg gttccccggg    60
acagtcagt                                                           69

<210> SEQ ID NO 335
<211> LENGTH: 70
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 335
cctctgactg agtgcacaga gtgctttaac ccaaccggct agtgttagcg gtstccccgg    60
ggcagagggt                                                          70

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 336
cctctgactg agtgcacaga gtgc                                          24

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 337
gggaggatgg agactgggtc                                               20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 338
gggaagatgg agactgggtc                                                  20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gggagagtgg agactgagtc                                                  20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gggtgcctgg agactgcgtc                                                  20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gggtggctgg agactgcgtc                                                  20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gggagtctgg agactgggtc                                                  20

<210> SEQ ID NO 343
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gggaggatgg agactgggtc atctggatgt cttgtgcact gtgacagagg                 50

<210> SEQ ID NO 344
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 344
gggaagatgg agactgggtc atctggatgt cttgtgcact gtgacagagg         50

<210> SEQ ID NO 345
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gggagagtgg agactgggtc atctggatgt cttgtgcact gtgacagagg         50

<210> SEQ ID NO 346
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gggtgcctgg agactgggtc atctggatgt cttgtgcact gtgacagagg         50

<210> SEQ ID NO 347
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gggtggctgg agactgggtc atctggatgt cttgtgcact gtgacagagg         50

<210> SEQ ID NO 348
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gggagtctgg agactgggtc atctggatgt cttgtgcact gtgacagagg         50

<210> SEQ ID NO 349
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
cctctgtcac agtgcacaag acatccagat gacccagtct cc                 42

<210> SEQ ID NO 350
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
```

```
cctctgtcac agtgcacaag ac                                              22
```

<210> SEQ ID NO 351
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351

```
acactctccc ctgttgaagc tctt                                            24
```

<210> SEQ ID NO 352
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 352

```
tccggagctt cagatctgtt tgcctttttg tggggtggtg cagatcgcgt tacggagatc     60
gaccgactgc ttgagcaaaa gccacgctta actgctgatc aggcatggga tgttattcgc    120
caaaccagtc gtcaggatct taacctgagg cttttttac ctactctgca agcagcgaca    180
tctggtttga cacagagcga tccgcgtcgt cagttggtag aaacattaac acgttgggat    240
ggcatcaatt tgcttaatga tgatggtaaa acctggcagc agccaggctc tgccatcctg    300
aacgtttggc tgaccagtat gttgaagcgt accgtagtgg ctgccgtacc tatgccattt    360
gataagtggt acagcgccag tggctacgaa acaacccagg acggcccaac tggttcgctg    420
aatataagtg ttggagcaaa aattttgtat gaggcggtgc agggagacaa atcaccaatc    480
ccacaggcgg ttgatctgtt tgctgggaaa ccacagcagg aggttgtgtt ggctgcgctg    540
gaagatacct gggagactct tccaaacgc tatggcaata atgtgagtaa ctggaaaaca    600
cctgcaatgg ccttaacgtt ccgggcaaat aatttctttg gtgtaccgca ggccgcagcg    660
gaagaaacgc gtcatcaggc ggagtatcaa accgtggaa cagaaaacga tatgattgtt    720
ttctcaccaa cgacaagcga tcgtcctgtg cttgcctggg atgtggtcgc acccggtcag    780
agtggggttta tgctcccga tggaacagtt gataagcact atgaagatca gctgaaaatg    840
tacgaaaatt ttggccgtaa gtcgctctgg ttaacgaagc aggatgtgga ggcgcataag    900
gagtcgtcta ga                                                        912
```

<210> SEQ ID NO 353
<211> LENGTH: 6680
<212> TYPE: DNA
<213> ORGANISM: Unknown
<220> FEATURE:
<223> OTHER INFORMATION: Description of Unknown: pCES5 polynucleotide

<400> SEQUENCE: 353

```
gacgaaaggg cctcgtgata cgcctatttt tataggttaa tgtcatgata ataatggttt     60
cttagacgtc aggtggcact tttcggggaa atgtgcgcgg aaccccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttgctc acccagaaac gctggtgaaa gtaaaagatg   300
```

```
ctgaagatca gttgggtgcc cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagacccegt agaaaagatc aaaggatctt cttgagatcc ttttttttctg cgcgtaatct   1260
gctgcttgca acaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctgaa cggggggtt   1560
cgtgcataca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggccttt   1860
gctggccttt tgctcacatg ttctttcctg cgttatcccc tgattctgtg ataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcaccccca ggctttacac tttatgcttc   2160
cggctcgtat gttgtgtgga attgtgagcg ataacaatt tcacacagga aacagctatg   2220
accatgatta cgccaagctt tggagccttt ttttttggaga ttttcaacgt gaaaaaatta   2280
ttattcgcaa ttcctttagt tgttcctttc tattctcaca gtgcacaggt ccaactgcag   2340
gtcgacctcg agatcaaacg tggaactgtg gctgcaccat ctgtcttcat cttcccgcca   2400
tctgatgagc agttgaaatc tggaactgcc tctgttgtgt gcctgctgaa taacttctat   2460
cccagagagg ccaaagtaca gtggaaggtg gataacgccc tccaatcggg taactcccag   2520
gagagtgtca cagagcagga cagcaaggac agcacctaca gcctcagcag cccctgacg   2580
ctgagcaaag cagactacga gaaacacaaa gtctacgcct gcgaagtcac ccatcagggc   2640
ctgagttcac cggtgacaaa gagcttcaac aggggagagt gttaataagg cgcgccaatt   2700
```

```
ctatttcaag gagacagtca taatgaaata cctattgcct acggcagccg ctggattgtt   2760
attactcgcg gcccagccgg ccatggccga agttcaattg ttagagtctg gtggcggtct   2820
tgttcagcct ggtggttctt tacgtctttc ttgcgctgct tccggagctt cagatctgtt   2880
tgccttttg tgggtggtg cagatcgcgt tacggagatc gaccgactgc ttgagcaaaa   2940
gccacgctta actgctgatc aggcatggga tgttattcgc caaaccagtc gtcaggatct   3000
taacctgagg ctttttttac ctactctgca agcagcgaca tctggtttga cacagagcga   3060
tccgcgtcgt cagttggtag aaacattaac acgttgggat ggcatcaatt tgcttaatga   3120
tgatggtaaa acctggcagc agccaggctc tgccatcctg aacgtttggc tgaccagtat   3180
gttgaagcgt accgtagtgg ctgccgtacc tatgccattt gataagtggt acagcgccag   3240
tggctacgaa acaacccagg acggcccaac tggttcgctg aatataagtg ttggagcaaa   3300
aattttgtat gaggcggtgc agggagacaa atcaccaatc ccacaggcgg ttgatctgtt   3360
tgctgggaaa ccacagcagg aggttgtgtt ggctgcgctg aagatacct gggagactct   3420
ttccaaacgc tatggcaata atgtgagtaa ctggaaaaca cctgcaatgg ccttaacgtt   3480
ccgggcaaat aatttctttg gtgtaccgca ggccgcagcg gaagaaacgc gtcatcaggc   3540
ggagtatcaa aaccgtggaa cagaaaacga tatgattgtt ttctcaccaa cgacaagcga   3600
tcgtcctgtg cttgcctggg atgtggtcgc acccggtcag agtgggttta ttgctcccga   3660
tggaacagtt gataagcact atgaagatca gctgaaaatg tacgaaaatt ttggccgtaa   3720
gtcgctctgg ttaacgaagc aggatgtgga ggcgcataag gagtcgtcta gagacaactc   3780
taagaatact ctctacttgc agatgaacag cttaagtctg agcattcggt ccgggcaaca   3840
ttctccaaac tgaccagacg acacaaacgg cttacgctaa atcccgcgca tgggatggta   3900
aagaggtggc gtctttgctg gcctggactc atcagatgaa ggccaaaaat tggcaggagt   3960
ggacacagca ggcagcgaaa caagcactga ccatcaactg gtactatgct gatgtaaacg   4020
gcaatattgg ttatgttcat actggtgctt atccagatcg tcaatcaggc catgatccgc   4080
gattaccgt cctggtacg ggaaaatggg actggaaagg ctattgcct tttgaaatga   4140
acccctaaggt gtataacccc cagaagctag cctgcggctt cggtcaccgt tcaagcgcc   4200
tccaccaagg gcccatcggt cttcccctg gcaccctcct ccaagagcac ctctggggc   4260
acagcggccc tgggctgcct ggtcaaggac tacttcccg aaccggtgac ggtgtcgtgg   4320
aactcaggcg ccctgaccag cggcgtccac accttcccgg ctgtcctaca gtcctcagga   4380
ctctactccc tcagcagcgt agtgaccgtg ccctccagca gcttgggcac ccagacctac   4440
atctgcaacg tgaatcacaa gcccagcaac accaaggtgg acaagaaagt tgagcccaaa   4500
tcttgtgcgc ccgcacatca tcatcaccat cacggggccg cagaacaaaa actcatctca   4560
gaagaggatc tgaatggggc cgcatagact gttgaaagtt gtttagcaaa acctcataca   4620
gaaaattcat ttactaacgt ctggaaagac gacaaaactt tagatcgtta cgctaactat   4680
gagggctgtc tgtggaatgc tacaggcgtt gtggtttgta ctggtgacga aactcagtgt   4740
tacggtacat gggttcctat tgggcttgct atccctgaaa atgagggtgg tggctctgag   4800
ggtggcggtt ctgagggtgg cggttctgag gtggcggta ctaaacctcc tgagtacggt   4860
gatacaccta ttccgggcta tacttatatc aaccctctcg acggcactta tccgcctggt   4920
actgagcaaa accccgctaa tcctaatcct tctcttgagg agtctcagcc tcttaatact   4980
ttcatgtttc agaataatag gttccgaaat aggcaggggtg cattaactgt ttatacgggc   5040
```

| | | | |
|---|---|---|---|
| actgttactc aaggcactga ccccgttaaa acttattacc agtacactcc tgtatcatca | 5100 |
| aaagccatgt atgacgctta ctggaacggt aaattcagag actgcgcttt ccattctggc | 5160 |
| tttaatgagg atccattcgt tgtgaatat caaggccaat cgtctgacct gcctcaacct | 5220 |
| cctgtcaatg ctggcggcgg ctctggtggt ggttctggtg gcggctctga gggtggcggc | 5280 |
| tctgagggtg gcggttctga gggtggcggc tctgagggtg gcggttccgg tggcggctcc | 5340 |
| ggttccggtg atttttgatta tgaaaaaatg gcaaacgcta ataaggggc tatgaccgaa | 5400 |
| aatgccgatg aaaacgcgct acagtctgac gctaaaggca aacttgattc tgtcgctact | 5460 |
| gattacggtg ctgctatcga tggtttcatt ggtgacgttt ccggccttgc taatggtaat | 5520 |
| ggtgctactg gtgattttgc tggctctaat tcccaaatgg ctcaagtcgg tgacggtgat | 5580 |
| aattcacctt taatgaataa tttccgtcaa tatttacctt ctttgcctca gtcggttgaa | 5640 |
| tgtcgccctt atgtctttgg cgctggtaaa ccatatgaat tttctattga ttgtgacaaa | 5700 |
| ataaacttat tccgtggtgt ctttgcgttt cttttatatg ttgccacctt tatgtatgta | 5760 |
| ttttcgacgt ttgctaacat actgcgtaat aaggagtctt aataagaatt cactggccgt | 5820 |
| cgttttacaa cgtcgtgact gggaaaaccc tggcgttacc caacttaatc gccttgcagc | 5880 |
| acatccccct ttcgccagct ggcgtaatag cgaagaggcc cgcaccgatc gcccttccca | 5940 |
| acagttgcgc agcctgaatg gcgaatggcg cctgatgcgg tattttctcc ttacgcatct | 6000 |
| gtgcggtatt tcacaccgca tataaattgt aaacgttaat attttgttaa aattcgcgtt | 6060 |
| aaatttttgt taaatcagct cattttttaa ccaataggcc gaaatcggca aaatccctta | 6120 |
| taaatcaaaa gaatagcccg agatagggtt gagtgttgtt ccagtttgga acaagagtcc | 6180 |
| actattaaag aacgtggact ccaacgtcaa agggcgaaaa accgtctatc agggcgatgg | 6240 |
| cccactacgt gaaccatcac ccaaatcaag ttttttgggg tcgaggtgcc gtaaagcact | 6300 |
| aaatcggaac cctaaaggga gcccccgatt tagagcttga cggggaaagc cggcgaacgt | 6360 |
| ggcgagaaag gaagggaaga agcgaaagg agcgggcgct agggcgctgg caagtgtagc | 6420 |
| ggtcacgctg cgcgtaacca ccacacccgc cgcgcttaat gcgccgctac agggcgcgta | 6480 |
| ctatggttgc tttgacgggt gcagtctcag tacaatctgc tctgatgccg catagttaag | 6540 |
| ccagccccga cacccgccaa cacccgctga cgcgccctga cgggcttgtc tgctcccggc | 6600 |
| atccgcttac agacaagctg tgaccgtctc cgggagctgc atgtgtcaga ggttttcacc | 6660 |
| gtcatcaccg aaacgcgcga | 6680 |

<210> SEQ ID NO 354
<211> LENGTH: 286
<212> TYPE: PRT
<213> ORGANISM: Unknown
<220> FEATURE:
<223> OTHER INFORMATION: Description of Unknown: pCES5 polypeptide

<400> SEQUENCE: 354

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser

```
              65                  70                  75                  80
Arg Ile Asp Ala Gly Gln Glu Gln Leu Gly Arg Arg Ile His Tyr Ser
              85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
            115                 120                 125

Asp Asn Thr Ala Ala Asn Leu Leu Thr Thr Ile Gly Gly Pro Lys
            130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
            275                 280                 285

<210> SEQ ID NO 355
<211> LENGTH: 138
<212> TYPE: PRT
<213> ORGANISM: Unknown
<220> FEATURE:
<223> OTHER INFORMATION: Description of Unknown: pCES5 polypeptide

<400> SEQUENCE: 355

Met Lys Lys Leu Leu Phe Ala Ile Pro Leu Val Val Pro Phe Tyr Ser
1               5                   10                  15

His Ser Ala Gln Val Gln Leu Gln Val Asp Leu Glu Ile Lys Arg Gly
            20                  25                  30

Thr Val Ala Ala Pro Ser Val Phe Ile Phe Pro Pro Ser Asp Glu Gln
            35                  40                  45

Leu Lys Ser Gly Thr Ala Ser Val Val Cys Leu Leu Asn Asn Phe Tyr
50                  55                  60

Pro Arg Glu Ala Lys Val Gln Trp Lys Val Asp Asn Ala Leu Gln Ser
65                  70                  75                  80

Gly Asn Ser Gln Glu Ser Val Thr Glu Gln Asp Ser Lys Asp Ser Thr
                85                  90                  95

Tyr Ser Leu Ser Ser Thr Leu Thr Leu Ser Lys Ala Asp Tyr Glu Lys
            100                 105                 110

His Lys Val Tyr Ala Cys Glu Val Thr His Gln Gly Leu Ser Ser Pro
            115                 120                 125

Val Thr Lys Ser Phe Asn Arg Gly Glu Cys
            130                 135
```

<210> SEQ ID NO 356
<211> LENGTH: 48
<212> TYPE: PRT
<213> ORGANISM: Unknown
<220> FEATURE:
<223> OTHER INFORMATION: Description of Unknown: pCES5 polypeptide

<400> SEQUENCE: 356

Met Lys Tyr Leu Leu Pro Thr Ala Ala Gly Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

<210> SEQ ID NO 357
<211> LENGTH: 28
<212> TYPE: PRT
<213> ORGANISM: Unknown
<220> FEATURE:
<223> OTHER INFORMATION: Description of Unknown: pCES5 peptide

<400> SEQUENCE: 357

Ser Arg Asp Asn Ser Lys Asn Thr Leu Tyr Leu Gln Met Asn Ser Leu
1               5                   10                  15

Ser Leu Ser Ile Arg Ser Gly Gln His Ser Pro Thr
            20                  25

<210> SEQ ID NO 358
<211> LENGTH: 129
<212> TYPE: PRT
<213> ORGANISM: Unknown
<220> FEATURE:
<223> OTHER INFORMATION: Description of Unknown: pCES5 polypeptide

<400> SEQUENCE: 358

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Ala Ala Ala His His His His His His
            100                 105                 110

Gly Ala Ala Glu Gln Lys Leu Ile Ser Glu Glu Asp Leu Asn Gly Ala
        115                 120                 125

Ala

<210> SEQ ID NO 359
<211> LENGTH: 404
<212> TYPE: PRT
<213> ORGANISM: Unknown
<220> FEATURE:
<223> OTHER INFORMATION: Description of Unknown: pCES5 polypeptide

<400> SEQUENCE: 359

```
Thr Val Glu Ser Cys Leu Ala Lys Pro His Thr Glu Asn Ser Phe Thr
1               5                   10                  15

Asn Val Trp Lys Asp Asp Lys Thr Leu Asp Arg Tyr Ala Asn Tyr Glu
            20                  25                  30

Gly Cys Leu Trp Asn Ala Thr Gly Val Val Cys Thr Gly Asp Glu
        35                  40                  45

Thr Gln Cys Tyr Gly Thr Trp Val Pro Ile Gly Leu Ala Ile Pro Glu
    50                  55                  60

Asn Glu Gly Gly Gly Ser Gly Gly Gly Ser Gly Gly Gly Ser
65                  70                  75                  80

Glu Gly Gly Gly Thr Lys Pro Pro Glu Tyr Gly Asp Thr Pro Ile Pro
                85                  90                  95

Gly Tyr Thr Tyr Ile Asn Pro Leu Asp Gly Thr Tyr Pro Pro Gly Thr
            100                 105                 110

Glu Gln Asn Pro Ala Asn Pro Asn Pro Ser Leu Glu Glu Ser Gln Pro
        115                 120                 125

Leu Asn Thr Phe Met Phe Gln Asn Asn Arg Phe Arg Asn Arg Gln Gly
        130                 135                 140

Ala Leu Thr Val Tyr Thr Gly Thr Val Thr Gln Gly Thr Asp Pro Val
145                 150                 155                 160

Lys Thr Tyr Tyr Gln Tyr Thr Pro Val Ser Ser Lys Ala Met Tyr Asp
            165                 170                 175

Ala Tyr Trp Asn Gly Lys Phe Arg Asp Cys Ala Phe His Ser Gly Phe
            180                 185                 190

Asn Glu Asp Pro Phe Val Cys Glu Tyr Gln Gly Gln Ser Ser Asp Leu
        195                 200                 205

Pro Gln Pro Pro Val Asn Ala Gly Gly Gly Ser Gly Gly Gly Ser Gly
    210                 215                 220

Gly Gly Ser Glu Gly Gly Gly Ser Glu Gly Gly Gly Ser Glu Gly Gly
225                 230                 235                 240

Gly Ser Glu Gly Gly Gly Ser Gly Gly Gly Ser Gly Ser Gly Asp Phe
        245                 250                 255

Asp Tyr Glu Lys Met Ala Asn Ala Asn Lys Gly Ala Met Thr Glu Asn
            260                 265                 270

Ala Asp Glu Asn Ala Leu Gln Ser Asp Ala Lys Gly Lys Leu Asp Ser
        275                 280                 285

Val Ala Thr Asp Tyr Gly Ala Ala Ile Asp Gly Phe Ile Gly Asp Val
    290                 295                 300

Ser Gly Leu Ala Asn Gly Asn Gly Ala Thr Gly Asp Phe Ala Gly Ser
305                 310                 315                 320

Asn Ser Gln Met Ala Gln Val Gly Asp Gly Asp Asn Ser Pro Leu Met
            325                 330                 335

Asn Asn Phe Arg Gln Tyr Leu Pro Ser Leu Pro Gln Ser Val Glu Cys
        340                 345                 350

Arg Pro Tyr Val Phe Gly Ala Gly Lys Pro Tyr Glu Phe Ser Ile Asp
    355                 360                 365

Cys Asp Lys Ile Asn Leu Phe Arg Gly Val Phe Ala Phe Leu Leu Tyr
    370                 375                 380

Val Ala Thr Phe Met Tyr Val Phe Ser Thr Phe Ala Asn Ile Leu Arg
385                 390                 395                 400

Asn Lys Glu Ser
```

```
<210> SEQ ID NO 360
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 360
gacatccaga tgacccagtc tccatcctcc ctgtctgcat ctgtaggaga cagagtcacc      60
atcacttgc                                                             69

<210> SEQ ID NO 361
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 361
gacatccaga tgacccagtc tccatcctcc ctgtctgcat ctgtaggaga cagagtcacc      60
atcacttgc                                                             69

<210> SEQ ID NO 362
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 362
gacatccaga tgacccagtc tccatcctcc ctgtctgcat ctgtaggaga cagagtcacc      60
atcacttgc                                                             69

<210> SEQ ID NO 363
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 363
gacatccaga tgacccagtc tccatcctcc ctgtctgcat ctgtaggaga cagagtcacc      60
atcacttgc                                                             69

<210> SEQ ID NO 364
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 364
gacatccaga tgacccagtc tccatcctcc ctgtctgcat ctgtaggaga cagagtcacc      60
atcacttgc                                                             69

<210> SEQ ID NO 365
<211> LENGTH: 69
<212> TYPE: DNA
<213> ORGANISM: Unknown
```

```
<220> FEATURE:
<223> OTHER INFORMATION: Description of Unknown: Kappa FR1 GLGs
      oligonucleotide

<400> SEQUENCE: 365
aacatccaga tgacccagtc tccatctgcc atgtctgcat ctgtaggaga cagagtcacc    60
atcacttgt                                                            69

<210> SEQ ID NO 366
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 366
gacatccaga tgacccagtc tccatcctca ctgtctgcat ctgtaggaga cagagtcacc    60
atcacttgt                                                            69

<210> SEQ ID NO 367
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 367
gacatccaga tgacccagtc tccatcctca ctgtctgcat ctgtaggaga cagagtcacc    60
atcacttgt                                                            69

<210> SEQ ID NO 368
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 368
gccatccagt tgacccagtc tccatcctcc ctgtctgcat ctgtaggaga cagagtcacc    60
atcacttgc                                                            69

<210> SEQ ID NO 369
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 369
gccatccagt tgacccagtc tccatcctcc ctgtctgcat ctgtaggaga cagagtcacc    60
atcacttgc                                                            69

<210> SEQ ID NO 370
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide
```

-continued

```
<400> SEQUENCE: 370
gacatccaga tgacccagtc tccatcttcc gtgtctgcat ctgtaggaga cagagtcacc    60
atcacttgt                                                           69

<210> SEQ ID NO 371
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 371
gacatccaga tgacccagtc tccatcttct gtgtctgcat ctgtaggaga cagagtcacc    60
atcacttgt                                                           69

<210> SEQ ID NO 372
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 372
gacatccagt tgacccagtc tccatccttc ctgtctgcat ctgtaggaga cagagtcacc    60
atcacttgc                                                           69

<210> SEQ ID NO 373
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 373
gccatccgga tgacccagtc tccattctcc ctgtctgcat ctgtaggaga cagagtcacc    60
atcacttgc                                                           69

<210> SEQ ID NO 374
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 374
gccatccgga tgacccagtc tccatcctca ttctctgcat ctacaggaga cagagtcacc    60
atcacttgt                                                           69

<210> SEQ ID NO 375
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 375
gtcatctgga tgacccagtc tccatcctta ctctctgcat ctacaggaga cagagtcacc    60
```

```
<210> SEQ ID NO 376
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 376
gccatccaga tgacccagtc tccatcctcc ctgtctgcat ctgtaggaga cagagtcacc    60
atcacttgc                                                            69

<210> SEQ ID NO 377
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 377
gacatccaga tgacccagtc tccttccacc ctgtctgcat ctgtaggaga cagagtcacc    60
atcacttgc                                                            69

<210> SEQ ID NO 378
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 378
gatattgtga tgacccagac tccactctcc ctgcccgtca cccctggaga gccggcctcc    60
atctcctgc                                                            69

<210> SEQ ID NO 379
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 379
gatattgtga tgacccagac tccactctcc ctgcccgtca cccctggaga gccggcctcc    60
atctcctgc                                                            69

<210> SEQ ID NO 380
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 380
gatgttgtga tgactcagtc tccactctcc ctgcccgtca cccttggaca gccggcctcc    60
atctcctgc                                                            69

<210> SEQ ID NO 381
```

```
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 381
gatgttgtga tgactcagtc tccactctcc ctgcccgtca cccttggaca gccggcctcc      60
atctcctgc                                                             69

<210> SEQ ID NO 382
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 382
gatattgtga tgacccagac tccactctct ctgtccgtca ccccctggaca gccggcctcc    60 atctcctgc                                                             69

<210> SEQ ID NO 383
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 383
gatattgtga tgacccagac tccactctct ctgtccgtca ccctggaca gccggcctcc      60 atctcctgc                                                             69

<210> SEQ ID NO 384
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 384
gatattgtga tgactcagtc tccactctcc ctgcccgtca cccctggaga gccggcctcc    60
atctcctgc                                                             69

<210> SEQ ID NO 385
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 385
gatattgtga tgactcagtc tccactctcc ctgcccgtca cccctggaga gccggcctcc    60
atctcctgc                                                             69

<210> SEQ ID NO 386
<211> LENGTH: 69
<212> TYPE: DNA
<213> ORGANISM: Unknown
<220> FEATURE:
```

```
<223> OTHER INFORMATION: Description of Unknown: Kappa FR1 GLGs
      oligonucleotide

<400> SEQUENCE: 386
gatattgtga tgacccagac tccactctcc tcacctgtca cccttggaca gccggcctcc    60
atctcctgc                                                           69

<210> SEQ ID NO 387
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 387
gaaattgtgt tgacgcagtc tccaggcacc ctgtctttgt ctccagggga aagagccacc    60
ctctcctgc                                                           69

<210> SEQ ID NO 388
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 388
gaaattgtgt tgacgcagtc tccagccacc ctgtctttgt ctccagggga aagagccacc    60
ctctcctgc                                                           69

<210> SEQ ID NO 389
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 389
gaaatagtga tgacgcagtc tccagccacc ctgtctgtgt ctccagggga aagagccacc    60
ctctcctgc                                                           69

<210> SEQ ID NO 390
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 390
gaaatagtga tgacgcagtc tccagccacc ctgtctgtgt ctccagggga aagagccacc    60
ctctcctgc                                                           69

<210> SEQ ID NO 391
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 391
```

```
gaaattgtgt tgacacagtc tccagccacc ctgtctttgt ctccagggga aagagccacc    60
ctctcctgc                                                            69
```

<210> SEQ ID NO 392
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 392

```
gaaattgtgt tgacacagtc tccagccacc ctgtctttgt ctccagggga aagagccacc    60
ctctcctgc                                                            69
```

<210> SEQ ID NO 393
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 393

```
gaaattgtaa tgacacagtc tccagccacc ctgtctttgt ctccagggga aagagccacc    60
ctctcctgc                                                            69
```

<210> SEQ ID NO 394
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 394

```
gacatcgtga tgacccagtc tccagactcc ctggctgtgt ctctgggcga gagggccacc    60
atcaactgc                                                            69
```

<210> SEQ ID NO 395
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 395

```
gaaacgacac tcacgcagtc tccagcattc atgtcagcga ctccaggaga caaagtcaac    60
atctcctgc                                                            69
```

<210> SEQ ID NO 396
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 396

```
gaaattgtgc tgactcagtc tccagacttt cagtctgtga ctccaaagga gaaagtcacc    60
atcacctgc                                                            69
```

<210> SEQ ID NO 397
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 397
gaaattgtgc tgactcagtc tccagacttt cagtctgtga ctccaaagga gaaagtcacc    60
atcacctgc    69

<210> SEQ ID NO 398
<211> LENGTH: 69
<212> TYPE: DNA
<213> ORGANISM: Unknown
<220> FEATURE:
<223> OTHER INFORMATION: Description of Unknown: Kappa FR1 GLGs
      oligonucleotide

<400> SEQUENCE: 398
gatgttgtga tgacacagtc tccagctttc ctctctgtga ctccagggga gaaagtcacc    60
atcacctgc    69

<210> SEQ ID NO 399
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 399
cagtctgtgc tgacgcagcc gccctcagtg tctggggccc cagggcagag ggtcaccatc    60
tcctgc    66

<210> SEQ ID NO 400
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 400
cagtctgtgc tgactcagcc accctcagcg tctgggaccc ccgggcagag ggtcaccatc    60
tcttgt    66

<210> SEQ ID NO 401
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 401
cagtctgtgc tgactcagcc accctcagcg tctgggaccc ccgggcagag ggtcaccatc    60
tcttgt    66

<210> SEQ ID NO 402
<211> LENGTH: 66

<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 402
cagtctgtgt tgacgcagcc gccctcagtg tctgcggccc caggacagaa ggtcaccatc    60
tcctgc                                                               66

<210> SEQ ID NO 403
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 403
cagtctgccc tgactcagcc tccctccgcg tccgggtctc ctggacagtc agtcaccatc    60
tcctgc                                                               66

<210> SEQ ID NO 404
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 404
cagtctgccc tgactcagcc tcgctcagtg tccgggtctc ctggacagtc agtcaccatc    60
tcctgc                                                               66

<210> SEQ ID NO 405
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 405
cagtctgccc tgactcagcc tgcctccgtg tctgggtctc ctggacagtc gatcaccatc    60
tcctgc                                                               66

<210> SEQ ID NO 406
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 406
cagtctgccc tgactcagcc tccctccgtg tccgggtctc ctggacagtc agtcaccatc    60
tcctgc                                                               66

<210> SEQ ID NO 407
<211> LENGTH: 66
<212> TYPE: DNA
<213> ORGANISM: Unknown
<220> FEATURE:
<223> OTHER INFORMATION: Description of Unknown: Lambda FR1 GLG oligonucleotide

<400> SEQUENCE: 407
cagtctgccc tgactcagcc tgcctccgtg tctgggtctc ctggacagtc gatcaccatc    60
tcctgc                                                              66

<210> SEQ ID NO 408
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 408
tcctatgagc tgactcagcc accctcagtg tccgtgtccc aggacagac agccagcatc    60 acctgc                                                              66

<210> SEQ ID NO 409
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 409
tcctatgagc tgactcagcc actctcagtg tcagtggccc tgggacagac ggccaggatt    60
acctgt                                                              66

<210> SEQ ID NO 410
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 410
tcctatgagc tgacacagcc accctcggtg tcagtgtccc aggacaaac ggccaggatc    60 acctgc                                                              66

<210> SEQ ID NO 411
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 411
tcctatgagc tgacacagcc accctcggtg tcagtgtccc taggacagat ggccaggatc    60
acctgc                                                              66

<210> SEQ ID NO 412
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 412

```
tcttctgagc tgactcagga ccctgctgtg tctgtggcct tgggacagac agtcaggatc    60
acatgc                                                               66
```

<210> SEQ ID NO 413
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 413

```
tcctatgtgc tgactcagcc accctcagtg tcagtggccc aggaaagac ggccaggatt     60 acctgt                                                               66
```

<210> SEQ ID NO 414
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 414

```
tcctatgagc tgacacagct accctcggtg tcagtgtccc caggacagac agccaggatc    60
acctgc                                                               66
```

<210> SEQ ID NO 415
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 415

```
tcctatgagc tgatgcagcc accctcggtg tcagtgtccc caggacagac ggccaggatc    60
acctgc                                                               66
```

<210> SEQ ID NO 416
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 416

```
tcctatgagc tgacacagcc atcctcagtg tcagtgtctc cgggacagac agccaggatc    60
acctgc                                                               66
```

<210> SEQ ID NO 417
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 417

```
ctgcctgtgc tgactcagcc cccgtctgca tctgccttgc tgggagcctc gatcaagctc    60
acctgc                                                               66
```

<210> SEQ ID NO 418
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 418
cagcctgtgc tgactcaatc atcctctgcc tctgcttccc tgggatcctc ggtcaagctc    60
acctgc                                                                66

<210> SEQ ID NO 419
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 419
cagcttgtgc tgactcaatc gccctctgcc tctgcctccc tgggagcctc ggtcaagctc    60
acctgc                                                                66

<210> SEQ ID NO 420
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 420
cagcctgtgc tgactcagcc accttcctcc tccgcatctc ctggagaatc cgccagactc    60
acctgc                                                                66

<210> SEQ ID NO 421
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 421
caggctgtgc tgactcagcc ggcttccctc tctgcatctc ctggagcatc agccagtctc    60
acctgc                                                                66

<210> SEQ ID NO 422
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 422
cagcctgtgc tgactcagcc atcttcccat tctgcatctt ctggagcatc agtcagactc    60
acctgc                                                                66

<210> SEQ ID NO 423
<211> LENGTH: 66
<212> TYPE: DNA

<213> ORGANISM: Unknown
<220> FEATURE:
<223> OTHER INFORMATION: Description of Unknown: Lambda FR1 GLG
      oligonucleotide

<400> SEQUENCE: 423
aattttatgc tgactcagcc ccactctgtg tcggagtctc cggggaagac ggtaaccatc    60
tcctgc                                                              66

<210> SEQ ID NO 424
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 424
cagactgtgg tgactcagga gccctcactg actgtgtccc caggagggac agtcactctc    60
acctgt                                                              66

<210> SEQ ID NO 425
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 425
caggctgtgg tgactcagga gccctcactg actgtgtccc caggagggac agtcactctc    60
acctgt                                                              66

<210> SEQ ID NO 426
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 426
cagactgtgg tgacccagga gccatcgttc tcagtgtccc ctggagggac agtcacactc    60
acttgt                                                              66

<210> SEQ ID NO 427
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 427
cagcctgtgc tgactcagcc accttctgca tcagcctccc tgggagcctc ggtcacactc    60
acctgc                                                              66

<210> SEQ ID NO 428
<211> LENGTH: 66
<212> TYPE: DNA
<213> ORGANISM: Unknown
<220> FEATURE:
<223> OTHER INFORMATION: Description of Unknown: Lambda FR1 GLG
      oligonucleotide

<400> SEQUENCE: 428
caggcagggc tgactcagcc accctcggtg tccaagggct tgagacagac cgccacactc    60
acctgc    66

<210> SEQ ID NO 429
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, g, t, unknown or other

<400> SEQUENCE: 429
ggccnnnnng gcc    13

<210> SEQ ID NO 430
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 430
ccannnnnnt gg    12

<210> SEQ ID NO 431
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 431
gacnnnnnng tc    12

<210> SEQ ID NO 432
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 432
cgannnnnnt gc    12

<210> SEQ ID NO 433
<211> LENGTH: 11
<212> TYPE: DNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 433
gcannnnntg c                                                          11

<210> SEQ ID NO 434
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 434
ccannnnntg g                                                          11

<210> SEQ ID NO 435
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 435 gaannnnttc                                                            10

<210> SEQ ID NO 436
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, g, t, unknown or other

<400> SEQUENCE: 436
nnnnnngaga cg                                                         12

<210> SEQ ID NO 437
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 437
gtatccnnnn nn                                                    12

<210> SEQ ID NO 438
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 438 gatnnnnatc                                                       10

<210> SEQ ID NO 439
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 439
gacnnnnngt c                                                     11

<210> SEQ ID NO 440
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 440
ggtctcnnnn n                                                     11

<210> SEQ ID NO 441
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 441
gccnnnnngg c                                                     11

<210> SEQ ID NO 442
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (4)..(12)
<223> OTHER INFORMATION: a, c, g, t, unknown or other

<400> SEQUENCE: 442
ccannnnnnn nntgg                                                    15

<210> SEQ ID NO 443
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, g, t, unknown or other

<400> SEQUENCE: 443
nnnnnnnnnn ctcctc                                                   16

<210> SEQ ID NO 444
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, c, g, t, unknown or other

<400> SEQUENCE: 444
nnnnnnnnnt ccgcc                                                    15

<210> SEQ ID NO 445
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(15)
<223> OTHER INFORMATION: a, c, g, t, unknown or other

<400> SEQUENCE: 445
cacctgcnnn nnnnn                                                    15

<210> SEQ ID NO 446
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 446
cagctcnnnn nnnnnnn                                                  17

<210> SEQ ID NO 447
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 447
gaagacnnnn nnnnnnn                                                    17

<210> SEQ ID NO 448
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(17)
<223> OTHER INFORMATION: a, c, g, t, unknown or other

<400> SEQUENCE: 448
gcagcnnnnn nnnnnnn                                                    17

<210> SEQ ID NO 449
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: a, c, g, t, unknown or other

<400> SEQUENCE: 449
gaagacnnnn nn                                                         12

<210> SEQ ID NO 450
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 450
cttgagnnnn nnnnnnnnnn nn                                              22

<210> SEQ ID NO 451
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, c, g, t, unknown or other

<400> SEQUENCE: 451
```

-continued

```
acggcnnnn nnnnnnnn                                                    19

<210> SEQ ID NO 452
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, c, g, t, unknown or other

<400> SEQUENCE: 452 acggcnnnn nnnnnnnn                                                    18

<210> SEQ ID NO 453
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 453
actgggnnnn n                                                          11

<210> SEQ ID NO 454
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 454 ggatcnnnnn                                                            10

<210> SEQ ID NO 455
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, c, g, t, unknown or other

<400> SEQUENCE: 455
gcatcnnnnn n                                                          11

<210> SEQ ID NO 456
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (7)..(16)
<223> OTHER INFORMATION: a, c, g, t, unknown or other

<400> SEQUENCE: 456
gaggagnnnn nnnnnn                                                    16

<210> SEQ ID NO 457
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, c, g, t, unknown or other

<400> SEQUENCE: 457
gggacnnnnn nnnnnnnn                                                  19

<210> SEQ ID NO 458
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(14)
<223> OTHER INFORMATION: a, c, g, t, unknown or other

<400> SEQUENCE: 458
acctgcnnnn nnnn                                                      14

<210> SEQ ID NO 459
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 459
ggcggannnn nnnnnnn                                                   17

<210> SEQ ID NO 460
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 460
ctgaagnnnn nnnnnnnnnn nn                                             22

<210> SEQ ID NO 461
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, c, g, t, unknown or other

<400> SEQUENCE: 461
cccgcnnnnn n                                                           11

<210> SEQ ID NO 462
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(18)
<223> OTHER INFORMATION: a, c, g, t, unknown or other

<400> SEQUENCE: 462
ggatgnnnnn nnnnnnnn                                                    18

<210> SEQ ID NO 463
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(22)
<223> OTHER INFORMATION: a, c, g, t, unknown or other

<400> SEQUENCE: 463
ctggagnnnn nnnnnnnnnn nn                                               22

<210> SEQ ID NO 464
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(15)
<223> OTHER INFORMATION: a, c, g, t, unknown or other

<400> SEQUENCE: 464
gacgcnnnnn nnnnn                                                       15

<210> SEQ ID NO 465
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, c, g, t, unknown or other
```

<400> SEQUENCE: 465
ggtgannnnn nnn                                                          13

<210> SEQ ID NO 466
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, c, g, t, unknown or other

<400> SEQUENCE: 466
gaagannnnn nnn                                                          13

<210> SEQ ID NO 467
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 467 gagtcnnnnn                                                              10

<210> SEQ ID NO 468
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(26)
<223> OTHER INFORMATION: a, c, g, t, unknown or other

<400> SEQUENCE: 468
tccracnnnn nnnnnnnnnn nnnnnn                                            26

<210> SEQ ID NO 469
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(11)
<223> OTHER INFORMATION: a, c, g, t, unknown or other

<400> SEQUENCE: 469
cctcnnnnnn n                                                            11

<210> SEQ ID NO 470
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(18)
<223> OTHER INFORMATION: a, c, g, t, unknown or other

<400> SEQUENCE: 470
cccacannnn nnnnnnnn                                                18

<210> SEQ ID NO 471
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(14)
<223> OTHER INFORMATION: a, c, g, t, unknown or other

<400> SEQUENCE: 471
gcatcnnnnn nnnn                                                    14

<210> SEQ ID NO 472
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(13)
<223> OTHER INFORMATION: a, c, g, t, unknown or other

<400> SEQUENCE: 472
ggtgannnnn nnn                                                     13

<210> SEQ ID NO 473
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(12)
<223> OTHER INFORMATION: a, c, g, t, unknown or other

<400> SEQUENCE: 473
cccgnnnnnn nn                                                      12

<210> SEQ ID NO 474
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(19)
<223> OTHER INFORMATION: a, c, g, t, unknown or other

<400> SEQUENCE: 474
ggatgnnnnn nnnnnnnn                                                19

```
<210> SEQ ID NO 475
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 475
gaccgannnn nnnnnnn                                                 17

<210> SEQ ID NO 476
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 476
cacccannnn nnnnnnn                                                 17

<210> SEQ ID NO 477
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(17)
<223> OTHER INFORMATION: a, c, g, t, unknown or other

<400> SEQUENCE: 477
caarcannnn nnnnnnn                                                 17

<210> SEQ ID NO 478
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, g, t, unknown or other

<400> SEQUENCE: 478
gcnnnnnnng c                                                       11

<210> SEQ ID NO 479
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other
```

```
<400> SEQUENCE: 479 caynnnnrtg                                                              10

<210> SEQ ID NO 480
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(11)
<223> OTHER INFORMATION: a, c, g, t, unknown or other

<400> SEQUENCE: 480
gagtcnnnnn n                                                            11

<210> SEQ ID NO 481
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, g, t, unknown or other

<400> SEQUENCE: 481
nnnnnngaga c                                                            11

<210> SEQ ID NO 482
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 482 caynnnnrtc                                                              10

<210> SEQ ID NO 483
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: a, c, g, t, unknown or other

<400> SEQUENCE: 483 gtctcnnnnn                                                              10

<210> SEQ ID NO 484
<211> LENGTH: 11
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, g, t, unknown or other

<400> SEQUENCE: 484
nnnnnngact c                                                           11

<210> SEQ ID NO 485
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 485
acctgcnnnn n                                                           11

<210> SEQ ID NO 486
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
gacccagtct ccatcctcc                                                   19

<210> SEQ ID NO 487
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
gactcagtct ccactctcc                                                   19

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
gacgcagtct ccaggcacc                                                   19

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
gacgcagtct ccagccacc                                                   19
```

<210> SEQ ID NO 490
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gtctcctgga cagtcgatc                                                19

<210> SEQ ID NO 491
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
ggccttggga cagacagtc                                                19

<210> SEQ ID NO 492
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
gtctcctgga cagtcagtc                                                19

<210> SEQ ID NO 493
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
ggccccaggg cagagggtc                                                19

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, g, t, unknown or other

<400> SEQUENCE: 494
nnnnnnnnnn nnnnngtccc                                               20

<210> SEQ ID NO 495
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (7)..(10)
<223> OTHER INFORMATION: a, c, g, t, unknown or other

<400> SEQUENCE: 495 ctcttcnnnn                                                              10

<210> SEQ ID NO 496
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(7)
<223> OTHER INFORMATION: a, c, g, t, unknown or other

<400> SEQUENCE: 496
nnnnnnngcg gg                                                           12

<210> SEQ ID NO 497
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, g, t, unknown or other

<400> SEQUENCE: 497
gcannnnnnt cg                                                           12

<210> SEQ ID NO 498
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(9)
<223> OTHER INFORMATION: a, c, g, t, unknown or other

<400> SEQUENCE: 498
nnnnnnnnng caggt                                                        15

<210> SEQ ID NO 499
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, g, t, unknown or other

<400> SEQUENCE: 499
cgtctcnnnn n                                                            11

<210> SEQ ID NO 500
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, g, t, unknown or other

<400> SEQUENCE: 500
cctnnnnnag g                                                          11

<210> SEQ ID NO 501
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 501
tttttttttt ttttt                                                      15

<210> SEQ ID NO 502
<211> LENGTH: 46
<212> TYPE: DNA
<213> ORGANISM: Unknown
<220> FEATURE:
<223> OTHER INFORMATION: Description of Unknown: h3401-d8 KAPPA
      oligonucleotide

<400> SEQUENCE: 502
agccaccctg tctgtgtctc caggggaaag agccaccctc tcctgc                    46

<210> SEQ ID NO 503
<211> LENGTH: 9532
<212> TYPE: DNA
<213> ORGANISM: Unknown
<220> FEATURE:
<223> OTHER INFORMATION: Description of Unknown: MALIA3 polynucleotide

<400> SEQUENCE: 503
aatgctacta ctattagtag aattgatgcc acctttcag ctcgcgcccc aaatgaaaat      60
atagctaaac aggttattga ccatttgcga aatgtatcta atggtcaaac taaatctact   120
cgttcgcaga attgggaatc aactgttaca tggaatgaaa cttccagaca ccgtactta    180 gttgcatatt taaacatgt tgagctacag caccagattc agcaattaag ctctaagcca    240
tccgcaaaaa tgacctctta tcaaaaggag caattaaagg tactctctaa tcctgacctg   300
ttggagtttg cttccggtct ggttcgcttt gaagctcgaa ttaaaacgcg atatttgaag   360
tctttcgggc ttcctcttaa tcttttgat gcaatccgct tgcttctga ctataatagt     420 cagggtaaag acctgatttt tgatttatgg tcattctcgt tttctgaact gtttaaagca   480
tttgaggggg attcaatgaa tatttatgac gattccgcag tattggacgc tatccagtct   540
aaacatttta ctattacccc ctctggcaaa acttcttttg caaaagcctc tcgctatttt   600 ggttttttatc gtcgtctggt aaacgagggt tatgatagtg ttgctcttac tatgcctcgt   660 aattccttttt ggcgttatgt atctgcatta gttgaatgtg gtattcctaa atctcaactg   720
atgaatcttt ctacctgtaa taatgttgtt ccgttagttc gtttattaa cgtagatttt   780 tcttcccaac gtcctgactg gtataatgag ccagttctta aaatcgcata aggtaattca   840
caatgattaa agttgaaatt aaaccatctc aagcccaatt tactactcgt tctggtgttt   900
```

```
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattctttcg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
tttttggaga ttttcaacgt gaaaaaatta ttattcgcaa ttcctttagt tgttcctttc   1620
tattctcaca gtgcacagtc tgtcgtgacg cagccgccct cagtgtctgg ggccccaggg   1680
cagagggtca ccatctcctg cactgggagc agctccaaca tcggggcagg ttatgatgta   1740
cactggtacc agcagcttcc aggaacagcc cccaaactcc tcatctatgg taacagcaat   1800
cggccctcag gggtccctga ccgattctct ggctccaagt ctggcacctc agcctccctg   1860
gccatcactg gctccaggc tgaggatgag gctgattatt actgccagtc ctatgacagc   1920
agcctgagtg gcctttatgt cttcggaact gggaccaagg tcaccgtcct aggtcagccc   1980
aaggccaacc ccactgtcac tctgttcccg ccctcctctg aggagctcca agccaacaag   2040
gccacactag tgtgtctgat cagtgacttc tacccgggag ctgtgacagt ggcctggaag   2100
gcagatagca gccccgtcaa ggcgggagtg agaccacca caccctccaa acaaagcaac   2160
aacaagtacg cggccagcag ctatctgagc ctgacgcctg agcagtggaa gtcccacaga   2220
agctacagct gccaggtcac gcatgaaggg agcaccgtgg agaagacagt ggcccctaca   2280
gaatgttcat aataaaccgc ctccaccggg cgcgccaatt ctatttcaag agacagtca   2340
taatgaaata cctattgcct acggcagccg ctggattgtt attactcgcg gcccagccgg   2400
ccatggccga agttcaattg ttagagtctg gtggcggtct tgttcagcct ggtggttctt   2460
tacgtctttc ttgcgctgct tccggattca ctttctcttc gtacgctatg tcttgggttc   2520
gccaagctcc tggtaaaggt ttggagtggg ttctgctat ctctggttct ggtggcagta   2580
cttactatgc tgactccgtt aaaggtcgct tcactatctc tagagacaac tctaagaata   2640
ctctctactt gcagatgaac agcttaaggg ctgaggacac tgcagtctac tattgcgcta   2700
aagactatga aggtactggt tatgctttcg acatatgggg tcaaggtact atggtcaccg   2760
tctctagtgc ctccaccaag ggcccatcgg tcttccccct ggcaccctcc tccaagagca   2820
cctctggggg cacagcggcc ctgggctgcc tggtcaagga ctacttcccc gaaccggtga   2880
cggtgtcgtg gaactcaggc gccctgacca gcggcgtcca caccttcccg gctgtcctac   2940
agtctagcgg actctactcc ctcagcagcg tagtgaccgt gccctcttct agcttgggca   3000
cccagaccta catctgcaac gtgaatcaca agcccagcaa caccaaggtg gacaagaaag   3060
ttgagcccaa atcttgtgcg gccgctcatc accaccatca tcactctgct gaacaaaaac   3120
tcatctcaga agaggatctg aatggtgccg cagatatcaa cgatgatcgt atggctggcg   3180
ccgctgaaac tgttgaaagt tgtttagcaa aaccccatac agaaaattca tttactaacg   3240
```

```
tctggaaaga cgacaaaact ttagatcgtt acgctaacta tgagggttgt ctgtggaatg    3300
ctacaggcgt tgtagtttgt actggtgacg aaactcagtg ttacggtaca tgggttccta    3360
ttgggcttgc tatccctgaa aatgagggtg gtggctctga gggtggcggt tctgagggtg    3420
gcggttctga gggtggcggt actaaacctc ctgagtacgg tgatacacct attccgggct    3480
atacttatat caaccctctc gacggcactt atccgcctgg tactgagcaa aaccccgcta    3540
atcctaatcc ttctcttgag gagtctcagc ctcttaatac tttcatgttt cagaataata    3600
ggttccgaaa taggcagggg gcattaactg tttatacggg cactgttact caaggcactg    3660
accccgttaa aacttattac cagtacactc ctgtatcatc aaaagccatg tatgacgctt    3720
actggaacgg taaattcaga gactgcgctt tccattctgg ctttaatgaa gatccattcg    3780
tttgtgaata tcaaggccaa tcgtctgacc tgcctcaacc tcctgtcaat gctgcggcg    3840 gctctggtgg tggttctggt ggcggctctg agggtggtgg ctctgagggt ggcggttctg    3900
agggtggcgg ctctgaggga ggcggttccg gtggtggctc tggttccggt gattttgatt    3960
atgaaaagat ggcaaacgct aataaggggg ctatgaccga aaatgccgat gaaaacgcgc    4020
tacagtctga cgctaaaggc aaacttgatt ctgtcgctac tgattacggt gctgctatcg    4080
atggtttcat tggtgacgtt tccggccttg ctaatggtaa tggtgctact ggtgattttg    4140
ctggctctaa ttcccaaatg gctcaagtcg gtgacggtga taattcacct ttaatgaata    4200
atttccgtca atatttacct tccctccctc aatcggttga atgtcgccct tttgtcttta    4260
gcgctggtaa accatatgaa ttttctattg attgtgacaa aataaactta ttccgtggtg    4320
tctttgcgtt tcttttatat gttgccacct ttatgtatgt attttctacg tttgctaaca    4380
tactgcgtaa taaggagtct taatcatgcc agttcttttg ggtattccgt tattattgcg    4440
tttcctcggt ttccttctgg taactttgtt cggctatctg cttacttttc ttaaaaaggg    4500
cttcggtaag atagctattg ctatttcatt gtttcttgct cttattattg ggcttaactc    4560
aattcttgtg ggttatctct ctgatattag cgctcaatta ccctctgact tgttcaggg    4620 tgttcagtta attctcccgt ctaatgcgct tccctgtttt tatgttattc tctctgtaaa    4680
ggctgctatt ttcattttg acgttaaaca aaaaatcgtt tcttatttgg attgggataa    4740
ataatatggc tgtttatttt gtaactggca aattaggctc tggaaagacg ctcgttagcg    4800
ttggtaagat tcaggataaa attgtagctg ggtgcaaaat agcaactaat cttgatttaa    4860
ggcttcaaaa cctcccgcaa gtcgggaggt tcgctaaaac gcctcgcgtt cttagaatac    4920
cggataagcc ttctatatct gatttgcttg ctattgggcg cggtaatgat tcctacgatg    4980
aaaataaaaa cggcttgctt gttctcgatg agtgcggtac ttggtttaat acccgttctt    5040
ggaatgataa ggaaagacag ccgattattg attggtttct acatgctcgt aaattaggat    5100
gggatattat ttttcttgtt caggacttat ctattgttga taaacaggcg cgttctgcat    5160
tagctgaaca tgttgtttat tgtcgtcgtc tggacagaat tactttacct tttgtcggta    5220
ctttatattc tcttattact ggctcgaaaa tgcctctgcc taaattacat gttggcgttg    5280
ttaaatatgg cgattctcaa ttaagcccta ctgttgagcg ttggctttat actggtaaga    5340
atttgtataa cgcatatgat actaaacagg ctttttctag taattatgat tccggtgttt    5400
attcttattt aacgccttat ttatcacacg gtcggtattt caaaccatta aatttaggtc    5460
agaagatgaa attaactaaa atatatttga aaaagtttc tcgcgttctt tgtcttgcga    5520
ttggatttgc atcagcattt acatatagtt atataaccca acctaagccg gaggttaaaa    5580
aggtagtctc tcagacctat gattttgata aattcactat tgactcttct cagcgtctta    5640
```

```
atctaagcta tcgctatgtt ttcaaggatt ctaagggaaa attaattaat agcgacgatt    5700
tacagaagca aggttattca ctcacatata ttgatttatg tactgtttcc attaaaaaag    5760
gtaattcaaa tgaaattgtt aaatgtaatt aattttgttt tcttgatgtt tgtttcatca    5820
tcttcttttg ctcaggtaat tgaaatgaat aattcgcctc tgcgcgattt tgtaacttgg    5880
tattcaaagc aatcaggcga atccgttatt gtttctcccg atgtaaaagg tactgttact    5940
gtatattcat ctgacgttaa acctgaaaat ctacgcaatt tctttatttc tgttttacgt    6000
gctaataatt ttgatatggt tggttcaatt ccttccataa ttcagaagta taatccaaac    6060
aatcaggatt atattgatga attgccatca tctgataatc aggaatatga tgataattcc    6120
gctccttctg gtggtttctt tgttccgcaa aatgataatg ttactcaaac ttttaaaatt    6180
aataacgttc gggcaaagga tttaatacga gttgtcgaat tgtttgtaaa gtctaatact    6240
tctaaatcct caaatgtatt atctattgac ggctctaatc tattagttgt ttctgcacct    6300
aaagatattt tagataacct tcctcaattc ctttctactg ttgatttgcc aactgaccag    6360
atattgattg agggtttgat atttgaggtt cagcaaggtg atgctttaga ttttttcattt   6420 gctgctggct ctcagcgtgg cactgttgca ggcggtgtta atactgaccg cctcacctct    6480
gttttatctt ctgctggtgg ttcgttcggt attttaatg gcgatgtttt agggctatca    6540
gttcgcgcat aaagactaa tagccattca aaaatattgt ctgtgccacg tattcttacg    6600
ctttcaggtc agaagggttc tatctctgtt ggccagaatg tcccttttat tactggtcgt    6660
gtgactggtg aatctgccaa tgtaaataat ccatttcaga cgattgagcg tcaaaatgta    6720
ggtatttcca tgagcgtttt tcctgttgca atggctggcg gtaatattgt tctggatatt    6780
accagcaagg ccgatagttt gagttcttct actcaggcaa gtgatgttat tactaatcaa    6840
agaagtattg ctacaacggt taatttgcgt gatggacaga ctcttttact cggtggcctc    6900
actgattata aaaacacttc tcaagattct ggcgtaccgt tcctgtctaa aatcccttta    6960
atcggcctcc tgtttagctc ccgctctgat tccaacgagg aaagcacgtt atacgtgctc    7020
gtcaaagcaa ccatagtacg cgccctgtag cggcgcatta gcgcggcgg gtgtggtggt    7080 tacgcgcagc gtgaccgcta cacttgccag cgccctagcg cccgctcctt tcgctttctt    7140
cccttccttt ctcgccacgt tcgccggctt tccccgtcaa gctctaaatc ggggggctccc   7200 tttagggttc cgatttagtg ctttacggca cctcgacccc aaaaaacttg atttgggtga    7260
tggttcacgt agtgggccat cgccctgata cggttttt cgccctttga cgttggagtc    7320
cacgttcttt aatagtggac tcttgttcca aactggaaca acactcaacc ctatctcggg    7380
ctattctttt gatttataag gattttgcc gatttcggaa ccaccatcaa acaggatttt    7440
cgcctgctgg gcaaaccag cgtggaccgc ttgctgcaac tctctcaggg ccaggcggtg    7500
aagggcaatc agctgttgcc cgtctcactg gtgaaaagaa aaaccaccct ggatccaagc    7560
ttgcaggtgg cacttttcgg ggaaatgtgc gcggaacccc tatttgttta ttttttctaaa   7620 tacattcaaa tatgtatccg ctcatgagac aataaccctg ataaatgctt caataatatt    7680
gaaaaaggaa gagtatgagt attcaacatt tccgtgtcgc ccttattccc ttttttgcgg    7740
cattttgcct tcctgttttt gctcacccag aaacgctggt gaaagtaaaa gatgctgaag    7800
atcagttggg cgcacgagtg ggttacatcg aactggatct caacagcggt aagatccttg    7860
agagttttcg ccccgaagaa cgttttccaa tgatgagcac ttttaaagtt ctgctatgtc    7920
atacactatt atcccgtatt gacgccgggc aagagcaact cggtcgccgg gcgcggtatt    7980
```

```
ctcagaatga cttggttgag tactcaccag tcacagaaaa gcatcttacg gatggcatga    8040
cagtaagaga attatgcagt gctgccataa ccatgagtga taacactgcg gccaacttac    8100
ttctgacaac gatcggagga ccgaaggagc taaccgcttt tttgcacaac atggggatc     8160 atgtaactcg ccttgatcgt tgggaaccgg agctgaatga agccatacca aacgacgagc    8220
gtgacaccac gatgcctgta gcaatgccaa caacgttgcg caaactatta actggcgaac    8280
tacttactct agcttcccgg caacaattaa tagactggat ggaggcggat aaagttgcag    8340
gaccacttct gcgctcggcc cttccggctg gctggtttat tgctgataaa tctggagccg    8400
gtgagcgtgg gtctcgcggt atcattgcag cactggggcc agatggtaag ccctcccgta    8460
tcgtagttat ctacacgacg gggagtcagg caactatgga tgaacgaaat agacagatcg    8520
ctgagatagg tgcctcactg attaagcatt ggtaactgtc agaccaagtt tactcatata    8580
tactttagat tgatttaaaa cttcattttt aatttaaaag gatctaggtg aagatccttt    8640
ttgataatct catgaccaaa atcccttaac gtgagttttc gttccactgt acgtaagacc    8700
cccaagcttg tcgactgaat ggcgaatggc gctttgcctg gtttccggca ccagaagcgg    8760
tgccggaaag ctggctggag tgcgatcttc ctgaggccga tactgtcgtc gtcccctcaa    8820
actggcagat gcacggttac gatgcgccca tctacaccaa cgtaacctat cccattacgg    8880
tcaatccgcc gtttgttccc acggagaatc cgacgggttg ttactcgctc acatttaatg    8940
ttgatgaaag ctggctacag gaaggccaga cgcgaattat ttttgatggc gttcctattg    9000
gttaaaaaat gagctgattt aacaaaaatt taacgcgaat tttaacaaaa tattaacgtt    9060
tacaatttaa atatttgctt atacaatctt cctgtttttg gggcttttct gattatcaac    9120
cggggtacat atgattgaca tgctagtttt acgattaccg ttcatcgatt ctcttgtttg    9180
ctccagactc tcaggcaatg acctgatagc ctttgtagat ctctcaaaaa tagctaccct    9240
ctccggcatg aatttatcag ctagaacggt tgaatatcat attgatggtg atttgactgt    9300
ctccggcctt tctcaccctt ttgaatcttt acctacacat tactcaggca ttgcatttaa    9360
aatatatgag ggttctaaaa atttttatcc ttgcgttgaa ataaaggctt ctcccgcaaa    9420
agtattacag ggtcataatg ttttttggtac aaccgattta gctttatgct ctgaggcttt    9480
attgcttaat tttgctaatt ctttgccttg cctgtatgat ttattggatg tt            9532
```

<210> SEQ ID NO 504
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, g, t, unknown or other

<400> SEQUENCE: 504 gacnnngtc                                                              10

METHODS OF CONSTRUCTING LIBRARIES OF GENETIC PACKAGES THAT COLLECTIVELY DISPLAY THE MEMBERS OF A DIVERSE FAMILY OF PEPTIDES, POLYPEPTIDES OR PROTEINS

CROSS-REFERENCE TO RELATED APPLICATIONS

The present application is a divisional (and claims the benefit of priority under 35 USC 120) of U.S. Ser. No. 09/837,306, filed Apr. 17, 2001, now abandoned which claims the benefit of U.S. Ser. No. 60/198,069, filed Apr. 17, 2000, all of which are herein incorporated by reference.

The present invention relates to constructing libraries of genetic packages that display a member of a diverse family of peptides, polypeptides or proteins and collectively display at least a portion of the diversity of the family. In a preferred embodiment, the displayed polypeptides are human Fabs.

More specifically, the invention is directed to the methods of cleaving single-stranded nucleic acids at chosen locations, the cleaved nucleic acids encoding, at least in part, the peptides, polypeptides or proteins displayed on the genetic packages of the libraries of the invention. In a preferred embodiment, the genetic packages are filamentous phage or phagemids.

The present invention further relates to methods of screening the libraries of genetic packages that display useful peptides, polypeptides and proteins and to the peptides, polypeptides and proteins identified by such screening.

BACKGROUND OF THE INVENTION

It is now common practice in the art to prepare libraries of genetic packages that display a member of a diverse family of peptides, polypeptides or proteins and collectively display at least a portion of the diversity of the family. In many common libraries, the displayed peptides, polypeptides or proteins are related to antibodies. Often, they are Fabs or single chain antibodies.

In general, the DNAs that encode members of the families to be displayed must be amplified before they are cloned and used to display the desired member on the surface of a genetic package. Such amplification typically makes use of forward and backward primers.

Such primers can be complementary to sequences native to the DNA to be amplified or complementary to oligonucleotides attached at the 5' or 3' ends of that DNA. Primers that are complementary to sequences native to the DNA to be amplified are disadvantaged in that they bias the members of the families to be displayed. Only those members that contain a sequence in the native DNA that is substantially complementary to the primer will be amplified. Those that do not will be absent from the family. For those members that are amplified, any diversity within the primer region will be suppressed.

For example, in European patent 368,684 B1, the primer that is used is at the 5' end of the $V_H$ region of an antibody gene. It anneals to a sequence region in the native DNA that is said to be "sufficiently well conserved" within a single species. Such primer will bias the members amplified to those having this "conserved" region. Any diversity within this region is extinguished.

It is generally accepted that human antibody genes arise through a process that involves a combinatorial selection of V and J or V, D, and J followed by somatic mutations. Although most diversity occurs in the Complementary Determining Regions (CDRs), diversity also occurs in the more conserved Framework Regions (FRs) and at least some of this diversity confers or enhances specific binding to antigens (Ag). As a consequence, libraries should contain as much of the CDR and FR diversity as possible.

To clone the amplified DNAs for display on a genetic package of the peptides, polypeptides or proteins that they encode, the DNAs must be cleaved to produce appropriate ends for ligation to a vector. Such cleavage is generally effected using restriction endonuclease recognition sites carried on the primers. When the primers are at the 5' end of DNA produced from reverse transcription of RNA, such restriction leaves deleterious 5' untranslated regions in the amplified DNA. These regions interfere with expression of the cloned genes and thus the display of the peptides, polypeptides and proteins coded for by them.

SUMMARY OF THE INVENTION

It is an object of this invention to provide novel methods for constructing libraries of genetic packages that display a member of a diverse family of peptides, polypeptides or proteins and collectively display at least a portion of the diversity of the family. These methods are not biased toward DNAs that contain native sequences that are complementary to the primers used for amplification. They also enable any sequences that may be deleterious to expression to be removed from the amplified DNA before cloning and displaying.

It is another object of this invention to provide a method for cleaving single-stranded nucleic acid sequences at a desired location, the method comprising the steps of:
  (i) contacting the nucleic acid with a single-stranded oligonucleotide, the oligonucleotide being functionally complementary to the nucleic acid in the region in which cleavage is desired and including a sequence that with its complement in the nucleic acid forms a restriction endonuclease recognition site that on restriction results in cleavage of the nucleic acid at the desired location; and
  (ii) cleaving the nucleic acid solely at the recognition site formed by the complementation of the nucleic acid and the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

It is a further object of this invention to provide an alternative method for cleaving single-stranded nucleic acid sequences at a desired location, the method comprising the steps of:
  (i) contacting the nucleic acid with a partially double-stranded oligonucleotide, the single-stranded region of the oligonucleotide being functionally complementary to the nucleic acid in the region in which cleavage is desired, and the double-stranded region of the oligonucleotide having a Type II-S restriction endonuclease recognition site, whose cleavage site is located at a known distance from the recognition site; and
  (ii) cleaving the nucleic acid solely at the cleavage site formed by the complementation of the nucleic acid and the single-stranded region of the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

It is another objective of the present invention to provide a method of capturing DNA molecules that comprise a member of a diverse family of DNAs and collectively comprise at least a portion of the diversity of the family. These DNA molecules in single-stranded form have been cleaved by one of the methods of this invention. This method involves ligating the individual single-stranded DNA members of the family to a partially duplex DNA complex. The method comprises the steps of:

(i) contacting a single-stranded nucleic acid sequence that has been cleaved with a restriction endonuclease with a partially double-stranded oligonucleotide, the single-stranded region of the oligonucleotide being functionally complementary to the nucleic acid in the region that remains after cleavage, the double-stranded region of the oligonucleotide including any sequences necessary to return the sequences that remain after cleavage into proper reading frame for expression and containing a restriction endonuclease recognition site 5' of those sequences; and (ii) cleaving the partially double-stranded oligonucleotide sequence solely at the restriction endonuclease recognition site contained within the double-stranded region of the partially double-stranded oligonucleotide.

It is another object of this invention to prepare libraries, that display a diverse family of peptides, polypeptides or proteins and collectively display at least part of the diversity of the family, using the methods and DNAs described above.

It is an object of this invention to screen those libraries to identify useful peptides, polypeptides and proteins and to use those substances in human therapy.

TERMS

Figure 1:
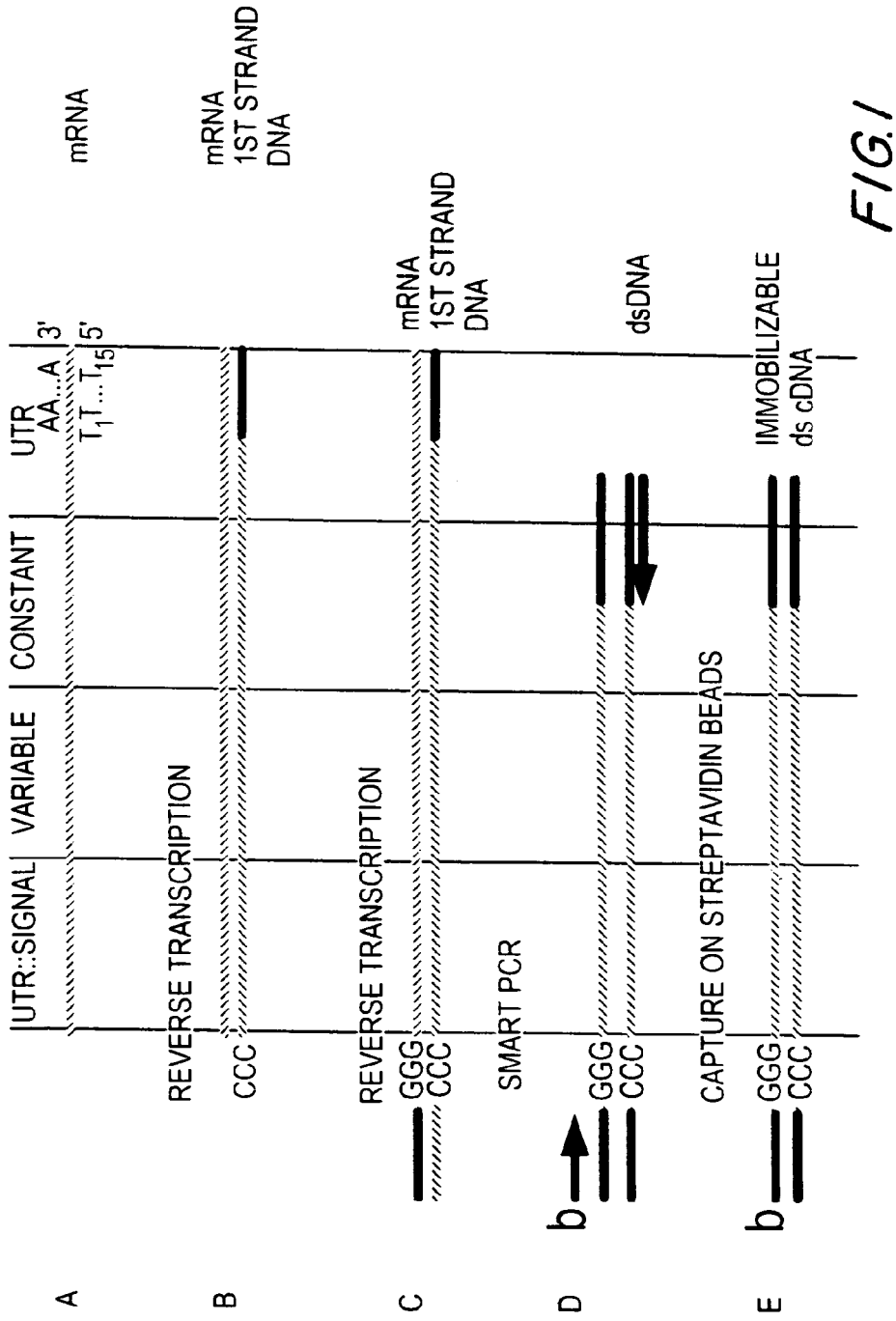
FIG. 1 is a schematic of various methods that may be employed to amplify VH genes without using primers specific for VH sequences.

In this application, the following terms and abbreviations are used:
Sense strand The upper strand of ds DNA as usually written. In the sense strand, 5'-ATG-3' codes for Met.
Antisense strand The lower strand of ds DNA as usually written. In the antisense strand, 3'-TAC-5' would correspond to a Met codon in the sense strand.
Forward primer: A "forward" primer is complementary to a part of the sense strand and primes for synthesis of a new antisense-strand molecule. "Forward primer" and "lower-strand primer" are equivalent.
Backward primer: A "backward" primer is complementary to a part of the antisense strand and primes for synthesis of a new sense-strand molecule. "Backward primer" and "top-strand primer" are equivalent.
Bases: Bases are specified either by their position in a vector or gene as their position within a gene by codon and base. For example, "89.1" is the first base of codon 89, 89.2 is the second base of codon 89.
Sv Streptavidin
Ap Ampicillin
$ap^R$ A gene conferring ampicillin resistance.
RE Restriction endonuclease
URE Universal restriction endonuclease
Functionally complementary Two sequences are sufficiently complementary so as to anneal under the chosen conditions.
RERS Restriction endonuclease recognition site
AA Amino acid
PCR Polymerization chain reaction
GLGs Germline genes
Ab Antibody: an immunoglobin. The term also covers any protein having a binding domain which is homologous to an immunoglobin binding domain. A few examples of antibodies within this definition are, inter alia, immunoglobin isotypes and the Fab, $F(ab^1)_2$, scfv, Fv, dAb and Fd fragments.
Fab Two chain molecule comprising an Ab light chain and part of a heavy-chain.
scFv A single-chain Ab comprising either VH::linker::VL or VL::linker::VH
w.t. Wild type
HC Heavy chain
LC Light chain
VK A variable domain of a Kappa light chain.
VH A variable domain of a heavy chain.
VL A variable domain of a lambda light chain.
In this application, all references referred to are specifically incorporated by reference.

DETAILED DESCRIPTION OF THE PREFERRED EMBODIMENTS

The nucleic acid sequences that are useful in the methods of this invention, i.e., those that encode at least in part the individual peptides, polypeptides and proteins displayed on the genetic packages of this invention, may be naturally occurring, synthetic or a combination thereof. They may be mRNA, DNA or cDNA. In the preferred embodiment, the nucleic acids encode antibodies. Most preferably, they encode Fabs.

The nucleic acids useful in this invention may be naturally diverse, synthetic diversity may be introduced into those naturally diverse members, or the diversity may be entirely synthetic. For example, synthetic diversity can be introduced into one or more CDRs of antibody genes.

Synthetic diversity may be created, for example, through the use of TRIM technology (U.S. Pat. No. 5,869,644). TRIM technology allows control over exactly which amino-acid types are allowed at variegated positions and in what proportions. In TRIM technology, codons to be diversified are synthesized using mixtures of trinucleotides. This allows any set of amino acid types to be included in any proportion.

Another alternative that may be used to generate diversified DNA is mixed oligonucleotide synthesis. With TRIM technology, one could allow Ala and Trp. With mixed oligonucleotide synthesis, a mixture that included Ala and Trp would also necessarily include Ser and Gly. The amino-acid types allowed at the variegated positions are picked with reference to the structure of antibodies, or other peptides, polypeptides or proteins of the family, the observed diversity in germline genes, the observed somatic mutations frequently observed, and the desired areas and types of variegation.

In a preferred embodiment of this invention, the nucleic acid sequences for at least one CDR or other region of the peptides, polypeptides or proteins of the family are cDNAs produced by reverse transcription from mRNA. More preferably, the mRNAs are obtained from peripheral blood cells, bone marrow cells, spleen cells or lymph node cells (such as B-lymphocytes or plasma cells) that express members of naturally diverse sets of related genes. More preferable, the mRNAs encode a diverse family of antibodies. Most preferably, the mRNAs are obtained from patients suffering from at least one autoimmune disorder or cancer. Preferably, mRNAs containing a high diversity of autoimmune diseases, such as systemic lupus erythematosus, systemic sclerosis, rheumatoid arthritis, antiphospholipid syndrome and vasculitis are used.

In a preferred embodiment of this invention, the cDNAs are produced from the mRNAs using reverse transcription. In this preferred embodiment, the mRNAs are separated from the cell and degraded using standard methods, such that only the full length (i.e., capped) mRNAs remain. The cap is then removed and reverse transcription used to produce the cDNAs.

The reverse transcription of the first (antisense) strand can be done in any manner with any suitable primer. See, e.g., H J de Haard et al., *Journal of Biolocical Chemistry*, 274(26): 18218-30 (1999). In the preferred embodiment of this invention where the mRNAs encode antibodies, primers that are complementary to the constant regions of antibody genes may be used. Those primers are useful because they do not generate bias toward subclasses of antibodies. In another embodiment, poly-dT primers may be used (and may be preferred for the heavy-chain genes). Alternatively, sequences complementary to the primer may be attached to the termini of the antisense strand.

In one preferred embodiment of this invention, the reverse transcriptase primer may be biotinylated, thus allowing the cDNA product to be immobilized on streptavidin (Sv) beads. Immobilization can also be effected using a primer labeled at the 5' end with one of a) free amine group, b) thiol, c) carboxylic acid, or d) another group not found in DNA that can react to form a strong bond to a known partner on an insoluble medium. If, for example, a free amine (preferably primary amine) is provided at the 5' end of a DNA primer, this amine can be reacted with carboxylic acid groups on a polymer bead using standard amide-forming chemistry. If such preferred immobilization is used during reverse transcription, the top strand RNA is degraded using well-known enzymes, such as a combination of RNAseH and RNAseA, either before or after immobilization.

The nucleic acid sequences useful in the methods of this invention are generally amplified before being used to display the peptides, polypeptides or proteins that they encode. Prior to amplification, the single-stranded DNAs may be cleaved using either of the methods described before. Alternatively, the single-stranded DNAs may be amplified and then cleaved using one of those methods.

Any of the well known methods for amplifying nucleic acid sequences may be used for such amplification. Methods that maximize, and do not bias, diversity are preferred. In a preferred embodiment of this invention where the nucleic acid sequences are derived from antibody genes, the present invention preferably utilizes primers in the constant regions of the heavy and light chain genes and primers to a synthetic sequence that are attached at the 5' end of the sense strand. Priming at such synthetic sequence avoids the use of sequences within the variable regions of the antibody genes. Those variable region priming sites generate bias against V genes that are either of rare subclasses or that have been mutated at the priming sites. This bias is partly due to suppression of diversity within the primer region and partly due to lack of priming when many mutations are present in the region complementary to the primer. The methods disclosed in this invention have the advantage of not biasing the population of amplified antibody genes for particular V gene types.

The synthetic sequences may be attached to the 5' end of the DNA strand by various methods well known for ligating DNA sequences together. RT CapExtention is one preferred method.

In RT CapExtention (derived from Smart PCR(TM), a short overlap (5'- . . . GGG-3' in the upper-strand primer (USP-GGG) complements 3'-CCC. . . . 5' in the lower strand) and reverse transcriptases are used so that-the reverse complement of the upper-strand primer is attached to the lower strand.

In a preferred embodiment of this invention, the upper strand or lower strand primer may be also biotinylated or labeled at the 5' end with one of a) free amino group, b) thiol, c) carboxylic acid and d) another group not found in DNA that can react to form a strong bond to a known partner as an insoluble medium. These can then be used to immobilize the labeled strand after amplification. The immobilized DNA can-be either single or double-stranded.

FIG. 1 shows a schematic of the amplification of VH genes. FIG. 1, Panel A shows a primer specific to the poly-dT region of the 3' UTR priming synthesis of the first, lower strand. Primers that bind in the constant region are also suitable. Panel B shows the lower strand extended at its 3' end by three Cs that are not complementary to the mRNA. Panel C shows the result of annealing a synthetic top-strand primer ending in three GGGs that hybridize to the 3' terminal CCCs and extending the reverse transcription extending the lower strand by the reverse complement of the synthetic primer sequence. Panel D shows the result of PCR amplification using a 5' biotinylated synthetic top-strand primer that replicates the 5' end of the synthetic primer of panel C and a bottom-strand primer complementary to part of the constant domain. Panel E shows immobilized double-stranded (ds) cDNA obtained by using a 5'-biotinylated top-strand primer.

Figure 2:
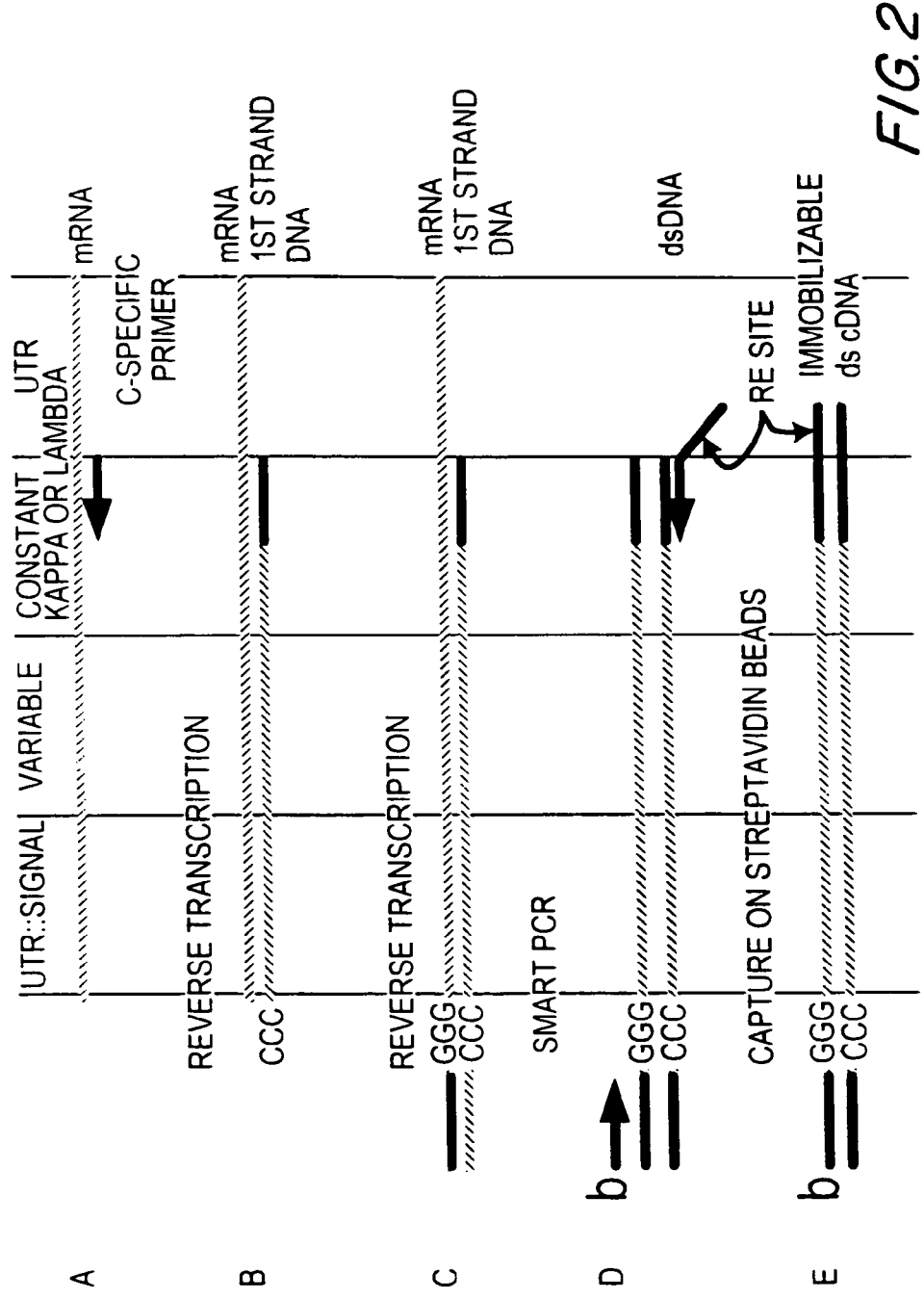
FIG. 2 is a schematic of various methods that may be employed to amplify VL genes without using VL sequences.

FIG. 2 shows a similar schematic for amplification of VL genes. FIG. 2, Panel A shows a primer specific to the constant region at or near the 3' end priming synthesis of the first, lower strand. Primers that bind in the poly-dT region are also suitable. Panel B shows the lower strand extended at its 3' end by three Cs that are not complementary to the mRNA. Panel C shows the result of annealing a synthetic top-strand primer ending in three GGGs that hybridize to the 3' terminal CCCs and extending the reverse transcription extending the lower strand by the reverse complement of the synthetic primer sequence. Panel D shows the result of PCR amplification using a 5' biotinylated synthetic top-strand primer that replicates the 5' end of the synthetic primer of panel C and a bottom-strand primer complementary to part of the constant domain. The bottom-strand primer also contains a useful restriction endonuclease site, such as AscI. Panel E shows immobilized ds cDNA obtained by using a 5'-biotinylated top-strand primer.

In FIGS. 1 and 2, each V gene consists of a 5' untranslated region (UTR) and a secretion signal, followed by the variable region, followed by a constant region, followed by a 3' untranslated region (which typically ends in poly-A). An initial primer for reverse transcription may be complementary to the constant region or to the poly A segment of the 3'-UTR. For human heavy-chain genes, a primer of 15 T (SEQ ID NO: 501) is preferred. Reverse transcriptases attach several C residues to the 3' end of the newly synthesized DNA. RT CapExtention exploits this feature. The reverse transcription reaction is first run with only a lower-strand primer. After about 1 hour, a primer ending in GGG (USP-GGG) and more RTase are added. This causes the lower-strand cDNA to be extended by the reverse complement of the USP-GGG up to the final GGG. Using one primer identical to part of the attached synthetic sequence and a second primer complementary to a region of known sequence at the 3' end of the sense strand, all the V genes are amplified irrespective of their V gene subclass.

After amplification, the DNAs of this invention are rendered single-stranded. For example, the strands can be separated by using a biotinylated primer, capturing the biotinylated product on streptavidin beads, denaturing the DNA, and washing away the complementary strand. Depending on which end of the captured DNA is wanted, one will choose to. immobilize either the upper (sense) strand or the lower (antisense) strand.

To prepare the single-stranded amplified DNAs for cloning into genetic packages so as to effect display of the peptides, polypeptides or proteins encoded, at least in part, by those DNAs, they must be manipulated to provide ends suitable for cloning and expression. In particular, any 5' untranslated regions and mammalian signal sequences must be removed and replaced, in frame, by a suitable signal sequence that functions in the display host. Additionally, parts of the variable domains (in antibody genes) may be removed and replaced by synthetic segments containing synthetic diversity. The diversity of other gene families may likewise be expanded with synthetic diversity.

According to the methods of this invention, there are two ways to manipulate the single-stranded amplified DNAs for cloning. The first method comprises the steps of:
  (i) contacting the nucleic acid with a single-stranded oligonucleotide, the oligonucleotide being functionally complementary to the nucleic acid in the region in which cleavage is desired and including a sequence that with its complement in the nucleic acid forms a restriction endonuclease recognition site that on restriction results in cleavage of the nucleic acid at the desired location; and
  (ii) cleaving the nucleic acid solely at the recognition site formed by the complementation of the nucleic acid and the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

In this first method, short oligonucleotides are annealed to the single-stranded DNA so that restriction endonuclease recognition sites formed within the now locally double-stranded regions of the DNA can be cleaved. In particular, a recognition site that occurs at the same position in a substantial fraction of the single-stranded DNAs is identical.

For antibody genes, this can be done using a catalog of germline sequences. See, e.g., the MRC Centre for Protein Engineering website. Updates can be obtained from this site under the heading "Amino acid and nucleotide sequence alignments." For other families, similar comparisons exist and may be used to select appropriate regions for cleavage and to maintain diversity.

For example, Table 195 depicts the DNA sequences of the FR3 regions of the 51 known human VH germline genes. In this region, the genes contain restriction endonuclease recognition sites shown in Table 200. Restriction endonucleases that cleave a large fraction of germline genes at the same site are preferred over endonucleases that cut at a variety of sites. Furthermore, it is preferred that there be only one site for the restriction endonucleases within the region to which the short oligonucleotide binds on the single-stranded DNA, e.g., about 10 bases on either side of the restriction endonuclease recognition site.

An enzyme that cleaves downstream in FR3 is also more preferable because it captures fewer mutations in the framework. This may be advantageous is some cases. However, it is well known that framework mutations exist and confer and enhance antibody binding. The present invention, by choice of appropriate restriction site, allows all or part of FR3 diversity to be captured. Hence, the method also allows extensive diversity to be captured.

Finally, in the methods of this invention restriction endonucleases that are active between about 45° and about 75° C. are used. Preferably enzymes that are active above 50° C., and more preferably active about 55° C., are used. Such temperatures maintain the nucleic acid sequence to be cleaved in substantially single-stranded form.

Enzymes shown in Table 200 that cut many of the heavy chain FR3 germline genes at a single position include: MaeIII (24@4), Tsp45I(21@4), HphI(44@5), BsaJI(23@65), AluI (23@47), BlpI(21@48), DdeI(29@58), BglII(10@61), MslI (44@72), BsiEI(23@74), EaeI(23@74), EagI(23@74), HaeII(25@75), Bst4CI(51@86), HpyCH4III(51@86), HinfI (38@2), MlyI(18@2), PleI(18@2), MnlI(31@67), HpyCH4V(21@44), BsmAI(16@11), BpmI(19@12), XmnI (12@30), and SacI(11@51). (The notation used means, for example, that BsmAI cuts 16 of the FR3 germline genes with a restriction endonuclease recognition site beginning at base 11 of FR3.)

For cleavage of human heavy chains in FR3, the preferred restriction endonucleases are: Bst4CI (or TaaI or HpyCH4III), BipI, HpyCH4V, and MslI. Because ACNGT (the restriction endonuclease recognition site for Bst4CI, TaaI, and HpyCH4III) is found at a consistent site in all the human FR3 germline genes, one of those enzymes is the most preferred for capture of heavy chain CDR3 diversity. BlpI and HpyCH4V are complementary. BipI cuts most members of the VH1 and VH4 families while HpyCH4V cuts most members of the VH3, VH5, VH6, and VH7 families. Neither enzyme cuts VH2s, but this is a very small family, containing only three members. Thus, these enzymes may also be used in preferred embodiments of the methods of this invention.

The restriction endonucleases HpyCH4III, Bst4CI, and TaaI all recognize 5'-ACnGT-3' and cut upper strand DNA after n and lower strand DNA before the base complementary to n. This is the most preferred restriction endonuclease recognition site for this method on human heavy chains because it is found in all germline genes. Furthermore, the restriction endonuclease recognition region (ACnGT) matches the second and third bases of a tyrosine codon (tay) and the following cysteine codon (tqy) as shown in Table 206. These codons are highly conserved, especially the cysteine in mature antibody genes.

Table 250 E shows the distinct oligonucleotides of length 22 (except the last one which is of length 20) bases. Table 255 C shows the analysis of 1617 actual heavy chain antibody genes. Of these, 1511 have the site and match one of the candidate oligonucleotides to within 4 mismatches. Eight oligonucleotides account for most of the matches and are given in Table 250 F.1. The 8 oligonucleotides are very similar so that it is likely that satisfactory cleavage will be achieved with only one oligonucleotide (such as H43.77.97.1-02#1) by adjusting temperature, pH, salinity, and the like. One or two oligonucleotides may likewise suffice whenever the germline gene sequences differ very little and especially if they differ very little close to the restriction endonuclease recognition region to be cleaved. Table 255 D shows a repeat analysis of 1617 actual heavy chain antibody genes using only the 8 chosen oligonucleotides. This shows that 1463 of the sequences match at least one of the oligonucleotides to within 4 mismatches and have the site as expected. Only 7 sequences have a second HpyCH4III restriction endonuclease recognition region in this region.

Another illustration of choosing an appropriate restriction endonuclease recognition site involves cleavage in FR1 of human heavy chains. Cleavage in FR1 allows capture of the entire CDR diversity of the heavy chain.

The germline genes for human heavy chain FR1 are shown in Table 217. Table 220 shows the restriction endonuclease recognition sites found in human germline genes FR1s. The preferred sites are BsgI(GTGCAG;39@4), BsoFI(GCngc; 43@6,11@9,2@3,1@12), TseI (Gcwgc;43@6,11@9,2@3, 1@12), MspA1I(CMGckg;46@7,2@1), PvuII(CAGctg; 46@7,2@1), AluI(AGct;48@82@2), DdeI(Ctnag;22@52, 9@48), HphI(tcacc;22@80), BssKI(Nccngg;35@39,2@40), BsaJI(Ccnngg;32@40,2@41), BstNI(CCwgg;33@40), ScrFI(CCngg;35@40,2@41), EcoO109I(RGgnccy;22@46, 11@43), Sau96I(Ggncc;23@47,11@44), AvaII(Ggwcc; 23@47,4@44), PpuMI(RGgwccy;22@46,4@43), BsmFI (gtccc;20@48), HinfI(Gantc;34@16,21@56,21@77), TfiI (21@77), M-ZyI(GAGTC;34@16), MlyI(gactc;21@56), and AlwNI(CAGnnnctg;22@68). The more preferred sites are MspAI and PvuII. MspAI and PvuII have 46 sites at 7-12 and 2 at 1-6. To avoid cleavage at both sites, oligonucleotides are used that do not fully cover the site at 1-6. Thus, the DNA will not be cleaved at that site. We have shown that DNA that extends 3, 4, or 5 bases beyond a PvuII-site can be cleaved efficiently.

Another illustration of choosing an appropriate restriction endonuclease recognition site involves cleavage in FRi of human kappa light chains. Table 300 shows the human kappa FRl germline genes and Table 302 shows restriction endonuclease recognition sites that are found in a substantial number of human kappa FRl germline genes at consistent locations. Of the restriction endonuclease recognition sites listed, BsmAI and PflFI are the most preferred enzymes. BsmAI sites are found at base 18 in 35 of 40 germline genes. PflFI sites are found in 35 of 40 germline genes at base 12.

Another example of choosing an appropriate restriction endonuclease recognition site involves cleavage in FR1 of the human lambda light chain. Table 400 shows the 31 known human lambda FR1 germline gene sequences. Table 405 shows restriction endonuclease recognition sites found in human lambda FR1 germline genes. HinfI and DdeI are the most preferred restriction endonucleases for cutting human lambda chains in FR1.

After the appropriate site or sites for cleavage are chosen, one or more short oligonucleotides are prepared so as to functionally complement, alone or in combination, the chosen recognition site. The oligonucleotides also include sequences that flank the recognition site in the majority of the amplified genes. This flanking region allows the sequence to anneal to the single-stranded DNA sufficiently to allow cleavage by the restriction endonuclease specific for the site chosen.

The actual length and sequence of the oligonucleotide depends on the recognition site and the conditions to be used for contacting and cleavage. The length must be sufficient so that the oligonucleotide is functionally complementary to the single-stranded DNA over a large enough region to allow the two strands to associate such that cleavage may occur at the chosen temperature and solely at the desired location.

Typically, the oligonucleotides of this preferred method of the invention are about 17 to about 30 nucleotides in length. Below about 17 bases, annealing is too weak and above 30 bases there can be a loss of specificity. A preferred length is 18 to 24 bases.

Oligonucleotides of this length need not be identical complements of the germline genes. Rather, a few mismatches taken may be tolerated. Preferably, however, no more than 1-3 mismatches are allowed. Such mismatches do not adversely affect annealing of the oligonucleotide to the single-stranded DNA. Hence, the two DNAs are said to be functionally complementary.

The second method to manipulate the amplified single-stranded DNAs of this invention for cloning comprises the steps of:
 (i) contacting the nucleic acid with a partially double-stranded oligonucleotide, the single-stranded region of the oligonucleotide being functionally complementary to the nucleic acid in the region in which cleavage is desired, and the double-stranded region of the oligonucleotide having a Type II-S restriction endonuclease recognition site, whose cleavage site is located at a known distance from the recognition site; and
 (ii) cleaving the nucleic acid solely at the cleavage site formed by the complementation of the nucleic acid and the single-stranded region of the oligonucleotide;
the contacting and the cleaving steps being performed at a temperature sufficient to maintain the nucleic acid in substantially single-stranded form, the oligonucleotide being functionally complementary to the nucleic acid over a large enough region to allow the two strands to associate such that cleavage may occur at the chosen temperature and at the desired location, and the cleavage being carried out using a restriction endonuclease that is active at the chosen temperature.

This second method employs Universal Restriction Endonucleases ("URE"). UREs are partially double-stranded oligonucleotides. The single-stranded portion or overlap of the URE consists of a DNA adapter that is functionally complementary to the sequence to be cleaved in the single-stranded DNA. The double-stranded portion consists of a type II-S restriction endonuclease recognition site.

The URE method of this invention is specific and precise and can tolerate some (e.g., 1-3) mismatches in the complementary regions, i.e., it is functionally complementary to that region. Further, conditions under which the URE is used can be adjusted so that most of the genes that are amplified can be cut, reducing bias in the library produced from those genes.

The sequence of the single-stranded DNA adapter or overlap portion of the URE typically consists of about 14-22 bases. However, longer or shorter adapters may be used. The size depends on the ability of the adapter to associate with its functional complement in the single-stranded DNA and the temperature used for contacting the URE and the single-stranded DNA at the temperature used for cleaving the DNA with the type II-S enzyme. The adapter must be functionally complementary to the single-stranded DNA over a large enough region to allow the two strands to associate such that the cleavage may occur at the chosen temperature and at the desired location. We prefer singe-stranded or overlap portions of 14-17 bases in length, and more preferably 18-20 bases in length.

The site chosen for cleavage using the URE is preferably one that is substantially conserved in the family of amplified DNAs. As compared to the first cleavage method of this invention, these sites do not need to be endonuclease recognition sites. However, like the first method, the sites chosen can be synthetic rather than existing in the native DNA. Such sites may be chosen by references to the sequences of known antibodies or other families of genes. For example, the sequences of many germline genes are reported at the MRC Centre for Protein Engineering website. For example, one preferred site occurs near the end of FR3--codon 89 through the second base of codon 93. CDR3 begins at codon 95.

The sequences of 79 human heavy-chain genes are also available at the National Center for Biotechnology Information (NCBI) website.

This site can be used to identify appropriate sequences for URE cleavage according to the methods of this invention. See, e.g., Table 8B.

Most preferably, one or more sequences are identified using these sites or other available sequence information. These sequences together are present in a substantial fraction of the amplified DNAs. For example, multiple sequences could be used to allow for known diversity in germline genes or for frequent somatic mutations. Synthetic degenerate sequences could also be used. Preferably, a sequence(s) that occurs in at least 65% of genes examined with no more than 2-3 mismatches is chosen URE single-stranded adapters or overlaps are then made to be complementary to the chosen regions. Conditions for using the UREs are determined empirically. These conditions should allow cleavage of DNA that contains the functionally complementary sequences with no more than 2 or 3 mismatches but that do not allow cleavage of DNA lacking such sequences.

As described above, the double-stranded portion of the URE includes a Type II-S endonuclease recognition site. Any Type II-S enzyme that is active at a temperature necessary to maintain the single-stranded DNA substantially in that form and to allow the single-stranded DNA adapter portion of the URE to anneal long enough to the single-stranded DNA to permit cleavage at the desired site may be used.

The preferred Type II-S enzymes for use in the URE methods of this invention provide asymmetrical cleavage of the single-stranded DNA. Among these are the enzymes listed in Table 800. The most preferred Type II-S enzyme is FokI.

When the preferred Fok I containing URE is used, several conditions are preferably used to effect cleavage:
1) Excess of the URE over target DNA should be present to activate the enzyme. URE present only in equimolar amounts to the target DNA would yield poor cleavage of ssDNA because the amount of active enzyme available would be limiting.
2) An activator may be used to activate part of the FokI enzyme to dimerize without causing cleavage. Examples of appropriate activators are shown in Table 510.
3) The cleavage reaction is performed at a temperature between 45-75° C., preferably above 50° C. and most preferably above 55° C.

The UREs used in the prior art contained a 14-base single-stranded segment, a 10-base stem (containing a FokI site), followed by the palindrome of the 10-base stem. While such UREs may be used in the methods of this invention, the preferred UREs of this invention also include a segment of three to eight bases (a loop) between the FokI restriction endonuclease recognition site containing segments. In the preferred embodiment, the stem (containing the FokI site) and its palindrome are also longer than 10 bases. Preferably, they are 10-14 bases in length. Examples of these "lollipop" URE adapters are shown in Table 5.

One example of using a URE to cleave an single-stranded DNA involves the FR3 region of human heavy chain. Table 508 shows an analysis of 840 full-length mature human heavy chains with the URE recognition sequences shown. The vast majority (718/840=0.85) will be recognized with 2 or fewer mismatches using five UREs (VHS881-1.1, VHS881-1.2, VHS881-2.1, VHS881-4.1, and VHS881-9.1). Each has a 20-base adaptor sequence to complement the germline gene, a ten-base stem segment containing a FokI site, a five base loop, and the reverse complement of the first stem segment. Annealing those adapters, alone or in combination, to single-stranded antisense heavy chain DNA and treating with FokI in the presence of, e.g., the activator FOKIact, will lead to cleavage of the antisense strand at the position indicated.

Another example of using a URE(s) to cleave a single-stranded DNA involves the FR1 region of the human Kappa light chains. Table 512 shows an analysis of 182 full-length human kappa chains for matching by the four 19-base probe sequences shown. Ninety-six percent of the sequences match one of the probes with 2 or fewer mismatches. The URE adapters shown in Table 512 are for cleavage of the sense strand of kappa chains. Thus, the adaptor sequences are the reverse complement of the germline gene sequences. The URE consists of a ten-base stem, a five base loop, the reverse complement of the stem and the complementation sequence. The loop shown here is TTGTT, but other sequences could be used. Its function is to interrupt the palindrome of the stems so that formation of a lollypop monomer is favored over dimerization. Table 512 also shows where the sense strand is cleaved.

Another example of using a URE to cleave a single-stranded DNA involves the human lambda light chain. Table 515 shows analysis of 128 human lambda light chains for matching the four 19-base probes shown. With three or fewer mismatches, 88 of 128 (69%) of the chains match one of the probes. Table 515 also shows URE adapters corresponding to these probes. Annealing these adapters to upper-strand ssDNA of lambda chains and treatment with FokI in the presence of FOKIact at a temperature at or above 45° C. will lead to specific and precise cleavage of the chains.

The conditions under which the short oligonucleotide sequences of the first method and the UREs of the second method are contacted with the single-stranded DNAs may be empirically determined. The conditions must be such that the single-stranded DNA remains in substantially single-stranded form. More particularly, the conditions must be such that the single-stranded DNA does not form loops that may interfere with its association with the oligonucleotide sequence or the URE or that may themselves provide sites for cleavage by the chosen restriction endonuclease.

The effectiveness and specificity of short oligonucleotides (first method) and UREs (second method) can be adjusted by controlling the concentrations of the URE adapters/oligonucleotides and substrate DNA, the temperature, the pH, the concentration of metal ions, the ionic strength, the concentration of chaotropes (such as urea and formamide), the concentration of the restriction endonuclease(e.g., FokI), and the time of the digestion. These conditions can be optimized with synthetic oligonucleotides having: 1) target germline gene sequences, 2) mutated target gene sequences, or 3) somewhat related non-target sequences. The goal is to cleave most of the target sequences and minimal amounts of non-targets.

In the preferred embodiment of this invention, the single-stranded DNA is maintained in substantially that form using a temperature between 45° C. to 75° C. More preferably, a temperature between 50° C. and 60° C., most preferably between 55° C. and 60° C., is used. These temperatures are employed both when contacting the DNA with the oligonucleotide or URE and when cleaving the DNA using the methods of this invention.

The two cleavage methods of this invention have several advantages. The first method allows the individual members of the family of single-stranded DNAs to be cleaved solely at one substantially conserved endonuclease recognition site. The method also does not require an endonuclease recognition site to be built in to the reverse transcription or amplification primers. Any native or synthetic site in the family can be used.

The second method has both of these advantages. In addition, the URE method allows the single-stranded DNAs to be cleaved at positions where no endonuclease recognition site naturally occurs or has been synthetically constructed.

Most importantly, both cleavage methods permit the use of 5' and 3' primers so as to maximize diversity and then cleavage to remove unwanted or deleterious sequences before cloning and display.

After cleavage of the amplified DNAs using one of the methods of this invention, the DNA is prepared for cloning. This is done by using a partially duplexed synthetic DNA adapter, whose terminal sequence is based on the specific cleavage site at which the amplified DNA has been cleaved.

The synthetic DNA is designed such that when it is ligated to the cleaved single-stranded DNA, it allows that DNA to be expressed in the correct reading frame so as to display the desired peptide, polypeptide or protein on the surface of the genetic package. Preferably, the double-stranded portion of the adapter comprises the sequence of several codons that encode the amino acid sequence characteristic of the family of peptides, polypeptides or proteins up to the cleavage site. For human heavy chains, the amino acids of the 3-23 framework are preferably used to provide the sequences required for expression of the cleaved DNA.

Preferably, the double-stranded portion of the adapter is about 12 to 100 bases in length. More preferably, about 20 to 100 bases are used. The double-standard region of the adapter also preferably contains at least one endonuclease recognition site useful for cloning the DNA into a suitable display vector (or a recipient vector used to archive the diversity). This endonuclease restriction site may be native to the germline gene sequences used to extend the DNA sequence. It may be also constructed using degenerate sequences to the native germline gene sequences. Or, it may be wholly synthetic.

The single-stranded portion of the adapter is complementary to the region of the cleavage in the single-stranded DNA. The overlap can be from about 2 bases up to about 15 bases. The longer the overlap, the more efficient the ligation is likely to be. A preferred length for the overlap is 7 to 10. This allows some mismatches in the region so that diversity in this region may be captured.

The single-stranded region or overlap of the partially duplexed adapter is advantageous because it allows DNA cleaved at the chosen site, but not other fragments to be captured. Such fragments would contaminate the library with genes encoding sequences that will not fold into proper antibodies and are likely to be non-specifically sticky.

One illustration of the use of a partially duplexed adaptor in the methods of this invention involves ligating such adaptor to a human FR3 region that has been cleaved, as described above, at 5'-ACnGT-3' using HpyCH4III, Bst4CI or TaaI.

Table 250 F.2 shows the bottom strand of the double-stranded portion of the adaptor for ligation to the cleaved bottom-strand DNA. Since the HpyCH4III-Site is so far to the right (as shown in Table 206), a sequence that includes the AflII-site as well as the XbaI site can be added. This bottom strand portion of the partially-duplexed adaptor, H43.XAExt, incorporates both XbaI and AflII-sites. The top strand of the double-stranded portion of the adaptor has neither site (due to planned mismatches in the segments opposite the XbaI and AflII-Sites of H43.XAExt), but will anneal very tightly to H43.XAExt. H43AExt contains only the AflII-site and is to be used with the top strands H43.ABr1 and H43.ABr2 (which have intentional alterations to destroy the AflII-site).

After ligation, the desired, captured DNA can be PCR amplified again, if desired, using in the preferred embodiment a primer to the downstream constant region of the antibody gene and a primer to part of the double-standard region of the adapter. The primers may also carry restriction endonuclease sites for use in cloning the amplified DNA.

After ligation, and perhaps amplification, of the partially double-stranded adapter to the single-stranded amplified DNA, the composite DNA is cleaved at chosen 5' and 3' endonuclease recognition sites.

The cleavage sites useful for cloning depend on the phage or phagemid into which the cassette will be inserted and the available sites in the antibody genes. Table 1 provides restriction endonuclease data for 75 human light chains. Table 2 shows corresponding data for 79 human heavy chains. In each Table, the endonucleases are ordered by increasing frequency of cutting. In these Tables, Nch is the number of chains cut by the enzyme and Ns is the number of sites (some chains have more than one site).

From this analysis, SfiI, NotI, AflII, ApaLI, and AscI are very suitable. SfiI and NotI are preferably used in pCES1 to insert the heavy-chain display segment. ApaLI and AscI are preferably used in pCES! to insert the light-chain display segment.

BstEII-sites occur in 97% of germ-line JH genes. In rearranged V genes, only 54/79 (68%) of heavy-chain genes contain a BstEII-Site and 7/61 of these contain two sites. Thus, 47/79 (59%) contain a single BstEII-Site. An alternative to using BstEII is to cleave via UREs at the end of JH and ligate to a synthetic oligonucleotide that encodes part of CH1.

One example of preparing a family of DNA sequences using the methods of this invention involves capturing human CDR 3 diversity. As described above, mRNAs from various autoimmune patients is reverse transcribed into lower strand cDNA. After the top strand RNA is degraded, the lower strand is immobilized and a short oligonucleotide used to cleave the cDNA upstream of CDR3. A partially duplexed synthetic DNA adapter is then annealed to the DNA and the DNA is amplified using a primer to the adapter and a primer to the constant region (after FR4). The DNA is then cleaved using BstEII (in FR4) and a restriction endonuclease appropriate to the partially double-stranded adapter (e.g., Xba I and AflII (in FR3)). The DNA is then ligated into a synthetic VH skeleton such as 3-23.

One example of preparing a single-stranded DNA that was cleaved using the URE method involves the human Kappa chain. The cleavage site in the sense strand of this chain is depicted in Table 512. The oligonucleotide kapextURE is annealed to the oligonucleotides (kaBR01UR, kaBR02UR, kaBR03UR, and kaBR04UR) to form a partially duplex DNA. This DNA is then ligated to the cleaved soluble kappa chains. The ligation product is then amplified using primers kapextUREPCR and CKForeAsc (which inserts a AscI site after the end of C kappa). This product is then cleaved with ApaLI and AscI and ligated to similarly cut recipient vector.

Another example involves the cleavage illustrated in Table 515. After cleavage, an extender (ON_LamEx133) and four bridge oligonucleotides (ON_LamB1-133, ON_LamB2-133, ON_LamB3-133, and ON_LamB4-133) are annealed to form a partially duplex DNA. That DNA is ligated to the cleaved lambda-chain sense strands. After ligation, the DNA is amplified with ON_Lam133PCR and a forward primer specific to the lambda constant domain, such as CL2ForeAsc or CL7ForeAsc (Table 130).

In human heavy chains, one can cleave almost all genes in FR4 (downstream, i.e. toward the 3' end of the sense strand, of CDR3) at a BstEII-Site that occurs at a constant position in a very large fraction of human heavy-chain V genes. One then needs a site in FR3, if only CDR3 diversity is to be captured, in FR2, if CDR2 and CDR3 diversity is wanted, or in FR1, if all the CDR diversity is wanted. These sites are preferably inserted as part of the partially double-stranded adaptor.

The preferred process of this invention is to provide recipient vectors having sites that allow cloning of either light or heavy chains. Such vectors are well known and widely used in the art. A preferred phage display vector in accordance with this invention is phage MALIA3. This displays in gene III. The sequence of the phage MALIA3 is shown in Table 120A (annotated) and Table 120B (condensed).

The DNA encoding the selected regions of the light or heavy chains can be transferred to the vectors using endonucleases that cut either light or heavy chains only very rarely. For example, light chains may be captured with ApaLI and AscI. Heavy-chain genes are preferably cloned into a recipient vector having SfiI, NcoI, XbaI, AflII, BstEII, ApaI, and NotI sites. The light chains are preferably moved into the library as ApaLI-AscI fragments. The heavy chains are preferably moved into the library as SfiI-NotI fragments.

Most preferably, the display is had on the surface of a derivative of M13 phage. The most preferred vector contains all the genes of M13, an antibiotic resistance gene, and the display cassette. The preferred vector is provided with restriction sites that allow introduction and excision of members of the diverse family of genes, as cassettes. The preferred vector is stable against rearrangement under the growth conditions used to amplify phage.

In another embodiment of this invention, the diversity captured by the methods of the present invention may be displayed in a phagemid vector (e.g., pCESI) that displays the peptide, polypeptide or protein on the III protein. Such vectors may also be used to store the diversity for subsequent display using other vectors or phage.

In another embodiment, the mode of display may be through a short linker to three possible anchor domains. One anchor domain being the final portion of M13 III ("IIIstump"), a second anchor being the full length III mature protein, and the third being the M13 VIII mature protein.

The IIIstump fragment contains enough of M13 III to assemble into phage but not the domains involved in mediating infectivity. Because the w.t. III and VIII proteins are present, the phage is unlikely to delete the antibody genes and phage that do delete these segments receive only a very small growth advantage. For each of the anchor domains, the DNA encodes the w.t. AA sequence, but differs from the w.t. DNA sequence to a very high extent. This will greatly reduce the potential for homologous recombination between the display anchor and the w.t. gene that is also present.

Most preferably, the present invention uses a complete phage carrying an antibiotic-resistance gene (such as an ampicillin-resistance gene) and the display cassette. Because the w.t. iii and viii genes are present, the w.t. proteins are also present. The display cassette is transcribed from a regulatable promoter (e.g., $P_{LacZ}$) Use of a regulatable promoter allows control of the ratio of the fusion display gene to the corresponding w.t. coat protein. This ratio determines the average number of copies of the display fusion per phage (or phagemid) particle.

Another aspect of the invention is a method of displaying peptides, polypeptides or proteins (and particularly Fabs) on filamentous phage. In the most preferred embodiment this method displays FABs and comprises:

a) obtaining a cassette capturing a diversity of segments of DNA encoding the elements:
$P_{reg}$::RBS1::SS1::VL::CL::stop::RBS2::SS2::VH::CH1::linker::anchor::stop::,
where $P_{reg}$ is a regulatable promoter, RBS1 is a first ribosome binding site, SS1 is a signal sequence operable in the host strain, VL is a member of a diverse set of light-chain variable regions, CL is a light-chain constant region, stop is one or more stop codons, RBS2 is a second ribosome binding site, SS2 is a second signal sequence operable in the host strain, VH is a member of a diverse set of heavy-chain variable regions, CH1 is an antibody heavy-chain first constant domain, linker is a sequence of amino acids of one to about 50 residues, anchor is a protein that will assemble into the filamentous phage particle and stop is a second example of one or more stop codons; and b) positioning that cassette within the phage genome to maximize the viability of the phage and to minimize the potential for deletion of the cassette or parts thereof.

The DNA encoding the anchor protein in the above preferred cassette should be designed to encode the same (or a closely related) amino acid sequence as is found in one of the coat proteins of the phage, but with a distinct DNA sequence. This is to prevent unwanted homologous recombination with the w.t. gene. In addition, the cassette should be placed in the intergenic region. The positioning and orientation of the display cassette can influence the behavior of the phage.

In one embodiment of the invention, a transcription terminator may be placed after the second stop of the display cassette above (e.g., Trp). This will reduce interaction between the display cassette and other genes in the phage antibody display vector (PADV).

In another embodiment of the methods of this invention, the phage or phagemid can display proteins other than Fab, by replacing the Fab portions indicated above, with other protein genes.

Various hosts can be used for growth of the display phage or phagemids of this invention. Such hosts are well known in the art. In the preferred embodiment, where Fabs are being displayed, the preferred host should grow at 30° C. and be RecA- (to reduce unwanted genetic recombination) and EndA- (to make recovery of RF DNA easier). It is also preferred that the host strain be easily transformed by electroporation.

XL1-Blue MRF' satisfies most of these preferences, but does not grow well at 30° C. XL1-Blue MRF' does grow slowly at 380C and thus is an acceptable host. TG-1 is also an acceptable host although it is RecA- and EncA'. XL1-Blue MRF' is more preferred for the intermediate host used to accumulate diversity prior to final construction of the library.

After display, the libraries of this invention may be screened using well known and conventionally used techniques. The selected peptides, polypeptides or proteins may then be used to treat disease. Generally, the peptides, polypeptides or proteins for use in therapy or in pharmaceutical compositions are produced by isolating the DNA encoding the desired peptide, polypeptide or protein from the member of the library selected. That DNA is then used in conventional methods to produce the peptide, polypeptides or protein it encodes in appropriate host cells, preferably mammalian host cells, e.g., CHO cells. After isolation, the peptide, polypeptide or protein is used alone or with pharmaceutically acceptable compositions in therapy to treat disease.

EXAMPLES

Example 1

Capturing Kappa Chains with BsmAI

A repertoire of human-kappa chain mRNAs was prepared by treating total or poly(A+) RNA isolated from a collection of patients having various autoimmune diseases with calf intestinal phosphatase to remove the 5'-phosphate from all molecules that have them, such as ribosomal RNA, fragmented mRNA, tRNA and genomic DNA. Full length mRNA (containing a protective 7-methyl cap structure) is unaffected. The RNA is then treated with tobacco acid pyrophosphatase to remove the cap structure from full length mRNAs leaving a 5'-monophosphate group.

Full length mRNA's were modified with an adaptor at the 5' end and then reversed transcribed and amplified using the GeneRACEh method and kit (Invitrogen). A 5' biotinylated primer complementary to the adaptor and a 3' primer complementary to a portion of the construct region were used.

Figure 3:
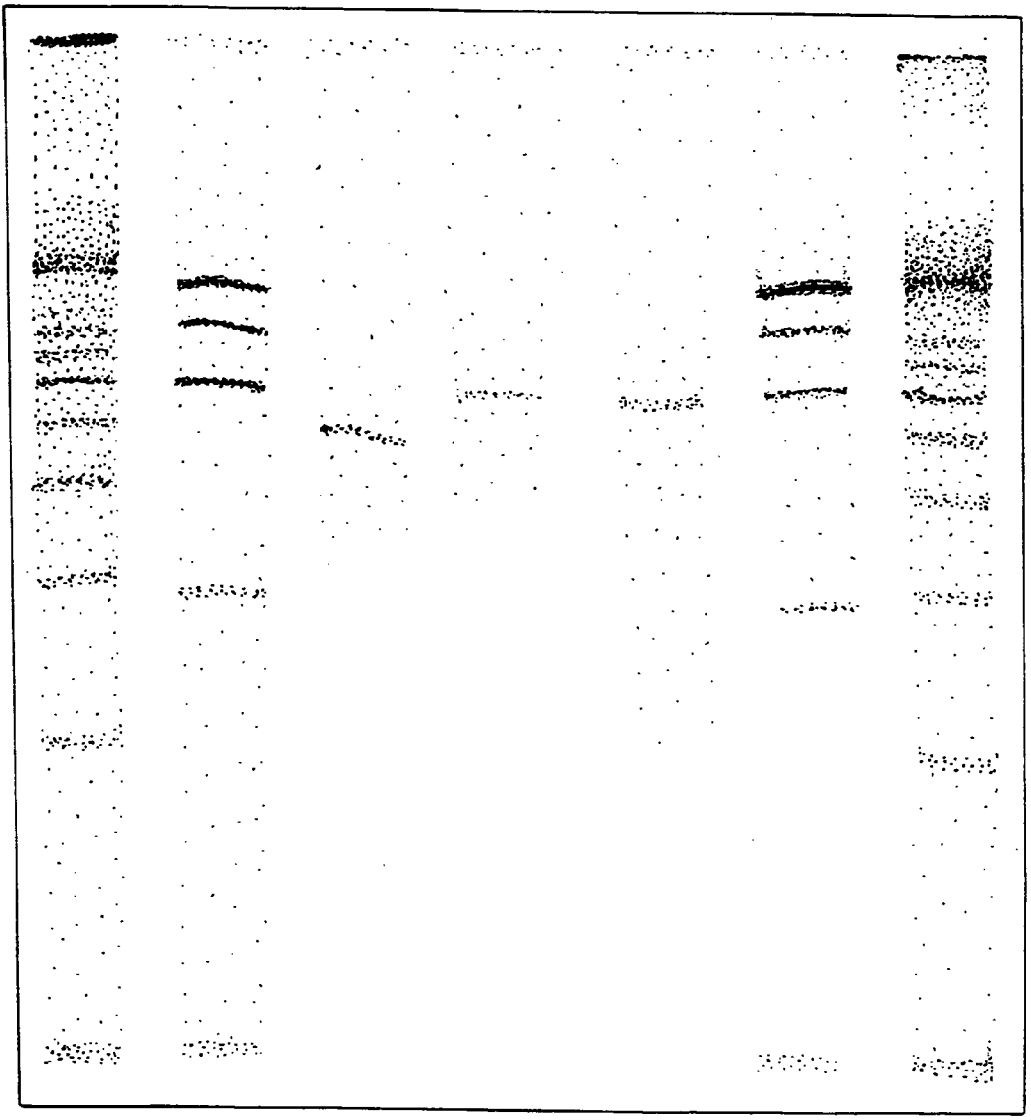
FIG. 3 depicts gel analysis of cleaved kappa DNA from Example 2.
Figure 4:
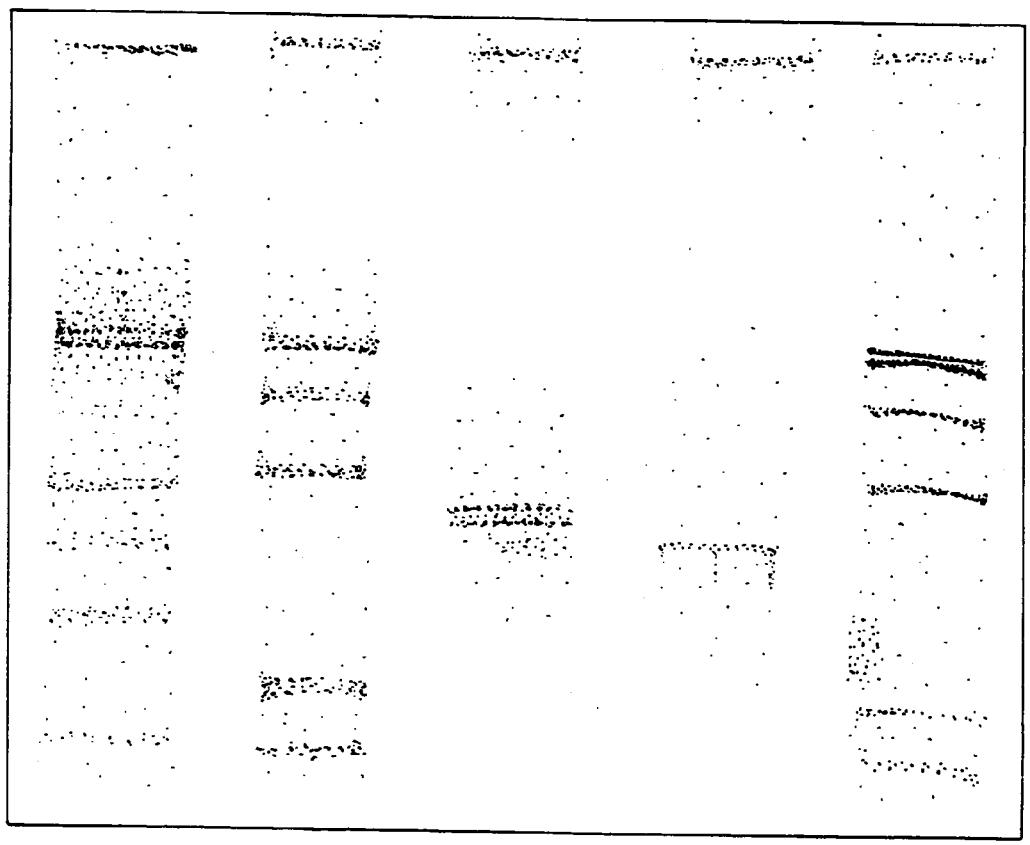
FIG. 4 depicts gel analysis of cleaved kappa DNA from Example 2.

Approximately 2 micrograms (ug) of human kappa-chain (Igkappa) gene RACE material with biotin attached to 5'-end of. upper strand was immobilized on 200 microliters (µL) of Seradyn magnetic beads. The lower strand was removed by washing the DNA with 2 aliquots 200 µL of 0.1 M NaOH (pH 13) for 3 minutes for the first aliquot followed by 30 seconds for the second aliquot. The beads were neutralized with 200 µL of 10 mM Tris (pH 7.5) 100 mM NaCl. The short oligonucleotides shown in Table 525 were added in 40 fold molar excess in 100 µL of NEB buffer 2 (50 mM NaCl, 10 mM Tris-HCl, 10 mM MgCl$_2$, 1 mM dithiothreitol pH 7.9) to the dry beads. The mixture was incubated at 95° C. for 5 minutes then cooled down to 55° C. over 30 minutes. Excess oligonucleotide was washed away with 2 washes of NEB buffer 3 (100 mM NaCl, 50 mM Tris-HCl, 10 mM MgCl$_2$, 1 mM dithiothreitol pH 7.9). Ten units of BsmAI (NEB) were added in NEB buffer 3 and incubated for 1 h at 55° C. The cleaved downstream DNA was collected and purified over a Qiagen PCR purification column (FIGS. 3 and 4).

A partially double-stranded adaptor was prepared using the oligonucleotide shown in Table 525. The adaptor was added to the single-stranded DNA in 100 fold molar excess along with 1000 units of T4 DNA ligase (NEB) and incubated overnight at 16° C. The excess oligonucleotide was removed with a Qiagen PCR purification column. The ligated material was amplified by PCR using the primers kapPCRt1 and kapfor shown in Table 525 for 10 cycles with the program shown in Table 530.

Figure 5:
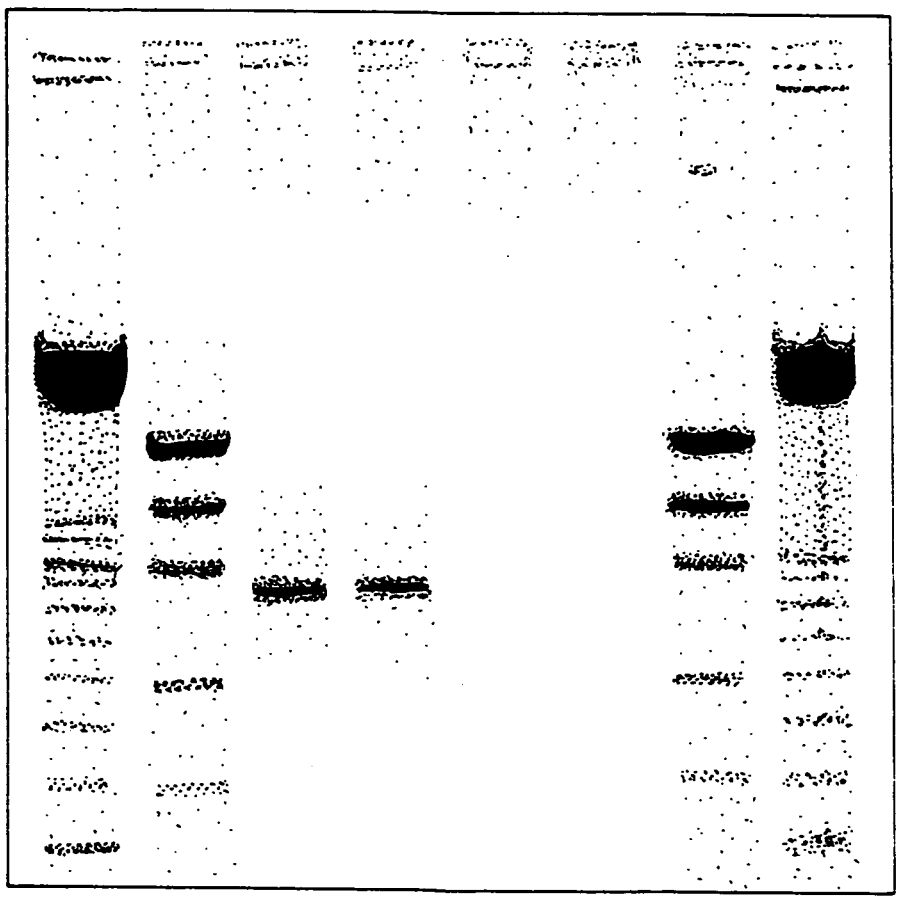
FIG. 5 depicts gel analysis of amplified kappa DNA from Example 2.
Figure 6:
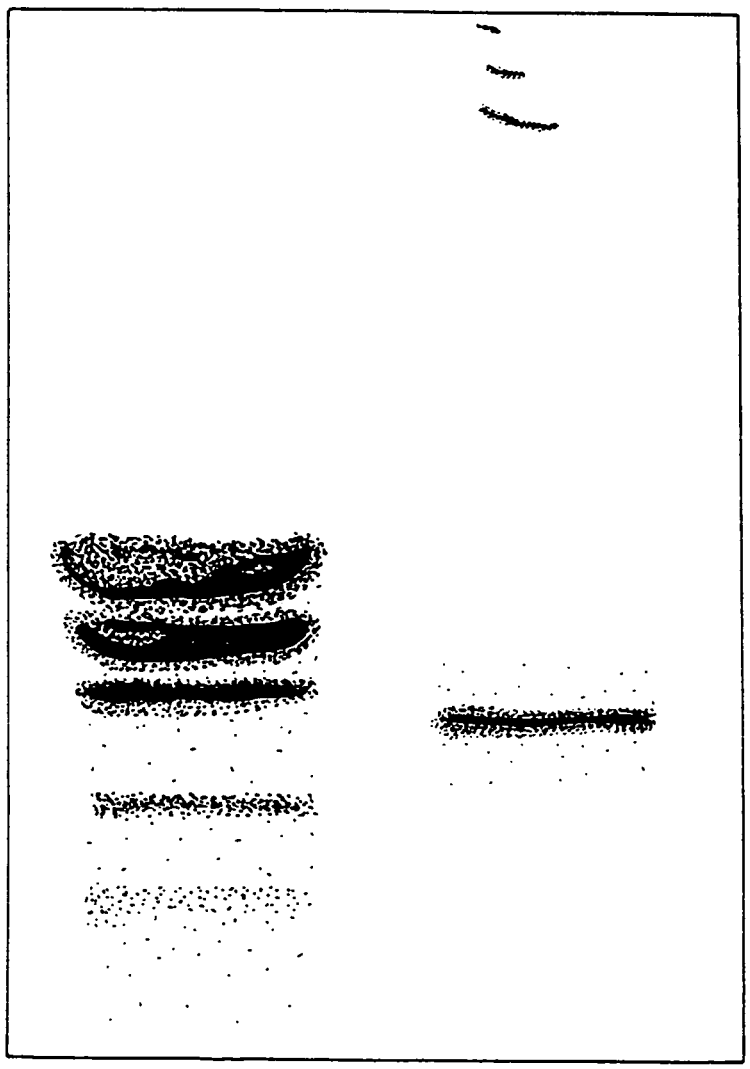
FIG. 6 depicts gel purified amplified kappa DNA from Example 2.

The soluble PCR product was run on a gel and showed a band of approximately 700 n, as expected (FIGS. 5 and 6). The DNA was cleaved with enzymes ApaLI and AscI, gel purified, and ligated to similarly cleaved vector pCES1. The presence of the correct size insert was checked by PCR in several clones as shown in FIG. 15.

Table 500 shows the DNA sequence of a kappa light chain captured by this procedure. Table 501 shows a second sequence captured by this procedure. The closest bridge sequence was complementary to the sequence 5'-agccacc-3', but the sequence captured reads 5'-Tgccacc-3', showing that some mismatch in the overlapped region is tolerated.

Example 2

Construction of Synthetic CDR1 and CDR2 Diversity in V-3-23 VH Framework

A synthetic Complementary Determinant Region (CDR) 1 and 2 diversity was constructed in the 3-23 VH framework in a two step process: first, a vector containing the 3-23 VH framework was constructed, and then, a synthetic CDR 1 and 2 was assembled and cloned into this vector.

For construction of the V3-23 framework, 8 oligos and two PCR primers (long oligonucleotides: TOPFR1A, BOTFR1B, BOTFR2, BOTFR3, F06, BOTFR4, ON-vgCl, and ON-vgC2 and primers: SFPRMET and BOTPCRPRIM, shown in Table 600) that overlap were designed based on the Genebank sequence of V323 VH. The design incorporated at least one useful restriction site in each framework region, as shown in Table 600. In Table 600, the segments that were synthesized are shown as bold, the overlapping regions are underscored, and the PCR priming regions at each end are underscored. A mixture of these 8 oligos was combined at a final concentration of 2.5 uM in a 20 ul Polymerase Chain Reaction (PCR) reaction. The PCR mixture contained 200 uM dNTPs, 2.5 mM MgCl$_2$, 0.02 U Pfu Turbo™ DNA Polymerase, 1 U Qiagen HotStart Taq DNA Polymerase, and 1× Qiagen PCR buffer. The PCR program consisted of 10 cycles of 94° C. for 30s, 55° C. for 30s, and 72° C. for 30s. The assembled V3-23 DNA sequence was then amplified, using 2.5 ul of a 10-fold dilution from the initial PCR in 100 ul PCR reaction. The PCR reaction contained 200 uM dNTPs, 2.5 mM MgCl$_2$, 0.02 U Pfu Turbo™, DNA Polymerase, 1 U Qiagen HotStart Taq DNA Polymerase, 1× Qiagen PCR Buffer and 2 outside primers (SFPRMET and BOTPCRPRIM) at a concentration of 1 uM. The PCR program consisted of 23 cycles at 94° C. for 30s, 55° C. for 30s, and 72° C. for 60s. The V3-23 VH DNA sequence was digested and cloned into pCES1 (phagemid vector) using the SfiI and BstEII restriction endonuclease sites (All restriction enzymes mentioned herein were supplied by New England BioLabs, Beverly, Mass. and used as per manufacturer's instructions).

Stuffer sequences (shown in Table 610 and Table 620) were introduced into pCES1 to replace CDR1/CDR2 sequences (900 bases between BspEI and XbaI RE sites) and CDR3 sequences (358 bases between AflII and BstEII), prior to cloning the CDR1/CDR2 diversity. The new vector is pCES5 and its sequence is given in Table 620. Having stuffers in place of the CDRs avoids the risk that a parental sequence would be over-represented in the library. The CDR1-2 stuffer contains restriction sites for BglII, Bsu36I, BclI, XcmI, MluI, PvuII, HpaI, and HincII, the underscored sites being unique within the vector pCES5. The stuffer that replaces CDR3 contains the unique restriction endonuclease site RsrII. The stuffer sequences are fragments from the penicillase gene of *E. coli*.

For the construction of the CDR1 and CDR2 diversity, 4 overlapping oligonucleotides (ON-vgCl, ON_Br12, ON_CD2Xba, and ON-vgC2, shown in Table 600 and Table 630) encoding CDR1/2, plus flanking regions, were designed. A mix of these 4 oligos was combined at a final concentration of 2.5 uM in a 40 ul PCR reaction. Two of the 4 oligos contained variegated sequences positioned at the CDR1 and the CDR2. The PCR mixture contained 200 uM dNTPs, 2.5 U Pwo DNA Polymerase (Roche), and 1× Pwo PCR buffer with 2 mM MgSO$_4$. The PCR program consisted of 10 cycles at 94° C. for 30s, 60° C. for 30s, and 72° C. for 60s. This assembled CDR1/2 DNA sequence was amplified, using 2.5 ul of the mixture in 100 ul PCR reaction. The PCR reaction contained 200 uM dNTPs, 2.5 U Pwo DNA Polymerase, 1× Pwo PCR Buffer with 2 mM MgSO$_4$ and 2 outside primers at a concentration of 1 uM. The PCR program consisted of 10 cycles at 94° C. for 30s, 60° C. for 30s, and 72° C. for 60s. These variegated sequences were digested and cloned into the V3-23 framework in place of the CDR1/2 stuffer.

We obtained approximately 7×10$^7$ independent transformants. Into this diversity, we can clone CDR3 diversity either from donor populations or from synthetic DNA.

Table 1 discloses SEQ ID NOS: 429-444, respectively, in order of appearance.

Table 2 discloses SEQ ID NOS 429, 442, 432, 441, 438-439, 433, 437, 431, 434, 436, 430, 435, 440 and 443-444, respectively, in order of appearance.

Table 5 discloses SEQ ID NOS: 15-24, 1-8, 15-16 and 9-10, respectively, in order of appearance.

Table 130 discloses SEQ ID NOS: 34-41, respectively, in order of appearance.

Table 195 discloses SEQ ID NOS: 42-92, respectively, in order of appearance.

Table 250 discloses SEQ ID NOS 93-110 and 112-177, respectively, in order of appearance.

Table 510 discloses SEQ ID NOS: 178-182, respectively, in order of appearance.

Table 600 discloses SEQ ID NOS: 183-191, residues 1 to 23 of SEQ ID NO: 191 and 192-193, respectively, in order of appearance.

Table 800 discloses SEQ ID NOS: 445-452, 437, 453-469, 467 and 470-477, respectively, in order of appearance.

Table 120 discloses SEQ ID NOS 194, 111 and 195-200, respectively in order of appearance.

Table 120B discloses SEQ ID NO: 503.

Table 200 discloses SEQ ID NOS: 478-481 and 435, respectively, in order of appearance.

Table 206 discloses SEQ ID NOS: 202, 435, 201, 203, and 482, respectively, in order of appearance.

Table 217 discloses SEQ ID NOS: 204-254, respectively, in order of appearance.

Table 220 discloses SEQ ID NOS: 483 and 481, respectively, in order of appearance.

Table 255A discloses SEQ ID NOS: 255-263, 255-263 and 255-263, respectively, in order of appearance. Table 255B discloses SEQ ID NOS: 264-277, 264-277 and 264-277, respectively, in order of appearance. Table 255C discloses SEQ ID NOS: 278-301 and 278-301, respectively, in order of appearance. Table 255D discloses SEQ ID NOS: 278-280, 291-292, 299-300, 161, 278-280, 291-292, 299-300 and 301, respectively, in order of appearance.

Table 300 discloses SEQ ID NOS: 302 and 360-398, respectively, in order of appearance.

Table 400 discloses SEQ ID NOS: 303, and 399-428, respectively, in order of appearance.

Table 405 discloses SEQ ID NOS: 484, 480, 478 and 485, respectively, in order of appearance.

Table 500 discloses SEQ ID NOS: 305 and 304, respectively, in order of appearance.

Table 501 discloses SEQ ID NOS 307, 306 and 502, respectively, in order of appearance.

Table 508 discloses residues 1-20 of SEQ ID NOS: 308-312 respectively, residues 1-20 of SEQ ID NOS: 308-312 respectively, SEQ ID NOS: 308-312, residues 21-45 of SEQ ID NOS: 308-312, SEQ ID NOS: 313-316, respectively, in order of appearance.

Table 512 discloses SEQ ID NOS: 486-489, 317-320, 486-489 and 321-326, respectively, in order of appearance.

Table 515 discloses SEQ ID NOS: 490-493, 327-330, 490-493 and 331-336, respectively, in order of appearance.

Table 525 discloses SEQ ID NOS: 337-351, respectively, in order of appearance.

Table 610 discloses SEQ ID NO: 352.

Table 620 discloses SEQ ID NOS 438, 433, 494, 504, 495-496, 437, 497, 441, 440, 439, 439, 439, 434, 498, 485, 429, 442, 499, 436, 443, 456, 500, 430, 354, 353 and 355-359, respectively, in order of appearance.

Table 630 discloses SEQ ID NOS: 11-14, respectively, in order of appearance.

It will be understood that the foregoing is only illustrative of the principles of this invention and that various modifications can be made by those skilled in the art without departing from the scope of and sprit of the invention.

TABLE 1

| Cleavage of 75 human light chains. | | | | |
|---|---|---|---|---|
| Enzyme | Recognition* | Nch | Ns | Planned location of site |
| AfeI | AGCgct | 0 | 0 | |
| AflII | Cttaag | 0 | 0 | HC FR3 |
| AgeI | Accggt | 0 | 0 | |
| AscI | GGcgcgcc | 0 | 0 | After LC |
| BglII | Agatct | 0 | 0 | |
| BsiWI | Cgtacg | 0 | 0 | |
| BspDI | ATcgat | 0 | 0 | |
| BssHII | Gcgcgc | 0 | 0 | |
| BstBI | TTcgaa | 0 | 0 | |
| DraIII | CACNNNgtg | 0 | 0 | |
| EagI | Cggccg | 0 | 0 | |
| FseI | GGCCGGcc | 0 | 0 | |
| FspI | TGCgca | 0 | 0 | |
| HpaI | GTTaac | 0 | 0 | |
| MfeI | Caattg | 0 | 0 | HC FR1 |
| MluI | Acgcgt | 0 | 0 | |
| NcoI | Ccatgg | 0 | 0 | Heavy chain signal |
| NheI | Gctagc | 0 | 0 | HC/anchor linker |
| NotI | GCggccgc | 0 | 0 | In linker after HC |
| NruI | TCGcga | 0 | 0 | |
| PacI | TTAATtaa | 0 | 0 | |
| PmeI | GTTTaaac | 0 | 0 | |
| PmlI | CACgtg | 0 | 0 | |
| PvuI | CGATcg | 0 | 0 | |
| SacII | CCGCgg | 0 | 0 | |
| SalI | Gtcgac | 0 | 0 | |
| SfiI | GGCCNNNNnggcc | 0 | 0 | Heavy Chain signal |
| SgfI | GCGATcgc | 0 | 0 | |
| SnaBI | TACgta | 0 | 0 | |
| StuI | AGGcct | 0 | 0 | |
| XbaI | Tctaga | 0 | 0 | HC FR3 |
| AatII | GACGTc | 1 | 1 | |
| AclI | AAcgtt | 1 | 1 | |
| AseI | ATtaat | 1 | 1 | |
| BsmI | GAATGCN | 1 | 1 | |
| BspEI | Tccgga | 1 | 1 | HC FR1 |
| BstXI | CCANNNNntgg | 1 | 1 | HC FR2 |
| DrdI | GACNNNNnngtc | 1 | 1 | |
| HindIII | Aagctt | 1 | 1 | |
| PciI | Acatgt | 1 | 1 | |
| SapI | gaagagc | 1 | 1 | |

TABLE 1-continued

Cleavage of 75 human light chains.

| Enzyme | Recognition* | Nch | Ns | Planned location of site |
|---|---|---|---|---|
| ScaI | AGTact | 1 | 1 | |
| SexAI | Accwggt | 1 | 1 | |
| SpeI | Actagt | 1 | 1 | |
| TliI | Ctcgag | 1 | 1 | |
| XhoI | Ctcgag | 1 | 1 | |
| BcgI | cgannnnnntgc | 2 | 2 | |
| BlpI | GCtnagc | 2 | 2 | |
| BssSI | Ctcgtg | 2 | 2 | |
| BstAPI | GCANNNNntgc | 2 | 2 | |
| EspI | GCtnagc | 2 | 2 | |
| KasI | Ggcgcc | 2 | 2 | |
| PflMI | CCANNNNntgg | 2 | 2 | |
| XmnI | GAANNnnttc | 2 | 2 | |
| ApaLI | Gtgcac | 3 | 3 | LC signal seq |
| NaeI | GCCggc | 3 | 3 | |
| NgoMI | Gccggc | 3 | 3 | |
| PvuII | CAGctg | 3 | 3 | |
| RsrII | CGgwccg | 3 | 3 | |
| BsrBI | GAGcgg | 4 | 4 | |
| BsrDI | GCAATGNNn | 4 | 4 | |
| BstZ17I | GTAtac | 4 | 4 | |
| EcoRI | Gaattc | 4 | 4 | |
| SphI | GCATGc | 4 | 4 | |
| SspI | AATatt | 4 | 4 | |
| AccI | GTmkac | 5 | 5 | |
| BclI | Tgatca | 5 | 5 | |
| BsmBI | Nnnnnngagacg | 5 | 5 | |
| BsrGI | Tgtaca | 5 | 5 | |
| DraI | TTTaaa | 6 | 6 | |
| NdeI | CAtatg | 6 | 6 | HC FR4 |
| SwaI | ATTTaaat | 6 | 6 | |
| BamHI | Ggatcc | 7 | 7 | |
| SacI | GAGCTc | 7 | 7 | |
| BciVI | GTATCCNNNNNN | 8 | 8 | |
| BsaBI | GATNNnnatc | 8 | 8 | |
| NsiI | ATGCAt | 8 | 8 | |
| Bsp120I | Gggccc | 9 | 9 | CH1 |
| ApaI | GGGCCc | 9 | 9 | CH1 |
| PspOOMI | Gggccc | 9 | 9 | |
| BspHI | Tcatga | 9 | 11 | |
| EcoRV | GATatc | 9 | 9 | |
| AhdI | GACNNNnngtc | 11 | 11 | |
| BbsI | GAAGAC | 11 | 14 | |
| PsiI | TTAtaa | 12 | 12 | |
| BsaI | GGTCTCNnnnn | 13 | 15 | |
| XmaI | Cccggg | 13 | 14 | |
| AvaI | Cycgrg | 14 | 16 | |
| BglI | GCCNNNNnggc | 14 | 17 | |
| AlwNI | CAGNNNctg | 16 | 16 | |
| BspMI | ACCTGC | 17 | 19 | |
| XcmI | CCANNNNNnnnntgg | 17 | 26 | |
| BstEII | Ggtnacc | 19 | 22 | HC FR4 |
| Sse8387I | CCTGCAgg | 20 | 20 | |
| AvrII | Cctagg | 22 | 22 | |
| HincII | GTYrac | 22 | 22 | |
| BsgI | GTGCAG | 27 | 29 | |
| MscI | TGGcca | 30 | 34 | |
| BseRI | NNnnnnnnnnctcctc | 32 | 35 | |
| Bsu36I | CCtnagg | 35 | 37 | |
| PstI | CTGCAg | 35 | 40 | |
| EciI | nnnnnnnnntccgcc | 38 | 40 | |
| PpuMI | RGgwccy | 41 | 50 | |
| StyI | Ccwwgg | 44 | 73 | |
| EcoO109I | RGgnccy | 46 | 70 | |
| Acc65I | Ggtacc | 50 | 51 | |
| KpnI | GGTACc | 50 | 51 | |
| BpmI | ctccag | 53 | 82 | |
| AvaII | Ggwcc | 71 | 124 | |

*cleavage occurs in the top strand after the last upper-case base. For REs that cut palindromic sequences, the lower strand is cut at the symmetrical site.

TABLE 2

Cleavage of 79 human heavy chains

| Enzyme | Recognition | Nch | Ns | Planned location of site |
|---|---|---|---|---|
| AfeI | AGCgct | 0 | 0 | |
| AflII | Cttaag | 0 | 0 | HC FR3 |
| AscI | GGcgcgcc | 0 | 0 | After LC |
| BsiWI | Cgtacg | 0 | 0 | |
| BspDI | ATcgat | 0 | 0 | |
| BssHII | Gcgcgc | 0 | 0 | |
| FseI | GGCCGGcc | 0 | 0 | |
| HpaI | GTTaac | 0 | 0 | |
| NheI | Gctagc | 0 | 0 | HC Linker |
| NotI | GCggccgc | 0 | 0 | In linker, HC/anchor |
| NruI | TCGcga | 0 | 0 | |
| NsiI | ATGCAt | 0 | 0 | |
| PacI | TTAATtaa | 0 | 0 | |
| PciI | Acatgt | 0 | 0 | |
| PmeI | GTTTaaac | 0 | 0 | |
| PvuI | CGATcg | 0 | 0 | |
| RsrII | CGgwccg | 0 | 0 | |
| SapI | gaagagc | 0 | 0 | |
| SfiI | GGCCNNNNnggcc | 0 | 0 | HC signal seq |
| SgfI | GCGATcgc | 0 | 0 | |
| SwaI | ATTTaaat | 0 | 0 | |
| AclI | AAcgtt | 1 | 1 | |
| AgeI | Accggt | 1 | 1 | |
| AseI | ATtaat | 1 | 1 | |
| AvrII | Cctagg | 1 | 1 | |
| BsmI | GAATGCN | 1 | 1 | |
| BsrBI | GAGcgg | 1 | 1 | |
| BsrDI | GCAATGNNn | 1 | 1 | |
| DraI | TTTaaa | 1 | 1 | |
| FspI | TGCgca | 1 | 1 | |
| HindIII | Aagctt | 1 | 1 | |
| MfeI | Caattg | 1 | 1 | HC FR1 |
| NaeI | GCCggc | 1 | 1 | |
| NgoMI | Gccggc | 1 | 1 | |
| SpeI | Actagt | 1 | 1 | |
| Acc65I | Ggtacc | 2 | 2 | |
| BstBI | TTcgaa | 2 | 2 | |
| KpnI | GGTACc | 2 | 2 | |
| MluI | Acgcgt | 2 | 2 | |
| NcoI | Ccatgg | 2 | 2 | In HC signal seq |
| NdeI | CAtatg | 2 | 2 | HC FR4 |
| PmlI | CACgtg | 2 | 2 | |
| XcmI | CCANNNNNnnnntgg | 2 | 2 | |
| BcgI | cgannnnnntgc | 3 | 3 | |
| BclI | Tgatca | 3 | 3 | |
| BglI | GCCNNNNnggc | 3 | 3 | |
| BsaBI | GATNNnnatc | 3 | 3 | |
| BsrGI | Tgtaca | 3 | 3 | |
| SnaBI | TACgta | 3 | 3 | |
| Sse8387I | CCTGCAgg | 3 | 3 | |
| ApaLI | Gtgcac | 4 | 4 | LC Signal/FR1 |
| BspHI | Tcatga | 4 | 4 | |
| BssSI | Ctcgtg | 4 | 4 | |
| PsiI | TTAtaa | 4 | 5 | |
| SphI | GCATGc | 4 | 4 | |
| AhdI | GACNNNnngtc | 5 | 5 | |
| BspEI | Tccgga | 5 | 5 | HC FR1 |
| MscI | TGGcca | 5 | 5 | |
| SacI | GAGCTc | 5 | 5 | |
| ScaI | AGTact | 5 | 5 | |
| SexAI | Accwggt | 5 | 6 | |
| SspI | AATatt | 5 | 5 | |
| TliI | Ctcgag | 5 | 5 | |
| XhoI | Ctcgag | 5 | 5 | |
| BbsI | GAAGAC | 7 | 8 | |
| BstAPI | GCANNNNntgc | 7 | 8 | |
| BstZ17I | GTAtac | 7 | 7 | |
| EcoRV | GATatc | 7 | 7 | |
| EcoRI | Gaattc | 8 | 8 | |
| BlpI | GCtnagc | 9 | 9 | |
| Bsu36I | CCtnagg | 9 | 9 | |
| DraIII | CACNNNgtg | 9 | 9 | |
| EspI | GCtnagc | 9 | 9 | |
| StuI | AGGcct | 9 | 13 | |
| XbaI | Tctaga | 9 | 9 | HC FR3 |

TABLE 2-continued

Cleavage of 79 human heavy chains

| Enzyme | Recognition | Nch | Ns | Planned location of site |
|---|---|---|---|---|
| Bsp120I | Gggccc | 10 | 11 | CH1 |
| ApaI | GGGCCc | 10 | 11 | CH1 |
| PspOOMI | Gggccc | 10 | 11 | |
| BciVI | GTATCCNNNNNN | 11 | 11 | |
| SalI | Gtcgac | 11 | 12 | |
| DrdI | GACNNNNnngtc | 12 | 12 | |
| KasI | Ggcgcc | 12 | 12 | |
| XmaI | Cccggg | 12 | 14 | |
| BglII | Agatct | 14 | 14 | |
| HincII | GTYrac | 16 | 18 | |
| BamHI | Ggatcc | 17 | 17 | |
| PflMI | CCANNNNntgg | 17 | 18 | |
| BsmBI | Nnnnnngagacg | 18 | 21 | |
| BstXI | CCANNNNNntgg | 18 | 19 | HC FR2 |
| XmnI | GAANNnnttc | 18 | 18 | |
| SacII | CCGCgg | 19 | 19 | |
| PstI | CTGCAg | 20 | 24 | |
| PvuII | CAGctg | 20 | 22 | |
| AvaI | Cycgrg | 21 | 24 | |
| EagI | Cggccg | 21 | 22 | |
| AatII | GACGTc | 22 | 22 | |
| BspMI | ACCTGC | 27 | 33 | |
| AccI | GTmkac | 30 | 43 | |
| StyI | Ccwwgg | 36 | 49 | |
| AlwNI | CAGNNNctg | 38 | 44 | |
| BsaI | GGTCTCNnnnn | 38 | 44 | |
| PpuMI | RGgwccy | 43 | 46 | |
| BsgI | GTGCAG | 44 | 54 | |
| BseRI | NNnnnnnnnnctcctc | 48 | 60 | |
| EciI | nnnnnnnnntccgcc | 52 | 57 | |
| BstEII | Ggtnacc | 54 | 61 | HC Fr4, 47/79 have one |
| EcoO109I | RGgnccy | 54 | 86 | |
| BpmI | ctccag | 60 | 121 | |
| AvaII | Ggwcc | 71 | 140 | |

TABLE 5

Use of FokI as "Universal Restriction Enzyme"

FokI - for dsDNA, | represent site of cleavage

```
                      site of cleavage
         5'-cacGGATGtg--nnnnnnn|nnnnnnn-3' (SEQ ID NO:15)
         3'-gtgCCTACac--nnnnnnnnnnn|nnn-5' (SEQ ID NO:16)
                       RECOG
                       NITion of FokI
```

Case I

```
         5'-...gtg|tatt-actgtgc..substrate....-3' (SEQ ID NO:17)
         3'-cac-ataa|tgacacg ┐
                             gtGTAGGcac\
                            5'- caCATCCgtg/
```

Case II

```
                   5'-...gtgtatt|agac-tgc..substrate....-3' (SEQ ID NO:19)
                       ┌ cacataa-tctg|acg-5'
         /gtgCCTACac
         \cacGGATGtg-3' (SEQ ID NO:20)
```

Case III (Case I rotated 180 degrees)

```
         /gtgCCTACac-5'
         \cacGGATGtg ┐
                      gtgtctt|acag-tcc-3' Adapter (SEQ ID NO:21)
              3'-...cacagaa-tgtc|agg..substrate....-5' (SEQ ID NO:22)
```

Case IV (Case II rotated 180 degrees)

```
                     3'- gtGTAGGcac\  (SEQ ID NO:23)
                      ┌ caCATCCgtg/
         5'-gag|tctc-actgagc
         Substrate 3'-...ctc-agag|tgactcg...-5' (SEQ ID NO:24)
```

Improved FokI adapters

FokI - for dsDNA, | represents sites of cleavage

Case II

Stem 11, loop 5, stem 11, recognition 17

```
         5'-...catgtg|tatt-actgtgc..Substrate....-3'
         3'- gtacac-ataa|tgacacg ┐            ┌T┐
                                  gtGTAGGcacG    T
                                 5'- caCATCCgtgc   C
                                                └TT┘
```

Case II

Stem 10, loop 5, stem 10, recognition 18

```
                          5'-...gtgtatt|agac-tgctgcc..Substrate....-3'
                   ┌T┐     ┌ cacataa-tctg|acgacg-5'
                   T     gtgCCTACac
                   C     cacGGATGtg-3'
                   └TT┘
```

Case III (Case I rotated 180 degrees)

Stem 11, loop 5, stem 11, recognition 20

```
         ┌T┐
         T    TgtgCCTACac-5'
         G    AcacGGATGtg ┐
         └TT┘              gtgtctt|acag-tccattctg-3' Adapter
                      3'-...cacagaa-tgtc|aggtaagac..substrate....-5'
```

Case IV (Case II rotated 180 degrees)

Stem 11, loop 4, stem 11, recognition 17

```
                                             ┌T┐
                     3'- gtGTAGGcacc            T
                     ┌ caCATCCgtgg
         5'-atcgag|tctc-actgagc               └ T ┘
         Substrate 3'-...tagctc-agag|tgactcg...-5'
```

BseRI

| sites of cleavage

```
         5'-cacGAGGAGnnnnnnnnnnn|nnnnn-3'
         3'-gtgctcctcnnnnnnnn|nnnnnnn-5'
             RECOG
             NITion of BseRI
```

Stem 11, loop 5, recognition 19

```
                  3'-.......gaacat|cg-ttaagccagta.....5'
         ┌T-T┐             cttgta-gc|aattcggtcat-3'
         C       GCTGAGGAGTC ┘
         T       cagactcctcag-5'      An adapter for BseRI to cleave the
         └T ──┘                        substrate above.
```

TABLE 8

Matches to URE FR3 adapters in 79 human HC.
A. List of Heavy-chains genes sampled

| | | | | |
|---|---|---|---|---|
| AF008566 | af103343 | HSA235676 | HSU92452 | HSZ93860 |
| AF035043 | AF103367 | HSA235675 | HSU94412 | HSZ93863 |
| AF103026 | AF103368 | HSA235674 | HSU94415 | MCOMFRAA |
| af103033 | AF103369 | HSA235673 | HSU94416 | MCOMFRVA |
| AF103061 | AF103370 | HSA240559 | HSU94417 | S82745 |
| Af103072 | af103371 | HSCB201 | HSU94418 | S82764 |
| af103078 | AF103372 | HSIGGVHC | HSU96389 | S83240 |

TABLE 8-continued

Matches to URE FR3 adapters in 79 human HC.
A. List of Heavy-chains genes sampled

| | | | | |
|---|---|---|---|---|
| AF103099 | AF158381 | HSU44791 | HSU96391 | SABVH369 |
| AF103102 | E05213 | HSU44793 | HSU96392 | SADEIGVH |
| AF103103 | E05886 | HSU82771 | HSU96395 | SAH2IGVH |
| AF103174 | E05887 | HSU82949 | HSZ93849 | SDA3IGVH |
| AF103186 | HSA235661 | HSU82950 | HSZ93850 | SIGVHTTD |
| af103187 | HSA235664 | HSU82952 | HSZ93851 | SUK4IGVH |
| AF103195 | HSA235660 | HSU82961 | HSZ93853 | |
| af103277 | HSA235659 | HSU86522 | HSZ93855 | |
| af103286 | HSA235678 | HSU86523 | HSZ93857 | |
| AF103309 | HSA235677 | | | |

TABLE 8 B

Testing all distinct GLGs from bases 89.1 to 93.2 of the heavy variable domain

| Id | Nb | 0 | 1 | 2 | 3 | 4 | | SEQ ID NO: |
|---|---|---|---|---|---|---|---|---|
| 1 | 38 | 15 | 11 | 10 | 0 | 2 | Seq1 gtgtattactgtgc | 25 |
| 2 | 19 | 7 | 6 | 4 | 2 | 0 | Seq2 gtAtattactgtgc | 26 |
| 3 | 1 | 0 | 0 | 1 | 0 | 0 | Seq3 gtgtattactgtAA | 27 |
| 4 | 7 | 1 | 5 | 1 | 0 | 0 | Seq4 gtgtattactgtAc | 28 |
| 5 | 0 | 0 | 0 | 0 | 0 | 0 | Seq5 Ttgtattactgtgc | 29 |
| 6 | 0 | 0 | 0 | 0 | 0 | 0 | Seq6 TtgtatCactgtgc | 30 |
| 7 | 3 | 1 | 0 | 1 | 1 | 0 | Seq7 ACAtattactgtgc | 31 |
| 8 | 2 | 0 | 2 | 0 | 0 | 0 | Seq8 ACgtattactgtgc | 32 |
| 9 | 9 | 2 | 2 | 4 | 1 | 0 | Seq9 ATgtattactgtac | 33 |
| Group | | 26 | 26 | 21 | 4 | 2 | | |
| Cumulative | | 26 | 52 | 73 | 77 | 79 | | |

TABLE 8C

Most important URE recognition seqs in FR3 Heavy

1 VHSzy1 GTGtattactgtgc (ON_SHC103) (SEQ ID NO: 25)
2 VHSzy2 GTAtattactgtgc (ON_SHC323) (SEQ ID NO: 26)
3 VHSzy4 GTGtattactgtac (ON_SHC349) (SEQ ID NO: 28)
4 VHSzy9 ATGtattactgtgc (ON_SHC5a) (SEQ ID NO: 33)

TABLE 8D testing 79 human HC V genes with four probes

Number of sequences.......... 79
Number of bases.............. 29143

Number of mismatches

| Id | Best | 0 | 1 | 2 | 3 | 4 | 5 | | |
|---|---|---|---|---|---|---|---|---|---|
| 1 | 39 | 15 | 11 | 10 | 1 | 2 | 0 | Seq1 gtgtattactgtgc | (SEQ ID NO: 25) |
| 2 | 22 | 7 | 6 | 5 | 3 | 0 | 1 | Seq2 gtAtattactgtgc | (SEQ ID NO: 26) |
| 3 | 7 | 1 | 5 | 1 | 0 | 0 | 0 | Seq4 gtgtattactgtAc | (SEQ ID NO: 28) |
| 4 | 11 | 2 | 4 | 4 | 1 | 0 | 0 | Seq9 ATatattactgtgc | (SEQ ID NO: 33) |
| Group | | 25 | 26 | 20 | 5 | 2 | | | |
| Cumulative | | 25 | 51 | 71 | 76 | 78 | | | |

One sequence has five mismatches with sequences 2, 4, and 9; it is scored as best for 2.
Id is the number of the adapter.
Best is the number of sequence for which the identified adapter was the best available.
The rest of the table shows how well the sequences match the adapters. For example, there are 11 sequences that match VHSzy1(Id = 1) with 2 mismatches and are worse for all other adapters. In this sample, 90% come within 2 bases of one of the four adapters.

TABLE 130

PCR primers for amplification of human Ab genes

| | |
|---|---|
| (HuIgMFOR) | 5'-tgg aag agg cac gtt ctt ttc ttt-3' |
| !(HuIgMFOREtop) | 5'-aaa gaa aag aac gtg cct ctt cca-3' = reverse complement |
| (HuCkFOR) | 5'-aca ctc tcc cct gtt gaa gct ctt-3' |
| (NuCL2FOR) | 5'-tga aca ttc tgt agg ggc cac tg-3' |
| (HuCL7FOR) | 5'-aga gca ttc tgc agg ggc cac tg-3' |
| !Kappa | |
| (CKForeAsc) | 5'-acc gcc tcc acc ggg cgc gcc tta tta aca ctc tcc cct gtt-gaa gct ctt-3' |
| (CL2ForeAsc) | 5'-acc gcc tcc acc ggg cgc gcc tta tta tga aca ttc tgt-agg ggc cac tg-3' |
| (CL7ForeAsc) | 5'-acc gcc tcc acc ggg cgc gcc tta tta aga gca ttc tgc-agg ggc cac tg-3' |

TABLE 195

Human GLG FR3 sequences

! VH1
! 66 67 68 69 70 71 72 73 74 75 76 77 78 79 80 agg gtc acc atg acc agg gac acg tcc atc agc aca gcc tac atg

! 81 82 82a 82b 82c 83 84 85 86 87 88 89 90 91 92 gag ctg agc agg ctg aga tct gac gac acg gcc gtg tat tac tgt

TABLE 195-continued

Human GLG FR3 sequences

! 93 94 95 gcg aga ga ! 1-02# 1 aga gtc acc att acc agg gac aca tcc gcg agc aca
gcc tac atg gag ctg agc agc ctg aga tct gaa gac acg gct gtg
tat tac tgt gcg aga ga ! 1-03# 2 aga gtc acc atg acc agg aac acc tcc ata agc aca
gcc tac atg gag ctg agc agc ctg aga tct gag gac acg gcc gtg
tat tac tgt gcg aga gg ! 1-08# 3 aga gtc acc atg acc aca gac aca tcc acg agc aca
gcc tac atg gag ctg agg agc ctg aga tct gac gac acg gcc gtg
tat tac tgt gcg aga ga ! 1-18# 4 aga gtc acc atg acc gag gac aca tct aca gac aca
gcc tac atg gag ctg agc agc ctg aga tct gag gac acg gcc gtg
tat tac tgt gca aca ga ! 1-24# 5 aga gtc acc att acc agg gac agg tct atg agc aca
gcc tac atg gag ctg agc agc ctg aga tct gag gac aca gcc atg
tat tac tgt gca aga ta ! 1-45# 6 aga gtc acc atg acc agg gac acg tcc acg agc aca
gtc tac atg gag ctg agc agc ctg aga tct gag gac acg gcc gtg
tat tac tgt gcg aga ga ! 1-46# 7 aga gtc acc att acc agg gac atg tcc aca agc aca
gcc tac atg gag ctg agc agc ctg aga tcc gag gac acg gcc gtg
tat tac tgt gcg gca ga ! 1-58# 8 aga gtc acg att acc gcg gac gaa tcc acg agc aca
gcc tac atg gag ctg agc agc ctg aga tct gag gac acg gcc gtg
tat tac tgt gcg aga ga ! 1-69# 9 aga gtc acg att acc gcg gac aaa tcc acg agc aca
gcc tac atg gag ctg agc agc ctg aga tct gag gac acg gcc gtg
tat tac tgt gcg aga ga ! 1-e# 10 aga gtc acc ata acc gcg gac acg tct aca gac aca
gcc tac atg

TABLE 195-continued

Human GLG FR3 sequences gag ctg agc agc ctg aga tct gag gac acg gcc gtg
tat tac tgt gca aca ga ! 1-f# 11

! VH2
agg ctc acc atc acc aag gac acc tcc aaa aac cag
gtg gtc ctt aca atg acc aac atg gac cct gtg aca gcc aca
tat tac tgt gca cac aga c ! 2-05# 12 agg ctc acc atc tcc aag gac acc tcc aaa agc cag
gtg gtc ctt acc atg acc aac atg gac cct gtg aca gcc aca
tat tac tgt gca cgg ata c ! 2-26# 13 agg ctc acc atc tcc aag gac acc tcc aaa aac cag
gtg gtc ctt aca atg acc aac atg gac cct gtg aca gcc acg
tat tac tgt gca cgg ata c ! 2-70# 14

! VH3
cga ttc acc atc tcc aga gac aac gcc aag aac tca
ctg tat ctg caa atg aac agc ctg aga gcc gag gac acg gct gtg
tat tac tgt gcg aga ga ! 3-07# 15 cga ttc acc atc tcc aga gac aac gcc aag aac tcc
ctg tat ctg caa atg aac agt ctg aga gct gag gac acg gcc ttg
tat tac tgt gca aaa gat a ! 3-09# 16 cga ttc acc atc tcc agg gac aac gcc aag aac tca
ctg tat ctg caa atg aac agc ctg aga gcc gag gac acg gcc gtg
tat tac tgt gcg aga ga ! 3-11# 17 cga ttc acc atc tcc aga gaa aat gcc aag aac tcc
ttg tat ctt caa atg aac agc ctg aga gcc ggg gac acg gct gtg
tat tac tgt gca aga ga ! 3-13# 18 aga ttc acc atc tca aga gat gat tca aaa aac acg
ctg tat ctg caa atg aac agc ctg aaa acc gag gac aca gcc gtg
tat tac tgt acc aca ga ! 3-15# 19 cga ttc acc atc tcc aga gac aac gcc aag aac tcc
ctg tat ctg caa atg aac agt ctg aga gcc gag gac acg gcc ttg
tat cac tgt TABLE 195-continued Human GLG FR3 sequences gcg aga ga ! 3-20# 20 cga ttc acc atc tcc aga gac aac gcc aag aac tca
ctg tat ctg caa atg aac agc ctg aga gcc gag gac acg gct gtg
tat tac tgt gcg aga ga ! 3-21# 21 cgg ttc acc atc tcc aga gac aat tcc aag aac acg
ctg tat ctg caa atg aac agc ctg aga gcc gag gac acg gcc gta
tat tac tgt gcg aaa ga ! 3-23# 22 cga ttc acc atc tcc aga gac aat tcc aag aac acg
ctg tat ctg caa atg aac agc ctg aga gct gag gac acg gct gtg
tat tac tgt gcg aaa ga ! 3-30# 23 cga ttc acc atc tcc aga gac aat tcc aag aac acg
ctg tat ctg caa atg aac agc ctg aga gct gag gac acg gct gtg
tat tac tgt gcg aga ga ! 3303# 24 cga ttc acc atc tcc aga gac aat tcc aag aac acg
ctg tat ctg caa atg aac agc ctg aga gct gag gac acg gct gtg
tat tac tgt gcg aaa ga ! 3305# 25 cga ttc acc atc tcc aga gac aat tcc aag aac acg
ctg tat ctg caa atg aac agc ctg aga gcc gag gac acg gct gtg
tat tac tgt gcg aga ga ! 3-33# 26 cga ttc acc atc tcc aga gac aac agc aaa aac tcc
ctg tat ctg caa atg aac agt ctg aga act gag gac acc gcc ttg
tat tac tgt gca aaa gat a ! 3-43# 27 cga ttc acc atc tcc aga gac aat gcc aag aac tca
ctg tat ctg caa atg aac agc ctg aga gac gag gac acg gct gtg
tat tac tgt gcg aga ga ! 3-48# 28 aga ttc acc atc tca aga gat ggt tcc aaa agc atc
gcc tat ctg caa atg aac agc ctg aaa acc gag gac aca gcc gtg
tat tac tgt act aga ga ! 3-49# 29 cga ttc acc atc tcc aga gac aat tcc aag aac acg
ctg tat ctt

TABLE 195-continued

Human GLG FR3 sequences caa atg aac agc ctg aga gcc gag gac acg gcc gtg
tat tac tgt gcg aga ga ! 3-53# 30 aga ttc acc atc tcc aga gac aat tcc aag aac acg
ctg tat ctt caa atg ggc agc ctg aga gct gag gac atg gct gtg
tat tac tgt gcg aga ga ! 3-64# 31 aga ttc acc atc tcc aga gac aat tcc aag aac acg
ctg tat ctt caa atg aac agc ctg aga gct gag gac acg gct gtg
tat tac tgt gcg aga ga ! 3-66# 32 aga ttc acc atc tca aga gat gat tca aag aac tca
ctg tat ctg caa atg aac agc ctg aaa acc gag gac acg gcc gtg
tat tac tgt gct aga ga ! 3-72# 33 agg ttc acc atc tcc aga gat gat tca aag aac acg
gcg tat ctg caa atg aac agc ctg aaa acc gag gac acg gcc gtg
tat tac tgt act aga ca ! 3-73# 34 cga ttc acc atc tcc aga gac aac gcc aag aac acg
ctg tat ctg caa atg aac agt ctg aga gcc gag gac acg gct gtg
tat tac tgt gca aga ga ! 3-74# 35 aga ttc acc atc tcc aga gac aat tcc aag aac acg
ctg cat ctt caa atg aac agc ctg aga gct gag gac acg gct gtg
tat tac tgt aag aaa ga ! 3-d# 36

! VH4
cga gtc acc ata tca gta gac aag tcc aag aac cag
ttc tcc ctg aag ctg agc tct gtg acc gcc gcg gac acg gcc gtg
tat tac tgt gcg aga ga ! 4-04# 37 cga gtc acc atg tca gta gac acg tcc aag aac cag
ttc tcc ctg aag ctg agc tct gtg acc gcc gtg gac acg gcc gtg
tat tac tgt gcg aga aa ! 4-28# 38 cga gtt acc ata tca gta gac acg tct aag aac cag
ttc tcc ctg aag ctg agc tct gtg act gcc gcg gac acg gcc gtg
tat tac tgt TABLE 195-continued Human GLG FR3 sequences gcg aga ga ! 4301# 39 cga gtc acc ata tca gta gac agg tcc aag aac cag
ttc tcc ctg aag ctg agc tct gtg acc gcc gcg gac acg gcc gtg
tat tac tgt gcc aga ga ! 4302# 40 cga gtt acc ata tca gta gac acg tcc aag aac cag
ttc tcc ctg aag ctg agc tct gtg act gcc gca gac acg gcc gtg
tat tac tgt gcc aga ga ! 4304# 41 cga gtt acc ata tca gta gac acg tct aag aac cag
ttc tcc ctg aag ctg agc tct gtg act gcc gcg gac acg gcc gtg
tat tac tgt gcg aga ga ! 4-31# 42 cga gtc acc ata tca gta gac acg tcc aag aac cag
ttc tcc ctg aag ctg agc tct gtg acc gcc gcg gac acg gct gtg
tat tac tgt gcg aga ga ! 4-34# 43 cga gtc acc ata tcc gta gac acg tcc aag aac cag
ttc tcc ctg aag ctg agc tct gtg acc gcc gca gac acg gct gtg
tat tac tgt gcg aga ca ! 4-39# 44 cga gtc acc ata tca gta gac acg tcc aag aac cag
ttc tcc ctg aag ctg agc tct gtg acc gct gcg gac acg gcc gtg
tat tac tgt gcg aga ga ! 4-59# 45 cga gtc acc ata tca gta gac acg tcc aag aac cag
ttc tcc ctg aag ctg agc tct gtg acc gct gcg gac acg gcc gtg
tat tac tgt gcg aga ga ! 4-61# 46 cga gtc acc ata tca gta gac acg tcc aag aac cag
ttc tcc ctg aag ctg agc tct gtg acc gcc gca gac acg gcc gtg
tat tac tgt gcg aga ga ! 4-b# 47

! VH5
cag gtc acc atc tca gcc gac aag tcc atc agc acc
gcc tac ctg cag tgg agc agc ctg aag gcc tcg gac acc gcc atg
tat tac tgt gcg aga ca ! 5-51# 48 cac gtc acc atc tca gct gac aag tcc atc agc act
gcc tac ctg cag tgg agc agc ctg aag gcc tcg gac acc gcc atg
tat tac tgt gcg aga ! 5-a# 49

! VH6
cga ata acc atc aac cca gac aca tcc aag aac cag
ttc tcc ctg cag ctg aac tct gtg act ccc gag gac acg gct gtg
tat tac tgt gca aga ga ! 6-1# 50

! VH7
cgg ttt gtc ttc tcc ttg gac acc tct gtc agc acg
gca tat ctg cag atc tgc agc cta aag gct gag gac act gcc gtg
tat tac tgt gcg aga ga ! 74.1# 51

TABLE 250

REdaptors, Extenders, and Bridges used for Cleavage and Capture of
Human Heavy Chains in FR3.

A: HpyCH4V Probes of actual human HC genes

!HpyCH4V in FR3 of human HC, bases 35-56; only those with TGca site

TGca; 10,

RE recognition:tgca of length 4 is expected at 10

| | | |
|---|---|---|
| 1 | 6-1 | agttctccctgcagctgaactc |
| 2 | 3-11,3-07,3-21,3-72,3-48 | cactgtatctgcaaatgaacag |
| 3 | 3-09,3-43,3-20 | ccctgtatctgcaaatgaacag |
| 4 | 5-51 | ccgcctacctgcagtggagcag |
| 5 | 3-15,3-30,3-30.5,3-30.3,3-74,3-23,3-33 | cgctgtatctgcaaatgaacag |
| 6 | 7-4.1 | cggcatatctgcagatctgcag |

TABLE 250-continued

REdaptors, Extenders, and Bridges used for Cleavage and Capture of Human Heavy Chains in FR3.

```
7                                       3-73 cggcgtatctgcaaatgaacag 8                                       5-a  ctgcctacctgcagtggagcag 9                                       3-49 tcgcctatctgcaaatgaacag
```

B: HpyCH4V REdaptors, Extenders, and Bridges
B.1 REdaptors

! Cutting HC lower strand:

! TmKeller for 100 mM NaCl, zero formamide

| ! Edapters for cleavage | | $T_m^W$ | $T_m^K$ |
|---|---|---|---|
| (ON_HCFR36-1) | 5'-agttctcccTGCAgctgaactc-3' | 68.0 | 64.5 |
| (ON_HCFR36-1A) | 5'-ttctcccTGCAgctgaactc-3' | 62.0 | 62.5 |
| (ON_HCFR36-1B) | 5'-ttctcccTGCAgctgaac-3' | 56.0 | 59.9 |
| (ON_HCFR33-15) | 5'-cgctgtatcTGCAaatgaacag-3' | 64.0 | 60.8 |
| (ON_HCFR33-15A) | 5'-ctgtatcTGCAaatgaacag-3' | 56.0 | 56.3 |
| (ON_HCFR33-15B) | 5'-ctgtatcTGCAaatgaac-3' | 50.0 | 53.1 |
| (ON_HCFR33-11) | 5'-cactgtatcTGCAaatgaacag-3' | 62.0 | 58.9 |
| (ON_HCFR35-51) | 5'-ccgcctaccTGCAgtggagcag-3' | 74.0 | 70.1 |

!

B.2 Segment of synthetic 3-23 gene into which captured CDR3 is to be cloned

!                    XbaI...

!D323*  cgCttcacTaag tcT aga gac aaC tcT aag aaT acT ctC taC

!       scab........ designed gene 3-23 gene................

!

!      HpyCH4V

!     .. ..          AflII...

!      Ttg caG atg aac agc TtA agG . . .

!      .......................... . . .

!

B.3 Extender and Bridges
! Extender (bottom strand):

!

(ON_HCHpyEx01)    5'-cAAgTAgAgAgTATTcTTAgAgTTgTcTcTAgAcTTAgTgAAgcg-3'

! ON_HCHpyEX01 is the reverse complement of

! 5'-cgCttcacTaag tcT aga gac aaC tcT aag aaT acT ctC taC Ttg-3'

!

! Bridges (top strand, 9-base overlap):

!

(ON_HCHpyBr016-1)   5'-cgCttcacTaag tcT aga gac aaC tcT aag-
                    aaT acT ctC taC Ttg CAgctgaac-3' (3'-term C is blocked)

!

! 3-15 et al. + 3-11

TABLE 250-continued

REdaptors, Extenders, and Bridges used for Cleavage and Capture of
Human Heavy Chains in FR3.

```
(ON_HCHpyBr023-15)   5'-cgCttcacTaag tcT aga gac aaC tcT aag-
                       aaT acT ctC taC Ttg CAaatgaac-3'(3'-term C is blocked)
!
! 5-51

(ON_HCHpyBr045-51)   5'-cgCttcacTaag tcT aga gac aaC tcT aag-
                       aaT acT ctC taC Ttg CAgtggagc-3'(3'-term C is blocked)
!
! PCR primer (top strand)
!
(ON_HCNpyPCR)        5'-cgCttcacTaag tcT aga gac-3'
!
C: BlpI Probes from human HC GLGs
  1              1-58,1-03,1-08,1-69,1-24,1-45,1-46,1-f,1-e  acatggaGcTGAGCagcctgag
  2                                                   1-02   acatggaGCTGAGCaggctgag
  3                                                   1-18   acatggagctgaggagcctgag
  4                                                 5-51,5-a acctgcagtggagcagcctgaa
  5                                            3-15,3-73,3-49,3-72 atctgcaaatgaacagcctgaa
  6        3303,3-33,3-07,3-11,3-30,3-21,3-23,3305,3-48  atctgcaaatgaacagcctgag
  7                                        3-20, 3-74,3-09,3-43 atctgcaaatgaacagtctgag
  8                                                   74.1   atctgcagatctgcagcctaaa
  9                                        3-66,3-13,3-53,3-d atcttcaaatgaacagcctgag
 10                                                   3-64   atcttcaaatgggcagcctgag
 11     4301,4-28,4302,4-04,4304,4-31,4-34,4-39,4-59,4-61,4b  ccctgaagGCTGAGCtctgtgac
 12                                                   6-1    ccctgcagctgaactctgtgac
 13                                                2-70,2-05 tccttacaatgaccaacatgga
 14                                                   2-26   tccttaccatgaccaacatgga
```

D: BlpI REdaptors, Extenders, and Bridges
D.1 REdaptors

|  |  | $T_m^W$ | $T_m^K$ |
|---|---|---|---|
| (BlpF3HC1-58) | 5'-ac atg gaG CTG AGC agc ctg ag-3' | 70 | 66.4 |
| (BlpF3HC6-1) | 5'-cc ctg aag ctg agc tct gtg ac-3' | 70 | 66.4 |

! BlpF3HC6-
1 matches 4-30.1,
not 6-1.

D.2 Segment of synthetic 3-23 gene into which captured CDR3 is to be cloned

```
!                              BlpI
!              XbaI...                                . ... ...
!D323  cgCttcacTaag TCT AGA gac aaC tcT aag aaT acT ctC taC Ttg caG atg aac
!
!              AflII...
!              agC TTA AGG
```

TABLE 250-continued

REdaptors, Extenders, and Bridges used for Cleavage and Capture of Human Heavy Chains in FR3.

```
D.3 Extender and Bridges
! Bridges (BlpF3Br1)      5'-cgCttcacTcag tcT aga gaT aaC AGT aaA aaT acT TtG-
                taC Ttg caG Ctg a|GC agc ctg-3'

(BlpF3Br2)      5'-cgCttcacTcag tcT aga gaT aaC AGT aaA aaT acT TtG-
                taC Ttg caG Ctg a|gc tct gtg-3'

!                              | lower strand is cut here

! Extender (BlpF3Ext)      5'-
TcAgcTgcAAgTAcAAAgTATTTTTAcTgTTATcTcTAgAcTgAgTgAAgcg-3'

! BlpF3Ext is the reverse complement of:

! 5'-cgCttcacTcag tcT aga gaT aaC AGT aaA aaT acT TtG taC Ttg caG Ctg a-3'

!

(BlpF3PCR)      5'-cgCttcacTcag tcT aga gaT aaC-3'

E: HpyCH4III Distinct GLG sequences surrounding site, bases 77-98
  1   102#1,118#4,146#7,169#9,1e#10,311#17,353#30,404#37,4301 ccgtgtattactgtgcgagaga 2   103#2,307#15,321#21,3303#24,333#26,348#28,364#31,366#32 ctctctattactgtgcgagaga 3                                                   108#3   ccgtgtattactgtgcgagagg 4                                            124#5,1f#11    ccgtgtattactgtgcaacaga 5                                                   145#6   ccatgtattactgtgcaagata 6                                                   158#8   ccgtgtattactgtgcggcaga 7                                                  205#12   ccacatattactgtgcacacag 8                                                  226#13   ccacatattactgtgcacggat 9                                                  270#14   ccacgtattactgtgcacggat 10                                         309#16,343#27    ccttatattactgtgcaaaaga 11                                    313#18,374#35,61#50    ctgtgtattactgtgcaagaga 12                                                  315#19   ccgtgtattactgtaccacaga 13                                                  320#20   ccttgtatcactgtgcgagaga 14                                                  323#22   ccgtatattactgtgcgaaaga 15                                         330#23,3305#25   ctgtgtattactgtgcgaaaga 16                                                  349#29   ccgtgtattactgtactagaga 17                                                  372#33   ccgtgtattactctgctagaga 18                                                  373#34   ccgtgtattactgtactagaca 19                                                   3d#36   ctgtgtattactgtaagaaaga 20                                                  428#38   ccgtgtattactgtgcgagaaa 21                                         4302#40,4304#41  ccgtgtattactgtgccagaga 22                                                  439#44   ctgtgtattactgtgcgagaca 23                                                  551#48   ccatgtattactgtgcgagaca 24                                                   5a#49   ccatgtattactgtgcgaga
```

TABLE 250-continued

REdaptors, Extenders, and Bridges used for Cleavage and Capture of Human Heavy Chains in FR3.

```
F: HpyCH4III REdaptors, Extenders, and Bridges
 F.1 REdaptors
 ! ONs for cleavage of HC(lower) in FR3(bases 77-97)

! For cleavage with HpyCH4III, Bst4CI, or TaaI

! cleavage is in lower chain before base 88.

!                77 788 888 888 889 999 999 9
 !                78 901 234 567 890 123 456 7      T_m^W         T_m^K
 (H43.77.97.1-02#1) 5'-cc gtg tat tAC TGT gcg aga g-3'    64            62.6

(H43.77.97.1-03#2) 5'-ct gtg tat tAC TGT gcg aga g-3'    62            60.6

(H43.77.97.108#3)  5'-cc gtg tat tAC TGT gcg aga g-3'    64            62.6

(H43.77.97.323#22) 5'-cc gta tat tac tgt gcg aaa g-3'    60            58.7

(H43.77.97.330#23) 5'-ct gtg tat tac tgt gcg aaa g-3'    60            58.7

(H43.77.97.439#44) 5'-ct gtg tat tac tgt gcg aga c-3'    62            60.6

(H43.77.97.551#48) 5'-cc atg tat tac tgt gcg aga c-3'    62            60.6

(H43.77.97.5a#49)  5'-cc atg tat tAC TGT gcg aga  -3'    58            58.3

F.2 Extender and Bridges
 ! XbaI and AflII sites in bridges are bunged (H43.XABr1)      5'-ggtgtagtga-

|TCT|AGt|gac|aac|tct|aag|aat|act|ctc|tac|ttg|cag|atg|-

|aac|agC|TTt|AGg|gct|gag|gac|aCT|GCA|Gtc|tac|tat tgt gcg aga-3'

(H43.XABr2)      5'-ggtgtagtga-

|TCT|AGt|gac|aac|tct|aag|aat|act|ctc|tac|ttg|cag|atg|-

|aac|agC|TTt|AGg|gct|gag|gac|aCT|GCA|Gtc|tac|tat tgt gcg aaa-3'

(H43.XAExt)      5'-ATAgTAgAcT gcAgTgTccT cAgcccTTAA gcTgTTcATc TgcAAgTAgAgAgTATTcTT AgAgTTgTcT cTAgATcAcT AcAcc-3'

!H43.XAExt is the reverse complement of
! 5'-ggtgtagtga-

!   |TCT|AGA|gac|aac|tct|aag|aat|act|ctc|tac|ttg|cag|atg|-

!   |aac|agC|TTA|AGg|gct|gag|gac|aCT|GCA|Gtc|tac|tat-3'

(H43.XAPCR)     5'-ggtgtagtga |TCT|AGA|gac|aac-3'

! XbaI and AflII sites in bridges are bunged (H43.ABr1)       5'-ggtgtagtga-

|aac|agC|TTt|AGg|gct|gag|gac|aCT|GCA|Gtc|tac|tat tgt gcg aga-3'

(H43.ABr2)       5'-ggtgtagtga-

|aac|agC|TTt|AGg|gct|gag|gac|aCT|GCA|Gtc|tac|tat tgt gcg aaa-3'

(H43.AExt)      5'-ATAgTAgAcTgcAgTgTccTcAgcccTTAAgcTgTTTcAcTAcAcc-3'

!(H43.AExt) is the reverse complement of 5'-ggtgtagtga-

!     |aac|agC|TTA|AGg|gct|gag|gac|aCT|GCA|Gtc|tac|tat-3'

(H43.APCR)      5'-ggtgtagtga |aac|agC|TTA|AGg|gct|g-3'
```

```
(FOKlact)    5'-cAcATccgTg TTgTT cAcggATgTg-3'
(VHEx881)    5'-AATAgTAgAc TgcAgTgTcc TcAgcccTTA
                AgcTgTTcAT cTgcAAgTAg-
                AgAgTATTCT TAgAgTTgTc TcTAgAcTTA
                gTgAAgcg-3'
! note that VHEx881 is the reverse complement of
  the ON below
!      [RC] 5'-cgCttcacTaag-
!              Scab........
!              Synthetic 3-23 as in Table 206
!              |TCT|AGA|gac|aac|tct|aag|aat-
!              |act|ctc|tac|ttg|cag|atg|-
!              XbaI...
!              |aac|agC|TTA|AGg|gct|gag|gac-
!              |aCT|GCA|Gtc|tac|tat|t-3'
```

```
                                -continued
!                               AflII...
(VHBA881)    5'-cgCttcacTaag-
                |TCT|AGA|gac|aac|tct|aag|aat-
                |act|ctc|tac|ttg|cag|atg|-
                |aac|agC|TTA|AGg|gct|gag|gac-
                |aCT|GCA|Gtc|tac|tat|tgt gcg
                ag-3'
(VHBB881)    5'-cgCttcacTaag-
                |TCT|AGA|gac|aac|tct|aag|aat-
                |act|ctc|tac|ttg|cag|atg|-
                |aac|agC|TTA|AGg|gct|gag|gac-
                |aCT|GCA|Gtc|tac|tat|tgt Acg
                ag-3'
(VH881PCR)   5'-cgCttcacTaag|TCT|AGA|gac|aac-3'
```

TABLE 600

V3-23 VH framework with variegated codons shown

```
!
!                     17  18  19  20  21  22
!                     A   Q   P   A   M   A
              5'-ctg tct gaa cG GCC cag ccG GCC atg gcc       29
              3'-gac aga ctt gc cgg gtc ggc cgg tac cgg
!                  Scab.........SfiI.............
!                       NgoMI...
!                          NcoI....
!
!                     FR1 (DP47/V3-23)--------------
!                     23  24  25  26  27  28  29  30
!                     E   V   Q   L   L   E   S   G
              gaa|gtt|CAA|TTG|tta|gag|tct|ggt|                53
!             ctt|caa|gtt|aac|aat|ctc|aga|cca|
!                       | MfeI  |
!
! --------------FR1----------------------------------
! 31  32  33  34  35  36  37  38  39  40  41  42  43  44  45
!  G   G   L   V   Q   P   G   G   S   L   R   L   S   C   A
  |ggc|ggt|ctt|gtt|cag|cct|ggt|ggt|tct|tta|cgt|ctt|tct|tgc|gct|   98
! |ccg|cca|gaa|caa|gtc|gga|cca|cca|aga|aat|gca|gaa|aga|acg|cga|
!
! Sites to be varied--->       ***     ***     ***
! ----FR1---------------->|...CDR1...............|---FR2------
```

TABLE 600-continued

V3-23 VH framework with variegated codons shown

```
! 46  47  48  49  50  51  52  53  54  55  56  57  58  59  60
!  A   S   G   F   T   F   S   S   Y   A   M   S   W   V   R
  |gct|TCC|GGA|ttc|act|ttc|tct|tCG|TAC|Gct|atg|tct|tgg|gtt|cgC|     143
! |cga|agg|cct|aag|tga|aag|aga|agc|atg|cga|tac|aga|acc|caa|gcg|
!     | BspEI |             | BsiWI|                     |BstXI.
!
!                  Sites to be varies--->  ***       *** ***
! --------FR2--------------------------->|...CDR2........
! 61  62  63  64  65  66  67  68  69  70  71  72  73  74  75
!  Q   A   P   G   K   G   L   E   W   V   S   A   I   S   G
  |CAa|gct|ccT|GGt|aaa|ggt|ttg|gag|tgg|gtt|tct|gct|atc|tct|ggt|     188
! |gtt|cga|gga|cca|ttt|cca|aac|ctc|acc|caa|aga|cga|tag|aga|cca|
! ...BstXI     |
!
!                  ***    ***
! .....CDR2..........................................|---FR3---
! 76  77  78  79  80  81  82  83  84  85  86  87  88  89  90
!  S   G   G   S   T   Y   Y   A   D   S   V   K   G   R   F
  |tct|ggt|ggc|agt|act|tac|tat|gct|gac|tcc|gtt|aaa|ggt|cgc|ttc|     233
! |aga|cca|ccg|tca|tga|atg|ata|cga|ctg|agg|caa|ttt|cca|gcg|aag|
!
! --------FR3-----------------------------------------------
! 91  92  93  94  95  96  97  98  99  100 101 102 103 104 105
!  T   I   S   R   D   N   S   K   N   T   L   Y   L   Q   M
  |act|atc|TCT|AGA|gac|aac|tct|aag|aat|act|ctc|tac|ttg|cag|atg|     278
! |tga|tag|aga|tct|ctg|ttg|aga|ttc|tta|tga|gag|atg|aac|gtc|tac|
!           | XbaI |
!
! ---FR3-------------------------------------------------->|
! 106 107 108 109 110 111 112 113 114 115 116 117 118 119 120
!  N   S   L   R   E   D   T   A   V   Y   Y   C   A   K
  |aac|agC|TTA|AGg|gct|gag|gac|aCT|GCA|Gtc|tac|tat|tgc|gct|aaa|     323
! |ttg|tcg|aat|tcc|cga|ctc|ctg|tga|cgt|cag|atg|ata|acg|cga|ttt|
!       |AflII |           | PstI |
!
! .......CDR3..................|----FR4-----------------
! 121 122 123 124 125 126 127 128 129 130 131 132 133 134 135
!  D   Y   E   G   T   G   Y   A   F   D   I   W   G   Q   G
  |gac|tat|gaa|ggt|act|ggt|tat|gct|ttc|gaC|ATA|TGg|ggt|caa|ggt|     368
! |ctg|ata|ctt|cca|tga|cca|ata|cga|aag|ctg|tat|acc|cca|gtt|cca|
!                                    | NdeI |
!
```

TABLE 600-continued

V3-23 VH framework with variegated codons shown

```
! --------------FR4---------->|
!  136 137 138 139 140 141 142

!   T   M   V   T   V   S   S

|act|atG|GTC|ACC|gtc|tct|agt-                                    389

! |tga|tac|cag|tgg|cag|aga|tca-

!         | BstEII |

!

!                143 144 145 146 147 148 149 150 151 152

!                 A   S   T   K   G   P   S   V   F   P gcc tcc acc aaG GGC CCa tcg GTC TTC ccc-3'        419

!                cgg agg tgg ttc ccg ggt agc cag aag ggg-5'

!                            Bsp120I.      BbsI...(2/2)

!                            ApaI....

(SFPRMET)    5'-ctg tct gaa cG GCC cag ccG-3'

(TOPFR1A)    5'-ctg tct gaa cG GCC cag ccG GCC atg gccgaa|gtt|CAA|TTG|tta|gag|tct|ggt|-

|ggc|ggt|ctt|gtt|cag|cct|ggt|ggt|tct|tta-3'

(BOTFR1B)                3'-caa|gtc|gga|cca|cca|aga|aat|gca|gaa|aga|acg|cga|-

|cga|agg|cct|aag|tga|aag-5' ! bottom strand (BOTFR2)     3'-acc|caa|gcg|-

|gtt|cga|gga|cca|ttt|cca|aac|ctc|acc|caa|aga|-5' ! bottom strand (BOTFR3)     3'- a|cga|ctg|agg|caa|ttt|cca|gcg|aag|-

|tga|tag|aga|tct|ctg|ttg|aga|ttc|tta|tga|gag|atg|aac|gtc|tac|-

|ttg|tcg|aat|tcc|cga|ctc|ctg|tga-5'

(F06)        5'-gC|TTA|AGg|gct|gag|gac|aCT|GCA|Gtc|tac|tat|tgc|gct|aaa|-

|gac|tat|gaa|ggt|act|ggt|tat|gct|ttc|gaC|ATA|TGg|ggt|c-3'

(BOTFR4)     3'-cga|aag|ctg|tat|acc|cca|gtt|cca|-

|tga|tac|cag|tgg|cag|aga|tcacgg agg tgg ttc ccg ggt agc cag aag ggg-5' ! bottom strand (BOTPRCPRIM)             3'-gg ttc ccg ggt agc cag aag ggg-5'

!

! CDR1 diversity

!

(ON-vgC1)    5'-|gct|TCC|GGA|ttc|act|ttc|tct|<1>|TAC|<1>|atg|<1>|-

!                                   CDR1.................6859

|tgg|gtt|cgC|CAa|gct|ccT|GG-3'

!

!<1> stands for an equamolar mix of {ADEFGHIKLMNPQRSTVWY}; no C

!                         (this is not a sequence)
```

TABLE 600-continued

V3-23 VH framework with variegated codons shown

```
!
! CDR2 diversity
!
(ON-vgC2)    5'-ggt|ttg|gag|tgg|gtt|tct|<2>|atc|<2>|<3>|-
!                                CDR2..........
             |tct|ggt|ggc|<1>|act|<1>|tat|gct|gac|tcc|gtt|aaa|gg-3'
!            CDR2.................................................
! <1> is an equimolar mixture of {ADEFGHIKLMNPQRSTVWY}; no C
! <2> is an equimolar mixture of {YRWVGS}; no ACDEFHIKLMNPQT
! <3> is an equimolar mixture of {PS}; no ACDEFGHIKLMNQRTVWY
```

TABLE 800

(new)
The following list of enzymes was taken from
http://rebase.neb.com/cgi-bin/asymmlist.
I have removed the enzymes that a) cut within the
recognition, b) cut on both sides of the recognition,
or c) have fewer than 2 bases between recognition and
closest cut site.
REBASE Enzymes
Apr. 13, 2001
Type II restriction enzymes with asymmetric recognition
sequences:

| Enzymes | Recognition Sequence | Isoschizomers | Suppliers |
|---|---|---|---|
| AarI | CACCTGCNNNN^NNNN_ | — | y |
| AceIII | CAGCTCNNNNNNN^NNNN_ | — | — |
| Bbr7I | GAAGACNNNNNNN^NNNN_ | — | — |
| BbvI | GCAGCNNNNNNNN^NNNN_ | — | y |
| BbvII | GAAGACNN^NNNN_ | — | — |
| Bce83I | CTTGAGNNNNNNNNNNNNNNNN_NN^ | — | — |
| BceAI | ACGGCNNNNNNNNNNNN^NN_ | — | y |
| BcefI | ACGGCNNNNNNNNNNNN^N_ | — | — |
| BciVI | GTATCCNNNNN_N^ | BfuI | y |
| BfiI | ACTGGGNNNN_N^ | BmrI | y |
| BinI | GGATCNNNN^N | | |
| BscAI | GCATCNNNN^NN_ | — | — |
| BseRI | GAGGAGNNNNNNNN_NN^ | — | y |
| BsmFI | GGGACNNNNNNNNNN^NNNN_ | BspLU11III | y |
| BspMI | ACCTGCNNNN^NNNN_ | Acc36I | y |
| EciI | GGCGGANNNNNNNNN_NN^ | — | y |
| Eco57I | CTGAAGNNNNNNNNNNNNNN_NN^ | BspKT5I | y |
| FauI | CCCGCNNNN^NN_ | BstFZ438I | y |
| FokI | GGATGNNNNNNNNN^NNNN_ | BstPZ418I | y |
| GsuI | CTGGAGNNNNNNNNNNNNNNNN_NN^ | — | y |

TABLE 800-continued (new)
The following list of enzymes was taken from
http://rebase.neb.com/cgi-bin/asymmlist.
I have removed the enzymes that a) cut within the
recognition, b) cut on both sides of the recognition,
or c) have fewer than 2 bases between recognition and
closest cut site.
REBASE Enzymes
Apr. 13, 2001
Type II restriction enzymes with asymmetric recognition
sequences:

| Enzymes | Recognition Sequence | Isoschizomers | Suppliers |
|---|---|---|---|
| HgaI | GACGCNNNNN^NNNNN_ | — | y |
| HphI | GGTGANNNNNNN_N^ | AsuHPI | y |
| MboII | GAAGANNNNNNN_N^ | — | y |
| MlyI | GAGTCNNNNN^ | SchI | y |
| MmeI | TCCRACNNNNNNNNNNNNNNNNNNNN_NN^ | — | — |
| MnlI | CCTCNNNNNN_N^ | — | y |
| PleI | GAGTCNNNN^N_ | PpsI | y |
| RleAI | CCCACANNNNNNNNN_NNN^ | — | — |
| SfaNI | GCATCNNNNN^NNNN_ | BspST5I | y |
| SspD5I | GGTGANNNNNNNN^ | — | — |
| Sth132I | CCCGNNNN^NNNN_ | — | — |
| StsI | GGATGNNNNNNNNNN^NNNN_ | — | — |
| TaqII | GACCGANNNNNNNNN_NN^, CACCCANNNNNNNNN_NN^ | — | — |
| Tth111II | CAARCANNNNNNNNN_NN^ | — | — |
| UbaPI | CGAACG | — | — |

The notation is ^ means cut the upper strand and _ means cut the lower strand. If the upper and lower strand are cut at the same place, then only ^ appears.

TABLE 120

MALIA3, annotated

! MALIA3 9532 bases

!------------------------------------------------------------------

1 aat gct act act att agt aga att gat gcc acc ttt tca gct cgc gcc
!       gene ii continued
     49 cca aat gaa aat ata gct aaa cag gtt att gac cat ttg cga aat gta
     97 tct aat ggt caa act aaa tct act cgt tcg cag aat gga aa tca act
    145 gtt aca tgg aat gaa act tcc aga cac cgt act tta gtt gca tat tta
    193 aaa cat gtt gag cta cag cac cag att cag caa tta agc tct aag cca
    241 tcc gca aaa atg acc tct tat caa aag gag caa tta aag gta ctc tct
    289 aat cct gac ctg ttg gag ttt gct tcc ggt ctg gtt cgc ttt gaa gct
    337 cga att aaa acg cga tat ttg aag tct ttc ggg ctt cct ctt aat ctt
    385 ttt gat gca atc cgc ttt gct tct gac tat aat agt cag ggt aaa gac
    433 ctg att ttt gat tta tgg tca ttc tcg ttt tct gaa ctg ttt aaa gca

TABLE 120-continued

MALIA3, annotated

```
  481 ttt gag ggg gat tca ATG aat att tat gac gat tcc gca gta ttg gac
!         RBS?......    Start gene x, ii continues
  529 gct atc cag tct aaa cat ttt act att acc ccc tct ggc aaa act tct
  577 ttt gca aaa gcc tct cgc tat ttt ggt ttt tat cgt cgt ctg gta aac
  625 gag ggt tat gat agt gtt gct ctt act atg cct cgt aat tcc ttt tgg
  673 cgt tat gta tct gca tta gtt gaa tgt ggt att cct aaa tct caa ctg
  721 atg aat ctt tct acc tgt aat aat gtt gtt ccg tta gtt cgt ttt att
  769 aac gta gat ttt tct tcc caa cgt cct gac tgg tat aat gag cca gtt
  817 ctt aaa atc gca TAA
!                   End X & II
  832 ggtaattca ca
!
!       M1              E5              Q10              T15
  843 ATG att aaa gtt gaa att aaa cca tct caa gcc caa ttt act act cgt
!     Start gene V
!
!       S17            S20             P25              E30
  891 tct ggt gtt tct cgt cag ggc aag cct tat tca ctg aat gag cag ctt
!
!              V35             E40              V45
  939 tgt tac gtt gat ttg ggt aat gaa tat ccg gtt ctt gtc aag att act
!
!         D50             A55              L60
  987 ctt gat gaa ggt cag cca gcc tat gcg cct ggt cTG TAC Acc gtt cat
!                                                 BsrGI...
!       L65             V70             S75                    R80
 1035 ctg tcc tct ttc aaa gtt ggt cag ttc ggt tcc ctt atg att gac cgt
!
!                       P85    K87 end of V
 1083 ctg cgc ctc gtt ccg gct aag TAA C
!
      1108 ATG gag cag gtc gcg gat ttc gac aca att tat cag gcg atg
!         Start gene VII
!
 1150 ata caa atc tcc gtt gta ctt tgt ttc gcg ctt ggt ata atc
!
!                       VII and IX overlap.
!                 ..... S2  V3  L4  V5                    310
```

TABLE 120-continued

MALIA3, annotated

```
  1192 gct ggg ggt caa agA TGA gt gtt tta gtg tat tct ttc gcc tct ttc gtt
!                       End VII
!                           |start IX
!      L13       W15                  G20             T25               E29
  1242 tta ggt tgg tgc ctt cgt agt ggc att acg tat ttt acc cgt tta atg gaa
!
  1293 act tcc tc
!
!        .... stop of IX IX and VIII overlap by four bases
  1301 ATG aaa aag tct tta gtc ctc aaa gcc tct gta gcc gtt gct acc ctc
!        Start signal sequence of viii.
!
  1349 gtt ccg atg ctg tct ttc gct gct gag ggt gac gat ccc gca aaa gcg
!                             mature VIII --->
  1397 gcc ttt aac tcc ctg caa gcc tca gcg acc gaa tat atc ggt tat gcg
  1445 tgg gcg atg gtt gtt gtc att
  1466 gtc ggc gca act atc ggt atc aag ctg ttt aag
  1499 aaa ttc acc tcg aaa gca ! 1515
!        ........... -35  ..
!
  1517       agc tga taaaccgat acaattaaag gctccttttg
!                      ..... -10   ...
!
  1552 gagccttttt ttttGGAGAt ttt ! S.D. underlined
!
!        <------III signal sequence ----------------------------->
!        M    K    K    L    L    F    A    I    P    L    V
  1575 caac GTG aaa aaa tta tta ttc gca att cct tta gtt ! 1611
!
!   V    P    F    Y    S    H    S    A    Q
  1612 gtt cct ttc tat tct cac aGT gcA Cag tCT
!                              ApaLI...
!
  1642 GTC GTG ACG CAG CCG CCC TCA GTG TCT GGG GCC CCA GGG CAG
       AGG GTC ACC ATC TCC TGC ACT GGG AGC AGC TCC AAC ATC GGG GCA
!         BstEII...
  1729 GGT TAT GAT GTA CAC TGG TAC CAG CAG CTT CCA GGA ACA GCC CCC AAA
  1777 CTC CTC ATC TAT GGT AAC AGC AAT CGG CCC TCA GGC GTC CCT GAC CGA
  1825 TTC TCT GGC TCC AAG TCT GGC ACC TCA GCC TCC CTG GCC ATC ACT
```

TABLE 120-continued

MALIA3, annotated

```
1870 GGG CTC CAG GCT GAG GAT GAG GCT GAT TAT

1900 TAC TGC CAG TCC TAT GAC AGC AGC CTG AGT

1930 GGC CTT TAT GTC TTC GGA ACT GGG ACC AAG GTC ACC GTC

!                                              BstEII...

1969 CTA GGT CAG CCC AAG GCC AAC CCC ACT GTC ACT

2002 CTG TTC CCG CCC TCC TCT GAG GAG CTC CAA GCC AAC AAG GCC ACA CTA

2050 GTG TGT CTG ATC AGT GAC TTC TAC CCG GGA GCT GTG ACA GTG CCC TGG

2098 AAG GCA GAT AGC AGC CCC GTC AAG GCG GGA GTG GAG ACC ACC ACA CCC

2146 TCC AAA CAA AGC AAC AAC AAG TAC GCG GCC AGC AGC TAT CTG AGC CTG

2194 ACG CCT GAG CAG TGG AAG TCC CAC AGA AGC TAC AGC TGC CAG GTC ACG

2242 CAT GAA GGG AGC ACC GTG GAG AAG ACA GTG GCC CCT ACA GAA TGT TCA

2290 TAA TAA ACCG CCTCCACCGG GCGCGCCAAT TCTATTTCAA GGAGACAGTC ATA

!                          AscI.....

!

!    PelB signal----------------------------------------->

!    M   K   Y   L   L   P   T   A   A   A   G   L   L   L   L

2343 ATG AAA TAC CTA TTG CCT ACG GCA GCC GCT GGA TTG TTA TTA CTC

!

!    16  17  18  19  20      21  22

!    A   A   Q   P   A       M   A 2388 gcG GCC cag ccG GCC     atg gcc

!        SfiI.............

!            NgoMI...(1/2)

!                   NcoI.........

!

!                           FR1(DP47/V3-23)---------------

!                           23  24  25  26  27  28  29  30

!                           E   V   Q   L   L   E   S   G 2409                        gaa|gtt|CAA|TTG|tta|gag|tct|ggt|

!                                  |MfeI   |

!

!    --------------FR1---------------------------------

!    31  32  33  34  35  36  37  38  39  40  41  42  43  44  45

!    G   G   L   V   Q   P   G   G   S   L   R   L   S   C   A

2433 |ggc|ggt|ctt|gtt|cag|cct|ggt|ggt|tct|tta|cgt|ctt|tct|tgc|gct|

!

!    ----FR1--------------->|...CDR1................|---FR2------

!    46  47  48  49  50  51  52  53  54  55  56  57  58  59  60

!    A   S   G   F   T   F   S   S   Y   A   M   S   W   V   R
```

TABLE 120-continued

MALIA3, annotated

```
2478 |gct|TCC|GGA|ttc|act|ttc|tct|tCG|TAC|Gct|atg|tct|tgg|gtt|cgC|
!        | BspEI  |                   | BsiWI|                  |BstXI.
!
!        --------FR2-------------------------->|...CDR2.........
!         61   62   63   64   65   66   67   68   69   70   71   72   73   74   75
!          Q    A    P    G    K    G    L    E    W    V    S    A    I    S    G
2523 |cAa|gct|ccT|GGt|aaa|ggt|ttg|gag|tgg|gtt|tct|gct|atc|tct|ggt|
!    ...BstXI           |
!
!        ....CDR2...........................................|---FR3---
!         76   77   78   79   80   81   82   83   84   85   86   87   88   89   90
!          S    G    G    S    T    Y    Y    A    D    S    V    K    G    R    F
2568 |tct|ggt|ggc|agt|act|tac|tat|gct|gac|tcc|gtt|aaa|ggt|cgc|ttc|
!
!
!        --------FR3------------------------------------------
!         91   92   93   94   95   96   97   98   99  100  101  102  103  104  105
!          T    I    S    R    D    N    S    K    N    T    L    Y    L    Q    M
2613 |act|atc|TCT|AGA|gac|aac|tct|aag|aat|act|ctc|tac|ttg|cag|atg|
!             | XbaI  |
!
!        ---FR3------------------------------------------------>|
!        106  107  108  109  110  111  112  113  114  115  116  117  118  119  120
!          N    S    L    R    A    E    D    T    A    V    Y    Y    C    A    K
2658 |aac|agC|TTA|AGg|gct|gag|gac|aCT|GCA|Gtc|tac|tat|tgc|gct|aaa|
!             |AflII  |              | PstI  |
!
!        .......CDR3................|----FR4-----------------
!        121  122  123  124  125  126  127  128  129  130  131  132  133  134  135
!          D    Y    E    G    T    G    Y    A    F    D    I    W    G    Q    G
2703 |gac|tat|gaa|ggt|act|ggt|tat|gct|ttc|gaC|ATA|TGg|ggt|caa|ggt|
!                                         | NdeI  |(1/4)
!
!        --------------FR4---------->|
!        136  137  138  139  140  141  142
!          T    M    V    T    V    S    S
2748 |act|atG|GTC|ACC|gtc|tct|agt
!            | BstEII |
! From BstEII onwards, pV323 is same as pCES1, except as noted.
```

TABLE 120-continued

MALIA3, annotated

! BstEII sites may occur in light chains; not likely to be unique in final
! vector.
!

```
                    143 144 145 146 147 148 149 150 151 152
!                    A   S   T   K   G   P   S   V   F   P
   2769             gcc tcc acc aaG GGC CCa tcg GTC TTC ccc
!                                   Bsp120I.     BbsI...(2/2)
!                                   ApaI....
!
!       153 154 155 156 157 158 159 160 161 162 163 164 165 166 167
!        L   A   P   S   S   K   S   T   S   G   G   T   A   A   L
   2799 ctg gca ccC TCC TCc aag agc acc tct ggg ggc aca gcg gcc ctg
!              BseRI...(2/2)
!
!       168 169 170 171 172 173 174 175 176 177 178 179 180 181 182
!        G   C   L   V   K   D   Y   F   P   E   P   V   T   V   S
   2844 ggc tgc ctg GTC AAG GAC TAC TTC CCc gaA CCG GTg acg gtg tcg
!                                                AgeI....
!
!       183 184 185 186 187 188 189 190 191 192 193 194 195 196 197
!        W   N   S   G   A   L   T   S   G   V   H   T   F   P   A
   2889 tgg aac tca GGC GCC ctg acc agc ggc gtc cac acc ttc ccg gct
!              KasI...(1/4)
!
!           198 199 200 201 202 203 204 205 206 207 208 209 210 211 212
!            V   L   Q   S   S   G   L   Y   S   L   S   S   V   V   T
   2934 gtc cta cag tCt agc GGa ctc tac tcc ctc agc agc gta gtg acc
!                   (Bsu36I...) (knocked out)
!
!           213 214 215 216 217 218 219 220 221 222 223 224 225 226 227
!            V   P   S   S   S   L   G   T   Q   T   Y   I   C   N   V
   2979 gtg ccC tCt tct agc tTG Ggc acc cag acc tac atc tgc aac gtg
!                   (BstXI..........)N.B. destruction of BstXI & BpmI sites.
!
!           228 229 230 231 232 233 234 235 236 237 238 239 240 241 242
!            N   H   K   P   S   N   T   K   V   D   K   K   V   E   P
   3024 aat cac aag ccc agc aac acc aag gtg gac aag aaa gtt gag ccc
!
!       243 244 245
```

TABLE 120-continued

MALIA3, annotated

```
!       K   S   C   A   A   A   H   H   H   H   H   H   S   A
  3069 aaa tct tgt GCG GCC GCt cat cac cac cat cat cac tct gct
!                       NotI......
!
!       E   Q   K   L   I   S   E   E   D   L   N   G   A   A
  3111 gaa caa aaa ctc atc tca gaa gag gat ctg aat ggt gcc gca
!
!
!       D   I   N   D   D   R   M       A   S   G   A
  3153 GAT ATC aac gat gat cgt atg     gct AGC ggc gcc
!       rEK cleavage site..........     NheI... KasI...
!       EcoRV..
!
! Domain 1 -------------------------------------------------------
!       A   E   T   V   E   S   C   L   A
  3183 gct gaa act gtt gaa agt tgt tta gca
!
!
!       K   P   H   T   E   I   S   F
  3210 aaa ccc cat aca gaa aat tca ttt
!
!       T   N   V   W   K   D   D   K   T
  3234 aCT AAC GTC TGG AAA GAC GAC AAA ACt
!
!       L   D   R   Y   A   N   Y   E   G   C   L   W   N   A   T   G   V
  3261 tta gat cgt tac gct aac tat gag ggt tgt ctg tgG AAT GCt aca ggc gtt
!                                                       BsmI____
!
!       V   V   C   T   G   D   E   T   Q   C   Y   G   T   W   V   P   I
  3312 gta gtt tgt act ggt GAC GAA ACT CAG TGT TAC GGT ACA TGG GTT cct att
!
!       G   L   A   I   P   E   N
  3363 ggg ctt gct atc cct gaa aat
!
! L1 linker -------------------------------------
!       E   G   G   G   S   E   G   G   G   S
  3384 gag ggt ggt ggc tct gag ggt ggc ggt tct
!
!       E   G   G   G   S   E   G   G   G   T
```

TABLE 120-continued

MALIA3, annotated

```
  3414 gag ggt ggc ggt tct gag ggt ggc ggt act
!
! Domain 2 -----------------------------------
  3444 aaa cct cct gag tac ggt gat aca cct att ccg ggc tat act tat atc aac
  3495 cct ctc gac ggc act tat ccg cct ggt act gag caa aac ccc gct aat cct
  3546 aat cct tct ctt GAG GAG tct cag cct ctt aat act ttc atg ttt cag aat
!                     BseRI__
  3597 aat agg ttc cga aat agg cag ggg gca tta act gtt tat acg ggc act
  3645 gtt act caa ggc act gac ccc gtt aaa act tat tac cag tac act cct
  3693 gta tca tca aaa gcc atg tat gac gct tac tgg aac ggt aaa ttC AGA
!                                                                  AlwNI
  3741 GAC TGc gct ttc cat tct ggc ttt aat gaa gat cca ttc gtt tgt gaa
!         AlwNI
  3789 tat caa ggc caa tcg tct gac ctg cct caa cct cct gtc aat gct
!
  3834 ggc ggc ggc tct
! start L2 ---------------------------------------------------------------
  3846 ggt ggt ggt tct
  3858 ggt ggc ggc tct
  3870 gag ggt ggt ggc tct gag ggt ggc ggt tct
  3900 gag ggt ggc ggc tct gag gga ggc ggt tcc
  3930 ggt ggt ggc tct ggt    ! end L2
!
! Domain 3 ---------------------------------------------------------------
!      S   G   D   F   D   Y   E   K   M   A   N   A   N   K   G   A
  3945 tcc ggt gat ttt gat tat gaa aag atg gca aac gct aat aag ggg gct
!
!      M   T   E   N   A   D   E   N   A   L   Q   S   D   A   K   G
  3993 atg acc gaa aat gcc gat gaa aac gcg cta cag tct gac gct aaa ggc
!
!      K   L   D   S   V   A   T   D   Y   G   A   A   I   D   G   F
  4041 aaa ctt gat tct gtc gct act gat tac ggt gct gct atc gat ggt ttc
!
!      I   G   D   V   S   G   L   A   N   G   N   G   A   T   G   D
  4089 att ggt gac gtt tcc ggc ctt gct aat ggt aat ggt gct act ggt gat
!
!      F   A   G   S   N   S   Q   M   A   Q   V   G   D   G   D   N
  4137 ttt gct ggc tct aat tcc caa atg gct caa gtc ggt gac ggt gat aat
!
```

TABLE 120-continued

MALIA3, annotated

```
!       S   P   L   M   N   N   F   R   Q   Y   L   P   S   L   P   Q
   4185 tca cct tta atg aat aat ttc cgt caa tat tta cct tcc ctc cct caa
!
!       S   V   E   C   R   P   F   V   F   S   A   G   K   P   Y   E
   4233 tcg gtt gaa tgt cgc cct ttt gtc ttt agc gct ggt aaa cca tat gaa
!
!       F   S   I   D   C   D   K   I   N   L   F   R
   4281 ttt tct att gat tgt gac aaa ata aac tta ttc cgt
!                                               End Domain 3
!
!       G   V   F   A   F   L   L   Y   V   A   T   F   M   Y   V   F140
   4317 ggt gtc ttt gcg ttt ctt tta tat gtt gcc acc ttt atg tat gta ttt
!       start transmembrane segment
!
!       S   T   F   A   N   I   L
   4365 tct acg ttt gct aac ata ctg
!
!       R   N   K   E   S
   4386 cgt aat aag gag tct TAA ! stop of iii
!       Intracellular anchor.
!
!          M1  P2   V    L   L5   G    I    P    L   L10  L    R    F    L   G15
   4404 tc ATG cca gtt ctt ttg ggt att ccg tta tta ttg cgt ttc ctc ggt
!          Start VI
!
   4451 ttc ctt ctg gta act ttg ttc ggc tat ctg ctt act ttt ctt aaa aag
   4499 ggc ttc ggt aag ata gct att gct att tca ttg ttt ctt gct ctt att
   4547 att ggg ctt aac tca att ctt gtg ggt tat ctc tct gat att agc gct
   4595 caa tta ccc tct gac ttt gtt cag ggt gtt cag tta att ctc ccg tct
   4643 aat gcg ctt ccc tgt ttt tat gtt att ctc tct gta aag gct gct att
   4691 ttc att ttt gac gtt aaa caa aaa atc gtt tct tat ttg gat tgg gat
!
!              M1  A2  V3      F5              L10            G13
   4739 aaa TAA t ATG gct gtt tat ttt gta act ggc aaa tta ggc tct gga
!          end VI    Start gene I
!
!          14  15  16  17  18  19  20  21  22  23  24  25  26  27  28
!          K   T   L   V   S   V   G   K   I   Q   D   K   I   V   A
```

TABLE 120-continued

MALIA3, annotated

```
4785 aag acg ctc gtt agc gtt ggt aag att cag gat aaa att gta gct 29  30  31  32  33  34  35  36  37  38  39  40  41  42  43
        G   C   K   I   A   T   N   L   D   L   R   L   Q   N   L
4830 ggg tgc aaa ata gca act aat ctt gat tta agg ctt caa aac ctc 44  45  46  47  48  49  50  51  52  53  54  55  56  57  58
        P   Q   V   G   R   F   A   K   T   P   R   V   L   R   I
4875 ccg caa gtc ggg agg ttc gct aaa acg cct cgc gtt ctt aga ata 59  60  61  62  63  64  65  66  67  68  69  70  71  72  73
        P   D   K   P   S   I   S   D   L   L   A   I   G   R   G
4920 ccg gat aag cct tct ata tct gat ttg ctt gct att ggg cgc ggt 74  75  76  77  78  79  80  81  82  83  84  85  86  87  88
        N   D   S   Y   D   E   N   K   N   G   L   L   V   L   D
4965 aat gat tcc tac gat gaa aat aaa aac ggc ttg ctt gtt ctc gat 89  90  91  92  93  94  95  96  97  98  99 100 101 102 103
        E   C   G   T   W   F   N   T   R   S   W   N   D   K   E
5010 gag tgc ggt act tgg ttt aat acc cgt tct tgg aat gat aag gaa 104 105 106 107 108 109 110 111 112 113 114 115 116 117 118
        R   Q   P   I   I   D   W   F   L   H   A   R   K   L   G
5055 aga cag ccg att att gat tgg ttt cta cat gct cgt aaa tta gga 119 120 121 122 123 124 125 126 127 128 129 130 131 132 133
        W   D   I   I   F   L   V   Q   D   L   S   I   V   D   K
5100 tgg gat att att ttt ctt gtt cag gac tta tct att gtt gat aaa 134 135 136 137 138 139 140 141 142 143 144 145 146 147 148
        Q   A   R   S   A   L   A   E   H   V   V   Y   C   R   R
5145 cag gcg cgt tct gca tta gct gaa cat gtt gtt tat tgt cgt cgt 149 150 151 152 153 154 155 156 157 158 159 160 161 162 163
        L   D   R   I   T   L   P   F   V   G   T   L   Y   S   L
5190 ctg gac aga att act tta cct ttt gtc ggt act tta tat tct ctt 164 165 166 167 168 169 170 171 172 173 174 175 176 177 178
```

TABLE 120-continued

MALIA3, annotated

```
!          I   T   G   S   K   M   P   L   P   K   L   H   V   G   V
      5235 att act ggc tcg aaa atg cct ctg cct aaa tta cat gtt ggc gtt
!
!          179 180 181 182 183 184 185 186 187 188 189 190 191 192 193
!          V   K   Y   G   D   S   Q   L   S   P   T   V   E   R   W
      5280 gtt aaa tat ggc gat tct caa tta agc cct act gtt gag cgt tgg
!
!          194 195 196 197 198 199 200 201 202 203 204 205 206 207 208
!          L   Y   T   G   K   N   L   Y   N   A   Y   D   T   K   Q
      5325 ctt tat act ggt aag aat ttg tat aac gca tat gat act aaa cag
!
!          209 210 211 212 213 214 215 216 217 218 219 220 221 222 223
!          A   F   S   S   N   Y   D   S   G   V   Y   S   Y   L   T
      5370 gct ttt tct agt aat tat gat tcc ggt gtt tat tct tat tta acg
!
!          224 225 226 227 228 229 230 231 232 233 234 235 236 237 238
!          P   Y   L   S   H   G   R   Y   F   K   P   L   N   L   G
      5415 cct tat tta tca cac ggt cgg tat ttc aaa cca tta aat tta ggt
!
!          239 240 241 242 243 244 245 246 247 248 249 250 251 252 253
!          Q   K   M   K   L   T   K   I   Y   L   K   K   F   S   R
      5460 cag aag atg aaa tta act aaa ata tat ttg aaa aag ttt tct cgc
!
!          254 255 256 257 258 259 260 261 262 263 264 265 266 267 268
!          V   L   C   L   A   I   G   F   A   S   A   F   T   Y   S
      5505 gtt ctt tgt ctt gcg att gga ttt gca tca gca ttt aca tat agt
!
!          269 270 271 272 273 274 275 276 277 278 279 280 281 282 283
!          Y   I   T   Q   P   K   P   E   V   K   K   V   V   S   Q
      5550 tat ata acc caa cct aag ccg gag gtt aaa aag gta gtc tct cag
!
!          284 285 286 287 288 289 290 291 292 293 294 295 296 297 298
!          T   Y   D   F   D   K   F   T   I   D   S   S   Q   R   L
      5595 acc tat gat ttt gat aaa ttc act att gac tct tct cag cgt ctt
!
!          299 300 301 302 303 304 305 306 307 308 309 310 311 312 313
!          N   L   S   Y   R   Y   V   F   K   D   S   K   G   K   L
```

TABLE 120-continued

MALIA3, annotated

```
5640 aat cta agc tat cgc tat gtt ttc aag gat tct aag gga aaa TTA
!                                                           PacI
!
!      314 315 316 317 318 319 320 321 322 323 324 325 326 327 328
!       I   N   S   D   D   L   Q   K   Q   G   Y   S   L   T   Y
5685 ATT AAt agc gac gat tta cag aag caa ggt tat tca ctc aca tat
!    PacI
!
!      329 330 331 332 333 334 335 336 337 338 339 340 341 342 343
!       i   I   D   L   C   T   V   S   I   K   K   G   N   S   N   E
!      iv                                                      M1  K
5730 att gat tta tgt act gtt tcc att aaa aaa ggt aat tca aAT Gaa
!                                                           Start IV
!
!      344 345 346 347 348 349
!       i   I   V   K   C   N  .End of I
!      iv  L3  L   N5  V   17  N    F   V10
5775     att gtt aaa tgt aat TAA T TTT GTT
! IV continued.....
5800 ttc ttg atg ttt gtt tca tca tct tct ttt gct cag gta att gaa atg
5848 aat aat tcg cct ctg cgc gat ttt gta act tgg tat tca aag caa tca
5896 ggc gaa tcc gtt att gtt tct ccc gat gta aaa ggt act gtt act gta
5944 tat tca tct gac gtt aaa cct gaa aat cta cgc aat ttc ttt att tct
5992 gtt tta cgt gct aat aat ttt gat atg gtt ggt tca att cct tcc ata
6040 att cag aag tat aat cca aac aat cag gat tat att gat gaa ttg cca
6088 tca tct gat aat cag gaa tat gat gat aat tcc gct cct tct ggt ggt
6136 ttc ttt gtt ccg caa aat gat aat gtt act caa act ttt aaa att aat
6184 aac gtt cgg gca aag gat tta ata cga gtt gtc gaa ttg ttt gta aag
6232 tct aat act tct aaa tcc tca aat gta tta tct att gac ggc tct aat
6280 cta tta gtt gtt TCT gca cct aaa gat att tta gat aac ctt cct caa
!                        ApaLI removed
6328 ttc ctt tct act gtt gat ttg cca act gac cag ata ttg att gag ggt
6376 ttg ata ttt gag gtt cag caa ggt gat gct tta gat ttt tca ttt gct
6424 gct ggc tct cag cgt ggc act gtt gca ggc ggt gtt aat act gac cgc
6472 ctc acc tct gtt tta tct tct gct ggt ggt tcg ttc ggt att ttt aat
6520 ggc gat gtt tta ggg cta tca gtt cgc gca tta aag act aat agc cat
6568 tca aaa ata ttg tct gtg cca cgt att ctt acg ctt tca ggt cag aag
6616 ggt tct atc tct gtT GGC CAg aat gtc cct ttt att act ggt cgt gtg
```

TABLE 120-continued

MALIA3, annotated

```
!                      MscI___
6664 act ggt gaa tct gcc aat gta aat aat cca ttt cag acg att gag cgt
6712 caa aat gta ggt att tcc atg agc gtt ttt cct gtt gca atg gct ggc
6760 ggt aat att gtt ctg gat att acc agc aag gcc gat agt ttg agt tct
6808 tct act cag gca agt gat gtt att act aat caa aga agt att gct aca
6856 acg gtt aat ttg cgt gat gga cag act ctt tta ctc ggt ggc ctc act
6904 gat tat aaa aac act tct caa gat tct ggc gta ccg ttc ctg tct aaa
6952 atc cct tta atc ggc ctc ctg ttt agc tcc cgc tct gat tcc aac gag
7000 gaa agc acg tta tac gtg ctc gtc aaa gca acc ata gta cgc gcc ctg
7048 TAG cggcgcatt
!   End IV
7060 aagcgcggcg ggtgtggtgg ttacgcgcag cgtgaccgct acacttgcca gcgccctagc
7120 gcccgctcct ttcgctttct tcccttcctt tctcgccacg ttcGCCGGCt ttccccgtca
!                                                  NgoMI_
7180 agctctaaat cggggctcc ctttagggtt ccgatttagt gctttacggc acctcgaccc
7240 caaaaaactt gatttgggtg atggttCACG TAGTGggcca tcgccctgat agacggtttt
!                        DraIII___
7300 tcgcccttG ACGTTGGAGT Ccacgttctt taatagtgga ctcttgttcc aaactggaac
!          DrdI_____
7360 aacactcaac cctatctcgg gctattcttt tgatttataa gggattttgc cgatttcgga
7420 accaccatca aacaggattt tcgcctgctg gggcaaacca gcgtggaccg cttgctgcaa
7480 ctctctcagg gccaggcggt gaagggcaat CAGCTGttgc cCGTCTCact ggtgaaaaga
!                                  PvuII.    BsmBI.
7540 aaaaccaccc tGGATCC AAGCTT
!            BamHI  HindIII (1/2)
!         Insert carrying bla gene
7563    gcaggtg gcacttttcg gggaaatgtg cgcggaaccc
7600 ctatttgttt attttctaa atacattcaa atatGTATCC gctcatgaga caataaccct
!                          BciVI
7660 gataaatgct tcaataatat tgaaaaAGGA AGAgt
!                   RBS.?...
!    Start bla gene
7695 ATG agt att caa cat ttc cgt gtc gcc ctt att ccc ttt ttt gcg gca ttt
7746 tgc ctt cct gtt ttt gct cac cca gaa acg ctg gtg aaa gta aaa gat gct
7797 gaa gat cag ttg ggC gCA CGA Gtg ggt tac atc gaa ctg gat ctc aac agc
!              BsssI...
!         ApaLI removed
7848 ggt aag atc ctt gag agt ttt cgc ccc gaa gaa cgt ttt cca atg atg agc
7899 act ttt aaa gtt ctg cta tgt cat aca cta tta tcc cgt att gac gcc ggg
```

TABLE 120-continued

MALIA3, annotated

```
7950 caa gaG CAA CTC GGT CGc cgg gcg cgg tat tct cag aat gac ttg gtt gAG
!            BcgI_____                                           ScaI
8001 TAC Tca cca gtc aca gaa aag cat ctt acg gat ggc atg aca gta aga gaa
!    ScaI_
8052 tta tgc agt gct gcc ata acc atg agt gat aac act gcg gcc aac tta ctt
8103 ctg aca aCG ATC Gga gga ccg aag gag cta acc gct ttt ttg cac aac atg
!                PvuI___
8154 ggg gat cat gta act cgc ctt gat cgt tgg gaa ccg gag ctg aat gaa gcc
8205 ata cca aac gac gag cgt gac acc acg atg cct gta gca atg cca aca acg
8256 tTG CGC Aaa cta tta act ggc gaa cta ctt act cta gct tcc cgg caa caa
!    FspI....
!
8307 tta ata gac tgg atg gag gcg gat aaa gtt gca gga cca ctt ctg cgc tcg
8358 GCC ctt ccG GCt ggc tgg ttt att gct gat aaa tct gga gcc ggt gag cgt
!    BglI_____
8409 gGG TCT Cgc ggt atc att gca gca ctg ggg cca gat ggt aag ccc tcc cgt
!    BsaI___
8460 atc gta gtt atc tac acG ACg ggg aGT Cag gca act atg gat gaa cga aat
!                         AhdI_____
8511 aga cag atc gct gag ata ggt gcc tca ctg att aag cat tgg TAA ctgt
!                                                           stop
8560 cagaccaagt ttactcatat atactttaga ttgatttaaa acttcatttt taatttaaaa
8620 ggatctaggt gaagatcctt tttgataatc tcatgaccaa aatcccttaa cgtgagtttt
8680 cgttccactg tacgtaagac cccc
8704 AAGCTT   GTCGAC tgaa tggcgaatgg cgctttgcct
!    HindIII  SalI..
!    (2/2)   HincII
8740 ggtttccggc accagaagcg gtgccggaaa gctggctgga gtgcgatctt
!
8790 CCTGAGG
!    Bsu36I_
8797      ccgat actgtcgtcg tcccctcaaa ctggcagatg
8832 cacggttacg atgcgcccat ctacaccaac gtaacctatc ccattacggt caatccgccg
8892 tttgttccca cggagaatcc gacgggttgt tactcgctca catttaatgt tgatgaaagc
8952 tggctacagg aaggccagac gcgaattatt tttgatggcg ttcctattgg ttaaaaaatg
9012 agctgattta acaaaaattt aacgcgaatt ttaacaaaat attaacgttt acaATTTAAA
!                                                            SwaI...
9072 Tatttgctta tacaatcttc ctgttttttgg ggcttttctg attatcaacc GGGGTAcat
!                                                           RBS?
```

TABLE 120-continued

MALIA3, annotated

```
9131 ATG att gac atg cta gtt tta cga tta ccg ttc atc gat tct ctt gtt tgc
!    Start gene II 9182 tcc aga ctc tca ggc aat gac ctg ata gcc ttt gtA GAT CTc tca aaa ata
!                                                    BglII...

9233 gct acc ctc tcc ggc atg aat tta tca gct aga acg gtt gaa tat cat att 9284 gat ggt gat ttg act gtc tcc ggc ctt tct cac cct ttt gaa tct tta cct 9335 aca cat tac tca ggc att gca ttt aaa ata tat gag ggt tct aaa aat ttt 9386 tat cct tgc gtt gaa ata aag gct tct ccc gca aaa gta tta cag ggt cat 9437 aat gtt ttt ggt aca acc gat tta gct tta tgc tct gag gct tta ttg ctt 9488 aat ttt gct aat tct ttg cct tgc ctg tat gat tta ttg gat gtt ! 9532
! gene II continues
```

| TABLE 120B |
|---|
| Sequence of MALIA3, condensed<br>LOCUS MALIA3 9532 CIRCULAR<br>ORIGIN |

```
   1 AATGCTACTA CTATTAGTAG AATTGATGCC ACCTTTTCAG
     CTCGCGCCCC AAATGAAAAT

61 ATAGCTAAAC AGGTTATTGA CCATTTGCGA AATGTATCTA
     ATGGTCAAAC TAAATCTACT

121 CGTTCGCAGA ATTGGGAATC AACTGTTACA TGGAATGAAA
     CTTCCAGACA CCGTACTTTA

181 GTTGCATATT TAAAACATGT TGAGCTACAG CACCAGATTC
     AGCAATTAAG CTCTAAGCCA

241 TCCGCAAAAA TGACCTCTTA TCAAAAGGAG CAATTAAAGG
     TACTCTCTAA TCCTGACCTG

301 TTGGAGTTTG CTTCCGGTCT GGTTCGCTTT GAAGCTCGAA
     TTAAAACGCG ATATTTGAAG

361 TCTTTCGGGC TTCCTCTTAA TCTTTTTGAT GCAATCCGCT
     TTGCTTCTGA CTATAATAGT

421 CAGGGTAAAG ACCTGATTTT TGATTTATGG TCATTCTCGT
     TTTCTGAACT GTTTAAAGCA

481 TTTGAGGGGG ATTCAATGAA TATTTATGAC GATTCCGCAG
     TATTGGACGC TATCCAGTCT

541 AAACATTTTA CTATTACCCC CTCTGGCAAA ACTTCTTTTG
     CAAAAGCCTC TCGCTATTTT

601 GGTTTTTATC GTCGTCTGGT AAACGAGGGT TATGATAGTG
     TTGCTCTTAC TATGCCTCGT

661 AATTCCTTTT GGCGTTATGT ATCTGCATTA GTTGAATGTG
     GTATTCCTAA ATCTCAACTG

721 ATGAATCTTT CTACCTGTAA TAATGTTGTT CCGTTAGTTC
     GTTTTATTAA CGTAGATTTT

781 TCTTCCCAAC GTCCTGACTG GTATAATGAG CCAGTTCTTA
     AAATCGCATA AGGTAATTCA

841 CAATGATTAA AGTTGAAATT AAACCATCTC AAGCCCAATT
     TACTACTCGT TCTGGTGTTT

901 CTCGTCAGGG CAAGCCTTAT TCACTGAATG AGCAGCTTTG
     TTACGTTGAT TTGGGTAATG

961 AATATCCGGT TCTTGTCAAG ATTACTCTTG ATGAAGGTCA
     GCCAGCCTAT GCGCCTGGTC

1021 TGTACACCGT TCATCTGTCC TCTTTCAAAG TTGGTCAGTT
     CGGTTCCCTT ATGATTGACC

1081 GTCTGCGCCT CGTTCCGGCT AAGTAACATG GAGCAGGTCG
     CGGATTTCGA CACAATTTAT

1141 CAGGCGATGA TACAAATCTC CGTTGTACTT TGTTTCGCGC
     TTGGTATAAT CGCTGGGGGT

1201 CAAAGATGAG TGTTTTAGTG TATTCTTTCG CCTCTTTCGT
     TTTAGGTTGG TGCCTTCGTA

1261 GTGGCATTAC GTATTTTACC CGTTTAATGG AAACTTCCTC
     ATGAAAAAGT CTTTAGTCCT

1321 CAAAGCCTCT GTAGCCGTTG CTACCCTCGT TCCGATGCTG
     TCTTTCGCTG CTGAGGGTGA

1381 CGATCCCGCA AAAGCGGCCT TTAACTCCCT GCAAGCCTCA
     GCGACCGAAT ATATCGGTTA

1441 TGCGTGGGCG ATGGTTGTTG TCATTGTCGG CGCAACTATC
     GGTATCAAGC TGTTTAAGAA

1501 ATTCACCTCG AAAGCAAGCT GATAAACCGA TACAATTAAA
     GGCTCCTTTT GGAGCCTTTT

1561 TTTTTGGAGA TTTTCAACGT GAAAAAATTA TTATTCGCAA
     TTCCTTTAGT TGTTCCTTTC

1621 TATTCTCACA GTGCACAGTC TGTCGTGACG CAGCCGCCCT
     CAGTGTCTGG GGCCCCAGGG

1681 CAGAGGGTCA CCATCTCCTG CACTGGGAGC AGCTCCAACA
     TCGGGGCAGG TTATGATGTA

1741 CACTGGTACC AGCAGCTTCC AGGAACAGCC CCCAAACTCC
     TCATCTATGG TAACAGCAAT
```

TABLE 120B-continued

Sequence of MALIA3, condensed
LOCUS MALIA3 9532 CIRCULAR
ORIGIN

```
1801 CGGCCCTCAG GGGTCCCTGA CCGATTCTCT GGCTCCAAGT
     CTGGCACCTC AGCCTCCCTG

1861 GCCATCACTG GGCTCCAGGC TGAGGATGAG GCTGATTATT
     ACTGCCAGTC CTATGACAGC

1921 AGCCTGAGTG GCCTTTATGT CTTCGGAACT GGGACCAAGG
     TCACCGTCCT AGGTCAGCCC

1981 AAGGCCAACC CCACTGTCAC TCTGTTCCCG CCCTCCTCTG
     AGGAGCTCCA AGCCAACAAG

2041 GCCACACTAG TGTGTCTGAT CAGTGACTTC TACCCGGGAG
     CTGTGACAGT GGCCTGGAAG

2101 GCAGATAGCA GCCCCGTCAA GGCGGGAGTG GAGACCACCA
     CACCCTCCAA ACAAAGCAAC

2161 AACAAGTACG CGGCCAGCAG CTATCTGAGC CTGACGCCTG
     AGCAGTGGAA GTCCCACAGA

2221 AGCTACAGCT GCCAGGTCAC GCATGAAGGG AGCACCGTGG
     AGAAGACAGT GCCCCCTACA

2281 GAATGTTCAT AATAAACCGC CTCCACCGGG CGCGCCAATT
     CTATTTCAAG GAGACAGTCA

2341 TAATGAAATA CCTATTGCCT ACGGCAGCCG CTGGATTGTT
     ATTACTCGCG GCCCAGCCGG

2401 CCATGGCCGA AGTTCAATTG TTAGAGTCTG GTGGCGGTCT
     TGTTCAGCCT GGTGGTTCTT

2461 TACGTCTTTC TTGCGCTGCT TCCGGATTCA CTTTCTCTTC
     GTACGCTATG TCTTGGGTTC

2521 GCCAAGCTCC TGGTAAAGGT TTGGAGTGGG TTTCTGCTAT
     CTCTGGTTCT GGTGGCAGTA

2581 CTTACTATGC TGACTCCGTT AAAGGTCGCT TCACTATCTC
     TAGAGACAAC TCTAAGAATA

2641 CTCTCTACTT GCAGATGAAC AGCTTAAGGG CTGAGGACAC
     TGCAGTCTAC TATTGCGCTA

2701 AAGACTATGA AGGTACTGGT TATGCTTTCG ACATATGGGG
     TCAAGGTACT ATGGTCACCG

2761 TCTCTAGTGC CTCCACCAAG GGCCCATCGG TCTTCCCCCT
     GGCACCCTCC TCCAAGAGCA

2821 CCTCTGGGGG CACAGCGGCC CTGGGCTGCC TGGTCAAGGA
     CTACTTCCCC GAACCGGTGA

2881 CGGTGTCGTG GAACTCAGGC GCCCTGACCA GCGGCGTCCA
     CACCTTCCCG GCTGTCCTAC

2941 AGTCTAGCGG ACTCTACTCC CTCAGCAGCG TAGTGACCGT
     GCCCTCTTCT AGCTTGGGCA

3001 CCCAGACCTA CATCTGCAAC GTGAATCACA AGCCCAGCAA
     CACCAAGGTG GACAAGAAAG

3061 TTGAGCCCAA ATCTTGTGCG GCCGCTCATC ACCACCATCA
     TCACTCTGCT GAACAAAAAC

3121 TCATCTCAGA AGAGGATCTG AATGGTGCCG CAGATATCAA
     CGATGATCGT ATGGCTGGCG

3181 CCGCTGAAAC TGTTGAAAGT TGTTTAGCAA AACCCCATAC
     AGAAAATTCA TTTACTAACG

3241 TCTGGAAAGA CGACAAAACT TTAGATCGTT ACGCTAACTA
     TGAGGGTTGT CTGTGGAATG

3301 CTACAGGCGT TGTAGTTTGT ACTGGTGACG AAACTCAGTG
     TTACGGTACA TGGGTTCCTA

3361 TTGGGCTTGC TATCCCTGAA AATGAGGGTG GTGGCTCTGA
     GGGTGGCGGT TCTGAGGGTG

3421 GCGGTTCTGA GGGTGGCGGT ACTAAACCTC CTGAGTACGG
     TGATACACCT ATTCCGGGCT

3481 ATACTTATAT CAACCCTCTC GACGGCACTT ATCCGCCTGG
     TACTGAGCAA AACCCCGCTA

3541 ATCCTAATCC TTCTCTTGAG GAGTCTCAGC CTCTTAATAC
     TTTCATGTTT CAGAATAATA

3601 GGTTCCGAAA TAGGCAGGGG GCATTAACTG TTTATACGGG
     CACTGTTACT CAAGGCACTG

3661 ACCCCGTTAA AACTTATTAC CAGTACACTC CTGTATCATC
     AAAAGCCATG TATGACGCTT

3721 ACTGGAACGG TAAATTCAGA GACTGCGCTT CCATTCTGG
     CTTTAATGAA GATCCATTCG

3781 TTTGTGAATA TCAAGGCCAA TCGTCTGACC TGCCTCAACC
     TCCTGTCAAT GCTGGCGGCG

3841 GCTCTGGTGG TGGTTCTGGT GGCGGCTCTG AGGGTGGTGG
     CTCTGAGGGT GGCGGTTCTG

3901 AGGGTGGCGG CTCTGAGGGA GGCGGTTCCG GTGGTGGCTC
     TGGTTCCGGT GATTTTCATT

3961 ATGAAAAGAT GGCAAACGCT AATAAGGGGG CTATGACcGA
     AAATGCCGAT GAAAACGCGC

4021 TACAGTCTGA CGCTAAAGGC AAACTTGATT CTGTCGCTAC
     TGATTACGGT GCTGCTATCG

4081 ATGGTTTCAT TGGTGACGTT TCCGGCCTTG CTAATGGTAA
     TGGTGCTACT GGTGATTTTG

4141 CTGGCTCTAA TTCCCAAATG GCTCAAGTCG GTGACGGTGA
     TAATTCACCT TTAATCAATA

4201 ATTTCCGTCA ATATTTACCT TCCCTCCCTC AATCGGTTGA
     ATGTCGCCCT TTTGTCTTTA

4261 GCGCTGGTAA ACCATATGAA TTTTCTATTG ATTGTGACAA
     AATAAACTTA TTCCGTGGTG

4321 TCTTTGCGTT TCTTTTATAT GTTGCCACCT TTATGTATCT
     ATTTTCTACG TTTGCTAACA

4381 TACTGCGTAA TAAGGAGTCT TAATCATGCC AGTTCTTTTG
     GGTATTCCGT TATTATTGCG

4441 TTTCCTCGGT TTCCTTCTGG TAACTTTGTT CGGCTATCTG
     CTTACTTTTC TTAAAAGGG

4501 CTTCGGTAAG ATAGCTATTG CTATTTCATT GTTTCTTGCT
     CTTATTATTG GGCTTAACTC

4561 AATTCTTGTG GGTTATCTCT CTGATATTAG CGCTCAATTA
     CCCTCTGACT TTGTTCAGGG

4621 TGTTCAGTTA ATTCTCCCGT CTAATGCGCT TCCCTGTTTT
     TATGTTATTC TCTCTGTAAA

4681 GGCTGCTATT TTCATTTTTG ACGTTAAACA AAAAATCGTT
     TCTTATTTGG ATTGGGATAA

4741 ATAATATGGC TGTTTATTTT GTAACTGGCA AATTAGGCTC
     TGGAAAGACG CTCGTTAGCG
```

TABLE 120B-continued

Sequence of MALIA3, condensed
LOCUS MALIA3 9532 CIRCULAR
ORIGIN

```
4801 TTGGTAAGAT TCAGGATAAA ATTGTAGCTG GGTGCAAAAT
     AGCAACTAAT CTTGATTTAA

4861 GGCTTCAAAA CCTCCCGCAA GTCGGGAGGT TCGCTAAAAC
     GCCTCGCGTT CTTAGAATAC

4921 CGGATAAGCC TTCTATATCT GATTTGCTTG CTATTGGGCG
     CGGTAATGAT TCCTACGATG

4981 AAAATAAAAA CGGCTTGCTT GTTCTCGATG AGTGCGGTAC
     TTGGTTTAAT ACCCGTTCTT

5041 GGAATGATAA GGAAAGACAG CCGATTATTG ATTGGTTTCT
     ACATGCTCGT AAATTAGGAT

5101 GGGATATTAT TTTTCTTGTT CAGGACTTAT CTATTGTTGA
     TAAACAGGCG CGTTCTGCAT

5161 TAGCTGAACA TGTTGTTTAT TGTCGTCGTC TGGACAGAAT
     TACTTTACCT TTTGTCGGTA

5221 CTTTATATTC TCTTATTACT GGCTCGAAAA TGCCTCTGCC
     TAAATTACAT GTTGGCGTTG

5281 TTAAAATATGG CGATTCTCAA TTAAGCCCTA CTGTTGAGCG
     TTGGCTTTAT ACTGGTAAGA

5341 ATTTGTATAA CGCATATGAT ACTAAACAGG CTTTTTCTAG
     TAATTATGAT TCCGGTGTTT

5401 ATTCTTATTT AACGCCTTAT TTATCACACG GTCGGTATTT
     CAAACCATTA AATTTAGGTC

5461 AGAAGATGAA ATTAACTAAA ATATATTTGA AAAAGTTTTC
     TCGCGTTCTT TGTCTTGCGA

5521 TTGGATTTGC ATCAGCATTT ACATATAGTT ATATAACCCA
     ACCTAAGCCG GAGGTTAAAA

5581 AGGTAGTCTC TCAGACCTAT GATTTTGATA AATTCACTAT
     TGACTCTTCT CAGCGTCTTA

5641 ATCTAAGCTA TCGCTATGTT TTCAAGGATT CTAAGGGAAA
     ATTAATTAAT AGCGACGATT

5701 TACAGAAGCA AGGTTATTCA CTCACATATA TTGATTTATG
     TACTGTTTCC ATTAAAAAAG

5761 GTAATTCAAA TGAAATTGTT AAATGTAATT AATTTTGTTT
     TCTTGATGTT TGTTTCATCA

5821 TCTTCTTTTG CTCAGGTAAT TGAAATGAAT AATTCGCCTC
     TGCGCGATTT TGTAACTTGG

5881 TATTCAAAGC AATCAGGCGA ATCCGTTATT GTTTCTCCCG
     ATGTAAAAGG TACTGTTACT

5941 GTATATTGAT CTGACGTTAA ACCTGAAAAT CTACGCAATT
     TCTTTATTTC TGTTTTACGT

6001 GCTAATAATT TGATATGGT TGGTTCAATT CCTTCCATAA
     TTCAGAAGTA TAATCCAAAC

6061 AATCAGGATT ATATTGATGA ATTGCCATCA TCTGATAATC
     AGGAATATGA TGATAATTCC

6121 GCTCCTTCTG GTGGTTTCTT TGTTCCGCAA AATGATAATG
     TTACTCAAAC TTTTAAAATT

6181 AATAACGTTC GGGCAAGGA TTTAATACGA GTTGTCGAAT
     TGTTTGTAAA GTCTAATACT

6241 TCTAAATCCT CAAATGTATT ATCTATTGAC GGCTCTAATC
     TATTAGTTGT TTCTGCACCT
```

TABLE 120B-continued

Sequence of MALIA3, condensed
LOCUS MALIA3 9532 CIRCULAR
ORIGIN

```
6301 AAAGATATTT TAGATAACCT TCCTCAATTC CTTTCTACTG
     TTGATTTGCC AACTGACCAG

6361 ATATTGATTG AGGGTTTGAT ATTTGAGGTT CAGCAAGGTG
     ATGCTTTAGA TTTTTCATTT

6421 GCTGCTGGCT CTCAGCGTGG CACTGTTGCA GGCGGTGTTA
     ATACTGACCG CCTCACCTCT

6481 GTTTTATCTT CTGCTGGTGG TTCGTTCGGT ATTTTTAATG
     GCGATGTTTT AGGGCTATCA

6541 GTTCGCGCAT TAAAGACTAA TAGCCATTCA AAAATATTGT
     CTGTGCCACG TATTCTTACG

6601 CTTTCAGGTC AGAAGGGTTC TATCTCTGTT GGCCAGAATG
     TCCCTTTTAT TACTGGTCGT

6661 GTGACTGGTG AATCTGCCAA TGTAAATAAT CCATTTCAGA
     CGATTGAGCG TCAAAATGTA

6721 GGTATTTCCA TGAGCGTTTT TCCTGTTGCA ATGGCTGGCG
     GTAATATTGT TCTGGATATT

6781 ACCAGCAAGG CCGATAGTTT GAGTTCTTCT ACTCAGGCAA
     GTGATGTTAT TACTAATCAA

6841 AGAAGTATTG CTACAACGGT TAATTTGCGT GATGGACAGA
     CTCTTTTACT CGGTGGCCTC

6901 ACTGATTATA AAAACACTTC TCAAGATTCT GGCGTACCGT
     TCCTGTCTAA AATCCCTTTA

6961 ATCGGCCTCC TGTTTAGCTC CCGCTCTGAT TCCAACGAGG
     AAAGCACGTT ATACGTGCTC

7021 GTCAAAGCAA CCATAGTACG CGCCCTGTAG CGGCGCATTA
     AGCGCGGCGG GTGTGGTGGT

7081 TACGCGCAGC GTGACCGCTA CACTTGCCAG CGCCCTAGCG
     CCCGCTCCTT TCCCTTTCTT

7141 CCCTTCCTTT CTCGCCACGT TCGCCGGCTT TCCCCGTCAA
     GCTCTAAATC GGGGGCTCCC

7201 TTTAGGGTTC CGATTTAGTG CTTTACGGCA CCTCGACCCC
     AAAAAACTTG ATTTGGGTGA

7261 TGGTTCACGT AGTGGGCCAT CGCCCTGATA GACGGTTTTT
     CGCCCTTTGA CGTTGGAGTC

7321 CACGTTCTTT AATAGTGGAC TCTTGTTCCA AACTGGAACA
     ACACTCAACC CTATCTCGGG

7381 CTATTCTTTT GATTTATAAG GGATTTTGCC GATTTCGGAA
     CCACCATCAA ACAGGATTTT

7441 CGCCTGCTGG GGCAAACCAG CGTGGACCGC TTGCTGCAAC
     TCTCTCAGGG CCAGGCGGTG

7501 AAGGGCAATC AGCTGTTGCC CGTCTCACTG GTGAAAAGAA
     AAACCACCCT GGATCCAAGC

7561 TTGCAGGTGG CACTTTTCGG GGAAATGTGC GCGGAACCCC
     TATTTGTTTA TTTTTCTAAA

7621 TACATTCAAA TATGTATCCG CTCATGAGAC AATAACCCTG
     ATAAATGCTT CAATAATATT

7681 GAAAAAGGAA GAGTATGAGT ATTCAACATT TCCGTGTCGC
     CCTTATTCCC TTTTTTGCGG

7741 CATTTTGCCT TCCTGTTTTT GCTCACCCAG AAACGCTGGT
     GAAAGTAAAA GATGCTGAAG
```

TABLE 120B-continued

Sequence of MALIA3, condensed
LOCUS MALIA3 9532 CIRCULAR
ORIGIN

```
7801 ATCAGTTGGG CGCACGAGTG GGTTACATCG AACTGGATCT
     CAACAGCGGT AAGATCCTTG

7861 AGAGTTTTCG CCCCGAAGAA CGTTTTCCAA TGATGAGCAC
     TTTTAAAGTT CTGCTATGTC

7921 ATACACTATT ATCCCGTATT GACGCCGGGC AAGAGCAACT
     CGGTCGCCCG GCGCGGTATT

7981 CTCAGAATGA CTTGGTTGAG TACTCACCAG TCACAGAAAA
     GCATCTTACG GATGGCATGA

8041 CAGTAAGAGA ATTATGCAGT GCTGCCATAA CCATGAGTGA
     TAACACTGCG GCCAACTTAC

8101 TTCTGACAAC GATCGGAGGA CCGAAGGAGC TAACCGCTTT
     TTTGCACAAC ATGGGGGATC

8161 ATGTAACTCG CCTTGATCGT TGGGAACCCG AGCTGAATGA
     AGCCATACCA AACGACGAGC

8221 GTGACACCAC GATGCCTGTA GCAATGCCAA CAACGTTGCG
     CAAACTATTA ACTGGCGAAC

8281 TACTTACTCT AGCTTCCCGG CAACAATTAA TAGACTGGAT
     GGAGGCGGAT AAAGTTGCAG

8341 GACCACTTCT GCGCTCGGCC CTTCCGGCTG GCTGGTTTAT
     TGCTGATAAA TCTGGAGCCG

8401 GTGAGCGTGG GTCTCGCGGT ATCATTGCAG CACTGGGGCC
     AGATGGTAAG CCCTCCCGTA

8461 TCGTAGTTAT CTACACGACG GGGAGTCAGG CAACTATGGA
     TGAACGAAAT AGACAGATCG

8521 CTGAGATAGG TGCCTCACTG ATTAAGCATT GGTAACTGTC
     AGACCAAGTT TACTCATATA

8581 TACTTTAGAT TGATTTAAAA CTTCATTTTT AATTTAAAAG
     GATCTAGGTG AAGATCCTTT

8641 TTGATAATCT CATGACCAAA ATCCCTTAAC GTGAGTTTTC
     GTTCCACTGT ACCTAAGACC

8701 CCCAAGCTTG TCGACTGAAT GGCGAATGGC GCTTTGCCTG
     GTTTCCGGCA CCAGAAGCGG

8761 TGCCGGAAAG CTGGCTGGAG TGCGATCTTC CTGAGGCCGA
     TACTGTCGTC GTCCCCTCAA

8821 ACTGGCAGAT GCACGGTTAC GATGCGCCCA TCTACACCAA
     CGTAACCTAT CCCATTACGG

8881 TCAATCCGCC GTTTGTTCCC ACGGAGAATC CGACGGGTTG
     TTACTCGCTC ACATTTAATG

8941 TTGATGAAAG CTGGCTACAG GAAGGCCAGA CGCGAATTAT
     TTTTGATGGC GTTCCTATTG

9001 GTTAAAAAAT GAGCTGATTT AACAAAAATT TAACGCGAAT
     TTTAACAAAA TATTAACGTT

9061 TACAATTTAA ATATTTGCTT ATACAATCTT CCTGTTTTTG
     GGGCTTTTCT GATTATCAAC

9121 CGGGGTACAT ATGATTGACA TGCTAGTTTT ACGATTACCG
     TTCATCGATT CTCTTGTTTG

9181 CTCCAGACTC TCAGGCAATG ACCTGATAGC CTTTGTAGAT
     CTCTCAAAAA TAGCTACCCT

9241 CTCCGGCATG AATTTATCAG CTAGAACGGT TGAATATCAT
     ATTGATGGTG ATTTGACTCT

9301 CTCCGGCCTT TCTCACCCTT TTGAATCTTT ACCTACACAT
     TACTCAGGCA TTGCATTTAA

9361 AATATATGAG GGTTCTAAAA ATTTTTATCC TTGCGTTGAA
     ATAAAGGCTT CTCCCGCAAA

9421 AGTATTACAG GGTCATAATG TTTTTGGTAC AACCGATTTA
     GCTTTATGCT CTGAGGCTTT

9481 ATTGCTTAAT TTTGCTAATT CTTTGCCTTG CCTGTATGAT
     TTATTGGATG TT
```

TABLE 200

Enzymes that either cut 15 or more human GLGs or
have 5+-base recognition in FR3
Typical entry:

| REname | Recognition | #sites |
| --- | --- | --- |
| GLGid#:base# | GLGid#:base# | GLGid#:base#... |

BstEII    Ggtnacc    2
1:3    48:3
There are 2 hits at base# 3
MaeIII    gtnac    36
1:4    2:4    3:4    4:4    5:4    6:4
7:4    8:4    9:4    10:4    11:4    37:4
37:58    38:4    38:58    39:4    39:58    40:4
40:58    41:4    41:58    42:4    42:58    43:4
43:58    44:4    44:58    45:4    45:58    46:4
46:58    47:4    47:58    48:4    49:4    50:58
There are 24 hits at base# 4
Tsp45I    gtsac    33
1:4    2:4    3:4    4:4    5:4    6:4
7:4    8:4    9:4    10:4    11:4    37:4
37:58    38:4    38:58    39:4    39:58    40:58
41:58    42:58    43:4    43:58    44:4    44:58
45:4    45:58    46:4    46:58    47:4    47:58
48:4    49:4    50:58
There are 21 hits at base# 4
HphI    tcacc    45
1:5    2:5    3:5    4:5    5:5    6:5
7:5    8:5    11:5    12:5    12:11    13:5
14:5    15:5    16:5    17:5    18:5    19:5
20:5    21:5    22:5    23:5    24:5    25:5
26:5    27:5    28:5    29:5    30:5    31:5
32:5    33:5    34:5    35:5    36:5    37:5
38:5    40:5    43:5    44:5    45:5    46:5
47:5    48:5    49:5
There are 44 hits at base# 5
NlaIII    CATG    26
1:9    1:42    2:42    3:9    3:42    4:9
4:42    5:9    5:42    6:42    6:78    7:9
7:42    8:21    8:42    9:42    10:42    11:42
12:57    13:48    13:57    14:57    31:72    38:9
48:78    49:78
There are 11 hits at base# 42
There are 1 hits at base# 48 Could cause raggedness.
BsaJI    Ccnngg    37
1:14    2:14    5:14    6:14    7:14    8:14
8:65    9:14    10:14    11:14    12:14    13:14
14:14    15:65    17:14    17:65    18:65    19:65
20:65    21:65    22:65    26:65    29:65    30:65
33:65    34:65    35:65    37:65    38:65    39:65
40:65    42:65    43:65    48:65    49:65    50:65
51:14
There are 23 hits at base# 65
There are 14 hits at base# 14
AluI    AGct    42
1:47    2:47    3:47    4:47    5:47    6:47
7:47    8:47    9:47    10:47    11:47    16:63
23:63    24:63    25:63    31:63    32:63    36:63
<u>37:47</u>    <u>37:52</u>    <u>38:47</u>    <u>38:52</u>    <u>39:47</u>    <u>39:52</u>

TABLE 200-continued

Enzymes that either cut 15 or more human GLGs or have 5+-base recognition in FR3
Typical entry:

| REname | Recognition | #sites | | | |
|---|---|---|---|---|---|
| GLGid#:base# | GLGid#:base# | GLGid#:base#... | | | |
| 40:47 | 40:52 | 41:47 | 41:52 | 42:47 | 42:52 |
| 43:47 | 43:52 | 44:47 | 44:52 | 45:47 | 45:52 |
| 46:47 | 46:52 | 47:47 | 47:52 | 49:15 | 50:47 |

There are 23 hits at base# 47
There are 11 hits at base# 52 Only 5 bases from 47

| BlpI | GCtnagc | 21 | | | |
|---|---|---|---|---|---|
| 1:48 | 2:48 | 3:48 | 5:48 | 6:48 | 7:48 |
| 8:48 | 9:48 | 10:48 | 11:48 | 37:48 | 38:48 |
| 39:48 | 40:48 | 41:48 | 42:48 | 43:48 | 44:48 |
| 45:48 | 46:48 | 47:48 | | | |

There are 21 hits at base# 48

| MwoI | GCNNNNNnngc | 19 | | | |
|---|---|---|---|---|---|
| 1:48 | 2:28 | 19:36 | 22:36 | 23:36 | 24:36 |
| 25:36 | 26:36 | 35:36 | 37:67 | 39:67 | 40:67 |
| 41:67 | 42:67 | 43:67 | 44:67 | 45:67 | 46:67 |
| 47:67 | | | | | |

There are 10 hits at base# 67
There are 7 hits at base# 36

| DdeI | Ctnag | 71 | | | |
|---|---|---|---|---|---|
| 1:49 | 1:58 | 2:49 | 2:58 | 3:49 | 3:58 |
| 3:65 | 4:49 | 4:58 | 5:49 | 5:58 | 5:65 |
| 6:49 | 6:58 | 6:65 | 7:49 | 7:58 | 7:65 |
| 8:49 | 8:58 | 9:49 | 9:58 | 9:65 | 10:49 |
| 10:58 | 10:65 | 11:49 | 11:58 | 11:65 | 15:58 |
| 16:58 | 16:65 | 17:58 | 18:58 | 20:58 | 21:58 |
| 22:58 | 23:58 | 23:65 | 24:58 | 24:65 | 25:58 |
| 25:65 | 26:58 | 27:58 | 27:65 | 28:58 | 30:58 |
| 31:58 | 31:65 | 32:58 | 32:65 | 35:58 | 36:58 |
| 36:65 | 37:49 | 38:49 | 39:26 | 39:49 | 40:49 |
| 41:49 | 42:26 | 42:49 | 43:49 | 44:49 | 45:49 |
| 46:49 | 47:49 | 48:12 | 49:12 | 51:65 | |

There are 29 hits at base# 58
There are 22 hits at base# 49 Only nine base from 58
There are 16 hits at base# 65 Only seven bases from 58

| BglII | Agatct | 11 | | | |
|---|---|---|---|---|---|
| 1:61 | 2:61 | 3:61 | 4:61 | 5:61 | 6:61 |
| 7:61 | 9:61 | 10:61 | 11:61 | 51:47 | |

There are 10 hits at base# 61

| BstYI | Rgatcy | 12 | | | |
|---|---|---|---|---|---|
| 1:61 | 2:61 | 3:61 | 4:61 | 5:61 | 6:61 |
| 7:61 | 8:61 | 9:61 | 10:61 | 11:61 | 51:47 |

There are 11 hits at base# 61

| Hpyl88I | TCNga | 17 | | | |
|---|---|---|---|---|---|
| 1:64 | 2:64 | 3:64 | 4:64 | 5:64 | 6:64 |
| 7:64 | 8:64 | 9:64 | 10:64 | 11:64 | 16:57 |
| 20:57 | 27:57 | 35:57 | 48:67 | 49:67 | |

There are 11 hits at base# 64
There are 4 hits at base# 57
There are 2 hits at base# 67 Could be ragged.

| MslI | CAYNNnnRTG | 44 | | | |
|---|---|---|---|---|---|
| 1:72 | 2:72 | 3:72 | 4:72 | 5:72 | 6:72 |
| 7:72 | 8:72 | 9:72 | 10:72 | 11:72 | 15:72 |
| 17:72 | 18:72 | 19:72 | 21:72 | 23:72 | 24:72 |
| 25:72 | 26:72 | 28:72 | 29:72 | 30:72 | 31:72 |
| 32:72 | 33:72 | 34:72 | 35:72 | 36:72 | 37:72 |
| 38:72 | 39:72 | 40:72 | 41:72 | 42:72 | 43:72 |
| 44:72 | 45:72 | 46:72 | 47:72 | 48:72 | 49:72 |
| 50:72 | 51:72 | | | | |

There are 44 hits at base# 72

| BsiEI | CGRYcg | 23 | | | |
|---|---|---|---|---|---|
| 1:74 | 3:74 | 4:74 | 5:74 | 7:74 | 8:74 |
| 9:74 | 10:74 | 11:74 | 17:74 | 22:74 | 30:74 |
| 33:74 | 34:74 | 37:74 | 38:74 | 39:74 | 40:74 |
| 41:74 | 42:74 | 45:74 | 46:74 | 47:74 | |

There are 23 hits at base# 74

| EaeI | Yggccr | 23 | | | |
|---|---|---|---|---|---|
| 1:74 | 3:74 | 4:74 | 5:74 | 7:74 | 8:74 |
| 9:74 | 10:74 | 11:74 | 17:74 | 22:74 | 30:74 |
| 33:74 | 34:74 | 37:74 | 38:74 | 39:74 | 40:74 |
| 41:74 | 42:74 | 45:74 | 46:74 | 47:74 | |

There are 23 hits at base# 74

| EagI | Cggccg | 23 | | | |
|---|---|---|---|---|---|
| 1:74 | 3:74 | 4:74 | 5:74 | 7:74 | 8:74 |
| 9:74 | 10:74 | 11:74 | 17:74 | 22:74 | 30:74 |
| 33:74 | 34:74 | 37:74 | 38:74 | 39:74 | 40:74 |
| 41:74 | 42:74 | 45:74 | 46:74 | 47:74 | |

There are 23 hits at base# 74

| HaeIII | GGcc | 27 | | | |
|---|---|---|---|---|---|
| 1:75 | 3:75 | 4:75 | 5:75 | 7:75 | 8:75 |
| 9:75 | 10:75 | 11:75 | 16:75 | 17:75 | 20:75 |
| 22:75 | 30:75 | 33:75 | 34:75 | 37:75 | 38:75 |
| 39:75 | 40:75 | 41:75 | 42:75 | 45:75 | 46:75 |
| 47:75 | 48:63 | 49:63 | | | |

There are 25 hits at base# 75

| Bst4CI | ACNgt 65° C. | 63 | | Sites There is a third isoschimser | |
|---|---|---|---|---|---|
| 1:86 | 2:86 | 3:86 | 4:86 | 5:86 | 6:86 |
| 7:34 | 7:86 | 8:86 | 9:86 | 10:86 | 11:86 |
| 12:86 | 13:86 | 14:86 | 15:36 | 15:86 | 16:53 |
| 16:86 | 17:36 | 17:86 | 18:86 | 19:86 | 20:53 |
| 20:86 | 21:36 | 21:86 | 22:0 | 22:86 | 23:86 |
| 24:86 | 25:86 | 26:86 | 27:53 | 27:86 | 28:36 |
| 28:86 | 29:86 | 30:86 | 31:86 | 32:86 | 33:36 |
| 33:86 | 34:86 | 35:53 | 35:86 | 36:86 | 37:86 |
| 38:86 | 39:86 | 40:86 | 41:86 | 42:86 | 43:86 |
| 44:86 | 45:86 | 46:86 | 47:86 | 48:86 | 49:86 |
| 50:86 | 51:0 | 51:86 | | | |

There are 51 hits at base# 86 All the other sites are well away

| HpyCH4III | ACNgt | 63 | | | |
|---|---|---|---|---|---|
| 1:86 | 2:86 | 3:86 | 4:86 | 5:86 | 6:86 |
| 7:34 | 7:86 | 8:86 | 9:86 | 10:86 | 11:86 |
| 12:86 | 13:86 | 14:86 | 15:36 | 15:86 | 16:53 |
| 16:86 | 17:36 | 17:86 | 18:86 | 19:86 | 20:53 |
| 20:86 | 21:36 | 21:86 | 22:0 | 22:86 | 23:86 |
| 24:86 | 25:86 | 26:86 | 27:53 | 27:86 | 28:36 |
| 28:86 | 29:86 | 30:86 | 31:86 | 32:86 | 33:36 |
| 33:86 | 34:86 | 35:53 | 35:86 | 36:86 | 37:86 |
| 38:86 | 39:86 | 40:86 | 41:86 | 42:86 | 43:86 |
| 44:86 | 45:86 | 46:86 | 47:86 | 48:86 | 49:86 |
| 50:86 | 51:0 | 51:86 | | | |

There are 51 hits at base# 86

| HinfI | Gantc | 43 | | | |
|---|---|---|---|---|---|
| 2:2 | 3:2 | 4:2 | 5:2 | 6:2 | 7:2 |
| 8:2 | 9:2 | 9:22 | 10:2 | 11:2 | 15:2 |
| 16:2 | 17:2 | 18:2 | 19:2 | 19:22 | 20:2 |
| 21:2 | 23:2 | 24:2 | 25:2 | 26:2 | 27:2 |
| 28:2 | 29:2 | 30:2 | 31:2 | 32:2 | 33:2 |
| 33:22 | 34:22 | 35:2 | 36:2 | 37:2 | 38:2 |
| 40:2 | 43:2 | 44:2 | 45:2 | 46:2 | 47:2 |
| 50:60 | | | | | |

There are 38 hits at base# 2

| MlyI | GAGTCNNNNNn | 18 | | | |
|---|---|---|---|---|---|
| 2:2 | 3:2 | 4:2 | 5:2 | 6:2 | 7:2 |
| 8:2 | 9:2 | 10:2 | 11:2 | 37:2 | 38:2 |
| 40:2 | 43:2 | 44:2 | 45:2 | 46:2 | 47:2 |

There are 18 hits at base# 2

| PleI | gagtc | 18 | | | |
|---|---|---|---|---|---|
| 2:2 | 3:2 | 4:2 | 5:2 | 6:2 | 7:2 |
| 8:2 | 9:2 | 10:2 | 11:2 | 37:2 | 38:2 |
| 40:2 | 43:2 | 44:2 | 45:2 | 46:2 | 47:2 |

There are 18 hits at base# 2

| AciI | Ccgc | 24 | | | |
|---|---|---|---|---|---|
| 2:26 | 9:14 | 10:14 | 11:14 | 27:74 | 37:62 |
| 37:65 | 38:62 | 39:65 | 40:62 | 40:65 | 41:65 |
| 42:65 | 43:62 | 43:65 | 44:62 | 44:65 | 45:62 |
| 46:62 | 47:62 | 47:65 | 48:35 | 48:74 | 49:74 |

There are 8 hits at base# 62
There are 8 hits at base# 65
There are 3 hits at base# 14
There are 3 hits at base# 74
There are 1 hits at base# 26
There are 1 hits at base# 35

| -"- | Gcgg | 11 | | | |
|---|---|---|---|---|---|
| 8:91 | 9:16 | 10:16 | 11:16 | 37:67 | 39:67 |
| 40:67 | 42:67 | 43:67 | 45:67 | 46:67 | |

There are 7 hits at base# 67

TABLE 200-continued

Enzymes that either cut 15 or more human GLGs or have 5+-base recognition in FR3
Typical entry:

| REname | Recognition | #sites | | | |
|---|---|---|---|---|---|
| GLGid#:base# | GLGid#:base# | GLGid#:base#... | | | |

There are 3 hits at base# 16
There are 1 hits at base# 91
BsiHKAI    GWGCWc    20
2:30    4:30    6:30    7:30    9:30    10:30
12:89   13:89   14:89   37:51   38:51   39:51
40:51   41:51   42:51   43:51   44:51   45:51
46:51   47:51
There are 11 hits at base# 51
Bsp1286I   GDGCHc    20
2:30    4:30    6:30    7:30    9:30    10:30
12:89   13:89   14:89   37:51   38:51   39:51
40:51   41:51   42:51   43:51   44:51   45:51
46:51   47:51
There are 11 hits at base# 51
HgiAI    GWGCWc    20
2:30    4:30    6:30    7:30    9:30    10:30
12:89   13:89   14:89   37:51   38:51   39:51
40:51   41:51   42:51   43:51   44:51   45:51
46:51   47:51
There are 11 hits at base# 51
BsoFI    GCngc    26
2:53    3:53    5:53    6:53    7:53    8:53
8:91    9:53    10:53   11:53   31:53   36:36
37:64   39:64   40:64   41:64   42:64   43:64
44:64   45:64   46:64   47:64   48:53   49:53
50:45   51:53
There are 13 hits at base# 53
There are 10 hits at base# 64
TseI    Gcwgc    17
2:53    3:53    5:53    6:53    7:53    8:53
9:53    10:53   11:53   31:53   36:36   45:64
46:64   48:53   49:53   50:45   51:53
There are 13 hits at base# 53
MnlI    gagg    34
3:67    3:95    4:51    5:16    5:67    6:67
7:67    8:67    9:67    10:67   11:67   15:67
16:67   17:67   19:67   20:67   21:67   22:67
23:67   24:67   25:67   26:67   27:67   28:67
29:67   30:67   31:67   32:67   33:67   34:67
35:67   36:67   50:67   51:67
There are 31 hits at base# 67
HpyCH4V    TGca    34
5:90    6:90    11:90   12:90   13:90   14:90
15:44   16:44   16:90   17:44   18:90   19:44
20:44   21:44   22:44   23:44   24:44   25:44
26:44   27:44   27:90   28:44   29:44   33:44
34:44   35:44   35:90   36:38   48:44   49:44
50:44   50:90   51:44   51:52
There are 21 hits at base# 44
There are 1 hits at base# 52

AccI    GTmkac    13    5-base recognition
7:37    11:24   37:16   38:16   39:16   40:16
41:16   42:16   43:16   44:16   45:16   46:16
47:16
There are 11 hits at base# 16
SacII    CCGCgg    8    6-base recognition
9:14    10:14   11:14   37:65   39:65   40:65
42:65   43:65
There are 5 hits at base# 65
There are 3 hits at base# 14
TfiI    Gawtc    24
9:22    15:2    16:2    17:2    18:2    19:2
19:22   20:2    21:2    23:2    24:2    25:2
26:2    27:2    28:2    29:2    30:2    31:2
32:2    33:2    33:22   34:22   35:2    36:2
There are 20 hits at base# 2
BsmAI    Nnnnnngagac    19
15:11   16:11   20:11   21:11   22:11   23:11
24:11   25:11   26:11   27:11   28:11   28:56
30:11   31:11   32:11   35:11   36:11   44:87
48:87
There are 16 hits at base# 11
BpmI    ctccag    19
15:12   16:12   17:12   18:12   20:12   21:12
22:12   23:12   24:12   25:12   26:12   27:12
28:12   30:12   31:12   32:12   34:12   35:12
36:12
There are 19 hits at base# 12
XmnI    GAANNnnttc    12
37:30   38:30   39:30   40:30   41:30   42:30
43:30   44:30   45:30   46:30   47:30   50:30
There are 12 hits at base# 30
BsrI    NCcagt    12
37:32   38:32   39:32   40:32   41:32   42:32
43:32   44:32   45:32   46:32   47:32   50:32
There are 12 hits at base# 32
BanII    GRGCYc    11
37:51   38:51   39:51   40:51   41:51   42:51
43:51   44:51   45:51   46:51   47:51
There are 11 hits at base# 51
Ec1136I    GAGctc    11
37:51   38:51   39:51   40:51   41:51   42:51
43:51   44:51   45:51   46:51   47:51
There are 11 hits at base# 51
SacI    GAGCTc    11
37:51   38:51   39:51   40:51   41:51   42:51
43:51   44:51   45:51   46:51   47:51
There are 11 hits at base# 51

TABLE 206

Synthetic 3.23 FR3 of human heavy chains showning positions of possible cleavage sites

```
!Sites engineered into the synthetic gene are shown in upper case DNA
!with the RE name between vertical bars (as in | XbaI |).
!RERSs frequently found in GLGs are shown below the synthetic sequence
!with the name to the right (as in gtn ac = MaeIII(24), indicating that
!24 of the 51 GLGs contain the site).
!
!                                                    |---FR3---
!
!                                                    89  90    (codon # in
!
                                                     R   F     synthetic 3-23)
```

TABLE 206-continued

Synthetic 3.23 FR3 of human heavy chains showing positions of possible cleavage sites

```
                                                |cgc|ttc| 6
!Allowed DNA                                    |cgn|tty|
!                                               |agr|
!                                                ga ntc = HinfI(38)
!                                                ga gtc = PleI(18)
!                                                ga wtc = TfiI(20)
!                                                 gtn ac = MaeIII(24)
!                                                 gts ac = Tsp45I(21)
!                                                  tc acc = HphI(44)
!        --------FR3---------------------------------------------
!         91  92  93  94  95  96  97  98  99 100 101 102 103 104 105
!          T   I   S   R   D   N   K   N   T   L   Y   L   Q   M
           |act|atc|TCT|AGA|gac|aac|tct|aag|aat|act|ctc|tac|ttg|cag|atg|51
!allowed|acn|ath|tcn|cgn|gay|aay|tcn|aar|aay|acn|ttr|tay|ttr|car|atg|
!              |agy|agr|         |agy|             |ctn|   |ctn|
!              |  ga|gac = BsmAI(16)                ag ct = AluI(23)
!            c|tcc ag = BpmI(19)                  g ctn agc = BlpI(21)
!              |       |        g aan nnn ttc = XmnI(12)
!              | XbaI  |                          tg ca = HpyCH4V(21)
!        ---FR3------------------------------------------------>|
!        106 107 108 109 110 111 112 113 114 115 116 117 118 119 120
!          N   S   L   R   A   E   D   T   A   V   Y   Y   C   A   K
           |aac|agC|TTA|AGg|gct|gag|gac|aCT|GCA|Gtc|tac|tat|tgc|gct|aaa|  96
!allowed|aay|tcn|ttr|cgn|gcn|gar|gay|acn|gcn|gtn|tay|tay|tgy|gcn|aar|
!          |agy|ctn|agr|              |       |
!              |   |  cc nng g = BsaJI(23)       ac ngt = Bst4CI(51)
!              |  aga tct = BglII(10)     |     ac ngt = HpyCH4III(51)
!              | Rga tcY = BstYI(11)      |     ac ngt = TaaI(51)
!              |   |         c ayn nnn rtc = MslI(44)
!              |   |              cg ryc g = BsiEI(23)
!              |   |              yg gcc r = EaeI(23)
!              |   |              cg gcc g = EagI(23)
!              |   |              |g gcc = HaeIII(25)
!              |   |         gag g = MnlI(31)|
!              |AflII |          | PstI |
```

TABLE 217

Human HC GLG FR1 Sequences
VH Exon - Nucleotide sequence alignment

VH1
1-02   CAG GTG CAG CTG GTG CAG TCT GGG GCT GAG GTG
       AAG AAG CCT GGG GCC TCA GTG AAG

GTC TCC TGC AAG GCT TCT GGA TAC ACC TTC ACC 1-03   cag gtC cag ctT gtg cag tct ggg gct gag gtg
       aag aag cct ggg gcc tca gtg aag gtT tcc tgc aag gct tct gga tac acc ttc acT 1-08   cag gtg cag ctg gtg cag tct ggg gct gag gtg
       aag aag cct ggg gcc tca gtg aag gtc tcc tgc aag gct tct gga tac acc ttc acc 1-18   cag gtT cag ctg gtg cag tct ggA gct gag gtg
       aag aag cct ggg gcc tca gtg aag gtc tcc tgc aag gct tct ggT tac acc ttT acc 1-24   cag gtC cag ctg gtA cag tct ggg gct gag gtg
       aag aag cct ggg gcc tca gtg aag gtc tcc tgc aag gTt tcC gga tac acc Ctc acT 1-45   cag Atg cag ctg gtg cag tct ggg gct gag gtg
       aag aag Act ggg Tcc tca gtg aag gtT tcc tgc aag gct tcC gga tac acc ttc acc 1-46   cag gtg cag ctg gtg cag tct ggg gct gag gtg
       aag aag cct ggg gcc tca gtg aag gtT tcc tgc aag gcA tct gga tac acc ttc acc 1-58   caA Atg cag ctg gtg cag tct ggg Cct gag gtg
       aag aag cct ggg Acc tca gtg aag gtc tcc tgc aag gct tct gga tTc acc ttT acT 1-69   cag gtg cag ctg gtg cag tct ggg gct gag gtg
       aag aag cct ggg Tcc tcG gtg aag gtc tcc tgc aag gct tct gga GGc acc ttc aGc 1-e    cag gtg cag ctg gtg cag tct ggg gct gag gtg
       aag aag cct ggg Tcc tcG gtg aag gtc tcc tgc aag gct tct gga GGc acc ttc aGc 1-f    Gag gtC cag ctg gtA cag tct ggg gct gag gtg
       aag aag cct ggg gcT Aca gtg aaA Atc tcc tgc aag gTt tct gga tac acc ttc acc VH2
2-05   CAG ATC ACC TTG AAG GAG TCT GGT CCT ACG CTG
       GTG AAA CCC ACA CAG ACC CTC ACG

CTG ACC TGC ACC TTC TCT GGG TTC TCA CTC AGC 2-26   cag Gtc acc ttg aag gag tct ggt cct GTg ctg
       gtg aaa ccc aca Gag acc ctc acg ctg acc tgc acc Gtc tct ggg ttc tca ctc agc 2-70   cag Gtc acc ttg aag gag tct ggt cct Gcg ctg
       gtg aaa ccc aca cag acc ctc acA ctg acc tgc acc ttc tct ggg ttc tca ctc agc VH3
3-07   GAG GTG CAG CTG GTG GAG TCT GGG GGA GGC TTG
       GTC CAG CCT GGG GGG TCC CTG AGA

CTC TCC TGT GCA GCC TCT GGA TTC ACC TTT AGT 3-09   gaA gtg cag ctg gtg gag tct ggg gga ggc ttg
       gtA cag cct ggC Agg tcc ctg aga ctc tcc tgt gca gcc tct gga ttc acc ttt GAt 3-11   Cag gtg cag ctg gtg gag tct ggg gga ggc ttg
       gtc Aag cct ggA ggg tcc ctg aga ctc tcc tgt gca gcc tct gga ttc acc ttC agt 3-13   gag gtg cag ctg gtg gag tct ggg gga ggc ttg
       gtA cag cct ggg ggg tcc ctg aga ctc tcc tgt gca gcc tct gga ttc acc ttC agt 3-15   gag gtg cag ctg gtg gag tct ggg gga ggc ttg
       gtA Aag cct ggg ggg tcc ctT aga ctc tcc tgt gca gcc tct gga ttc acT ttC agt 3-20   gag gtg cag ctg gtg gag tct ggg gga ggT Gtg
       gtA cGg cct ggg ggg tcc ctg aga ctc tcc tgt gca gcc tct gga ttc acc ttt GAt 3-21   gag gtg cag ctg gtg gag tct ggg gga ggc Ctg
       gtc Aag cct ggg ggg tcc ctg aga ctc tcc tgt gca gcc tct gga ttc acc ttC agt 3-23   gag gtg cag ctg Ttg gag tct ggg gga agc ttg
       gtA cag cct ggg ggg tcc ctg aga ctc tcc tgt gca gcc tct gga ttc acc ttt agC 3-30   Cag gtg cag ctg gtg gag tct ggg gga ggc Gtg
       ctc cag cct ggg Agg tcc ctg aga ctc tcc tgt gca gcc tct gga ttc acc ttC agt 3-30.3 Cag gtg cag ctg gtg gag tct ggg gga ggc Gtg
       gtc cag cct ggg Agg tcc ctg aga ctc tcc tgt gca gcc tct gga ttc acc ttC agt 3-30.5 Cag gtg cag ctg gtg gag tct ggg gga ggc Gtg
       gtc cag cct ggg Agg tcc ctg aga ctc tcc tgt gca gcc tct gga ttc acc ttC agt 3-33   Cag gtg cag ctg gtg gag tct ggg gga ggc Gtg
       gtc cag cct ggg Agg tcc ctg aga ctc tcc tgt gca gcG tct gga ttc acc ttC agt 3-43   gaA gtg cag ctg gtg gag tct ggg gga gTc Gtg
       gtA cag cct ggg ggg tcc ctg aga ctc tcc tgt gca gcc tct gga ttc acc ttt GAt 3-48   gag gtg cag ctg gtg gag tct ggg gga ggc ttg
       gtA cag cct ggg ggg tcc ctg aga ctc tcc tgt gca gcc tct gga ttc acc ttC agt 3-49   gag gtg cag ctg gtg gag tct ggg gga ggc ttg
       gtA cag ccA ggg Cgg tcc ctg aga ctc tcc tgt Aca gcT tct gga ttc acc ttt Ggt 3-53   gag gtg cag ctg gtg gag Act ggA gga ggc ttg
       Atc cag cct ggg ggg tcc ctg aga ctc tcc tgt gca gcc tct ggG ttc acc GtC agt

TABLE 217-continued

Human HC GLG FR1 Sequences
VH Exon - Nucleotide sequence alignment 3-64  gag gtg cag ctg gtg gag tct ggg gga ggc ttg
      gtc cag cct ggg ggg tcc ctg aga ctc tcc tgt gca gcc tct gga ttc acc ttC agt 3-66  gag gtg cag ctg gtg gag tct ggg gga ggc ttg
      gtc cag cct ggg ggg tcc ctg aga ctc tcc tgt gca gcc tct gga ttc acc GtC agt 3-72  gag gtg cag ctg gtg gag tct ggg gga ggc ttg
      gtc cag cct ggA ggg tcc ctg aga ctc tcc tgt gca gcc tct gga ttc acc ttC agt 3-73  gag gtg cag ctg gtg gag tct ggg gga ggc ttg
      gtc cag cct ggg ggg tcc ctg aAa ctc tcc tgt gca gcc tct ggG ttc acc ttC agt 3-74  gag gtg cag ctg gtg gag tcC ggg gga ggc ttA
      gtT cag cct ggg ggg tcc ctg aga ctc tcc tgt gca gcc tct gga ttc acc ttC agt 3-d   gag gtg cag ctg gtg gag tct Cgg gga gTc ttg
      gtA cag cct ggg ggg tcc ctg aga ctc tcc tgt gca gcc tct gga ttc acc GtC agt VH4
4-04  CAG GTG CAG CTG CAG GAG TCG GGC CCA GGA CTG
      GTG AAG CCT TCG GGG ACC CTG TCC

CTC ACC TGC GCT GTC TCT GGT GGC TCC ATC AGC 4-28  cag gtg cag ctg cag gag tcg ggc cca gga ctg
      gtg aag cct tcg gAC acc ctg tcc ctc acc tgc gct gtc tct ggt TAc tcc atc agc 4-30.1 cag gtg cag ctg cag gag tcg ggc cca gga ctg
       gtg aag cct tcA CAg acc ctg tcc ctc acc tgc Act gtc tct ggt ggc tcc atc agc 4-30.2 cag Ctg cag ctg cag gag tcC ggc Tca gga ctg
       gtg aag cct tcA CAg acc ctg tcc ctc acc tgc gct gtc tct ggt ggc tcc atc agc 4-30.4 cag gtg cag ctg cag gag tcg ggc cca gga ctg
       gtg aag cct tcA CAg acc ctg tcc ctc acc tgc Act gtc tct ggt ggc tcc atc agc 4-31  cag gtg cag ctg cag gag tcg ggc cca gga ctg
      gtg aag cct tcA CAg acc ctg tcc ctc acc tgc Act gtc tct ggt ggc tcc atc agc 4-34  cag gtg cag ctA cag Cag tGg ggc Gca gga ctg
      Ttg aag cct tcg gAg acc ctg tcc ctc acc tgc gct gtc tAt ggt ggG tcc Ttc agT 4-39  cag Ctg cag ctg cag gag tcg ggc cca gga ctg
      gtg aag cct tcg gAg acc ctg tcc ctc acc tgc Act gtc tct ggt ggc tcc atc agc 4-59  cag gtg cag ctg cag gag tcg ggc cca gga ctg
      gtg aag cct tcg gAg acc ctg tcc ctc acc tgc Act gtc tct ggt ggc tcc atc agT 4-61  cag gtg cag ctg cag gag tcg ggc cca gga ctg
      gtg aag cct tcg gAg acc ctg tcc ctc acc tgc Act gtc tct ggt ggc tcc Gtc agc 4-b   cag gtg cag ctg cag gag tcg ggc cca gga ctg
      gtg aag cct tcg gAg acc ctg tcc ctc acc tgc gct gtc tct ggt TAc tcc atc agc VH5
5-51  GAG GTG CAG CTG GTG CAG TCT GGA GCA GAG GTG
      AAA AAG CCC GGG GAG TCT CTG AAG

ATC TCC TGT AAG GGT TCT GGA TAC AGC TTT ACC 5-a   gaA gtg cag ctg gtg cag tct gga gca gag gtg
      aaa aag ccc ggg gag tct ctg aGg atc tcc tgt aag ggt tct gga tac agc ttt acc VH6
6-1   CAG GTA CAG CTG CAG CAG TCA GGT CCA GGA CTG
      GTG AAG CCC TCG CAG ACC CTC TCA

CTC ACC TGT GCC ATC TCC GGG GAC AGT GTC TCT

VH7
7-4.1 CAG GTG CAG CTG GTG CAA TCT GGG TCT GAG TTG
      AAG AAG CCT GGG GCC TCA GTG AAG

GTT TCC TGC AAG GCT TCT GGA TAC ACC TTC ACT

TABLE 220

RERS sites in Human HC GLG FR1s where there are at least 20 GLGs cut

BsgI            GTGCAG          71 (cuts 16/14 bases to right)
 1:4    1:13    2:13    3:4     3:13    4:13
 6:13   7:4     7:13    8:13    9:4     9:13
10:4   10:13   15:4    15:65   16:4    16:65
17:4   17:65   18:4    18:65   19:4    19:65
20:4   20:65   21:4    21:65   22:4    22:65
23:4   23:65   24:4    24:65   25:4    25:65
26:4   26:65   27:4    27:65   28:4    28:65
29:4   30:4    30:65   31:4    31:65   32:4
32:65  33:4    33:65   34:4    34:65   35:4
35:65  36:4    36:65   37:4    38:4    39:4
41:4   42:4    43:4    45:4    46:4    47:4
48:4   48:13   49:4    49:13   51:4
There are 39 hits at base# 4
There are 21 hits at base# 65
-"-             ctgcac          9
12:63  13:63   14:63   39:63   41:63   42:63
44:63  45:63   46:63
BbvI            GCAGC           65
 1:6    3:6     6:6     7:6     8:6     9:6
10:6   15:6    15:67   16:6    16:67   17:6
17:67  18:6    18:67   19:6    19:67   20:6
20:67  21:6    21:67   22:6    22:67   23:6
23:67  24:6    24:67   25:6    25:67   26:6
26:67  27:6    27:67   28:6    28:67   29:6
30:6   30:67   31:6    31:67   32:6    32:67
33:6   33:67   34:6    34:67   35:6    35:67
36:6   36:67   37:6   38:6   39:6   40:6
41:6   42:6   43:6    44:6   45:6   46:6
47:6   48:6    49:6    50:12  51:6
There are 43 hits at base# 6 Bolded sites very near sites
listed below
There are 21 hits at base# 67
-"-             gctgc           13
37:9   38:9    39:9    40:3    40:9    41:9
42:9   44:3    44:9    45:9    46:9    47:9

TABLE 220-continued

RERS sites in Human HC GLG FR1s where there are at least 20 GLGs cut

50:9
There are 11 hits at base# 9
BsoFI         GCngc          78
| | | | | | |
|---|---|---|---|---|---|
| 1:6 | 3:6 | 6:6 | 7:6 | 8:6 | 9:6 |
| 10:6 | 15:6 | 15:67 | 16:6 | 16:67 | 17:6 |
| 17:67 | 18:6 | 18:67 | 19:6 | 19:67 | 20:6 |
| 20:67 | 21:6 | 21:67 | 22:6 | 22:67 | 23:6 |
| 23:67 | 24:6 | 24:67 | 25:6 | 25:67 | 26:6 |
| 26:67 | 27:6 | 27:67 | 28:6 | 28:67 | 29:6 |
| 30:6 | 30:67 | 31:6 | 31:67 | 32:6 | 32:67 |
| 33:6 | 33:67 | 34:6 | 34:67 | 35:6 | 35:67 |
| 36:6 | 36:67 | _37:6_ | _37:9_ | _38:6_ | _38:9_ |
| 39:6 | 39:9 | _40:3_ | _40:6_ | _40:9_ | 41:6 |
| 41:9 | 42:6 | 42:9 | 43:6 | _44:3_ | _44:6_ |
| _44:9_ | _45:6_ | _45:9_ | _46:6_ | _46:9_ | _47:6_ |
| _47:9_ | 48:6 | 49:6 | 50:9 | 50:12 | 51:6 |

There are 43 hits at base# 6 These often occur together.
There are 11 hits at base# 9
There are 2 hits at base# 3
There are 21 hits at base# 67
TseI          Gcwgc          78
| | | | | | |
|---|---|---|---|---|---|
| 1:6 | 3:6 | 6:6 | 7:6 | 8:6 | 9:6 |
| 10:6 | 15:6 | 15:67 | 16:6 | 16:67 | 17:6 |
| 17:67 | 18:6 | 18:67 | 19:6 | 19:67 | 20:6 |
| 20:67 | 21:6 | 21:67 | 22:6 | 22:67 | 23:6 |
| 23:67 | 24:6 | 24:67 | 25:6 | 25:67 | 26:6 |
| 26:67 | 27:6 | 27:67 | 28:6 | 28:67 | 29:6 |
| 30:6 | 30:67 | 31:6 | 31:67 | 32:6 | 32:67 |
| 33:6 | 33:67 | 34:6 | 34:67 | 35:6 | 35:67 |
| 36:6 | 36:67 | _37:6_ | _37:9_ | _38:6_ | _38:9_ |
| _39:6_ | _39:9_ | _40:3_ | _40:6_ | _40:9_ | _41:6_ |
| _41:9_ | _42:6_ | _42:9_ | 43:6 | _44:3_ | _44:6_ |
| _44:9_ | _45:6_ | _45:9_ | _46:6_ | _46:9_ | _47:6_ |
| _47:9_ | 48:6 | 49:6 | _50:9_ | _50:12_ | 51:6 |

There are 43 hits at base# 6 Often together.
There are 11 hits at base# 9
There are 2 hits at base# 3
There are 1 hits at base# 12
There are 21 hits at base# 67
MspAlI        CMGckg         48
| | | | | | |
|---|---|---|---|---|---|
| 1:7 | 3:7 | 4:7 | 5:7 | 6:7 | 7:7 |
| 8:7 | 9:7 | 10:7 | 11:7 | 15:7 | 16:7 |
| 17:7 | 18:7 | 19:7 | 20:7 | 21:7 | 22:7 |
| 23:7 | 24:7 | 25:7 | 26:7 | 27:7 | 28:7 |
| 29:7 | 30:7 | 31:7 | 32:7 | 33:7 | 34:7 |
| 35:7 | 36:7 | 37:7 | 38:7 | 39:7 | _40:1_ |
| _40:7_ | 41:7 | 42:7 | _44:1_ | _44:7_ | 45:7 |
| 46:7 | 47:7 | 48:7 | 49:7 | 50:7 | 51:7 |

There are 46 hits at base# 7
PvuII         CAGctg         48
| | | | | | |
|---|---|---|---|---|---|
| 1:7 | 3:7 | 4:7 | 5:7 | 6:7 | 7:7 |
| 8:7 | 9:7 | 10:7 | 11:7 | 15:7 | 16:7 |
| 17:7 | 18:7 | 19:7 | 20:7 | 21:7 | 22:7 |
| 23:7 | 24:7 | 25:7 | 26:7 | 27:7 | 28:7 |
| 29:7 | 30:7 | 31:7 | 32:7 | 33:7 | 34:7 |
| 35:7 | 36:7 | 37:7 | 38:7 | 39:7 | _40:1_ |
| _40:7_ | 41:7 | 42:7 | _44:1_ | _44:7_ | 45:7 |
| 46:7 | 47:7 | 48:7 | 49:7 | 50:7 | 51:7 |

There are 46 hits at base# 7
There are 2 hits at base# 1
AluI          AGct           54
| | | | | | |
|---|---|---|---|---|---|
| 1:8 | 2:8 | 3:8 | 4:8 | 4:24 | 5:8 |
| 6:8 | 7:8 | 8:8 | 9:8 | 10:8 | 11:8 |
| 15:8 | 16:8 | 17:8 | 18:8 | 19:8 | 20:8 |
| 21:8 | 22:8 | 23:8 | 24:8 | 25:8 | 26:8 |
| 27:8 | 28:8 | 29:8 | 29:69 | 30:8 | 31:8 |
| 32:8 | 33:8 | 34:8 | 35:8 | 36:8 | 37:8 |
| 38:8 | 39:8 | _40:2_ | _40:8_ | 41:8 | 42:8 |
| 43:8 | _44:2_ | _44:8_ | 45:8 | 46:8 | 47:8 |
| 48:8 | 48:82 | 49:8 | 49:82 | 50:8 | 51:8 |

There are 48 hits at base# 8
There are 2 hits at base# 2
DdeI          Ctnag          48
| | | | | | |
|---|---|---|---|---|---|
| 1:26 | 1:48 | 2:26 | 2:48 | 3:26 | 3:48 |
| 4:26 | 4:48 | 5:26 | 5:48 | 6:26 | 6:48 |
| 7:26 | 7:48 | 8:26 | 8:48 | 9:26 | 10:26 |
| 11:26 | 12:85 | 13:85 | 14:85 | 15:52 | 16:52 |
| 17:52 | 18:52 | 19:52 | 20:52 | 21:52 | 22:52 |
| 23:52 | 24:52 | 25:52 | 26:52 | 27:52 | 28:52 |
| 29:52 | 30:52 | 31:52 | 32:52 | 33:52 | 35:30 |
| 35:52 | 36:52 | 40:24 | 49:52 | 51:26 | 51:48 |

There are 22 hits at base# 52 52 and 48 never together.
There are 9 hits at base# 48
There are 12 hits at base# 26 26 and 24 never together.
HphI          tcacc          42
| | | | | | |
|---|---|---|---|---|---|
| 1:86 | 3:86 | 6:86 | 7:86 | 8:80 | 11:86 |
| 12:5 | 13:5 | 14:5 | 15:80 | 16:80 | 17:80 |
| 18:80 | 20:80 | 21:80 | 22:80 | 23:80 | 24:80 |
| 25:80 | 26:80 | 27:80 | 28:80 | 29:80 | 30:80 |
| 31:80 | 32:80 | 33:80 | 34:80 | 35:80 | 36:80 |
| 37:59 | 38:59 | 39:59 | 40:59 | 41:59 | 42:59 |
| 43:59 | 44:59 | 45:59 | 46:59 | 47:59 | 50:59 |

There are 22 hits at base# 80 80 and 86 never together
There are 5 hits at base# 86
There are 12 hits at base# 59
BssKI         Nccngg         50
| | | | | | |
|---|---|---|---|---|---|
| 1:39 | 2:39 | 3:39 | 4:39 | 5:39 | 7:39 |
| 8:39 | 9:39 | 10:39 | 11:39 | 15:39 | 16:39 |
| 17:39 | 18:39 | 19:39 | 20:39 | 21:29 | 21:39 |
| 22:39 | 23:39 | 24:39 | 25:39 | 26:39 | 27:39 |
| 28:39 | 29:39 | 30:39 | 31:39 | 32:39 | 33:39 |
| 34:39 | 35:19 | 35:39 | 36:39 | 37:24 | 38:24 |
| 39:24 | 41:24 | 42:24 | 44:24 | 45:24 | 46:24 |
| 47:24 | _48:39_ | _48:40_ | _49:39_ | _49:40_ | 50:24 |
| 50:73 | 51:39 | | | | |

There are 35 hits at base# 39 39 and 40 together twice.
There are 2 hits at base# 40
BsaJI         Ccnngg         47
| | | | | | |
|---|---|---|---|---|---|
| 1:40 | 2:40 | 3:40 | 4:40 | 5:40 | 7:40 |
| 8:40 | 9:40 | 9:47 | 10:40 | 10:47 | 11:40 |
| 15:40 | 18:40 | 19:40 | 20:40 | 21:40 | 22:40 |
| 23:40 | 24:40 | 25:40 | 26:40 | 27:40 | 28:40 |
| 29:40 | 30:40 | 31:40 | 32:40 | 34:40 | 35:20 |
| 35:40 | 36:40 | 37:24 | 38:24 | 39:24 | 41:24 |
| 42:24 | 44:24 | 45:24 | 46:24 | 47:24 | _48:40_ |
| _48:41_ | _49:40_ | _49:41_ | 50:74 | 51:40 | |

There are 32 hits at base# 40 40 and 41 together twice
There are 2 hits at base# 41
There are 9 hits at base# 24
There are 2 hits at base# 47
BstNI         CCwgg          44
PspGI         ccwgg
ScrFI($M.HpaII) CCwgg
| | | | | | |
|---|---|---|---|---|---|
| 1:40 | 2:40 | 3:40 | 4:40 | 5:40 | 7:40 |
| 8:40 | 9:40 | 10:40 | 11:40 | 15:40 | 16:40 |
| 17:40 | 18:40 | 19:40 | 20:40 | 21:30 | 21:40 |
| 22:40 | 23:40 | 24:40 | 25:40 | 26:40 | 27:40 |
| 28:40 | 29:40 | 30:40 | 31:40 | 32:40 | 33:40 |
| 34:40 | 35:40 | 36:40 | 37:25 | 38:25 | 39:25 |
| 41:25 | 42:25 | 44:25 | 45:25 | 46:25 | 47:25 |
| 50:25 | 51:40 | | | | |

There are 33 hits at base# 40
ScrFI         CCngg          50
| | | | | | |
|---|---|---|---|---|---|
| 1:40 | 2:40 | 3:40 | 4:40 | 5:40 | 7:40 |
| 8:40 | 9:40 | 10:40 | 11:40 | 15:40 | 16:40 |
| 17:40 | 18:40 | 19:40 | 20:40 | 21:30 | 21:40 |
| 22:40 | 23:40 | 24:40 | 25:40 | 26:40 | 27:40 |
| 28:40 | 29:40 | 30:40 | 31:40 | 32:40 | 33:40 |
| 34:40 | 35:20 | 35:40 | 36:40 | 37:25 | 38:25 |
| 39:25 | 41:25 | 42:25 | 44:25 | 45:25 | 46:25 |
| 47:25 | 48:40 | 48:41 | 49:40 | 49:41 | 50:25 |
| 50:74 | 51:40 | | | | |

There are 35 hits at base# 40
There are 2 hits at base# 41
EcoO109I      RGgnccy        34
| | | | | | |
|---|---|---|---|---|---|
| 1:43 | 2:43 | 3:43 | 4:43 | 5:43 | 6:43 |
| 7:43 | 8:43 | 9:43 | 10:43 | 15:46 | 16:46 |
| 17:46 | 18:46 | 19:46 | 20:46 | 21:46 | 22:46 |
| 23:46 | 24:46 | 25:46 | 26:46 | 27:46 | 28:46 |
| 30:46 | 31:46 | 32:46 | 33:46 | 34:46 | 35:46 |
| 36:46 | 37:46 | 43:79 | 51:43 | | |

TABLE 220-continued

RERS sites in Human HC GLG FR1s where there are at least 20 GLGs cut

There are 22 hits at base# 46 46 and 43 never together
There are 11 hits at base# 43
NlaIV          GGNcc          71
1:43    2:43    3:43    4:43    5:43    6:43
7:43    8:43    9:43    9:79    10:43   10:79
15:46   15:47   16:47   17:46   17:47   18:46
18:47   19:46   19:47   20:46   20:47   21:46
21:47   22:46   22:47   23:47   24:47   25:47
26:47   27:46   27:47   28:46   28:47   29:47
30:46   30:47   31:46   31:47   32:46   32:47
33:46   33:47   34:46   34:47   35:46   35:47
36:46   36:47   37:21   37:46   37:47   37:79
38:21   39:21   39:79   40:79   41:21   41:79
42:21   42:79   43:79   44:21   44:79   45:21
45:79   46:21   46:79   47:21   51:43
There are 23 hits at base# 47 46 & 47 often together
There are 17 hits at base# 46
There are 11 hits at base# 43
Sau96I         Ggncc          70
1:44    2:3     2:44    3:44    4:44    5:3     5:44    6:44
7:44    8:22    8:44    9:44    10:44   11:3    12:22   13:22
14:22   15:33   15:47   16:47   17:47   18:47   19:47   20:47
21:47   22:47   23:33   23:47   24:33   24:47   25:33   25:47
26:33   26:47   27:47   28:47   29:47   30:47   31:33   31:47
32:33   32:47   33:33   33:47   34:33   34:47   35:47   36:47
37:21   37:22   37:47   38:21   38:22   39:21   39:22   41:21
41:22   42:21   42:22   43:80   44:21   44:22   45:21   45:22
46:21   46:22   47:21   47:22   50:22   51:44
There are 23 hits at base# 47 These do not occur together.
There are 11 hits at base# 44
There are 14 hits at base# 22 These do occur together.
There are 9 hits at base# 21
BsmAI          GTCTCNnnnn     22
1:58    3:58    4:58    5:58    8:58    9:58
10:58   13:70   36:18   37:70   38:70   39:70
40:70   41:70   42:70   44:70   45:70   46:70
47:70   48:48   49:48   50:85
There are 11 hits at base# 70
-"-            Nnnnngagac     27
13:40   15:48   16:48   17:48   18:48   20:48
21:48   22:48   23:48   24:48   25:48   26:48
27:48   28:48   29:48   30:10   30:48   31:48
32:48   33:48   35:48   36:48   43:40   44:40
45:40   46:40   47:40
There are 20 hits at base# 48
AvaII          Ggwcc          44
Sau96I($M.HaeIII) Ggwcc       44
2:3     5:3     6:44    8:44    9:44    10:44
11:3    12:22   13:22   14:22   15:33   15:47
16:47   17:47   18:47   19:47   20:47   21:47
22:47   23:33   23:47   24:33   24:47   25:33
25:47   26:33   26:47   27:47   28:47   29:47
30:47   31:33   31:47   32:33   32:47   33:33
33:47   34:33   34:47   35:47   36:47   37:47
43:80   50:22
There are 23 hits at base# 47 44 & 47 never together
There are 4 hits at base# 44
PpuMI          RGgwccy        27
6:43    8:43    9:43    10:43   15:46   16:46
17:46   18:46   19:46   20:46   21:46   22:46
23:46   24:46   25:46   26:46   27:46   28:46
30:46   31:46   32:46   33:46   34:46   35:46
36:46   37:46   43:79
There are 22 hits at base# 46 43 and 46 never occur together.
There are 4 hits at base# 43
BsmFI          GGGAC          3
8:43    37:46   50:77
-"-            gtccc          33
15:48   16:48   17:48   1:0     1:0     20:48
21:48   22:48   23:48   24:48   25:48   26:48
27:48   28:48   29:48   30:48   31:48   32:48
33:48   34:48   35:48   36:48   37:54   38:54
39:54   40:54   41:54   42:54   43:54   44:54
45:54   46:54   47:54
There are 20 hits at base# 48
There are 11 hits at base# 54
HinfI          Gantc          80

8:77    12:16   13:16   14:16   15:16   15:56
15:77   16:16   16:56   16:77   17:16   17:56
17:77   18:16   18:56   18:77   19:16   19:56
19:77   20:16   20:56   20:77   21:16   21:56
21:77   22:16   22:56   22:77   23:16   23:56
23:77   24:16   24:56   24:77   25:16   25:56
25:77   26:16   26:56   26:77   27:16   27:26
27:56   27:77   28:16   28:56   28:77   29:16
29:56   29:77   30:56   31:16   31:56   31:77
32:16   32:56   32:77   33:16   33:56   33:77
34:16   35:16   35:56   35:77   36:16   36:26
36:56   36:77   37:16   38:16   39:16   40:16
41:16   42:16   44:16   45:16   46:16   47:16
48:46   49:46
There are 34 hits at base# 16
TfiI           Gawtc          21
8:77    15:77   16:77   17:77   18:77   19:77
20:77   21:77   22:77   23:77   24:77   25:77
26:77   27:77   28:77   29:77   31:77   32:77
33:77   35:77   36:77
There are 21 hits at base# 77
MlyI           GAGTC          38
12:16   13:16   14:16   15:16   16:16   17:16
18:16   19:16   20:16   21:16   22:16   23:16
24:16   25:16   26:16   27:16   27:26   28:16
29:16   31:16   32:16   33:16   34:16   35:16
36:16   36:26   37:16   38:16   39:16   40:16
41:16   42:16   44:16   45:16   46:16   47:16
48:46   49:46
There are 34 hits at base# 16
-"-            GACTC          21
15:56   16:56   17:56   18:56   19:56   20:56
21:56   22:56   23:56   24:56   25:56   26:56
27:56   28:56   29:56   30:56   31:56   32:56
33:56   35:56   36:56
There are 21 hits at base# 56
PleI           gagtc          38
12:16   13:16   14:16   15:16   16:16   17:16
18:16   19:16   20:16   21:16   22:16   23:16
24:16   25:16   26:16   27:16   27:26   28:16
29:16   31:16   32:16   33:16   34:16   35:16
36:16   36:26   37:16   38:16   39:16   40:16
41:16   42:16   44:16   45:16   46:16   47:16
48:46   49:46
There are 34 hits at base# 16
-"-            gactc          21
15:56   16:56   17:56   18:56   19:56   20:56
21:56   22:56   23:56   24:56   25:56   26:56
27:56   28:56   29:56   30:56   31:56   32:56
33:56   35:56   36:56
There are 21 hits at base# 56
AlwNI          CAGNNNctg      26
15:68   16:68   17:68   18:68   19:68   20:68
21:68   22:68   23:68   24:68   25:68   26:68
27:68   28:68   29:68   30:68   31:68   32:68
33:68   34:68   35:68   36:68   39:46   40:46
41:46   42:46
There are 22 hits at base# 68

TABLE 255

Analysis of frequency of matching REdaptors in actual V genes

A: HpyCH4V in HC at bases 35-56

| Id | Ntot | \<-- Number of mismatches --\> | | | | | | | | | | Number Cut | Id | Probe |
|---|---|---|---|---|---|---|---|---|---|---|---|---|---|---|
| | | 0 | 1 | 2 | 3 | 4 | 5 | 6 | 7 | 8 | 9 | 10 | | |
| 1 | 510 | 5 | 11 | 274 | 92 | 61 | 25 | 22 | 11 | 1 | 3 | 5 | 443 | 6-1 | agttctcccTGCAgctgaactc |
| 2 | 192 | 54 | 42 | 32 | 24 | 15 | 2 | 3 | 10 | 3 | 1 | 6 | 167 | 3-11 | cactgtatcTGCAaatgaacag |
| 3 | 58 | 19 | 7 | 17 | 6 | 5 | 1 | 0 | 1 | 0 | 2 | 0 | 54 | 3-09 | ccctgtatcTGCAaatgaacag |
| 4 | 267 | 42 | 33 | 9 | 8 | 8 | 82 | 43 | 22 | 8 | 11 | 1 | 100 | 5-51 | ccgcctaccTGCAgtggagcag |
| 5 | 250 | 111 | 59 | 41 | 24 | 7 | 5 | 1 | 0 | 0 | 2 | 0 | 242 | 3-15 | cgctgtatcTGCAaatgaacag |
| 6 | 7 | 0 | 2 | 0 | 1 | 0 | 0 | 0 | 0 | 0 | 4 | 0 | 3 | 7-4.1 | cggcatatcTGCAgatctgcag |
| 7 | 7 | 0 | 2 | 2 | 0 | 0 | 2 | 1 | 0 | 0 | 0 | 0 | 4 | 3-73 | cggcgtatcTGCAaatgaacag |
| 8 | 26 | 10 | 4 | 1 | 3 | 1 | 2 | 1 | 3 | 1 | 0 | 0 | 19 | 5-a | ctgcctaccTGCAgtggagcag |
| 9 | 21 | 8 | 2 | 3 | 1 | 6 | 1 | 0 | 0 | 0 | 0 | 0 | 20 | 3-49 | tcgcctatCTGCAaatgaacag |
| | 1338 | 249 | 162 | 379 | 149 | 103 | 120 | 71 | 47 | 13 | 23 | 12 | 1052 | | |
| | | 249 | 411 | 790 | 939 | | 1162 | | 1280 | | 1316 | | | | |
| | | | | | 1042 | | 1233 | | 1293 | | 1338 | | | | |

| Id | Probe | dotted probe |
|---|---|---|
| 6-1 | agttctcccTGCAgCtgaactc | agttctcccTGCAgctgaactc |
| 3-11 | cactgtatcTGCAaatgaacag | cac.g.at.....aa.....ag |
| 3-09 | ccctgtatcTGCAaatgaacag | ccc.g.at.....aa.....ag |
| 5-51 | ccgcctaccTGCAgtggagcag | ccgc..a........tg..g.ag |
| 3-15 | cgctgtatcTGCAaatgaacag | c.c.g.at.....aa.....ag |
| 7-4.1 | cggcatatcTGCAgatctgcag | c.gca.at......a.ctg.ag |
| 3-73 | cggcgtatcTGCAaatgaacag | c.gcg.at.....aa.....ag |
| 5-a | ctgcctaccTGCAgtggagcag | ctgc..a........tg..g.ag |
| 3-49 | tcgcctatCTGCAaatgaacag | tcgc..at.....aa.....ag |

Seqs with the expected RE site only.......1004
(Counts only cases with 4 or fewer mismatches)

Seqs with only an unexpected site.........  0

Seqs with both expected and unexpected....  48
(Counts only cases with 4 or fewer mismatches)

Seqs with no sites........................  0

B: BlpI in HC

| Id | Ntot | 0 | 1 | 2 | 3 | 4 | 5 | 6 | 7 | 8 | Ncut | Name | |
|---|---|---|---|---|---|---|---|---|---|---|---|---|---|
| 1 | 133 | 73 | 16 | 11 | 13 | 6 | 9 | 1 | 4 | 0 | 119 | 1-58 | acatggaGCTGAGCagcctgag |
| 2 | 14 | 11 | 1 | 0 | 0 | 0 | 0 | 1 | 0 | 1 | 12 | 1-02 | acatggagctgagcaggctgag |
| 3 | 34 | 17 | 8 | 2 | 6 | 1 | 0 | 0 | 0 | 0 | 0 | 1-18 | acatggagctgaggagcctgag |
| 4 | 120 | 50 | 32 | 16 | 10 | 9 | 1 | 1 | 1 | 0 | 2 | 5-51 | acctgcagtggagcagcctgaa |
| 5 | 55 | 13 | 11 | 10 | 17 | 3 | 1 | 0 | 0 | 0 | 0 | 3-15 | atctgcaaatgaacagcctgaa |
| 6 | 340 | 186 | 88 | 41 | 15 | 6 | 3 | 0 | 1 | 0 | 0 | 3303 | atctgcaaatgaacagcctgag |

TABLE 255-continued

Analysis of frequency of matching REdaptors in actual V genes

| | | | | | | | | | | | | | |
|---|---|---|---|---|---|---|---|---|---|---|---|---|---|
| 7 | 82 | 25 | 16 | 25 | 12 | 1 | 3 | 0 | 0 | 0 | 0 | 3-20 | atctgcaaatgaacagtctgag |
| 8 | 3 | 0 | 2 | 0 | 1 | 0 | 0 | 0 | 0 | 0 | 0 | 74.1 | atctgcagatctgcagcctaaa |
| 9 | 23 | 18 | 2 | 2 | 1 | 0 | 0 | 0 | 0 | 0 | 0 | 3-66 | atcttcaaatgaacagcctgag |
| 10 | 2 | 1 | 0 | 1 | 0 | 0 | 0 | 0 | 0 | 0 | 0 | 3-64 | atcttcaaatgggcagcctgag |
| 11 | 486 | 249 | 78 | 81 | 38 | 21 | 10 | 4 | 4 | 1 | 467 | 4301 | ccctgaagatgagctctgtgac |
| 12 | 16 | 6 | 3 | 1 | 0 | 1 | 1 | 3 | 1 | 0 | 1 | 6-1 | ccctgcagctgaactctgtgac |
| 13 | 28 | 15 | 8 | 2 | 2 | 1 | 0 | 0 | 0 | 0 | 0 | 2-70 | tccttacaatgaccaacatgga |
| 14 | 2 | 0 | 2 | 0 | 0 | 0 | 0 | 0 | 0 | 0 | 0 | 2-26 | tccttaccatgaccaacatgga |

601

| Name | Full sequence | Dot mode |
|---|---|---|
| 1-58 | acatggaGCTGAGCagcctgag | acatggaGCTGAGCagcctgag |
| 1-02 | acatggagctgagcaggctgag | ................g..... |
| 1-18 | acatggagctgaggagcctgag | .............g........ |
| 5-51 | acctgcagtggagcagcctgaa | ..c..c..tg...........a |
| 3-15 | atctgcaaatgaacagcctgaa | .tc...c..aa...a........a |
| 3-30.3 | atctgcaaatgaacagcctgag | .tc...c..aa...a.......... |
| 3-20 | atctgcaaatgaacagtctgag | .tc...c..aa...a....t...... |
| 7-4.1 | atctgcagatctgcagcctaaa | .tc...c..a.ct........a.a |
| 3-66 | atcttcaaatgaacagcctgag | .tc.tc.aa...a.......... |
| 3-64 | atcttcaaatgggcagcctgag | .tc.tc.aa...g.......... |
| 4-30.1 | ccctgaagctgagctctgtgac | c.c..a........tctg...c |
| 6-1 | ccctgcagctgaactctgtgac | c.c..c......a.tctg...c |
| 2-70 | tccttacaatgaccaacatgga | t.c.tacaa...c...a.a..ga |
| 2-26 | tccttaccatgaccaacatgga | t.c.tacca...c...a.a..ga |

Seqs with the expected RE site only....... 597
(counting sequences with 4 or fewer mismatches)

Seqs with only an unexpected site............... 2

Seqs with both expected and unexpected.......... 2

Seqs with no sites.............................. 686

C: HpyCH4III, Bst4CI, or TaaI in HC
In scoring whether the RE site of interest is present, only ONs that have 4 or fewer mismatches are counted.

Number of sequences.......... 1617

| Id | Ntot | 0 | 1 | 2 | 3 | 4 | 5 | 6 | 7 | 8 | Ncut | acngt | acngt |
|---|---|---|---|---|---|---|---|---|---|---|---|---|---|
| 1 | 244 | 78 | 92 | 43 | 18 | 10 | 1 | 2 | 0 | 0 | 241102 #1,1 | ccgtgtattACTGTgcgagaga | ccgtgtattactgtgcgagaga |
| 2 | 457 | 69 | 150 | 115 | 66 | 34 | 11 | 8 | 3 | 1 | 434103 #2,3 | ctgtgtattactgtgcgagaga | .t..................... |
| 3 | 173 | 52 | 45 | 36 | 22 | 14 | 3 | 0 | 0 | 1 | 169108 #3 | ccgtgtattactgtgcgagagg | .....................g |

TABLE 255-continued

Analysis of frequency of matching REdaptors in actual V genes

| | | | | | | | | | | | | |
|---|---|---|---|---|---|---|---|---|---|---|---|---|
| 4 | 16 | 0 | 3 | 2 | 2 | 1 | 6 | 0 | 1 | 1 | 8124 #5,1 | ccgtgtattactgtgcaacaga ................a.c... |
| 5 | 4 | 0 | 0 | 1 | 0 | 1 | 1 | 0 | 1 | 0 | 2145 #6 | ccatgtattactgtgcaagata ..a............a...t. |
| 6 | 15 | 1 | 0 | 1 | 0 | 6 | 4 | 1 | 1 | 1 | 8158 #8 | ccgtgtattactgtgcggcaga ................gc... |
| 7 | 23 | 4 | 8 | 5 | 2 | 2 | 1 | 1 | 0 | 0 | 21205 #12 | ccacatattactgtgcacacag ..aca..........acacag |
| 8 | 9 | 1 | 1 | 1 | 0 | 3 | 2 | 1 | 0 | 0 | 6226 #13 | ccacatattactgtgcacggat ..aca..........ac.gat |
| 9 | 7 | 1 | 3 | 1 | 1 | 0 | 0 | 1 | 0 | 0 | 6270 #14 | ccacgtattactgtgcacggat ..ac...........ac.gat |
| 10 | 23 | 7 | 3 | 5 | 5 | 2 | 1 | 0 | 0 | 0 | 22309 #16, | ccttgtattactgtgcaaaaga ..t............a.a... |
| 11 | 35 | 5 | 10 | 7 | 6 | 3 | 3 | 0 | 1 | 0 | 31313 #18, | ctgtgtattactgtgcaagaga .t.............a..... |
| 12 | 18 | 2 | 3 | 2 | 2 | 6 | 1 | 0 | 2 | 0 | 15315 #19 | ccgtgtattactgtaccacaga ..............a.c.c... |
| 13 | 3 | 1 | 2 | 0 | 0 | 0 | 0 | 0 | 0 | 0 | 3320 #20 | ccttgtatcactgtgcgagaga ..t......c............ |
| 14 | 117 | 29 | 23 | 28 | 22 | 8 | 4 | 2 | 1 | 0 | 110323 #22 | ccgtatattactgtgcgaaaga .....a.............a... |
| 15 | 75 | 21 | 25 | 13 | 9 | 1 | 4 | 2 | 0 | 0 | 69330 #23, | ctgtgtattactgtgcgaaaga .t.................a... |
| 16 | 14 | 2 | 2 | 2 | 3 | 0 | 3 | 1 | 1 | 0 | 9349 #29 | ccgtgtattactgtactagaga ..............a.t..... |
| 17 | 2 | 0 | 0 | 1 | 0 | 0 | 1 | 0 | 0 | 0 | 1372 #33 | ccgtgtattactgtgctagaga ..................t..... |
| 18 | 1 | 0 | 0 | 1 | 0 | 0 | 0 | 0 | 0 | 0 | 1373 #34 | ccgtgtattactgtactagaca ..............a.t...c. |
| 19 | 2 | 0 | 0 | 0 | 0 | 0 | 0 | 0 | 0 | 2 | 03d #36 | ctgtgtattactgtaagaaaga .t............aa..a.... |
| 20 | 34 | 4 | 9 | 9 | 4 | 5 | 3 | 0 | 0 | 0 | 31428 #38 | ccgtgtattactgtgcgagaaa .....................a. |
| 21 | 17 | 5 | 4 | 2 | 2 | 3 | 1 | 0 | 0 | 0 | 164302 #40 | ccgtgtattactgtgccagaga .................c..... |
| 22 | 75 | 15 | 17 | 24 | 7 | 10 | 1 | 1 | 0 | 0 | 73439 #44 | ctgtgtattactgtgcgagaca .t.................c. |
| 23 | 40 | 14 | 15 | 4 | 5 | 1 | 0 | 1 | 0 | 0 | 39551 #48 | ccatgtattactgtgcgagaaa ..a.................c. |
| 24 | 213 | 26 | 56 | 60 | 42 | 20 | 7 | 2 | 0 | 0 | 2045a #49 | ccatgtattactgtgcgagaAA ..a...............AA |

| | | | | | | | | | | |
|---|---|---|---|---|---|---|---|---|---|---|
| Group | | 337 | 471 | 363 | 218 | 130 | 58 | 23 | 11 | 6 |
| Cumulative | | 337 | 808 | 1171 | 1389 | 1519 | 1577 | 1600 | 1611 | 1617 |

Seqs with the expected RE site only.......1511

Seqs with only an unexpected site.........  0

```
                Seqs with both expected and unexpected.... 8
                Seqs with no sites...................... 0
            Analysis repeated using only 8 best REdaptors Id  Ntot  0    1    2   3   4   5   6   7  8+
1   301  78  101  54  32  16   9  10   1  0  281 102#1  ccgtgtattactgtgcgagaga
2   493  69  155 125  73  37  14  11   3  6  459 103#2  ctgtgtattactgtgcgagaga
3   189  52   45  38  23  18   5   4   1  3  176 108#3  ccgtgtattactgtgcgagagg
4   127  29   23  28  24  10   6   5   2  0  114 323#22 ccgtatattactgtgcgaaaga
5    78  21   25  14  11   1   4   2   0  0   72 330#23 ctgtgtattactgtgcgaaaga
6    79  15   17  25   8  11   1   2   0  0   76 439#44 ctgtgtattactgtgcgagaca
7    43  14   15   5   5   3   0   1   0  0   42 551#48 ccatgtattactgtgcgagaca
8   307  26   63  72  51  38  24  14  13  6  250 5a#49  ccatgtattactgtgcgaga 1  102#1  ccgtgtattactgtgcgagaga   ccgtgtattactgtgcgagaga
2  103#2  ctgtgtattactgtgcgagaga   .t....................
3  108#3  ccgtgtattactgtgcgagagg   .....................g
4  323#22 ccgtatattactgtgcgaaaga   ....a.............a...
5  330#23 ctgtgtattactgtgcgaaaga   .t................a...
6  439#44 ctgtgtattactgtgcgagaca   .t..................c.
7  551#48 ccatgtattactgtgcgagaca   ..a.................c.
8  5a#49  ccatgtattactgtgcgagaAA   ..a.................AA Seqs with the expected RE site only.......1463/1617
Seqs with only an unexpected site.........    0
Seqs with both expected and unexpected....    7
Seqs with no sites........................    0
```

TABLE 300

Kappa FR1 GLGs

! 1   2   3   4   5   6   7   8   9   10  11
  12

GAC ATC CAG ATG ACC CAG TCT CCA TCC TCC CTG
TCT 13  14  15  16  17  18  19  20  21  22  23

GCA TCT GTA GGA GAC AGA GTC ACC ATC ACT TGC  O12
!

GAC ATC CAG ATG ACC CAG TCT CCA TCC TCC CTG
TCT

GCA TCT GTA GGA GAC AGA GTC ACC ATC ACT TGC  O2
!

GAC ATC CAG ATG ACC CAG TCT CCA TCC TCC CTG
TCT

GCA TCT GTA GGA GAC AGA GTC ACC ATC ACT TGC  O18
!

GAC ATC CAG ATG ACC CAG TCT CCA TCC TCC CTG
TCT

TABLE 300-continued

Kappa FR1 GLGs

GCA TCT GTA GGA GAC AGA GTC ACC ATC ACT TGC  O8
!

GAC ATC CAG ATG ACC CAG TCT CCA TCC TCC CTG
TCT

GCA TCT GTA GGA GAC AGA GTC ACC ATC ACT TGC  A20
!

GAC ATC CAG ATG ACC CAG TCT CCA TCC TCC CTG
TCT

GCA TCT GTA GGA GAC AGA GTC ACC ATC ACT TGC  A30
!

AAC ATC CAG ATG ACC CAG TCT CCA TCT GCC ATG
TCT

GCA TCT GTA GGA GAC AGA GTC ACC ATC ACT TGT  L14
!

GAC ATC CAG ATG ACC CAG TCT CCA TCC TCA CTG
TCT

GCA TCT GTA GGA GAC AGA GTC ACC ATC ACT TGT  L1
!

TABLE 300-continued

Kappa FR1 GLGs

| | |
|---|---|
| GAC ATC CAG ATG ACC CAG TCT CCA TCC TCA CTG TCT | |
| GCA TCT GTA GGA GAC AGA GTC ACC ATC ACT TGT | L15 |
| GCC ATC CAG TTG ACC CAG TCT CCA TCC TCC CTG TCT | |
| GCA TCT GTA GGA GAC AGA GTC ACC ATC ACT TGC | L4 |
| GCC ATC CAG TTG ACC CAG TCT CCA TCC TCC CTG TCT | |
| GCA TCT GTA GGA GAC AGA GTC ACC ATC ACT TGC | L18 |
| GAC ATC CAG ATG ACC CAG TCT CCA TCT TCC GTG TCT | |
| GCA TCT GTA GGA GAC AGA GTC ACC ATC ACT TGT | L5 |
| GAC ATC CAG ATG ACC CAG TCT CCA TCT TCT GTG TCT | |
| GCA TCT GTA GGA GAC AGA GTC ACC ATC ACT TGT | L19 |
| GAC ATC CAG TTG ACC CAG TCT CCA TCC TTC CTG TCT | |
| GCA TCT GTA GGA GAC AGA GTC ACC ATC ACT TGC | L8 |
| GCC ATC CGG ATG ACC CAG TCT CCA TTC TCC CTG TCT | |
| GCA TCT GTA GGA GAC AGA GTC ACC ATC ACT TGC | L23 |
| GCC ATC CGG ATG ACC CAG TCT CCA TCC TCA TTC TCT | |
| GCA TCT ACA GGA GAC AGA GTC ACC ATC ACT TGT | L9 |
| GTC ATC TGG ATG ACC CAG TCT CCA TCC TTA CTC TCT | |
| GCA TCT ACA GGA GAC AGA GTC ACC ATC AGT TGT | L24 |
| GCC ATC CAG ATG ACC CAG TCT CCA TCC TCC CTG TCT | |
| GCA TCT GTA GGA GAC AGA GTC ACC ATC ACT TGC | L11 |
| GAC ATC CAG ATG ACC CAG TCT CCT TCC ACC CTG TCT | |
| GCA TCT GTA GGA GAC AGA GTC ACC ATC ACT TGC | L12 |
| GAT ATT GTG ATG ACC CAG ACT CCA CTC TCC CTG CCC | |
| GTC ACC CCT GGA GAG CCG GCC TCC ATC TCC TGC | O11 |
| GAT ATT GTG ATG ACC CAG ACT CCA CTC TCC CTG CCC | |
| GTC ACC CCT GGA GAG CCG GCC TCC ATC TCC TGC | O1 |
| GAT GTT GTG ATG ACT CAG TCT CCA CTC TCC CTG CCC | |
| GTC ACC CTT GGA CAG CCG GCC TCC ATC TCC TGC | A17 |
| GAT GTT GTG ATG ACT CAG TCT CCA CTC TCC CTG CCC | |
| GTC ACC CTT GGA CAG CCG GCC TCC ATC TCC TGC | A1 |
| GAT ATT GTG ATG ACC CAG ACT CCA CTC TCT CTG TCC | |
| GTC ACC CCT GGA CAG CCG GCC TCC ATC TCC TGC | A18 |
| GAT ATT GTG ATG ACC CAG ACT CCA CTC TCT CTG TCC | |
| GTC ACC CCT GGA CAG CCG GCC TCC ATC TCC TGC | A2 |
| GAT ATT GTG ATG ACT CAG TCT CCA CTC TCC CTG CCC | |
| GTC ACC CCT GGA GAG CCG GCC TCC ATC TCC TGC | A19 |
| GAT ATT GTG ATG ACC CAG TCT CCA CTC TCC CTG CCC | |
| GTC ACC CCT GGA GAG CCG GCC TCC ATC TCC TGC | A3 |
| GAT ATT GTG ATG ACC CAG ACT CCA CTC TCC TCA CCT | |
| GTC ACC CTT GGA CAG CCG GCC TCC ATC TCC TGC | A23 |
| GAA ATT GTG TTG ACG CAG TCT CCA GGC ACC CTG TCT | |
| TTG TCT CCA GGG GAA AGA GCC ACC CTC TCC TGC | A27 |
| GAA ATT GTG TTG ACG CAG TCT CCA GCC ACC CTG TCT | |
| TTG TCT CCA GGG GAA AGA GCC ACC CTC TCC TGC | A11 |
| GAA ATA GTG ATG ACG CAG TCT CCA GCC ACC CTG TCT | |
| GTG TCT CCA GGG GAA AGA GCC ACC CTC TCC TGC | L2 |
| GAA ATA GTG ATG ACG CAG TCT CCA GCC ACC CTG TCT | |
| GTG TCT CCA GGG GAA AGA GCC ACC CTC TCC TGC | L16 |
| GAA ATT GTG TTG ACA CAG TCT CCA GCC ACC CTG TCT | |
| TTG TCT CCA GGG GAA AGA GCC ACC CTC TCC TGC | L6 |
| GAA ATT GTG TTG ACA CAG TCT CCA GCC ACC CTG TCT | |
| TTG TCT CCA GGG GAA AGA GCC ACC CTC TCC TGC | L20 |

TABLE 300-continued

Kappa FR1 GLGs

| | |
|---|---|
| GAA ATT GTA ATG ACA CAG TCT CCA GCC ACC CTG TCT | 5 |
| TTG TCT CCA GGG GAA AGA GCC ACC CTC TCC TGC ! | L25 |
| GAC ATC GTG ATG ACC CAG TCT CCA GAC TCC CTG GCT | 10 |
| GTG TCT CTG GGC GAG AGG GCC ACC ATC AAC TGC ! | B3 |
| GAA ACG ACA CTC ACG CAG TCT CCA GCA TTC ATG TCA | 15 |
| GCG ACT CCA GGA GAC AAA GTC AAC ATC TCC TGC ! | B2 |
| GAA ATT GTG CTG ACT CAG TCT CCA GAC TTT CAG TCT | |
| GTG ACT CCA AAG GAG AAA GTC ACC ATC ACC TGC ! | A26 |
| GAA ATT GTG CTG ACT CAG TCT CCA GAC TTT CAG TCT | |
| GTG ACT CCA AAG GAG AAA GTC ACC ATC ACC TGC ! | A10 |
| GAT GTT GTG ATG ACA CAG TCT CCA GCT TTC CTC TCT | |
| GTG ACT CCA GGG GAG AAA GTC ACC ATC ACC TGC ! | A14 |

| | | MsII | FokI --> <-- --> | PflFI | BsrI | BsmAI | MnlI | HpyCH 4V |
|---|---|---|---|---|---|---|---|---|
| VKII | | | | | | | | |
| O11 | 1901–1969 | — | — | — | — | — | 1956 | — |
| O1 | 2001–2069 | — | — | — | — | — | 2056 | — |
| A17 | 2101–2169 | — | — | 2112 | — | 2118 | 2156 | — |
| A1 | 2201–2269 | — | — | 2212 | — | 2218 | 2256 | — |
| A18 | 2301–2369 | — | — | — | — | — | 2356 | — |
| A2 | 2401–2469 | — | — | — | — | — | 2456 | — |
| A19 | 2501–2569 | — | — | 2512 | — | 2518 | 2556 | — |
| A3 | 2601–2669 | — | — | 2612 | — | 2618 | 2656 | — |
| A23 | 2701–2769 | — | — | — | — | — | 2729 2756 | — |
| VKIII | | | | | | | | |
| A27 | 2801–2869 | — | — | 2812 | — | 2818 2839 | 2860 | — |
| A11 | 2901–2969 | — | — | 2912 | — | 2918 2939 | 2960 | — |
| L2 | 3001–3069 | — | — | 3012 | — | 3018 3039 | 3060 | — |
| L16 | 3101–3169 | — | — | 3112 | — | 3118 3139 | 3160 | — |
| L6 | 3201–3269 | — | — | 3212 | — | 3218 3239 | 3260 | — |
| L20 | 3301–3369 | — | — | 3312 | — | 3318 3339 | 3360 | — |
| L25 | 3401–3469 | — | — | 3412 | — | 3418 3439 | 3460 | — |
| VKIV | | | | | | | | |
| B3 | 3501–3569 | 3503 | — | 3512 | 3515 | 3518 3539 | 3551< | |
| VKV | | | | | | | | |
| B2 | 3601–3669 | — | — | 3649 | — | 3618 3647 | — | — |
| VKVI | | | | | | | | |
| A26 | 3701–3769 | — | — | 3712 | — | 3718 | — | — |
| A10 | 3801–3869 | — | — | 3812 | — | 3818 | — | — |
| A14 | 3901–3969 | — | — | 3912 | — | 3918 | 3930> | — |

Table 302 RERS sites found in Human Kappa FR1 GLG's, continued

| | | SfaNI | SfcI | HinfI | MlyI --> --> <-- | MaeIII Tsp45I same sites | HphI xx38 xx56 xx62 | HpaII MspI xx06 xx52 |
|---|---|---|---|---|---|---|---|---|
| VKI | | | | | | | | |
| O12 | 1–69 | 37 | 41 | 53 | 53 | 55 | 56 | — |
| O2 | 101–169 | 137 | 141 | 153 | 153 | 155 | 156 | — |
| O18 | 201–269 | 237 | 241 | 253 | 253 | 255 | 256 | — |
| O8 | 301–369 | 337 | 341 | 353 | 353 | 355 | 356 | — |
| A20 | 401–469 | 437 | 441 | 453 | 453 | 455 | 456 | — |
| A30 | 501–569 | 537 | 541 | 553 | 553 | 555 | 556 | — |
| L14 | 601–669 | 637 | 641 | 653 | 653 | 655 | 656 | — |
| L1 | 701–769 | 737 | 741 | 753 | 753 | 755 | 756 | — |
| L15 | 801–869 | 837 | 841 | 853 | 853 | 855 | 856 | — |
| L4 | 901–969 | 937 | 941 | 953 | 953 | 955 | 956 | — |
| L18 | 1001–1069 | 1037 | 1041 | 1053 | 1053 | 1055 | 1056 | — |
| L5 | 1101–1169 | 1137 | 1141 | 1153 | 1153 | 1155 | 1156 | — |

-continued

| | | | | | | | | |
|---|---|---|---|---|---|---|---|---|
| L19 | 1201–1269 | 1237 | 1241 | 1253 | 1253 | 1255 | 1256 | — |
| L8 | 1301–1369 | 1337 | 1341 | 1353 | 1353 | 1355 | 1356 | — |
| L23 | 1401–1469 | 1437 | 1441 | 1453 | 1453 | 1455 | 1456 | 1406 |
| L9 | 1501–1569 | 1537 | 1541 | 1553 | 1553 | 1555 | 1556 | 1506 |
| L24 | 1601–1669 | 1637 | 1641 | 1653 | 1653 | 1655 | 1656 | |
| L11 | 1701–1769 | 1737 | 1741 | 1753 | 1753 | 1755 | 1756 | |
| L12 | 1801–1869 | 1837 | 1841 | 1853 | 1853 | 1855 | 1856 | |
| VKII | | | | | | | | |
| O11 | 1901–1969 | — | — | 1918 | 1918 | 1937 | 1938 | 1952 |
| O1 | 2001–2069 | — | — | 2018 | 2018 | 2037 | 2038 | 2052 |
| A17 | 2101–2169 | — | — | 2112 | 2112 | 2137 | 2138 | 2152 |
| A1 | 2201–2269 | — | — | 2212 | 2212 | 2237 | 2238 | 2252 |
| A18 | 2301–2369 | — | — | 2318 | 2318 | 2337 | 2338 | 2352 |
| A2 | 2401–2469 | — | — | 2418 | 2418 | 2437 | 2438 | 2452 |
| A19 | 2501–2569 | — | — | 2512 | 2512 | 2537 | 2538 | 2552 |
| A3 | 2601–2669 | — | — | 2612 | 2612 | 2637 | 2638 | 2652 |
| A23 | 2701–2769 | — | — | 2718 | 2718 | 2737 | 2731* 2738* | — |
| VKIII | | | | | | | | |
| A27 | 2801–2869 | — | — | — | — | | | — |
| A11 | 2901–2969 | — | — | — | — | | | — |
| L2 | 3001–3069 | — | — | — | — | | | — |
| L16 | 3101–3169 | — | — | — | — | | | — |
| L6 | 3201–3269 | — | — | — | — | | | — |
| L20 | 3301–3369 | — | — | — | — | | | — |
| L25 | 3401–3469 | — | — | — | — | | | — |
| VKIV | | | | | | | | |
| B3 | 3501–3569 | — | — | 3525 | 3525 | | | — |
| VKV | | | | | | | | |
| B2 | 3601–3669 | — | — | 3639 | 3639 | | | — |
| VKVI | | | | | | | | |
| A26 | 3701–3769 | — | — | 3712 3739 | 3712 3739 | 3737 3755 | 3756 3762 | — |
| A10 | 3801–3869 | — | — | 3812 3839 | 3812 3839 | 3837 3855 | 3856 3862 | — |
| A14 | 3901–3969 | — | — | 3939 | 3939 | 3937 3955 | 3956 3962 | — |

Table 302 RERS sites found in Human Kappa FR1, continued

| | | BsaJI xx29 xx42 xx43 | BssKI (NstNI) xx22 xx30 xx43 | BpmI xx20 xx41 xx44 --> --> <-- | BsrFI Cac8I NaeI NgoMIV | HaeII | Tsp509I |
|---|---|---|---|---|---|---|---|
| VKI | | | | | | | |
| O12 | 1–69 | — | — | — | — | — | — |
| O2 | 101–169 | — | — | — | — | — | — |
| O18 | 201–269 | — | — | — | — | — | — |
| O8 | 301–369 | — | — | — | — | — | — |
| A20 | 401–469 | — | — | — | — | — | — |
| A30 | 501–569 | — | — | — | — | — | — |
| L14 | 601–669 | — | — | — | — | — | — |
| L1 | 701–769 | — | — | — | — | — | — |
| L15 | 801–869 | — | — | — | — | — | — |
| L4 | 901–969 | — | — | — | — | — | — |
| L18 | 1001–1069 | — | — | — | — | — | — |
| L5 | 1101–1169 | — | — | — | — | — | — |
| L19 | 1201–1269 | — | — | — | — | — | — |
| L8 | 1301–1369 | — | — | — | — | — | — |
| L23 | 1401–1469 | — | — | — | — | — | — |
| L9 | 1501–1569 | — | — | — | — | — | — |
| L24 | 1601–1669 | — | — | — | — | — | — |
| L11 | 1701–1769 | — | — | — | — | — | — |
| L12 | 1801–1869 | — | — | — | — | — | — |
| VKII | | | | | | | |
| O11 | 1901–1969 | 1942 | 1943 | 1944 | 1951 | 1954 | — |
| O1 | 2001–2069 | 2042 | 2043 | 2044 | 2051 | 2054 | — |
| A17 | 2101–2169 | 2142 | — | — | 2151 | 2154 | — |
| A1 | 2201–2269 | 2242 | — | — | 2251 | 2254 | — |
| A18 | 2301–2369 | 2342 | 2343 | — | 2351 | 2354 | — |
| A2 | 2401–2469 | 2442 | 2443 | — | 2451 | 2454 | — |
| A19 | 2501–2569 | 2542 | 2543 | 2544 | 2551 | 2554 | — |
| A3 | 2601–2669 | 2642 | 2643 | 2644 | 2651 | 2654 | — |
| A23 | 2701–2769 | 2742 | — | — | 2751 | 2754 | — |

| | | | | | | | |
|---|---|---|---|---|---|---|---|
| VKIII | | | | | | | |
| A27 | 2801–2869 | 2843 | 2822 2843 | 2820 2841 | — | — | 2803 |
| A11 | 2901–2969 | 2943 | 2943 | 2920 2941 | — | — | 2903 |
| L2 | 3001–3069 | 3043 | 3043 | 3041 | — | — | — |
| L16 | 3101–3169 | 3143 | 3143 | 3120 3141 | — | — | — |
| L6 | 3201–3269 | 3243 | 3243 | 3220 3241 | — | — | 3203 |
| L20 | 3301–3369 | 3343 | 3343 | 3320 3341 | — | — | 3303 |
| L25 | 3401–3469 | 3443 | 3443 | 3420 3441 | — | — | 3403 |
| VKIV | | | | | | | |
| B3 | 3501–3569 | 3529 | 3530 | 3520 | — | 3554 | |
| VKV | | | | | | | |
| B2 | 3601–3669 | | 3643 | 3620 3641 | — | — | |
| VKVI | | | | | | | |
| A26 | 3701–3769 | | — | 3720 | — | — | 3703 |
| A10 | 3801–3869 | | — | 3820 | — | — | 3803 |
| A14 | 3901–3969 | 3943 | 3943 | 3920 3941 | — | — | — |

TABLE 400

Lambda FR1 GLG sequences

! VL1
CAG TCT GTG CTG ACT CAG CCA CCC TCG GTG TCT GAA 1a
GCC CCC AGG CAG AGG GTC ACC ATC TCC TGT !

cag tct gtg ctg acG cag ccG ccc tcA gtg tct gGG 1e
gcc ccA Ggg cag agg gtc acc atc tcc tgC !

cag tct gtg ctg act cag cca ccc tcA cCg tct gGG 1c
Acc ccc Ggg cag agg gtc acc atc tcT tgt !

cag tct gtg ctg act cag cca ccc tcA cCg tct gGG 1g
Acc ccc Ggg cag agg gtc acc atc tcT tgt !

cag tct gtg Ttg acG cag ccG ccc tcA gtg tct gcG 1b
gcc ccA GgA cag aAg gtc acc atc tcc tgC !

! VL2
CAG TCT GCC CTG ACT CAG CCT CCC TCC GCG TCC GGG 2c
TCT CCT GGA CAG TCA GTC ACC ATC TCC TGC !

cag tct gcc ctg act cag cct cGc tcA gTg tcc ggg 2e
tct cct gga cag tca gtc acc atc tcc tgc !

cag tct gcc ctg act cag cct Gcc tcc gTg tcT ggg 2a2
tct cct gga cag tcG Atc acc atc tcc tgc !

cag tct gcc ctg act cag cct ccc tcc gTg tcc ggg 2d
tct cct gga cag tca gtc acc atc tcc tgc !

cag tct gcc ctg act cag cct Gcc tcc gTg tcT ggg 2b2
tct cct gga cag tcG Atc acc atc tcc tgc !

! VL3
TCC TAT GAG CTG ACT CAG CCA CCC TCA GTG TCC GTG 3r
TCC CCA GGA CAG ACA GCC AGC ATC ACC TGC !

tcc tat gag ctg act cag cca cTc tca gtg tcA gtg 3j
Gcc cTG gga cag acG gcc agG atT acc tgT !

tcc tat gag ctg acA cag cca ccc tcG gtg tcA gtg 3p
tcc cca gga caA acG gcc agG atc acc tgc !

tcc tat gag ctg acA cag cca ccc tcG gtg tcA gtg 3a
tcc cTa gga cag aTG gcc agG atc acc tgc !

tcT tCt gag ctg act cag GAC ccT GcT gtg tcT gtg 3l
Gcc TTG gga cag aca gTc agG atc acA tgc !

tcc tat gTg ctg act cag cca ccc tca gtg tcA gtg 3h
Gcc cca gga Aag acG gcc agG atT acc tgT !

tcc tat gag ctg acA cag cTa ccc tcG gtg tcA gtg 3e
tcc cca gga cag aca gcc agG atc acc tgc !

tcc tat gag ctg aTG cag cca ccc tcG gtg tcA gtg 3m
tcc cca gga cag acG gcc agG atc acc tgc !

tcc tat gag ctg acA cag cca Tcc tca gtg tcA gtg V2-19
tcT ccG gga cag aca gcc agG atc acc tgc !

! VL4
CTG CCT GTG CTG ACT CAG CCC CCG TCT GCA TCT GCC 4c
TTG CTG GGA GCC TCG ATC AAG CTC ACC TGC !

cAg cct gtg ctg act caA TcA TcC tct gcC tct gcT 4a
tCC ctg gga Tcc tcg Gtc aag ctc acc tgc !

cAg cTt gtg ctg act caA TcG ccC tct gcC tct gcc 4b
tCC ctg gga gcc tcg Gtc aag ctc acc tgc !

! VL5
CAG CCT GTG CTG ACT CAG CCA CCT TCC TCC TCC GCA 5e
TCT CCT GGA GAA TCC GCC AGA CTC ACC TGC !

cag Gct gtg ctg act cag ccG Gct tcc CTc tcT gca 5c
tct cct gga gCa tcA gcc agT ctc acc tgc !

TABLE 400-continued

Lambda FR1 GLG sequences

```
cag cct gtg ctg act cag cca Tct tcc CAT tcT gca    5b
tct Tct gga gCa tcA gTc aga ctc acc tgc !

! VL6
AAT TTT ATG CTG ACT CAG CCC CAC TCT GTG TCG GAG    6a
TCT CCG GGG AAG ACG GTA ACC ATC TCC TGC !

! VL7
CAG ACT GTG GTG ACT CAG GAG CCC TCA CTG ACT GTG    7a
TCC CCA GGA GGG ACA GTC ACT CTC ACC TGT !

cag Gct gtg gtg act cag gag ccc tca ctg act gtg    7b
tcc cca gga ggg aca gtc act ctc acc tgt !

! VL8
CAG ACT GTG GTG ACC CAG GAG CCA TCG TTC TCA GTG    8a
TCC CCT GGA GGG ACA GTC ACA CTC ACT TGT !

! VL9
CAG CCT GTG CTG ACT CAG CCA CCT TCT GCA TCA GCC    9a
TCC CTG GGA GCC TCG GTC ACA CTC ACC TGC !

! VL10
CAG GCA GGG CTG ACT CAG CCA CCC TCG GTG TCC AAG   10a
GGC TTG AGA CAG ACC GCC ACA CTC ACC TGC !
```

TABLE 405

RERSs found in human lambda FR1 GLGs

```
! There are 31 lambda GLGs
MlyI     NnnnnnGACTC        25
  1:6      3:6      4:6      6:6      7:6      8:6
  9:6     10:6     11:6     12:6     15:6     16:6
 20:6     21:6     22:6     23:6     23:50    24:6
 25:6     25:50    26:6     27:6     28:6     30:6
 31:6
There are 23 hits at base# 6
-"-      GAGTCNNNNNn         1
26:34
MwoI     GCNNNNNnngc        20
  1:9      2:9      3:9      4:9     11:9     11:56
 12:9     13:9     14:9     16:9     17:9     18:9
 19:9     20:9     23:9     24:9     25:9     26:9
 30:9     31:9
There are 19 hits at base# 9
HinfI    Gantc              27
  1:12     3:12     4:12     6:12     7:12     8:12
  9:12    10:12    11:12    12:12    15:12    16:12
 20:12    21:12    22:12    23:12    23:46    23:56
 24:12    25:12    25:56    26:12    26:34    27:12
 28:12    30:12    31:12
There are 23 hits at base# 12
PleI     gactc              25
  1:12     3:12     4:12     6:12     7:12     8:12
  9:12    10:12    11:12    12:12    15:12    16:12
 20:12    21:12    22:12    23:12    23:56    24:12
 25:12    25:56    26:12    27:12    28:12    30:12
 31:12
There are 23 hits at base# 12
-"-      gagtc               1
26:34
DdeI     Ctnag              32
  1:14     2:24     3:14     3:24     4:14     4:24
  5:24     6:14     7:14     7:24     8:14     9:14
 10:14    11:14    11:24    12:14    12:24    15:5
 15:14    16:14    16:24    19:24    20:14    23:14
```

TABLE 405-continued

RERSs found in human lambda FR1 GLGs

```
 24:14    25:14    26:14    27:14    28:14    29:30
 30:14    31:14
There are 21 hits at base# 14
BsaJI    Ccnngg             38
  1:23     1:40     2:39     2:40     3:39     3:40
  4:39     4:40     5:39    11:39    12:38    12:39
 13:23    13:39    14:23    14:39    15:38    16:39
 17:23    17:39    18:23    18:39    21:38    21:39
 21:47    22:38    22:39    22:47    26:40    27:39
 28:39    29:14    29:39    30:38    30:39    30:47
 31:23    31:32
There are 17 hits at base# 39
There are 5 hits at base# 38
There are 5 hits at base# 40 Makes cleavage ragged.
MnlI     cctc               35
  1:23     2:23     3:23     4:23     5:23     6:19
  6:23     7:19     8:23     9:19     9:23    10:23
 11:23    13:23    14:23    16:23    17:23    18:23
 19:23    20:47    21:23    21:29    21:47    22:23
 22:29    22:35    22:47    23:26    23:29    24:27
 27:23    28:23    30:35    30:47    31:23
There are 21 hits at base# 23
There are 3 hits at base# 19
There are 3 hits at base# 29
There are 1 hits at base# 26
There are 1 hits at base# 27 These could make cleavage ragged.
-"-      gagg                7
  1:48     2:48     3:48     4:48    27:44    28:44
 29:44
BssKI    Nccngg             39
  1:40     2:39     3:39     3:40     4:39     4:40
  5:39     6:31     6:39     7:31     7:39     8:39
  9:31     9:39    10:39    11:39    12:38    12:52
 13:39    13:52    14:52    16:39    16:52    17:39
 17:52    18:39    18:52    19:39    19:52    21:38
 22:38    23:39    24:39    26:39    27:39    28:39
 29:14    29:39    30:38
There are 21 hits at base# 39
There are 4 hits at base# 38
There are 3 hits at base# 31
There are 3 hits at base# 40 Ragged
BstNI    CCwgg              30
  1:41     2:40     5:40     6:40     7:40     8:40
  9:40    10:40    11:40    12:39    12:53    13:40
 13:53    14:53    16:40    16:53    17:40    17:53
 18:40    18:53    19:53    21:39    22:39    23:40
 24:40    27:40    28:40    29:15    29:40    30:39
There are 17 hits at base# 40
There are 7 hits at base# 53
There are 4 hits at base# 39
There are 1 hits at base# 41 Ragged
PspGI    ccwgg              30
  1:41     2:40     5:40     6:40     7:40     8:40
  9:40    10:40    11:40    12:39    12:53    13:40
 13:53    14:53    16:40    16:53    17:40    17:53
 18:40    18:53    19:53    21:39    22:39    23:40
 24:40    27:40    28:40    29:15    29:40    30:39
There are 17 hits at base# 40
There are 7 hits at base# 53
There are 4 hits at base# 39
There are 1 hits at base# 41
ScrFI    CCngg              39
  1:41     2:40     3:40     3:41     4:40     4:41
  5:40     6:32     6:40     7:32     7:40     8:40
  9:32     9:40    10:40    11:40    12:39    12:53
 13:40    13:53    14:53    16:40    16:53    17:40
 17:53    18:40    18:53    19:40    19:53    21:39
 22:39    23:40    24:40    26:40    27:40    28:40
 29:15    29:40    30:39
There are 21 hits at base# 40
There are 4 hits at base# 39
There are 3 hits at base# 41
MaeIII   gtnac              16
  1:52     2:52     3:52     4:52     5:52     6:52
  7:52     9:52    26:52    27:10    27:52    28:10
 28:52    29:10    29:52    30:52
There are 13 hits at base# 52
Tsp45I   gtsac              15
```

TABLE 405-continued

RERSs found in human lambda FR1 GLGs

| | | | | | |
|---|---|---|---|---|---|
| 1:52 | 2:52 | 3:52 | 4:52 | 5:52 | 6:52 |
| 7:52 | 9:52 | 27:10 | 27:52 | 28:10 | 28:52 |
| 29:10 | 29:52 | 30:52 | | | |
| There are 12 hits at base# 52 | | | | | |
| HphI | tcacc | | 26 | | |
| 1:53 | 2:53 | 3:53 | 4:53 | 5:53 | 6:53 |
| 7:53 | 8:53 | 9:53 | 10:53 | 11:59 | 13:59 |
| 14:59 | 17:59 | 18:59 | 19:59 | 20:59 | 21:59 |
| 22:59 | 23:59 | 24:59 | 25:59 | 27:59 | 28:59 |
| 30:59 | 31:59 | | | | |
| There are 16 hits at base# 59 | | | | | |
| There are 10 hits at base# 53 | | | | | |
| BspMI | ACCTGCNNNNn | | 14 | | |
| 11:61 | 13:61 | 14:61 | 17:61 | 18:61 | 19:61 |
| 20:61 | 21:61 | 22:61 | 23:61 | 24:61 | 25:61 |
| 30:61 | 31:61 | | | | |
| There are 14 hits at base# 61 Goes into CDR1 | | | | | |

TABLE 500 h3401-h2 captured Via CJ with BsmAI

```
! 1    2    3    4    5    6    7    8    9    10   11   12   13   14   15
! S    A    Q    D    I    Q    M    T    Q    S    P    A    T    L    S
  aGT  GCA  Caa  gac  atc  cag  atg  acc  cag  tct  cca  gcc  acc  ctg  tct
! ApaLI                                                    a    gcc  acc  !
L25,L6,L20,L2,L16,All ! Extender........................Bridge...
! 16   17   18   19   20   22   22   23   24   25   26   27   28   29   30
! V    S    P    G    E    R    A    T    L    S    C    R    A    S    Q
  gtg  tct  cca  ggg  gaa  agg  gcc  acc  ctc  tcc  tgc  agg  gcc  agt  cag
! 31   32   33   34   35   36   37   38   39   40   42   42   43   44   45
! S    V    S    N    N    L    A    W    Y    Q    Q    K    P    G    Q
  agt  gtt  agt  aac  aac  tta  gcc  tgg  tac  cag  cag  aaa  cct  ggc  cag
! 46   47   48   49   50   51   52   53   54   55   56   57   58   59   60
! V    P    R    L    L    I    Y    G    A    S    T    R    A    T    D
  gtt  ccc  agg  ctc  ctc  atc  tat  ggt  gca  tcc  acc  agg  gcc  act  gat
! 61   62   63   64   65   66   67   68   69   70   72   72   73   74   75
! I    P    A    R    F    S    G    S    G    S    G    T    D    F    T
  atc  cca  gcc  agg  ttc  agt  ggc  agt  ggg  tct  ggg  aca  gac  ttc  act
! 76   77   78   79   80   82   82   83   84   85   86   87   88   89   90
! L    T    I    S    R    L    E    P    E    D    F    A    V    Y    Y
  ctc  acc  atc  agc  aga  ctg  gag  cct  gaa  gat  ttt  gca  gtg  tat  tac
! 91   92   93   94   95   96   97   98   99   100  101  102  103  104  105
! C    Q    R    Y    G    S    S    P    G    W    T    F    G    Q    G
  tgt  cag  cgg  tat  ggt  agc  tca  ccg  ggg  tgg  acg  ttc  ggc  caa  ggg
! 106  107  108  109  110  111  122  113  114  115  116  117  118  119  120
! T    K    V    E    I    K    R    T    V    A    A    P    S    V    F
  acc  aag  gtg  gaa  atc  aaa  cga  act  gtg  gct  gca  cca  tct  gtc  ttc
! 121  122  123  124  125  126  127  128  129  130  131  132  133  134  135
! I    F    P    P    S    D    E    Q    L    K    S    G    T    A    S
  atc  ttc  ccg  cca  tct  gat  gag  cag  ttg  aaa  tct  gga  act  gcc  tct
! 136  137  138  139  140  142  142  143  144  145  146  147  148  149  150
```

TABLE 500-continued h3401-h2 captured Via CJ with BsmAI

| ! | V | V | C | L | L | N | N | F | Y | P | R | E | A | K | V |
|---|---|---|---|---|---|---|---|---|---|---|---|---|---|---|---|
|   | gtt | gtg | tgc | ctg | ctg | aat | aac | ttc | tat | ccc | aga | gag | gcc | aaa | gta |

| ! | 151 | 152 | 153 | 154 | 155 | 156 | 157 | 158 | 159 | 160 | 161 | 162 | 163 | 164 | 165 |
|---|---|---|---|---|---|---|---|---|---|---|---|---|---|---|---|
| ! | Q | W | K | V | D | N | A | L | Q | S | G | N | S | Q | E |
|   | cag | tgg | aag | gtg | gat | aac | gcc | ctc | caa | tcg | ggt | aac | tcc | cag | gag |

| ! | 166 | 167 | 168 | 169 | 170 | 171 | 172 | 173 | 174 | 175 | 176 | 177 | 178 | 179 | 180 |
|---|---|---|---|---|---|---|---|---|---|---|---|---|---|---|---|
| ! | S | V | T | E | Q | D | S | K | D | S | T | Y | S | L | S |
|   | agt | gtc | aca | gag | cag | gac | agc | aag | gac | agc | acc | tac | agc | ctc | agc |

| ! | 181 | 182 | 183 | 184 | 185 | 186 | 187 | 188 | 189 | 190 | 191 | 192 | 193 | 194 | 195 |
|---|---|---|---|---|---|---|---|---|---|---|---|---|---|---|---|
| ! | S | T | L | T | L | S | K | A | D | Y | E | K | H | K | V |
|   | agc | acc | ctg | acg | ctg | agc | aaa | gca | gac | tac | gag | aaa | cac | aaa | gtc |

| ! | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|
| ! | Y | A | C | E | V | T | H | Q | G | L | S | S | P | V | T |
|   | tac | gcc | tgc | gaa | gtc | acc | cat | cag | ggc | ctg | agc | tcg | cct | gtc | aca |

| ! | 211 | 212 | 213 | 214 | 215 | 216 | 217 | 218 | 219 | 220 | 221 | 222 | 223 |
|---|---|---|---|---|---|---|---|---|---|---|---|---|---|
| ! | K | S | F | N | K | G | E | C | K | G | E | F | A |
|   | aag | agc | ttc | aac | aaa | gga | gag | tgt | aag | ggc | gaa | ttc | gc..... |

TABLE 501 h3401-d8 KAPPA captured with CJ and BsmAI

| ! | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| ! | S | A | Q | D | I | Q | M | T | Q | S | P | A | T | L | S |
|   | aGT GCA Caa | gac | atc | cag | atg | acc | cag | tct | cct | gcc | acc | ctg | tct |

! ApaLI...Extender....................a gcc acc !
L25,L6,L20,L2,L16,A11

!                                             A GCC ACC CTG TCT ! L2

| ! | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|
| ! | V | S | P | G | E | R | A | T | L | S | C | R | A | S | Q |
|   | gtg | tct | cca | ggt | gaa | aga | gcc | acc | ctc | tcc | tgc | agg | gcc | agt | cag |
| ! | GTG | TCT | CCA | GGG | GAA | AGA | GCC | ACC | CTC | TCC | TGC |   | L2 |   |   |

| ! | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|
| ! | N | L | L | S | N | L | A | W | Y | Q | Q | K | P | G | Q |
|   | aat | ctt | ctc | agc | aac | tta | gcc | tgg | tac | cag | cag | aaa | cct | ggc | cag |

| ! | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|
| ! | A | P | R | L | L | I | Y | G | A | S | T | G | A | I | G |
|   | gct | ccc | agg | ctc | ctc | atc | tat | ggt | gct | tcc | acc | ggg | gcc | att | ggt |

| ! | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|
| ! | I | P | A | R | F | S | G | S | G | S | G | T | E | F | T |
|   | atc | cca | gcc | agg | ttc | agt | ggc | agt | ggg | tct | ggg | aca | gag | ttc | act |

TABLE 501-continued h3401-d8 KAPPA captured with CJ and BsmAI

```
!  76  77  78  79  80  81  82  83  84  85  86  87  88  89  90
!   L   T   I   S   S   L   Q   S   E   D   F   A   V   Y   F
   ctc acc atc agc agc ctg cag tct gaa gat ttt gca gtg tat ttc
!  91  92  93  94  95  96  97  98  99 100 101 102 103 104 105
!   C   Q   Q   Y   G   T   S   P   P   T   F   G   G   G   T
   tgt cag cag tat ggt acc tca ccg ccc act ttc ggc gga ggg acc
! 106 107 108 109 110 111 112 113 114 115 116 117 118 119 120
!   K   V   E   I   K   R   T   V   A   A   P   S   V   F   I
   aag gtg gag atc aaa cga act gtg gct gca cca tct gtc ttc atc
! 121 122 123 124 125 126 127 128 129 130 131 132 133 134 135
!   F   P   P   S   D   E   Q   L   K   S   G   T   A   S   V
   ttc ccg cca tct gat gag cag ttg aaa tct gga act gcc tct gtt
! 136 137 138 139 140 141 142 143 144 145 146 147 148 149 150
!   V   C   P   L   N   N   F   Y   P   R   E   A   K   V   Q
   gtg tgc ccg ctg aat aac ttc tat ccc aga gag gcc aaa gta cag
! 151 152 153 154 155 156 157 158 159 160 161 162 163 164 165
!   W   K   V   D   N   A   L   Q   S   G   N   S   Q   E   S
   tgg aag gtg gat aac gcc ctc caa tcg ggt aac tcc cag gag agt
! 166 167 168 169 170 171 172 173 174 175 176 177 178 179 180
!   V   T   E   Q   D   N   K   D   S   T   Y   S   L   S   S
   gtc aca gag cag gac aac aag gac agc acc tac agc ctc agc agc
! 181 182 183 184 185 186 187 188 189 190 191 192 193 194 195
!   T   L   T   L   S   K   V   D   Y   E   K   H   E   V   Y
   acc ctg acg ctg agc aaa gta gac tac gag aaa cac gaa gtc tac
! 196 197 198 199 200 201 202 203 204 205 206 207 208 209 210
!   A   C   E   V   T   H   Q   G   L   S   S   P   V   T   K
   gcc tgc gaa gtc acc cat cag ggc ctt agc tcg ccc gtc acg aag
! 211 212 213 214 215 216 217 218 219 220 221 222 223
!   S   F   N   R   G   E   C   K   K   E   F   V
   agc ttc aac agg gga gag tgt aag aaa gaa ttc gtt t
```

TABLE 508

Human heavy chains bases 88.1 to 94.2
Number of sequences.......... 840

| Id | Ntot | Number of Mismatchers | | | | | | | | Probe Name | Sequence............ | Dot form............ |
|---|---|---|---|---|---|---|---|---|---|---|---|---|
| | | 0 | 1 | 2 | 3 | 4 | 5 | 6 | 7 | | | |
| 1 | 364 | 152 | 97 | 76 | 26 | 7 | 4 | 2 | 0 | VHS881-1.1 | gctgtgtattactgtgcgag | gctgtgtattactgtgcgag |
| 2 | 265 | 150 | 60 | 33 | 13 | 5 | 4 | 0 | 0 | VHS881-1.2 | gccgtgtattactgtgcgag | ...c................ |

TABLE 508-continued

Human heavy chains bases 88.1 to 94.2
Number of sequences.......... 840

| 3 | 96 | 14 | 34 | 16 | 10 | 5 | 7 | 9 | 1VHS881-2.1 | gccgtatattactgtgcgag | ...c...a............. |
| 4 | 20 | 0 | 3 | 4 | 9 | 2 | 2 | 0 | 0VHS881-4.1 | gccgtgtattactgtacgag | ...c............a.... |
| 5 | 95 | 25 | 36 | 18 | 11 | 2 | 2 | 0 | 1VHS881-9.1 | gccatgtattactgtgcgag | ...ca................ |

```
     840 341 230 147 69 21 19 11  2

341 571 718 787 808 827 838 840

88 89 90 91 92 93 94 95 Codon number as in Table 195

Recognition........... Stem...... Loop. Stem......

(VHS881-1.1)  5'-gctgtgtat|tact-gtgcgag cAcATccgTg TTgTT cAcggATgTg-3'

(VHS881-1.2)  5'-gccgtgtat|tact-gtgcgag cAcATccgTg TTgTT cAcggATgTg-3'

(VHS881-2.1)  5'-gccgtatat|tact-gtgcgag cAcATccgTg TTgTT cAcggATgTg-3'

(VHS881-4.1)  5'-gccgtgtat|tact-gtacgag cAcATccgTg TTgTT cAcggATgTg-3'

(VHS881-9.1)  5'-gccatatat|tact-gtgcgag cAcATccgTg TTgTT cAcggATgTg-3'

| site of substrate cleavage (FOKlact)     5'-cAcATccgTg TTgTT cAcggATgTg-3'

(VHEx881)     5'-AATAgTAgAc TgcAgTgTcc TcAgcccTTA AgcTgTTcAT cTgcAAgTag-
                 AgAgTATTcT TAgAgTTgTc TcTAgAcTTA gTgAAgcg-3'

! note that VHEx881 is the reverse complement of the ON below

!         [RC] 5'-cgCttcacTaag-

!              Scab........

!              Synthetic 3-23 as in Table 206

!              |TCT|AGA|gac|aac|tct|aag|aat|act|ctc|tac|ttg|cag|atg|-

!              XbaI...

!              |aac|agC|TTa|AGg|gct|gag|gac|aCT|GCA|Tgc|tac|tat|t-3'

!                  AflII...

(VHBA881)     5'-cgCttcacTaag-

|TCT|AGA|gac|aac|tct|aag|aat|act|ctc|tac|ttg|cag|atg|-

|aac|agC|TTa|Agg|gct|gag|gac|aCT|GCA|Gtc|tac|tat|tgt gcg ag-3'

(VHBB881)     5'-cgCttcacTaag-

|TCT|AGA|gac|aac|tct|aag|aat|act|ctc|tac|ttg|cag|atg|-

|aac|agC|TTA|AGg|gct|gag|gac|aCT|GCA|Gtc|tac|tat|tgt Acg ag-3'

(VH881PCR)    5'-cgCttcacTaag|TCT|AGA|gac|aac-3'
```

TABLE 512

Kappa, bases 12-30

```
!
! ID Ntot  0  1  2  3  4  5  6  Name     Sequence........... Dot Form...........

!  1  84  40 21 20  1  2  0  0  SK12012  gacccagtctccatcctcc  gacccagtctccatcctcc
!  2  32  19  3  6  2  1  0  1  SK12A17  gactcagtctccactctcc  ...t.........ct....

!  3  26  17  8  1  0  0  0  0  SK12A27  gacgcagtctccaggcacc  ...g.........gg.a..
```

TABLE 512-continued

Kappa, bases 12-30

```
!
! ID Ntot 0  1  2  3  4  5  6 Name    Sequence.......... Dot Form...........

!  4  40 21 18  1  0  0  0 SK12A11 gacgcagtctccagccacc ...g.........g..a..

!     182 97 50 28  3  3  0  1

!        97 147 175 178 181 181 182

!
```

URE adapters:

```
!                       Stem...... Loop. Stem...... Recognition........
(SzKB1230-012)          5'-cAcATccgTg TTgTT cAcggATgTg ggAggATggAgAcTgggTc-3'
!              [RC]  5'-gacccagtctccatcctcc cAcATccgTg AAcAA cAcggATgTg-3'
!                       Recognition........ Stem...... loop. Stem......
!                                           FokI.            FokI.

!                       Stem...... Loop. Stem...... Recognition........
(SzKB1230-A17)          5'-cAcATccgTg TTgTT cAcggATgTg ggAgAgTggAgAcTgAgTc-3'
!              [RC]  5'-gactcagtctccactctcc cAcATccgTg AAcAA cAcggATgTg-3'
!                       Recognition........ Stem...... loop. Stem......
!                                           FokI.            FokI.

!                       Stem...... Loop. Stem...... Recognition........
(SzKB1230-A27)          5'-cAcATccgTg TTgTT cAcggATgTg ggTgccTggAgAcTgcgTc-3'
!              [RC]  5'-gacgcagtctccaggcacc cAcATccgTg AAcAA cAcggATgTg-3'
!                       Recognition........ Stem...... loop. Stem......
!                                           FokI.            FokI.

!                       Stem...... Loop. Stem...... Recognition........
(SzKB1230-A11)          5'-cAcATccgTg TTgTT cAcggATgTg ggTggcTggAgAcTgcgTc-3'
!              [RC]  5'-gacgcagtctccagccacc cAcATccgTg AAcAA cAcggATgTg-3'
!                       Recognition........ Stem...... loop. Stem......
!                                           FokI.            FokI.
```

What happens in the upper strand:

```
(SzKB1230-012*)    5'-gac cca gtc|tcc a-tc ctc c-3'
!                              | Site of cleavage in substrate
!
(SzKB1230-A17*)    5'-gac tca gtc|tcc a-ct ctc c-3'
!
(SzKB1230-A27*)    5'-gac gca gtc|tcc a-gg cac c-3'
!
(SzKB1230-A11*)    5'-gac gca gtc|tcc a-gc cac c-3'
(kapextURE)        5'-ccTctactctTgTcAcAgTgcAcAA gAc ATc cAg-3' !sense strand
                      Scab............ApaLI.
```

TABLE 512-continued

Kappa, bases 12-30

```
! ID       Ntot 0 1 2 3 4 5 6 Name       Sequence........... Dot Form...........

(kapextUREPCR)     5'-ccTctactctTgTcAcAgTg-3'
                        Scab.............
(kaBRO1UR)         5'-ggAggATggA cTggATgTcT TgTgcAcTgT gAcAAgAgTA gAgg-3'
!       [RC]       5'-ccTctactctTgTcAcAgTgcAcAA gAc ATc cAg tcc a-tc ctc c-3'
                   ON above is R.C. of this one
(kaBRO2UR)         5'-ggAgAgTggA cTggATgTcT TgTgcAcTgT gAcAAgAgTA gAgg-3'
!       [RC]       5'-ccTctactctTgTcAcAgTgcAcAA gAc ATc cAg tcc a-ct ctc c-3'
                   ON above is R.C. of this one
(kaBRO3UR)         5'-ggTgccTggA cTggATgTcT TgTgcAcTgT gAcAAgAgTA gAgg-3'
!       [RC]       5'-ccTctactctTgTcAcAgTgcAcAA gAc ATc cAg tcc a-gg cac c-3'
                   ON above is R.C. of this one
(kaBRO4UR)         5'-ggTggcTggA cTggATgTcT TgTgcAcTgT gAcAAgAgTA gAgg-3'
!       [RC]       5'-ccTctactctTgTcAcAgTgcAcAA gAc ATc cAg tcc a-gc cac c-3'
                   ON above is R.C. of this one
                        Scab.............ApaLI.
```

TABLE 515

Lambda URE adapters bases 13.3 to 19.3

```
! Number of sequences.......... 128
!
            Number of mismatches...............

! Id Ntot 0  1  2  3  4  5  6  7  8 Name       Sequence........... Dot form...........

! 1   58  45  7  1  0  0  0  2  2 1VL133-2a2  gtctcctggacagtcgatc  gtctcctggacagtcgatc ! 2   16  10  1  0  1  0  1  1  0 2VL133-31   ggccttgggacagacagtc  .g.cttg.......a.ag..

! 3   17   6  0  0  0  4  1  1  5 0VL133-2c   gtctcctggacagtcagtc  ................ag..

! 4   37   3  0 10  4  4  3  7  4 2VL133-1c   ggccccagggcagagggtc  .g.c..a..g...ag.g..

!    128  64  8 11  5  8  5 11 11  5
!         64 72 83 88 96 101 112 123 128
!
!                     Stem...... loop. Stem...... Recognition........
(VL133-2a2)          5'-cAcATccgTg TTgTT cAcggATgTg gATcgAcTgTccAggAgAc-3'
!           [RC]     5'-gtctcctggacagtcgatc cAcATccgTg AAcAA cAcggATgTg-3'
!                       Recognition........ Stem...... Loop. Stem......
!
!                     Stem...... loop. Stem...... Recognition........
```

TABLE 515-continued

Lambda URE adapters bases 13.3 to 19.3

```
(VL133-31)        5'-cAcATccgTg TTgTT cAcggATgTg gAcTgTcTgTcccAAggcc-3'
!
!            [RC] 5'-ggccttgggacagacagtc cAcATccgTg AAcAA cAcggATgTg-3'
!                     Recognition........ Stem...... Loop. Stem......
!
!
!                     Stem...... loop. Stem...... Recognition........
(VL133-2c)        5'-cAcATccgTg TTgTT cAcggATgTg gAcTgAcTgTccAggAgAc-3'
!
!            [RC] 5'-gtctcctggacagtcagtc cAcATccgTg AAcAA cAcggATgTg-3'
!                     Recognition........ Stem...... Loop. Stem......
!
!
!                     Stem...... loop. Stem...... Recognition........
(VL133-1c)        5'-cAcATccgTg TTgTT cAcggATgTg gAcccTcTgcccTggggcc-3'
!
!            [RC] 5'-ggccccagggcagagggtc cAcATccgTg AAcAA cAcggATgTg-3'
What happens in the top strand:
!                             | site of cleavage in the upper strand
(VL133-2a2*)      5'-g tct cct g|ga cag tcg atc
!
(VL133-31*)       5'-g gcc ttg g|ga cag aca gtc
!
(VL133-2c*)       5'-g tct cct g|ga cag tca gtc
!
(VL133-1c*)       5'-g gcc cca g|gg cag agg gtc
!
! The following Extenders and Bridges all encode the AA sequence of 2a2 for
codons 1-25
!                             1
(ON_LamEx133)  5'-ccTcTgAcTgAgT gcA cAg -
!
!                     2   3   4   5   6   7   8   9  10  11  12
                      AGt gcT TtA acC caA ccG gcT AGT gtT AGC ggT-
!
!                     13  14  15
                      tcC ccG g ! 2a2
!                                        1
(ON_LamB1-133) [RC] 5'-ccTcTgAcTgAgT gcA cAg -
!
!                     2   3   4   5   6   7   8   9  10  11  12
                      AGt gcT TtA acC caA ccG gcT AGT gtT AGC ggT-
!
!                     13  14  15
                      tcC ccG g ga cag tcg at-3' ! 2a2
! N.B. the actual seq is the reverse complement of the one shown.
!
(ON_LamB2-133) [RC] 5'-ccTcTgAcTgAgT gcA cAg -
!
```

TABLE 515-continued

Lambda URE adapters bases 13.3 to 19.3

```
!              2   3   4   5   6   7   8   9  10  11  12
              AGt gcT TtA acC caA ccG gcT AGT gtT AGC ggT-
!

!             13  14  15
              tcC ccG g ga cag aca gt-3' ! 31

!N.B. the actual seq is the reverse complement of the one shown.

!

!

(ON_LamB3-233) [RC] 5'-ccTcTgAcTgAgT gcA cAg -

!

!              2   3   4   5   6   7   8   9  10  11  12
              AGt gcT TtA acC caA ccG gcT AGT gtT AGC ggT-

!

!             13  14  15
              tcC ccG g ga cag tca gt -3' ! 2c

!N.B. the actual seq is the reverse complement of the one shown.

!

(ON_LamB4-133) [RC] 5'-ccTcTgAcTgAgT gcA cAg -

!

!              2   3   4   5   6   7   8   9  10  11  12
              AGt gcT TtA acC caA ccG gcT ACT gtT AGC ggT-

!

!             13  14  15
              tcC ccG g gg cag agg gt-3' ! 1c

! N.B. the actual seq is the reverse complement of the one shown.

!

(ON_Lam13PCR)   5'-ccTcTgAcTgAgT gcA cAg AGt gc-3'
```

TABLE 525

ONs used in Capture of kappa light chains using CJ method and BsmAI

All ONs are written 5' to 3'.
REdapters (6)
ON_2OSK15O12
gggAggATggAgAcTgggTc

ON_2OSK15L12
gggAAgATggAgAcTgggTc

ON_2OSK15A17
gggAgAgTggAgAcTgAgTc

ON_2OSK15A27
gggTgccTggAgAcTgcgTc

ON_2OSK15A11
gggTggcTggAgAcTgcgTc

ON_2OSK15B3
gggAgTcTggAgAcTgggTc

Bridges (6)
kapbri1O12
gggAggATggAgAcTgggTcATcTggATgTcTTgTgcAcTgTgAcAgAgg kapbri1L12
gggAAgATggAgAcTgggTcATcTggATgTcTTgTgcAcTgTgAcAgAgg kapbri1A17
gggAgAgTggAgAcTgggTcATcTggATgTcTTgTgcAcTgTgAcAgAgg kapbri1A27
gggTgccTggAgAcTgggTcATcTggATgTcTTgTgcAcTgTgAcAgAgg kapbri1A11
gggTggcTggAgAcTgggTcATcTggATgTcTTgTgcAcTgTgAcAgAgg kapbri1B3
gggAgTcTggAgAcTgggTcATcTggATgTcTTgTgcAcTgTgAcAgAgg

TABLE 525-continued

ONs used in Capture of kappa light chains using CJ method and BsmAI

Extender (5' biotinylated)
kapext1bio
ccTcTgTcAcAgTgcAcAAgAcATccAgATgAcccAgTcTcc Primers
kaPCRt1
ccTcTgTcAcAgTgcAcAAgAc kapfor
5'-aca ctc tcc cct gtt gaa gct ctt-3'

TABLE 530

PCR program for amplification of kappa DNA

| | |
|---|---|
| 95° C. | 5 minutes |
| 95° C. | 15 seconds |
| 65° C. | 30 seconds |
| 72° C. | 1 minute |
| 72° C. | 7 minutes |
| 4° C. | hold |

Reagents (100 ul reaction):

| | |
|---|---|
| Template | 50 ng |
| 10x turbo PCR buffer | 1x |
| turbo Pfu | 4 U |
| dNTPs | 200 μM each |
| kaPCRt1 | 300 nM |
| kapfor | 300 nM |

TABLE 610

Stuffer used in VH

```
  1  TCCGGAGCTT CAGATCTGTT TGCCTTTTTG TGGGGTGGTG
     CAGATCGCGT TACGGAGATC
```

TABLE 610-continued

Stuffer used in VH

```
 61  GACCGACTGC TTGAGCAAAA GCCACGCTTA ACTGCTGATC
     AGGCATGGGA TGTTATTCGC

121  CAAACCAGTC GTCAGGATCT TAACCTGAGG CTTTTTTTAC
     CTACTCTGCA AGCAGCGACA

181  TCTGGTTTGA CACAGAGCGA TCCGCGTCGT CAGTTGGTAG
     AAACATTAAC ACGTTGGGAT

241  GGCATCAATT TGCTTAATGA TGATGGTAAA ACCTGGCAGC
     AGCCAGGCTC TGCCATCCTG

301  AACGTTTGGC TGACCAGTAT GTTGAAGCGT ACCGTAGTGG
     CTGCCGTACC TATGCCATTT

361  GATAAGTGGT ACAGCGCCAG TGGCTACGAA ACAACCCAGG
     ACGGCCCAAC TGGTTCGCTG

421  AATATAAGTG TTGGAGCAAA AATTTTGTAT GAGGCGGTGC
     AGGGAGACAA ATCACCAATC

481  CCACAGGCGG TTGATCTGTT TGCTGGGAAA CCACAGCAGG
     AGGTTGTGTT GGCTGCGCTG

541  GAAGATACCT GGGAGACTCT TTCCAAACGC TATGGCAATA
     ATGTGAGTAA CTGGAAAACA

601  CCTGCAATGG CCTTAACGTT CCGGGCAAAT AATTTCTTTG
     GTGTACCGCA GGCCGCAGCG

661  GAAGAAACGC GTCATCAGGC GGAGTATCAA AACCGTGGAA
     CAGAAAACGA TATGATTGTT

721  TTCTCACCAA CGACAAGCGA TCGTCCTGTG CTTGCCTGGG
     ATGTGGTCGC ACCCGGTCAG

781  AGTGGGTTTA TTGCTCCCGA TGGAACAGTT GATAAGCACT
     ATGAAGATCA GCTGAAAATG

841  TACGAAAATT TTGGCCGTAA GTCGCTCTGG TTAACGAAGC
     AGGATGTGGA GGCGCATAAG

901  GAGTCGTCTA GA
```

TABLE 620

DNA sequence of pCES5

!pCES5 6680 bases = pCes4 with stuffers in CDR1-2 and CDR3 2000.12.13

!

!Ngene = 6680

!Useful REs (cut MAnoLI fewer than 3 times) 2000.06.05

!

!Non-cutters
!Acc65I Ggtacc      AfeI AGCgct       AvrII Cctagg

!BsaBI GATNNnnatc  BsiWI Cgtacg       BsmFI Nnnnnnnnnnnnnnnngtccc

!BsrGI Tgtaca      BstAPI GCANNNntgc  BstBI TTcgaa

!BstZ17I GTAtac    BtrI CACgtg        Ecl136I GAGctc

!EcoRV GATatc      FseI GGCCGGcc      KpnI GGTACc

!MscI TGGcca       NruI TCGcga        NsiI ATGCAt

!PacI TTAATtaa     PmeI GTTTaaac      PmlI CACgtg

!PpuMI RGgwccy     PshAI GACNNnngtc   SacI GAGCTc

TABLE 620-continued

| DNA sequence of pCES5 | | | | | | |
|---|---|---|---|---|---|---|
| !SacII | CCGCgg | SbfI | CCTGCAgg | SexAI | Accwggt | |
| !SgfI | GCGATcgc | SnaBI | TACgta | SpeI | Actagt | |
| !SphI | GCATGc | Sse8387I | CCTGCAgg | StuI | AGGcct | |
| !SwaI | ATTTaaat | XmaI | Cccggg | | | |
| ! | | | | | | |

```
!cutters
!Enzymes that cut more than 3 times.
!AlwNI    CAGNNNctg        5

!BsgI     ctgcac           4

!BsrFI    Rccggy           5

!EarI     CTCTTCNnnn       4

!FauI     nNNNNNNGCGGG    10

!
!Enzymes that cut from 1 to 3 times.
!
!Eco0109I RGgnccy          3    7 2636 4208

!BssSI    Ctcgtg           1   12

!-"-      Cacgag           1 1703

!BspHI    Tcatga           3   43  148 1156

!AatII    GACGTc           1   65

!BciVI    GTATCCNNNNNN     2  140 1667

!Eco57I   CTGAAG           1  301

!-"-      cttcag           2 1349

!AvaI     Cycgrg           3  319 2347 6137

!BsiHKAI  GWGCWc           3  401 2321 4245

!HgiAI    GWGCWc           3  401 2321 4245

!BcgI     gcannnnnntcg     1  461

!ScaI     AGTact           1  505

!PvuI     CGATcg           3  616 3598 5926

!FspI     TGCgca           2  763 5946

!BglI     GCCNNNNnggc      3  864 2771 5952

!BpmI     CTGGAG           1  898

!-"-      ctccag           1 4413

!BsaI     GGTCTCNnnnn      1  916

!AhdI     GACNNNnngtc      1  983

!Eam1105I GACNNNnngtc      1  983

!DrdI     GACNNNNNnngtc    3 1768 6197 6579

!SapI     gaagagc          1 1998

!PvuII    CAGctg           3 2054 3689 5896

!PflMI    CCANNNNntgg      3 2233 3943 3991

!HindIII  Aagctt           1 2235
```

TABLE 620-continued

| DNA sequence of pCES5 | | | |
|---|---|---|---|
| !ApaLI Gtgcac | 1 | 2321 | |
| !BspMI Nnnnnnnnngcaggt | 1 | 2328 | |
| !-"-   ACCTGCNNNNn | 2 | 3460 | |
| !PstI CTGCAg | 1 | 2335 | |
| !AccI GTmkac | 2 | 2341 | 2611 |
| !HincII GTYrac | 2 | 2341 | 3730 |
| !SalI Gtcgac | 1 | 2341 | |
| !TliI Ctcgag | 1 | 2347 | |
| !XhoI Ctcgag | 1 | 2347 | |
| !BbsI gtcttc | 2 | 2383 | 4219 |
| !BlpI GCtnagc | 1 | 2580 | |
| !EspI GCtnagc | 1 | 2580 | |
| !SgrAI CRccggyg | 1 | 2648 | |
| !AgeI Accggt | 2 | 2649 | 4302 |
| !AscI GGcgcgcc | 1 | 2689 | |
| !BssHII Gcgcgc | 1 | 2690 | |
| !sfiI GGCCNNNNnggac | 1 | 2770 | |
| !NaeI GCCggc | 2 | 2776 | 6349 |
| !NgoMIV Gccggc | 2 | 2776 | 6349 |
| !BtgI Ccrygg | 3 | 2781 3553 | 5712 |
| !DsaI Ccrygg | 3 | 2781 3553 | 5712 |
| !NcoI Ccatgg | 1 | 2781 | |
| !StyI Ccwwgg | 3 | 2781 4205 | 4472 |
| !MfeI Caattg | 1 | 2795 | |
| !BspEI Tccgga | 1 | 2861 | |
| !BglII Agatct | 1 | 2872 | |
| !BclI Tgatca | 1 | 2956 | |
| !Bsu36I CCtnagg | 3 | 3004 4143 | 4373 |
| !XcmI CCANNNNNnnnntgg | 1 | 3215 | |
| !MluI Acgcgt | 1 | 3527 | |
| !HpaI GTTaac | 1 | 3730 | |
| !XbaI Tctaga | 1 | 3767 | |
| ! | | | |
| !AflII Cttaag | 1 | 3811 | |
| !BsmI NGcattc | 1 | 3821 | |
| !-"-   GAATGCN | 1 | 4695 | |
| !RsrII CGgwccg | 1 | 3827 | |
| !NheI Gctagc | 1 | 4166 | |
| !BstEII Ggtnacc | 1 | 4182 | |

TABLE 620-continued

DNA sequence of pCES5

```
!BsmBI  CGTCTCNnnnn        2  4188 6625
!-"-    Nnnnnngagacg       1  6673
!ApaI   GGGCCc             1  4209
!BanII  GRGCYc             3  4209 4492 6319
!Bsp120I Gggccc            1  4209
!PspOMI Gggccc             1  4209
!BseRI  NNnnnnnnnnctcctc   1  4226
!-"-    GAGGAGNNNNNNNNNN   1  4957
!EcoNI  CCTNNnnnagg        1  4278
!PflFI  GACNnngtc          1  4308
!Tth111I GACNnngtc         1  4308
!KasI   Ggcgcc             2  4327 5967
!BstXI  CCANNNNNntgg       1  4415
!NotI   GCggccgc           1  4507
!EagI   Cggccg             1  4508
!BamHI  Ggatcc             1  5169
!BspDI  ATcgat             1  5476
!NdeI   CAtatg             1  5672
!EcoRI  Gaattc             1  5806
!PsiI   TTAtaa             1  6118
!DraIII CACNNNgtg          1  6243
!BsaAI  YACgtr             1  6246

!------------------------------------------------------------------

1 gacgaaaggg cCTCGTGata cgcctatttt tataggttaa tgtcatgata ataatggttt
!              BsssI.(1/2)
    61 cttaGACGTC aggtggcact tttcggggaa atgtgcgcgg aacccctatt tgtttatttt
!          AatII.
   121 tctaaataca ttcaaatatG TATCCgctca tgagacaata accctgataa atgcttcaat
!                    BciVI..(1 of 2)
   181 aatattgaaa aaggaagagt
!Base # 201 to 1061 = ApR gene from pUC119 with some RE sites removed
!
!        1   2   3   4   5   6   7   8   9  10  11  12  13  14  15
!       fM   S   I   Q   H   F   R   V   A   L   I   P   F   F   A
   201  atg agt att caa cat ttc cgt gtc gcc ctt att ccc ttt ttt gcg
!
!       16  17  18  19  20  21  22  23  24  25  26  27  28  29  30
!        A   F   C   L   P   V   F   A   H   P   E   T   L   V   K
```

TABLE 620-continued

DNA sequence of pCES5

```
246 gca ttt tgc ctt cct gtt ttt gct cac cca gaa acg ctg gtg aaa 31  32  33  34  35  36  37  38  39  40  41  42  43  44  45
      V   K   D   A   E   D   Q   L   G   A   R   V   G   Y   I
291 gta aaa gat gct gaa gat cag ttg ggt gcc cga gtg ggt tac atc 46  47  48  49  50  51  52  53  54  55  56  57  58  59  60
      E   L   D   L   N   S   G   K   I   L   E   S   F   R   P
336 gaa ctg gat ctc aac agc ggt aag atc ctt gag agt ttt cgc ccc 61  62  63  64  65  66  67  68  69  70  71  72  73  74  75
      E   E   R   F   P   M   M   S   T   F   K   V   L   L   C
381 gaa gaa cgt ttt cca atg atg agc act ttt aaa gtt ctg cta tgt 76  77  78  79  80  81  82  83  84  85  86  87  88  89  90
      G   A   V   L   S   R   I   D   A   G   Q   E   Q   L   G
426 ggc gcg gta tta tcc cgt att gac gcc ggg caa gaG CAa ctc ggT
                                                    BcgI...........

91  92  93  94  95  96  97  98  99 100 101 102 103 104 105
      R   R   I   H   Y   S   Q   N   D   L   V   E   Y   S   P
471 CGc cgc ata cac tat tct cag aat gac ttg gtt gAG TAC Tca cca
  ..BcgI......                                   ScaI....

106 107 108 109 110 111 112 113 114 115 116 117 118 119 120
      V   T   E   K   H   L   T   D   G   M   T   V   R   E   L
516 gtc aca gaa aag cat ctt acg gat ggc atg aca gta aga gaa tta 121 122 123 124 125 126 127 128 129 130 131 132 133 134 135
      C   S   A   A   I   T   M   S   D   N   T   A   A   N   L
561 tgc agt gct gcc ata acc atg agt gat aac act gcg gcc aac tta 136 137 138 139 140 141 142 143 144 145 146 147 148 149 150
      L   L   T   T   I   G   G   P   K   E   L   T   A   F   L
606 ctt ctg aca aCG ATC Gga gga ccg aag gag cta acc gct ttt ttg
                 PvuI.... (1/2)

151 152 153 154 155 156 157 158 159 160 161 162 163 164 165
      H   N   M   G   D   H   V   T   R   L   D   R   W   E   P
```

TABLE 620-continued

DNA sequence of pCES5

```
651 cac aac atg ggg gat cat gta act cgc ctt gat cgt tgg gaa ccg 166 167 168 169 170 171 172 173 174 175 176 177 178 179 180
         E   L   N   E   A   I   P   N   D   E   R   D   T   T   M
    696 gag ctg aat gaa gcc ata cca aac gac gag cgt gac acc acg atg 181 182 183 184 185 186 187 188 189 190 191 192 193 194 195
         P   V   A   M   A   T   T   L   R   K   L   L   T   G   E
    741 cct gta GCA ATG gca aca acg tTG CGC Aaa cta tta act ggc gaa
                BsrDI..(1/2)    FspI....(1/2)

196 197 198 199 200 201 202 203 204 205 206 207 208 209 210
         L   L   T   L   A   S   R   Q   Q   L   I   D   W   M   E
    786 cta ctt act cta gct tcc cgg caa caa tta ata gac tgg atg gag 211 212 213 214 215 216 217 218 219 220 221 222 223 224 225
         A   D   K   V   A   G   P   L   L   R   S   A   L   P   A
    831 gcg gat aaa gtt gca gga cca ctt ctg cgc tcg gcc ctt ccg gct 226 227 228 229 230 231 232 233 234 235 236 237 238 239 240
         G   W   F   I   A   D   K   S   G   A   G   E   R   G   S
    876 ggc tgg ttt att gct gat aaa tCT GGA Gcc ggt gag cgt gGG TCT
                                    BpmI....(1/2)            BsaI....

241 242 243 244 245 246 247 248 249 250 251 252 253 254 255
         R   G   I   I   A   A   L   G   P   D   G   K   P   S   R
    921 Cgc ggt atC ATT GCa gca ctg ggg cca gat ggt aag ccc tcc cgt
!BsaI......    BsrDI...(2/2)

256 257 258 259 260 261 262 263 264 265 266 267 268 269 270
         I   V   V   I   Y   T   T   G   S   Q   A   T   M   D   E
    966 atc gta gtt atc tac acG ACg ggg aGT Cag gca act atg gat gaa
                               AhdI...........

271 272 273 274 275 276 277 278 279 280 281 282 283 284 285
         R   N   R   Q   I   A   E   I   G   A   S   L   I   K   H
   1011 cga aat aga cag atc gct gag ata ggt gcc tca ctg att aag cat
```

TABLE 620-continued

DNA sequence of pCES5

```
!
!      286 287
!       W   .
  1056 tgg taa
  1062                                          ctgtcagac caagtttact
  1081 catatatact ttagattgat ttaaaacttc attttttaatt taaaaggatc taggtgaaga
  1141 tcctttttga taatctcatg accaaaatcc cttaacgtga gttttcgttc cactgagcgt
  1201 cagacccgt agaaaagatc aaaggatctt cttgagatcc ttttttttctg cgcgtaatct
  1261 gctgcttgca acaaaaaaa ccaccgctac cagcggtggt ttgtctgccg gatcaagagc
  1321 taccaactct ttttccgaag gtaactggct tcagcagagc gcagatacca aatactgtcc
  1381 ttctagtgta gccgtagtta ggccaccact tcaagaactc tgtagcaccg cctacatacc
  1441 tcgctctgct aatcctgtta ccagtggctg ctgccagtgg cgataagtcg tgtcttaccg
  1501 ggttggactc aagacgatag ttaccggata aggcgcagcg gtcgggctga acggggggtt
  1561 cgtgcataca gcccagcttg gagcgaacga cctacaccga actgagatac ctacagcgtg
  1621 agcattgaga aagcgccacg cttcccgaag ggagaaaggc ggacagGTAT CCggtaagcg
!                                                   BciVI..(2 of 2)
  1681 gcagggtcgg aacaggagag cgCACGAGg agcttccagg gggaaacgcc tggtatcttt
!                          BssSI.(2/2)
  1741 atagtcctgt cgggtttcgc cacctctgac ttgagcgtcg atttttgtga tgctcgtcag
  1801 gggggcggag cctatggaaa aacgccagca acgcggcctt tttacggttc ctggccttt
  1861 gctggccttt tgctcACATG Ttctttcctg cgttatcccc tgattctgtg gataaccgta
!                      PciI...
  1921 ttaccgcctt tgagtgagct gataccgctc gccgcagccg aacgaccgag cgcagcgagt
  1981 cagtgagcga ggaagcgGAA GAGCgcccaa tacgcaaacc gcctctcccc gcgcgttggc
!                      SapI....
  2041 cgattcatta atgCAGCTGg cacgacaggt ttcccgactg gaaagcgggc agtgagcgca
!                    PvuII.(1/3)
  2101 acgcaatTAA TGTgagttag ctcactcatt aggcacccca ggcTTTACAc tttatgcttc
!            ..-35..       Plac                   ..-10.
  2161 cggctcgtat gttgtgtgga attgtgagcg gataacaatt tcacaCAGGA AACAGCTATG
!                                                      M13Rev_seq_primer
  2221 ACcatgatta cgCCAAGCTT TGGagccttt ttttggaga ttttcaac
!             PflMI.......
!             Hind3.
!signal::linker::CLight
!
!      1   2   3   4   5   6   7   8   9   10  11  12  13  14  15
!      fM  K   K   L   L   F   A   I   P   L   V   V   P   F   Y
  2269 gtg aaa aaa tta tta ttc gca att cct tta gtt gtt cct ttc tat
```

TABLE 620-continued

DNA sequence of pCES5

```
!
!                      Linker.........................End of FR4
!      16  17  18  19      20  21  22  23  24  25  26  27  28  29  30
!      S   H   S   A       Q   V   Q   L   Q   V   D   L   E   I   K
    2314 tct cac aGT GCA    Cag gtc caa CTG CAG GTC GAC CTC GAG atc aaa
!              ApaLI......          PstI...        XhoI...
!                                   BspMI...
!                                           SalI...
!                                           AccI...(1/2)
!                                           HincII.(1/2)
!
!Vlight domains could be cloned in as ApaLI-XhoI fragments.
!VL-CL(kappa) segments can be cloned in as ApaLI-AscI fragments. <--------
!
!      Ckappa------------------------------------------------
!      31  32  33  34  35  36  37  38  39  40  41  42  43  44  45
!      R   G   T   V   A   A   P   S   V   F   I   F   P   P   S
    2359 cgt gga act gtg gct gca cca tct GTC TTC atc ttc ccg cca tct
!                                       BbsI...(1/2)
!
!      46  47  48  49  50  51  52  53  54  55  56  57  58  59  60
!      D   E   Q   L   K   S   G   T   A   S   V   V   C   L   L
    2404 gat gag cag ttg aaa tct gga act gcc tct gtt gtg tgc ctg ctg
!
!      61  62  63  64  65  66  67  68  69  70  71  72  73  74  75
!      N   N   F   Y   P   R   E   A   K   V   Q   W   K   V   D
    2449 aat aac ttc tat ccc aga gag gcc aaa gta cag tgg aag gtg gat
!
!      76  77  78  79  80  81  82  83  84  85  86  87  88  89  90
!      N   A   L   Q   S   G   N   S   Q   E   S   V   T   E   Q
    2494 aac gcc ctc caa tcg ggt aac tcc cag gag agt gtc aca gag cag
!
!      91  92  93  94  95  96  97  98  99 100 101 102 103 104 105
!      D   S   K   D   S   T   Y   S   L   S   S   T   L   T   L
    2539 gac agc aag gac agc acc tac agc ctc agc agc acc ctg acG CTG
!                                                               EspI...
!
!     106 107 108 109 110 111 112 113 114 115 116 117 118 119 120
!      S   K   A   D   Y   E   K   H   K   V   Y   A   C   E   V
```

TABLE 620-continued

DNA sequence of pCES5

```
  2584 AGC aaa gca gac tac gag aaa cac aaa GTC TAC gcc tgc gaa gtc
!....EspI....                              AccI...(2/2)
!
!      121 122 123 124 125 126 127 128 129 130 131 132 133 134 135
!       T   H   Q   G   L   S   S   P   V   T   K   S   F   N   R
  2629 acc cat cag ggc ctg agt tcA CCG GTg aca aag agc ttc aac agg
!                                   AgeI....(1/2)
!
!      136 137 138 139 140
!       G   E   C   .   .
  2674 gga gag tgt taa taa GG CGCGCCaatt
!                             AscI.....
!                              BssHII.
!
  2701 ctatttcaag gagacagtca ta
!
!PelB::3-23(stuffed)::CH1::III fusion gene
!
!      1   2   3   4   5   6   7   8   9   10  11  12  13  14  15
!       M   K   Y   L   L   P   T   A   A   A   G   L   L   L   L
  2723 atg aaa tac cta ttg cct acg gca gcc gct gga ttg tta tta ctc
!
!-------------------------------------------
!
!      16  17  18  19  20  21  22
!       A   A   Q   P   A   M   A
  2768 gcG GCC cag ccG GCC atg gcc
!         SfiI............
!               NgoMIV..(1/2)
!                     NcoI....
!
!                              FR1 (DP47/V3-23)---------------
!                             23  24  25  26  27  28  29  30
!                              E   V   Q   L   L   E   S   G
  2789                        gaa|gtt|CAA|TTG|tta|gag|tct|ggt|
!                                      |MfeI |
!
!      --------------FR1-------------------------------------
!      31  32  33  34  35  36  37  38  39  40  41  42  43  44  45
```

TABLE 620-continued

DNA sequence of pCES5

```
!       G   G   L   V   Q   P   G   G   S   L   R   L   S   C   A
  2813 |ggc|ggt|ctt|gtt|cag|cct|ggt|ggt|tct|tta|cgt|ctt|tct|tgc|gct|
!
!       ----FR1-----
!        46  47  48
!        A   S   G
  2858 |gct|TCC|GGA|
!            | BspEI |
!
!           Stuffer for CDR1, FR2, and CDR2---------------------------------->
!       There are no stop codons in this stuffer.
  2867                                                gcttcAGATC Tgtttgcctt
!                                                              BglII..
  2887 tttgtggggt ggtgcagatc gcgttacgga gatcgaccga ctgcttgagc aaaagccacg
  2947 cttaactgcT GATCAggcat gggatgttat tcgccaaacc agtcgtcagg atcttaacct
!            BclI...
  3007 gaggcttttt ttacctactc tgcaagcagc gacatctggt ttgacacaga gcgatccgcg
  3067 tcgtcagttg gtagaaacat taacacgttg ggatggcatc aatttgctta atgatgatgg
  3127 taaaacctgg cagcagccag gctctgccat cctgaacgtt tggctgacca gtatgttgaa
  3187 gcgtaccgta gtggctgccg tacctatgCC Atttgataag TGGtacagcg ccagtggcta
!                                       XcmI............
  3247 cgaaacaacc caggacggcc caactggttc gctgaatata agtgttggag caaaaatttt
  3307 gtatgaggcg gtgcagggag acaaatcacc aatcccacag gcggttgatc tgtttgctgg
  3367 gaaaccacag caggaggttg tgttggctgc gctggaagat acctgggaga ctctttccaa
  3427 acgctatggc aataatgtga gtaactggaa acacctgca atggccttaa cgttccgggc
  3487 aaataatttc tttggtgtac cgcaggccgc agcggaagaa ACGCGTcatc aggcggagta
!                                                              MluI..
  3547 tcaaaaccgt ggaacagaaa acgatatgat tgttttctca ccaacgacaa gcgatcgtcc
  3607 tgtgcttgcc tgggatgtgg tcgcacccgg tcagagtggg tttattgctc ccgatggaac
  3667 agttgataag cactatgaag atcagctgaa aatgtacgaa aattttggcc gtaagtcgct
!                                       PvuII.
  3727 ctgGTTAACg aagcaggatg tggaggcgca taaggagtcg
!           HpaI..
!           HincII(2/2)
!
!       --------FR3------------------------------------------
!                 4   5   6   7   8   9  10  11  12  13  14  15  16
!                93  94  95  96  97  98  99 100 101 102 103 104 105
!                 S   R   D   N   S   K   N   T   L   Y   L   Q   M
```

TABLE 620-continued

DNA sequence of pCES5

```
3767         |TCT|AGA|gac|aac|tct|aag|aat|act|ctc|tac|ttg|cag|atg|
             | XbaI |

---FR3------------------------------------------------>|

17  18  19  20

106 107 108 109

N   S   L   s   l   s   i   r   s   g
  3806 |aac|agC|TTA|AG t ctg agc att CGG TCC G
             |AflII |              RsrII..

q   h   s   p   t   .
  3834 gg caa cat tct cca aac tga   ccagacga cacaaacggc 3872 ttacgctaaa tcccgcgcat gggatggtaa agaggtggcg tctttgctgg cctggactca 3932 tcagatgaag gccaaaaatt ggcaggagtg gacacagcag gcagcgaaac aagcactgac 3992 catcaactgg tactatgctg atgtaaacgg caatattggt tatgttcata ctggtgctta 4052 tccagatcgt caatcaggcc atgatccgcg attacccgtt cctggtacgg gaaaatggga 4112 ctggaaaggg ctattgcctt ttgaaatgaa ccctaaggtg tataaccccc ag 4164       aa GCTAGC ctgcggcttc
                 NheI..

4182 G|GTC|ACC|                             gtc tca agc
         |BstEII |

136 137 138 139 140 141 142 143 144 145 146 147 148 149 150
       A   S   T   K   G   P   S   V   F   P   L   A   P   S   S
  4198 gcc tcc acc aag ggc cca tcg gtc ttc ccc ctg gca ccc tcc tcc 151 152 153 154 155 156 157 158 159 160 161 162 163 164 165
       K   S   T   S   C   G   T   A   A   L   G   C   L   V   K
  4243 aag agc acc tct ggg ggc aca gcg gcc ctg ggc tgc ctg gtc aag 166 167 168 169 170 171 172 173 174 175 176 177 178 179 180
       D   Y   F   P   E   P   V   T   V   S   W   N   S   G   A
  4288 gac tac ttc ccc gaa ccg gtg acg gtg tcg tgg aac tca ggc gcc 181 182 183 184 185 186 187 188 189 190 191 192 193 194 195
       L   T   S   G   V   H   T   F   P   A   V   L   Q   S   S
  4333 ctg acc agc ggc gtc cac acc ttc ccg gct gtc cta cag tcc tca
```

TABLE 620-continued

DNA sequence of pCES5

```
       196 197 198 199 200 201 202 203 204 205 206 207 208 209 210
        G   L   Y   S   L   S   S   V   V   T   V   P   S   S   S
4378 gga ctc tac tcc ctc agc agc gta gtg acc gtg ccc tcc agc agc 211 212 213 214 215 216 217 218 219 220 221 222 223 224 225
        L   G   T   Q   T   Y   I   C   N   V   N   H   K   P   S
4423 ttg ggc acc cag acc tac atc tgc aac gtg aat cac aag ccc agc 226 227 228 229 230 231 232 233 234 235 236 237 238
        N   T   K   V   D   K   K   V   E   P   K   S   C
4468 aac acc aag gtg gac aaG AAA GTT GAG CCC AAA TCT TGT
                             ON-TQHCforw.....................

Poly His linker
               139 140 141 142 143 144 145 146 147 148 149 150
                A   A   A   H   H   H   H   H   H   G   A   A
4507           GCG GCC GCa cat cat cat cac cat cac ggg gcc gca
               NotI......
               EagI....

151 152 153 154 155 156 157 158 159 160 161 162 163 164 165
        E   Q   K   L   I   S   E   E   D   L   N   G   A   A   .
4543 gaa caa aaa ctc atc tca gaa gag gat ctg aat ggg gcc gca tag Mature III---------------------------------------------->...
       166 167 168 169 170 171 172 173 174 175 176 177 178 179 180
        T   V   E   S   C   L   A   K   P   H   T   E   N   S   F
4588 act gtt gaa agt tgt tta gca aaa cct cat aca gaa aat tca ttt 181 182 183 184 185 186 187 188 189 190 191 192 193 194 195
        T   N   V   W   K   D   D   K   T   L   D   R   Y   A   N
4633 act aac gtc tgg aaa gac gac aaa act tta gat cgt tac gct aac 196 197 198 199 200 201 202 203 204 205 206 207 208 209 210
        Y   E   G   C   L   W   N   A   T   G   V   V   V   C   T
4678 tat gag ggc tgt ctg tgG AAT GCt aca ggc gtt gtg gtt tgt act
                             BsmI....

211 212 213 214 215 216 217 218 219 220 221 222 223 224 225
```

TABLE 620-continued

DNA sequence of pCES5

|     | G   | D   | E   | T   | Q   | C   | Y   | G   | T   | W   | V   | P   | I   | G   | L   |
|-----|-----|-----|-----|-----|-----|-----|-----|-----|-----|-----|-----|-----|-----|-----|-----|
| 4723 | ggt | gac | gaa | act | cag | tgt | tac | ggt | aca | tgg | gtt | cct | att | ggg | ctt |

|     | 226 | 227 | 228 | 229 | 230 | 231 | 232 | 233 | 234 | 235 | 236 | 237 | 238 | 239 | 240 |
|-----|-----|-----|-----|-----|-----|-----|-----|-----|-----|-----|-----|-----|-----|-----|-----|
|     | A   | I   | P   | E   | N   | E   | G   | G   | S   | E   | G   | G   | G   | S   |     |
| 4768 | gct | atc | cct | gaa | aat | gag | ggt | ggt | ggc | tct | gag | ggt | ggc | ggt | tct |

|     | 241 | 242 | 243 | 244 | 245 | 246 | 247 | 248 | 249 | 250 | 251 | 252 | 253 | 254 | 255 |
|-----|-----|-----|-----|-----|-----|-----|-----|-----|-----|-----|-----|-----|-----|-----|-----|
|     | E   | G   | G   | G   | S   | E   | G   | G   | T   | K   | P   | P   | E   | Y   |     |
| 4813 | gag | ggt | ggc | ggt | tct | gag | ggt | ggc | ggt | act | aaa | cct | cct | gag | tac |

|     | 256 | 257 | 258 | 259 | 260 | 261 | 262 | 263 | 264 | 265 | 266 | 267 | 268 | 269 | 270 |
|-----|-----|-----|-----|-----|-----|-----|-----|-----|-----|-----|-----|-----|-----|-----|-----|
|     | G   | D   | T   | P   | I   | P   | G   | Y   | T   | Y   | I   | N   | P   | L   | D   |
| 4858 | ggt | gat | aca | cct | att | ccg | ggc | tat | act | tat | atc | aac | cct | ctc | gac |

|     | 271 | 272 | 273 | 274 | 275 | 276 | 277 | 278 | 279 | 280 | 281 | 282 | 283 | 284 | 285 |
|-----|-----|-----|-----|-----|-----|-----|-----|-----|-----|-----|-----|-----|-----|-----|-----|
|     | G   | T   | Y   | P   | P   | G   | T   | E   | Q   | N   | P   | A   | N   | P   | N   |
| 4903 | ggc | act | tat | ccg | cct | ggt | act | gag | caa | aac | ccc | gct | aat | cct | aat |

|     | 286 | 287 | 288 | 289 | 290 | 291 | 292 | 293 | 294 | 295 | 296 | 297 | 298 | 299 | 300 |
|-----|-----|-----|-----|-----|-----|-----|-----|-----|-----|-----|-----|-----|-----|-----|-----|
|     | P   | S   | L   | E   | E   | S   | Q   | P   | L   | N   | T   | F   | M   | F   | Q   |
| 4948 | cct | tct | ctt | GAG | GAG | tct | cag | cct | ctt | aat | act | ttc | atg | ttt | cag |
|     |     |     |     | BseRI..(2/2) |

|     | 301 | 302 | 303 | 304 | 305 | 306 | 307 | 308 | 309 | 310 | 311 | 312 | 313 | 314 | 315 |
|-----|-----|-----|-----|-----|-----|-----|-----|-----|-----|-----|-----|-----|-----|-----|-----|
|     | N   | N   | R   | F   | R   | N   | R   | Q   | G   | A   | L   | T   | V   | Y   | T   |
| 4993 | aat | aat | agg | ttc | cga | aat | agg | cag | ggt | gca | tta | act | gtt | tat | acg |

|     | 316 | 317 | 318 | 319 | 320 | 321 | 322 | 323 | 324 | 325 | 326 | 327 | 328 | 329 | 330 |
|-----|-----|-----|-----|-----|-----|-----|-----|-----|-----|-----|-----|-----|-----|-----|-----|
|     | G   | T   | V   | T   | Q   | G   | T   | D   | P   | V   | K   | T   | Y   | Y   | Q   |
| 5038 | ggc | act | gtt | act | caa | ggc | act | gac | ccc | gtt | aaa | act | tat | tac | cag |

|     | 331 | 332 | 333 | 334 | 335 | 336 | 337 | 338 | 339 | 340 | 341 | 342 | 343 | 344 | 345 |
|-----|-----|-----|-----|-----|-----|-----|-----|-----|-----|-----|-----|-----|-----|-----|-----|
|     | Y   | T   | P   | V   | S   | S   | K   | A   | M   | Y   | D   | A   | Y   | W   | N   |
| 5083 | tac | act | cct | gta | tca | tca | aaa | gcc | atg | tat | gac | gct | tac | tgg | aac |

|     | 346 | 347 | 348 | 349 | 350 | 351 | 352 | 353 | 354 | 355 | 356 | 357 | 358 | 359 | 360 |
|-----|-----|-----|-----|-----|-----|-----|-----|-----|-----|-----|-----|-----|-----|-----|-----|
|     | G   | K   | F   | R   | D   | C   | A   | F   | H   | S   | G   | F   | N   | E   | D   |
| 5128 | ggt | aaa | ttc | aga | gac | tgc | gct | ttc | cat | tct | ggc | ttt | aat | gaG | GAT |

TABLE 620-continued

DNA sequence of pCES5

```
!                                                               BamHI..
!
!     361 362 363 364 365 366 367 368 369 370 371 372 373 374 375
!      P   F   V   C   E   Y   Q   G   Q   S   S   D   L   P   Q
   5173CCa ttc gtt tgt gaa tat caa ggc caa tcg tct gAC CTG Cct caa
!BamHI...                                          BspMI...(2/2)
!
!     376 377 378 379 380 381 382 383 384 385 386 387 388 389 390
                                                              S   G   G   G   S !G   G
   5218cct cct gtc aat gct ggc ggc ggc tct ggt ggt ggt tct ggt ggc
!
!     391 392 393 394 395 396 397 398 399 400 401 402 403 404 405
!      G   S   E   G   G   G   S   E   G   G   G   S   E   G   G
   5263ggc tct gag ggt ggc ggc tct gag ggt ggc ggt tct gag ggt ggc
!
!     406 407 408 409 410 411 412 413 414 415 416 417 418 419 420
!      G   S   E   G   G   G   S   G   G   S   G   S   G   D
   5308ggc tct gag ggt ggc ggt tcc ggt ggc ggc tcc ggt tcc ggt gat
!
!     421 422 423 424 425 426 427 428 429 430 431 432 433 434 435
!      F   D   Y   E   K   M   A   N   A   N   K   G   A   M   T
   5353ttt gat tat gaa aaa atg gca aac gct aat aag ggg gct atg acc
!
!     436 437 438 439 440 441 442 443 444 445 446 447 448 449 450
!      E   N   A   D   E   N   A   L   Q   S   D   A   K   G   K
   5398gaa aat gcc gat gaa aac gcg cta cag tct gac gct aaa ggc aaa
!
!     451 452 453 454 455 456 457 458 459 460 461 462 463 464 465
!      L   D   S   V   A   T   D   Y   G   A   A   I   D   G   F
   5443ctt gat tct gtc gct act gat tac ggt gct gct ATC GAT ggt ttc
!                                                          BspDI..
!
!     466 467 468 469 470 471 472 473 474 475 476 477 478 479 480
!      I   G   D   V   S   G   L   A   N   G   N   G   A   T   G
   5488att ggt gac gtt tcc ggc ctt gct aat ggt aat ggt gct act ggt
!
!     481 482 483 484 485 486 487 488 489 490 491 492 493 494 495
!      D   F   A   G   S   N   S   Q   M   A   Q   V   G   D   G
   5533gat ttt gct ggc tct aat tcc caa atg gct caa gtc ggt gac ggt
```

TABLE 620-continued

DNA sequence of pCES5

```
      496 497 498 499 500 501 502 503 504 505 506 507 508 509 510
       D   N   S   P   L   M   N   N   F   R   Q   Y   L   P   S
  5578 gat aat tca cct tta atg aat aat ttc cgt caa tat tta cct tct 511 512 513 514 515 516 517 518 519 520 521 522 523 524 525
       L   P   Q   S   V   E   C   R   P   Y   V   F   G   A   G
  5623 ttg cct cag tcg gtt gaa tgt cgc cct tat gtc ttt ggc gct ggt 526 527 528 529 530 531 532 533 534 535 536 537 538 539 540
       K   P   Y   E   F   S   I   D   C   D   K   I   N   L   F
  5668 aaa cCA TAT Gaa ttt tct att gat tgt gac aaa ata aac tta ttc
          NdeI....

541 542 543 544 545 546 547 548 549 550 551 552 553 554 555
       R   G   V   F   A   F   L   L   Y   V   A   T   F   M   Y
  5713 cgt ggt gtc ttt gcg ttt ctt tta tat gtt gcc acc ttt atg tat 556 557 558 559 560 561 562 563 564 565 566 567 568 569 570
       V   F   S   T   F   A   N   I   L   R   N   K   E   S   .
  5758 gta ttt tcg acg ttt gct aac ata ctg cgt aat aag gag tct taa 571
       .
  5803 taa GAATTC
            EcoRI.
  5812 actggccgt cgttttacaa cgtcgcgact gggaaaaccc tggcgttacc caacttaatc
  5871 gccttgcagc acatccccct ttcgccagct ggcgtaatag cgaagaggcc cgcacCGATC
                                                                  PvuI..
  5931 Gcccttccca acagtTGCGC Agcctgaatg gcgaatGGCG CCtgatgcgg tatttctcc
  !...PvuI...(3/3)         FspI...(2/2)          KasI...(2/2)
  5991 ttacgcatct gtgcggtatt tcacaccgca tataaattgt aaacgttaat attttgttaa
  6051 aattcgcgtt aaattttgt taaatcagct catttttaa ccaataggcc gaaatcggca
  6111 aaatcccTTA TAAatcaaaa gaatagcccg atagggtt gagtgttgtt ccagtttgga
             PsiI...
  6171 acaagagtcc actattaaag aacgtggact ccaacgtcaa agggcgaaaa accgtctatc
  6231 agggcgatgg ccCACtacGT Gaaccatcac ccaaatcaag ttttttgggg tcgaggtgcc
                 DraIII....
  6291 gtaaagcact aaatcggaac cctaaaggga gccccgatt cagagcttga cggggaaaGC
```

TABLE 620-continued

DNA sequence of pCES5

```
!                                                        NgoMIV..
6351 CGGCgaacgt ggcgagaaag gaagggaaga aagcgaaagg agcgggcgct agggcgctgg
!    ..NgoMIV.(2/2)
6411 caagtgtagc ggtcacgctg cgcgtaacca ccacacccgc cgcgcttaat gcgccgctac
6471 agggcgcgta ctatggttgc tttgacgggt gcagtctcag tacaatctgc tctgatgccg
6531 catagttaag ccagccccga caccsgccaa cacccgctga cgcgccctga cgggcttgtc
6591 tgctcccggc atccgcttac agacaagctg tgaccgtctc cgggagctgc atgtgtcaga
6651 ggttttcacc gtcatcaccg aaacgcgcga
```

TABLE 630

Oligonucleotides used to clone CDR1/2 diversity

All sequences are 5' to 3'.

1) ON_CD1Bsp, 30 bases

| A | c | c | T | c | A | c | T | g | g | C | T | T | c | c | g | g | A |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 |

| T | T | c | A | c | T | T | T | c | T | c | T |
|---|---|---|---|---|---|---|---|---|---|---|---|
| 19 | 20 | 21 | 22 | 23 | 24 | 25 | 26 | 27 | 28 | 29 | 30 |

2) ON_Br12, 42 bases

| A | g | A | A | A | c | c | c | A | c | T | c | c | A | A | A | c | c |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 |

| T | T | T | A | c | c | A | g | g | A | g | c | T | T | g | g | c | g |
|---|---|---|---|---|---|---|---|---|---|---|---|---|---|---|---|---|---|
| 19 | 20 | 21 | 22 | 23 | 24 | 25 | 26 | 27 | 28 | 29 | 30 | 31 | 32 | 33 | 34 | 35 | 36 |

| A | A | c | c | c | A |
|---|---|---|---|---|---|
| 37 | 38 | 39 | 40 | 41 | 42 |

3) ON_CD2Xba, 51 bases

| g | g | A | A | g | g | c | A | g | T | g | A | T | c | T | A | g | A |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 |

| g | A | T | A | g | T | g | A | A | g | c | g | A | c | c | T | T | T |
|---|---|---|---|---|---|---|---|---|---|---|---|---|---|---|---|---|---|
| 19 | 20 | 21 | 22 | 23 | 24 | 25 | 26 | 27 | 28 | 29 | 30 | 31 | 32 | 33 | 34 | 35 | 36 |

| A | A | c | g | g | A | g | T | c | A | g | c | A | T | A |
|---|---|---|---|---|---|---|---|---|---|---|---|---|---|---|
| 37 | 38 | 39 | 40 | 41 | 42 | 43 | 44 | 45 | 46 | 47 | 48 | 49 | 50 | 51 |

4) ON_BotXba, 23 bases

| g | g | A | A | g | g | c | A | g | T | g | A | T | c | T | A | g | A |
|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 |

| g | A | T | A | g |
|---|---|---|---|---|
| 19 | 20 | 21 | 22 | 23 |

---

We claim:

1. A method for preparing a nucleic acid, the method comprising the steps of:

(i) amplifying a nucleic acid that encodes a polypeptide using a primer complementary to at least part of a synthetic sequence located at the 5' terminus of the nucleic acid sequence;

(ii) rendering the amplified nucleic acid obtained from step (i) single-stranded;

(iii) hybridizing the single-stranded nucleic acid obtained from step (ii) with a single-stranded oligonucleotide to form a locally double-stranded region, wherein there is a single site for a restriction endonuclease within the locally double-stranded region;

(iv) forming a cleaved DNA complex by cleaving the locally double-stranded region formed by the hybridizing step (iii) with the restriction endonuclease at the single site for the restriction endonuclease to remove all unwanted 5' nucleotides from the amplified nucleic acid; and (v) cloning the cleaved DNA complex obtained from step (iv) a vector for expressing the polypeptide encoded by the nucleic acid;

wherein the hybridizing and the cleaving steps are performed at a temperature under which the single-stranded nucleic acid is maintained in substantially single-stranded form and associates with the single-stranded oligonucleotide to form the locally double-stranded region, and wherein the restriction endonuclease is active at the temperature.

2. The method according to claim 1, wherein the nucleic acid encodes at least a portion of an immunoglobulin.

3. The method according to claim 2, wherein the immunoglobulin comprises a Fab or single chain Fv.

4. The method according to claim 3, wherein the immunoglobulin comprises at least a portion of a heavy chain.

5. The method according to claim 4, wherein at least a portion of the heavy chain is human.

6. The method according to claim 3, wherein the immunoglobulin comprises at least a portion of FR1.

7. The method according to claim 6, wherein at least a portion of the FR1 is human.

8. The method according to claim 3, wherein the immunoglobulin comprises at least a portion of a light chain.

9. The method according to claim 8, wherein at least a portion of the light chain is human.

10. The method according to claim 2, wherein the immunoglobulin comprises at least a portion of a heavy chain.

11. The method according to claim 10, wherein at least a portion of the heavy chain is human.

12. The method according to claim 2, wherein the immunoglobulin comprises at least a portion of FR1.

13. The method according to claim 12, wherein at least a portion of the FR1 is human.

14. The method according to claim 2, Wherein the immunoglobulin comprises at least a portion of a light chain.

15. The method according to claim 14, Wherein at least a portion of the light chain is human.

16. The method according to claim 1, wherein the nucleic acid is at least in part derived from a patient suffering from at least one autoimmune disease or cancer.

17. The method according to claim 16, wherein the autoimmune disease is lupus erythematosus, systemic sclerosis, rheumatoid arthritis, antiphosolipid syndrome or vasculitis.

18. The method according to claim 16, wherein the nucleic acid is at least in part isolated from peripheral blood cells, bone marrow cells, spleen cells or lymph node cells.

19. The method according to claim 1, Wherein the temperature is between 45° C. and 75° C.

20. The method according to claim 19, wherein the temperature is between 50° C. and 60° C.

21. The method according to claim 20, wherein the temperature is between 55° C. and 60° C.

22. The method according to claim 1, wherein the length of the single-stranded oligonucleotide is between 17 and 30 bases.

23. The method according to claim 22, wherein the length of the single-stranded oligonucleotide is between 18 and 24 bases.

24. The method according to claim 1, wherein the restriction endonuclease is selected from the group consisting of TaaI MacIII, Tsp45I, HphI, BsaJI, AluI, BlpI, DdeI, BglII, MslI, BsiEI, EaeI, EagI, HaeIII, Bst4CI, HpyCH4III, HinfI, MlyI, PleI, MnlI, HpyCH4V, BsmAI, BpmI, XmnI, and SacI.

25. The method according to claim 24, wherein the restriction endonuclease is selected from the group consisting of Bst4CI, TaaI, HpyCH4III, BlpI, HpyCH4V and MslI.

26. The method of claim 1, wherein the vector is a. phage display vector.

27. The method of claim 1, wherein the cloning step is performed using a partially duplexed synthetic DNA adapter.

* * * * *